US008283334B2

(12) United States Patent
Bogdahn et al.

(10) Patent No.: US 8,283,334 B2
(45) Date of Patent: Oct. 9, 2012

(54) INHIBITORS OF TGF-R SIGNALING FOR TREATMENT OF CNS DISORDERS

(75) Inventors: Ulrich Bogdahn, Regensburg (DE);
Ludwig Aigner, Regensburg (DE);
Frank-Peter Wachs, Regensburg (DE);
Beate Winner, Regensburg (DE);
Jurgen Winkler, Lappersdorf (DE)

(73) Assignees: Ulrich Bogdahn, Regensburg (DE);
Ludwig Aigner, Salzburg (AT)

( * ) Notice: Subject to any disclaimer, the term of this patent is extended or adjusted under 35 U.S.C. 154(b) by 0 days.

(21) Appl. No.: 13/028,035

(22) Filed: Feb. 15, 2011

(65) Prior Publication Data

US 2011/0263678 A1 Oct. 27, 2011

Related U.S. Application Data

(62) Division of application No. 10/597,813, filed as application No. PCT/EP2005/001298 on Feb. 9, 2005, now Pat. No. 8,022,045.

(30) Foreign Application Priority Data

Feb. 9, 2004 (EP) .................................... 04002846

(51) Int. Cl.
*A61K 31/70* (2006.01)
*C07H 21/02* (2006.01)
*C07H 21/04* (2006.01)
(52) U.S. Cl. .......................... 514/44; 536/24.1; 536/24.5
(58) Field of Classification Search ................. 536/23.1, 536/24.1, 24.3, 24.33, 24.5
See application file for complete search history.

(56) References Cited

U.S. PATENT DOCUMENTS

2003/0064944 A1* 4/2003 Murray et al. .................. 514/44

FOREIGN PATENT DOCUMENTS

| EP | 1 133 988 | 9/2001 |
|---|---|---|
| WO | WO 93/19783 | 10/1993 |
| WO | WO 01/19161 | 3/2001 |
| WO | WO 03/000656 | 1/2003 |
| WO | WO 03/056013 | 7/2003 |

OTHER PUBLICATIONS

Sylvain Lesne et al., "Transforming Growth Factor-β1 Potentiates Amyloid-β Generationin Astrocytes and in Transgenic Mice" The Journal of Biological Chemistry, (2003), vol. 278, No. 20, pp. 18408-18418.

Amelia Sanchez-Capelo et al., "Transforming growth factor β1 overexpression in the nigrostriatal system increases the dopaminergic deficit of MPTP mice" Molecular and Cellular Neuroscience, (2003), vol. 23, pp. 614-625.

(Continued)

*Primary Examiner* — Terra Cotta Gibbs
(74) *Attorney, Agent, or Firm* — J.C. Patents

(57) ABSTRACT

The present invention relates to the use of oligonucleotides for the preparation of a pharmaceutical composition for the prevention or treatment of a disease, wherein neurogenesis and/or neuroregeneration has a beneficial effect, in particular a disease like Morbus Alzheimer, Morbus Parkinson, Lewy Body Dementia, Amyotrophic Lateral Sclerosis, Spinocerebellar Atrophies, Creutzfeldt Jakob Disease, Frontemporal Dementia, Morbus Pick, AIDS Dementia Complex, Vascular Dementia, Progressive Supranuclear Palsy, Corticobasal Degeneration, Multisystem-Atrophy, Hallervorden Spatz Disease, Huntington's disease, Stroke, Traumatic Brain and spinal cord Injury, Retinitis Pigmentosa, Macular Degeneration, Glaucoma, Cochlea Degeneration, Depression, Schizophrenia, Multiple Sclerosis, and developmental neurodegeneration.

4 Claims, 5 Drawing Sheets

OTHER PUBLICATIONS

Kerstin Krieglstein et al., "Reduction of endogenous transforming growth factors β prevents ontogenetic neuron death" Nature America Inc., (2000), vol. 3, No. 11, pp. 1085-1090.

Minori Higashiyama et al., "Inhibition by Transforming Growth Factor-β1 of the Cellular Action of Arginine Vasopressin in Cultured Rat Glomerular Mesangial Cells" Hypertension Research, (1999), vol. 22, pp. 173-180.

Christopher A. Baker et al., "Microglial Activation Varies in Different Models of Creutzfeldt-Jakob Disease" Journal of Virology, (1999), vol. 73, No. 6, pp. 5089-5097.

Tony Wyss-Coray et al., "Chronic Overproduction of Transforming Growth Factor-β1 by Astrocytes Promotes Alzheimer's Disease-Like Microvascular Degeneration in Transgenic Mice" American Journal of Pathology, (2000), vol. 156, No. 1, pp. 139-150.

Xiaoping Luo et al., "The Expression of Smads in Human Endometrium and Regulation and Induction in Endometrial Epithelial and Stromal Cells by Transforming Growth Factor-β" The Journal of Clinical Endocrinology & Metabolism, (2003), vol. 88, No. 10, pp. 4967-4976.

Anne E.G. Lenferink et al., "Expression of TFG-β Type II Receptor Antisense RNA Impairs TGF-β Signaling in Vitro and Promotes Mammary Gland Differentiation in Vivo" International Journal of Cancer, (2003), vol. 107, Issue 6, pp. 919-928.

Weipting Yu et al., "Evidence for Role of Transforming Growth Factor-β in RRR-α-Tocopheryl Succinate-Induced Apoptosis of Human MDA-MB-435 Breast Cancer Cells" Nutrition and Cancer, (1997), vol. 27, No. 3, pp. 267-278.

Wendy Yee et al., "Glucocorticoid-induced tropoelastin expression is mediated via transforming growth factor-$β_3$" The American Physiological Society, (1996), vol. 14, No. 6, pp. L992-1001L.

Sylviane Komesli et al., "Chimeric extracellular domain of type II transforming growth factor (TGF)-β receptor fused to the Fc region of human immunoglobulin as a TGF-β antagonist" European Journal of Biochemistry, (1998), vol. 254, pp. 505-513.

Frederick L. Hall et al., "Transforming growth factor-β type-II receptor signalling: intrinsic/associated casein kinase activity, receptor interactions and functional effects of blocking antibodies" Biochemical Journal, (1996), vol. 316, pp. 303-310.

Jason Liu et al., "Transforming Growth Factor β2, But Not β1 and β3, Is Critical for Early Rat Lung Branching" Developmental Dynamics, (2000), vol. 217, pp. 343-360.

Miroslava Ogorelkova et al., "Adenovirus-Delivered Antisense RNA and shRNA Exhibit Different Silencing Efficiencies for the Endogenous Transforming Growth Factor-β (TGF-β) Type II Receptor" Oligonucleotides, (2006), vol. 16, pp. 2-14.

Corline J.A. De Groot et al., "Expression of Transforming Growth factor (TGF)-β1, -β2, and -β3 Isoforms and TGF-β Type I and Type II Receptors in Multiple Sclerosis Lesions and Human Adule Astrocyte Cultures" Journal of Neuropathology and Experimental Neurology, (1999), vol. 58, No. 2, pp. 174-187.

Jia Luo et al., "Growth factor-mediated neural proliferation: target of ethanol toxicity" Brain Research, (1998), vol. 27, pp. 157-167.

Jia Luo et al., "Basic fibroblast growth factor- and platelet-derived growth factor-mediated cell proliferation in B104 neuroblastoma cells: effect of ethanol on cell cycle kinetics" Brain Research, (1997), vol. 770, pp. 139-150.

Natalie Milner et al., "Selecting effective antisense reagents on combinatorial oligonucleotide arrays" Nature Biotechnology, (1997), vol. 15, pp. 537-541.

Patricia Lagadec et al., "Evidence for Control of Nitric Oxide Synthesis by Intracellular Transforming Growth Factor-β1 in Tumor Cells" American Journal of Pathology, (1999), vol. 154, No. 6, pp. 1867-1876.

Jiangsong Zhao et al., "Abrogation of Transforming Growth Factor-β Type II Receptor Stimulates Embryonic Mouse Lung Branching Morphogenesis in Culture" Developmental Biology, (1996), vol. 180, pp. 242-257.

Blast Alignment of Sequence ID No. 3, dated Mar. 2, 2008.

Sequence of Tgf-$R_{II}$, NM_003242, PRI Mar. 9, 2007.

* cited by examiner

A)

B)

A)

B)

INHIBITORS OF TGF-R SIGNALING FOR TREATMENT OF CNS DISORDERS

CROSS-REFERENCE TO RELATED APPLICATION

This application is a divisional of, and claims the priority benefit of, U.S. application Ser. No. 10/597,813 filed on Apr. 13, 2007, now issued as U.S. Pat. No. 8,022,045, which is based on International Patent application PCT/EP2005/001298, filed on Feb. 9, 2005, which claims the priority benefit of European Patent application serial No. 04002846.6, filed on Feb. 9, 2004. The entirety of each of the above-mentioned patent applications is hereby incorporated by reference herein and made a part of this specification.

SPECIFICATION

The present invention relates to the use of oligonucleotides for the preparation of a pharmaceutical composition for the prevention or treatment of a disease, wherein neurogenesis and/or neuroregeneration has a beneficial effect, in particular a neurodegenerative disease like Morbus Alzheimer, Morbus Parkinson incl. Multisystem-Atrophy, Progressive Supranuclear Palsy, Corticobasal Degeneration, Lewy Body Dementia, Amyotrophic Lateral Sclerosis and other Motor Neuron Disorders, Huntington's disease, Spinocerebellar Atrophies, Creutzfeldt Jakob and other severe Prion Diseases, Frontemporal Dementia incl. Morbus Pick, AIDS Dementia Complex, Hallervorden Spatz Disease, Huntington's disease, a cerebrovascular disease like Vascular Dementia, Stroke, Traumatic Brain and spinal cord Injury, Retinitis Pigmentosa, Macular Degeneration, Glaucoma, Depression and Schizophrenia, and developmental disorders like Down's syndrome.

A number of severe neurodegenerative disorders have severe socioeconomic impact upon modern societies, e.g., disorders like Morbus Alzheimer, Developmental disorders with dementia (like Down's syndrome), Morbus Parkinson, Lewy Body Dementia, Frontemporal Dementia, Morbus Pick, Amyotrophic Lateral Sclerosis, Spinocerebellar Atrophies; Creutzfeldt Jakob Disease, AIDS Dementia Complex, Vascular Dementia, Progressive Supranuclear Palsy, Corticobasal Degeneration, Multisystem-Atrophy, Huntington's disease, Stroke, Traumatic Brain Injury, Retinitis Pigmentosa, Macular Degeneration, Glaucoma, Depression, Schizophrenia, and Multiple Sclerosis. The common pathophysiological cause is found in genetic, epigenetic or acquired defects—frequently resulting in aggregate formation or accumulation of cell debris—ultimately leading to progressive dysfunction and finally to neuronal or glial cell death and structural disintegration. Microglia cells and perivascular resting macrophages are attracted and activated, trying to clear the cell and tissue debris. This may happen in a very short span of time, as in Creutzfeldt Jacob Disease, or over decades, as e.g. in Parkinson's Disease or Multiple Sclerosis. The activated microglial/macrophage cell population releases a number of inflammatory cytokines into the extracellular matrix, draining these either into small venules or the CSF-space. Unfortunately, neurogenesis and neuroregeneration that could have an advantageous effect on the clinical course of these diseases described above (despite their individual specific pathophysiological mechanisms) is suppressed by so far unknown mechanisms. Thus, the technical problem underlying the present invention is to provide means suitable for treating or preventing neurodegenerative disorders or at least symptoms associated with said disorders by interfering with the suppression of neurogenesis and neuroregeneration.

The solution of the said technical problem is achieved by providing the embodiments characterized in the claims. The TGF-beta family of proteins, namely TGF-beta1, TGF-beta2 and TGF-beta3 with their specific cell surface receptors TGF RI, TGF RII, TGF RIII are known to act on several crucial aspects of embryonal and mainly mesenchymal/neuroektodermal organ development. They allow embryonal stem cells to differentiate into neuronal precursor cells, and are neuroprotective for injured mature neurons. It is further known that they have a critical impact upon hematopoetic stem cell differentiation, controlling proliferation and also differentiation. During the experiments leading to the present invention it was found that TGF-R, i.e. TGF RI and TGF RII are crucial factors involved in suppression of neurogenesis and neuroregeneration and, accordingly, a compound which is capable of interfering with this biological activity of TGF R or TGF RII is useful for the treatment/prevention of neurodegenerative disorders and/or neuroinflammatory disorders.

To summarize, as a result of the experiments leading to the present invention:

1. A physiological regulatory circuit has been recognized that accounts for the level of effective CNS-reneration by precursor-/stem cells, although of course the individual components have been known (TGF-β, TGF-RII, cerebrospinal fluid compartment, vitreous, endolymphatic fluid, neuronal precursor cells, etc). This circuit—with the crucial target molecule TGF-RII expressed at the ventricular wall—is responsible for the defunct neuroregeneration in the majority of CNS-pathology.

2. Interestingly the regulation takes places not via blood, lymphatics, or extracellular matrix but via fluid compartments (cerebrospinal fluid etc.), which have direct contact to neuronal cells and their precursors or stem cells.

3. A physiologically inhibitory circuit for neuronal/oligodendroglial or astrocytic renewal has been discovered as being an ideal target for strategies to repair damage within the CNS, overwhelmingly being applicable for almost all destructive pathology in the nervous system. From previous knowledge on TGF-β it has been tried rather to increase than decrease (see 5) TGF-β function in order to augment its known neuroprotective or immunosuppresive activities in the CNS: here we postulate to decrease its inhibitory function on stem cell renewal by blocking TGF-RII signalling at the ventricular wall.

4. Although for a long time it has been speculated that inflammatory processes play a significant role in neurodegeneration, and a relative large amount of preclinical and clinical data seem to support this idea, the master circuit is now being disclosed, that orchestrates all the single regulatory sub-circles, e.g. cytokines (IL-1, IL-6, IL-12) and others.

5. In addition, it might be noted that Nature has installed neuroprotection and an immunoprivileged CNS above neuroregeneration in priority: it has not been shown so far that the immunopriviliged and highly protected CNS (protected specifically against immune attacks and neuronal apoptosis), which is in significant part due to the TGF-β system, has deficits in neuroregeneration due to exactly this privilege and due to the same molecule TGF-β. The evolutionary concept seems to argue in favour for acute neuroprotection of a highly sophisticated CNS and its most complex functioning; in this context, individual neuroregeneration seems less important for evolution than neuroprotection of the individuum.

The Regulatory Circuit

Physiologically neurogenesis of the brain allows continuous repair/replacement of malfunctioning or ageing neuronal, oligodendroglial or astrocytic cells by respective precursor cells. Neurogenesis for repair in the brain is regulated by the TGF-β-TGF-R (especially TGF RII, but also TGF RI) system, via the cerebrospinal fluid; the main orchestrators are micoglial/macrophage lineage cells producing TGF-β and secreting it via extracellular space into the CSF (as well as within vitreous, endolymphatics) compartment, and neuronal precursor cells/stem cells, that receive this signal via CSF (as well as into vitreous, endolymphatics) through highly expressed TGF-RII or TGF-RI on their surface structures, or an ependymal lining with identical receptors. In the majority of CNS-pathology neurogenesis is severely impaired or malfunctioning. The regulation of neurogenesis is adjusted, usually suppressed (!) by the activation of microglial cells/macrophages from within the CNS, taking place in the context of any specific disease pathology. Activated microglial cells/macrophages by this route—CSF to subventrucolar zone/other neurogenic zones—suppress the regeneration of the neurodegenerating, acute and chronic inflammatory, hypoxic, atherosclerotic or ageing brain parenchyma. Not only neuronal differentiation is affected, but also oligodendroglial and astrocytic cell lineages. All molecules that interfere with this circuit to improve neuronal/oligodenroglial/astrocytic regeneration are claimed as treatment. Methods for diagnostics, prophylaxis, prevention or prognosis of CNS pathology employing this circuit are also of high importance, conceivably for monitoring the effects of therapeutic intervention.

Adult rodent neural stem and precursor cell cultures were treated with 10 ng/ml of recombinant human TGF-beta1 for 7 days. On day 7 cells were dissociated, counted by Trypan Blue exclusion assay and TGF-beta1 pre-treated cells were reseeded in with or without 10 ng/ml TGF-betaI. This procedure was performed every 7 days. The data are expressed as average cell numbers±SD from three experiments performed in triplicate.

Figure 3:
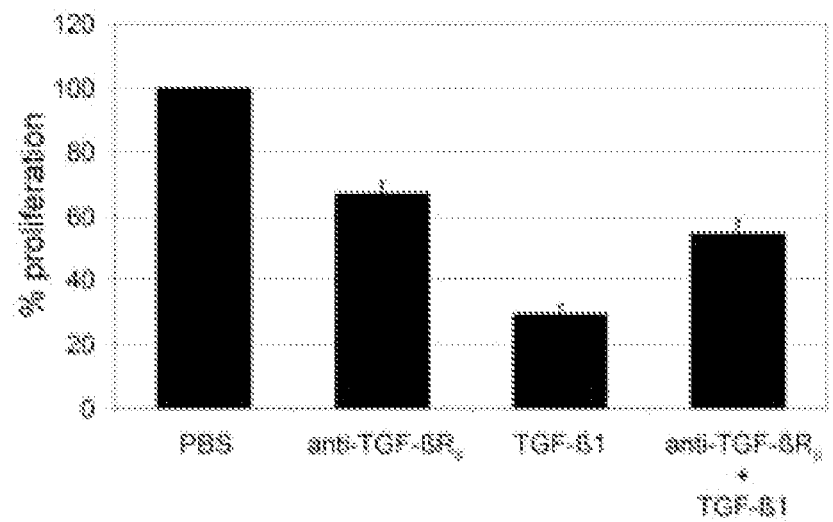

FIG. 3: Antibodies Against TGF-BetaRII can Reduce TGF-Beta1 Effects on Adult Rodent NSCs Adult rodent NSC cultures were treated with 10 ng/ml of recombinant human TGF-beta1 for 7 days in the presence or absence of anti-TGF-betaRII antibody (10 µg/ml). On day 7 viable cells were counted by Trypan Blue exclusion assay in a hemocytometer. The data are expressed as average cell numbers±SD from three experiments performed in triplicate.

Figure 4:
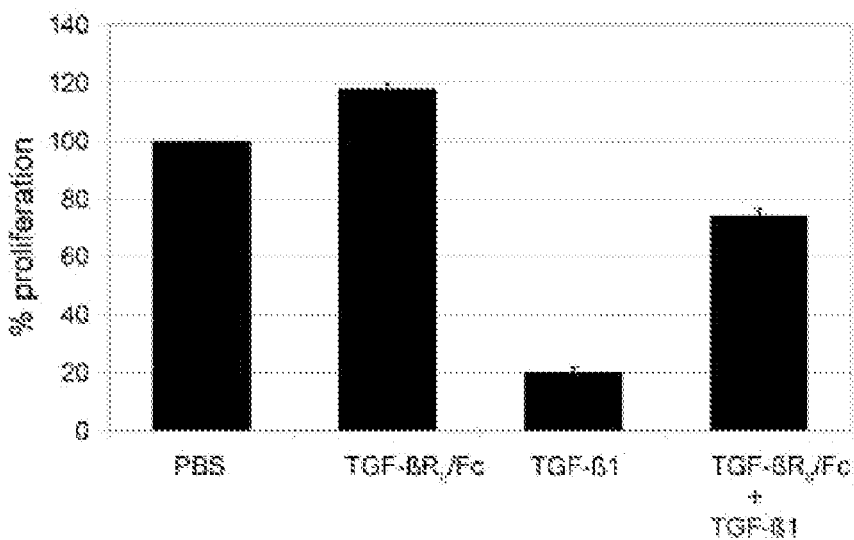

FIG. 4: Soluble TGF-RII Inhibits TGF-β1-Induced Suppression of NSC Proliferation Adult rodent NSC cultures were treated with 10 ng/ml of recombinant human TGF-beta1 for 7 days in the presence or absence of soluble anti-TGF-betaRII (500 ng/ml). On day 7 viable cells were counted by Trypan Blue exclusion assay in a hemocytometer. The data are expressed as average±SD from three experiments performed in triplicate.

FIG. 5:

TGF-β$R_{II}$-Expressing Cells can be Isolated Using Cell Sorting Techniques.

Adult rodent NSCs were prepared as described in example 1. Cells expressing TGF-bRII were purified using antibodies against TGF-bRII. About 20% of NSCs express the receptor and this cell population can be enriched by this approach.

Figure 6:
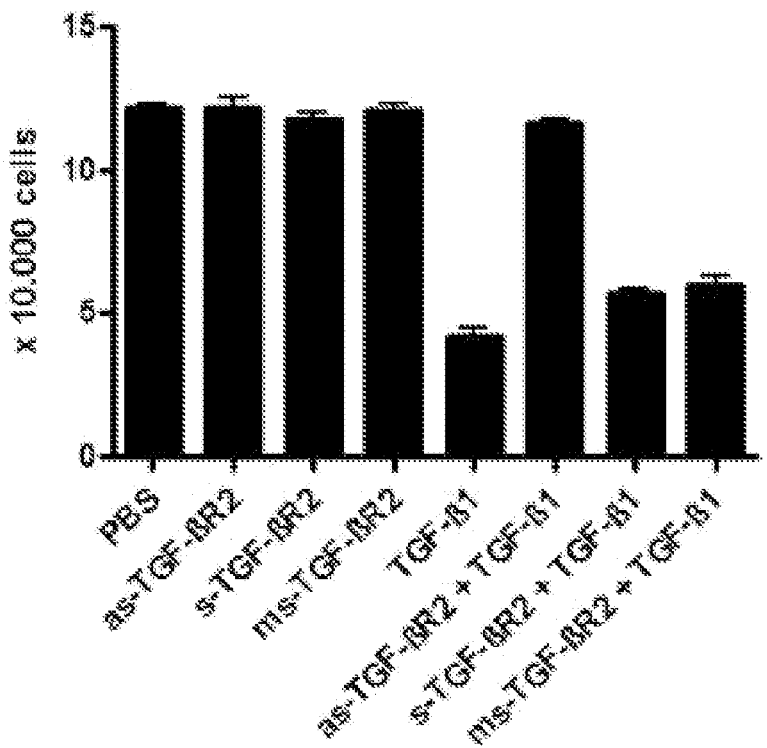

FIG. 6: Antisense Oligonucleotides Against TGF-βRII Inhibit the TGF-β1 Induced Down-Regulation of Adult Neural Stem and Precursor Proliferation In Vitro.

It was shown that the TGF-β1 induced inhibition of neural stem and precursor proliferation was completely and specifically blocked by the antisense treatment.

Figure 7:
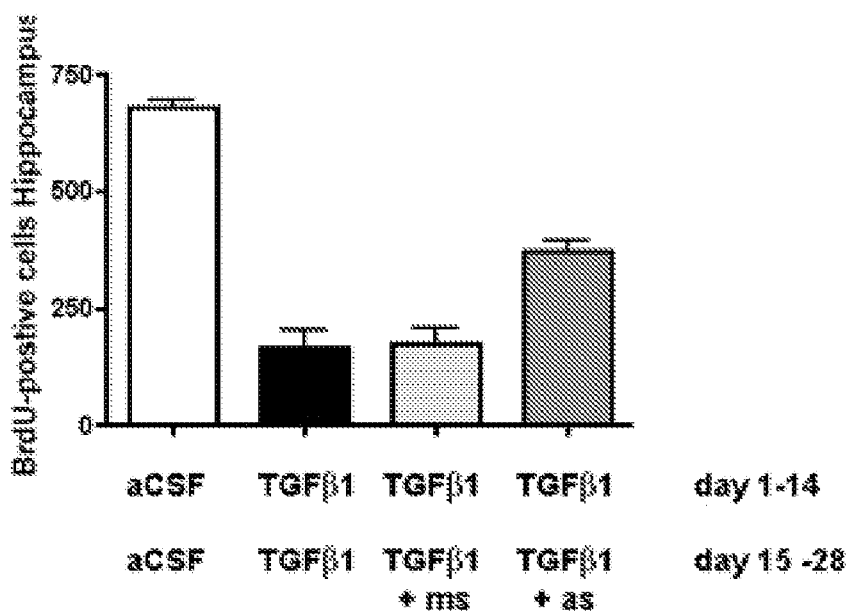
Figure 7:
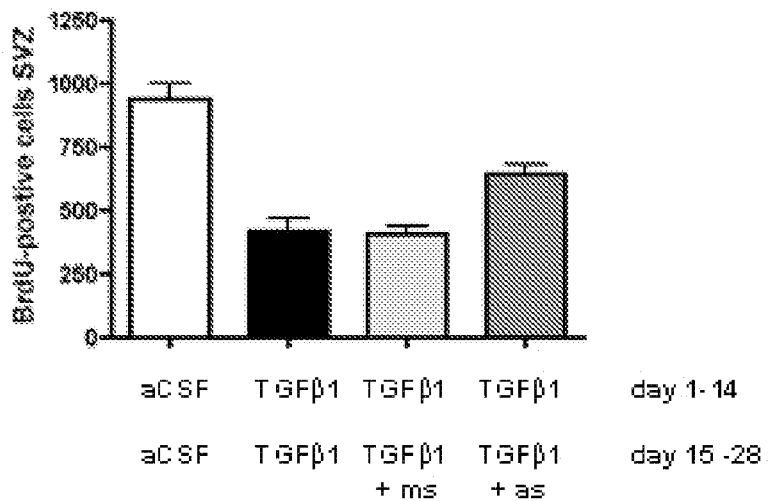

FIG. 7: In Vivo Treatment with TGF-RII Specific Antisense Oligonucleotides Rescues the TGF-β1 Induced Blockade of Cell Proliferation in the Adult Brain.

FIG. 7 demonstrates the TGF-β1 induced down-regulation of cell proliferation in the hippocampal dentate gyrus (FIG. 7A) and in the subventricular zone (FIG. 7B). Treatment with missense oligonucleotide did not block this effect, whereas antisense oligonucleotide treatment blocked the TGF-β1 effect (FIGS. 7A and B).

Figure 8:
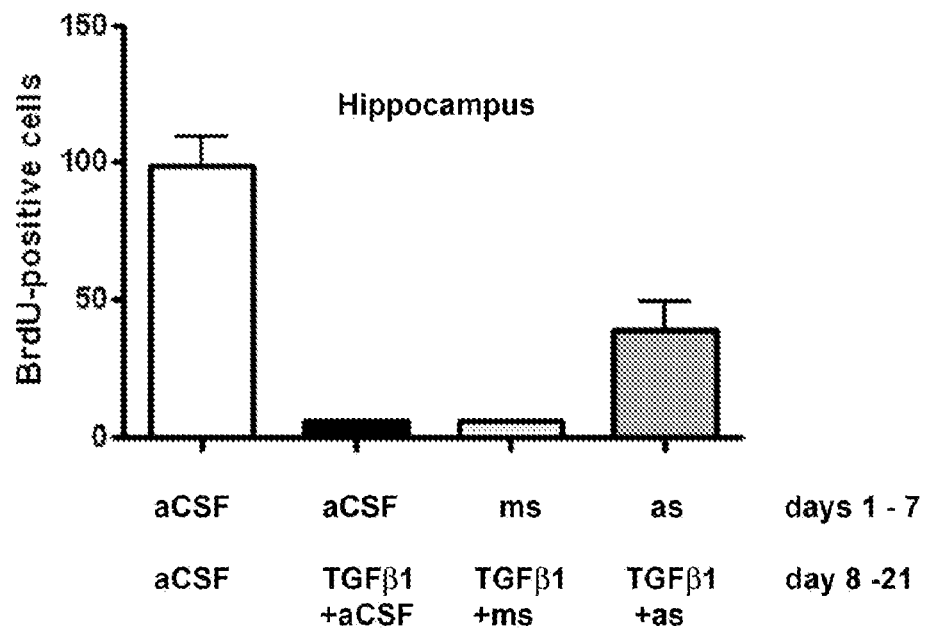
Figure 8:
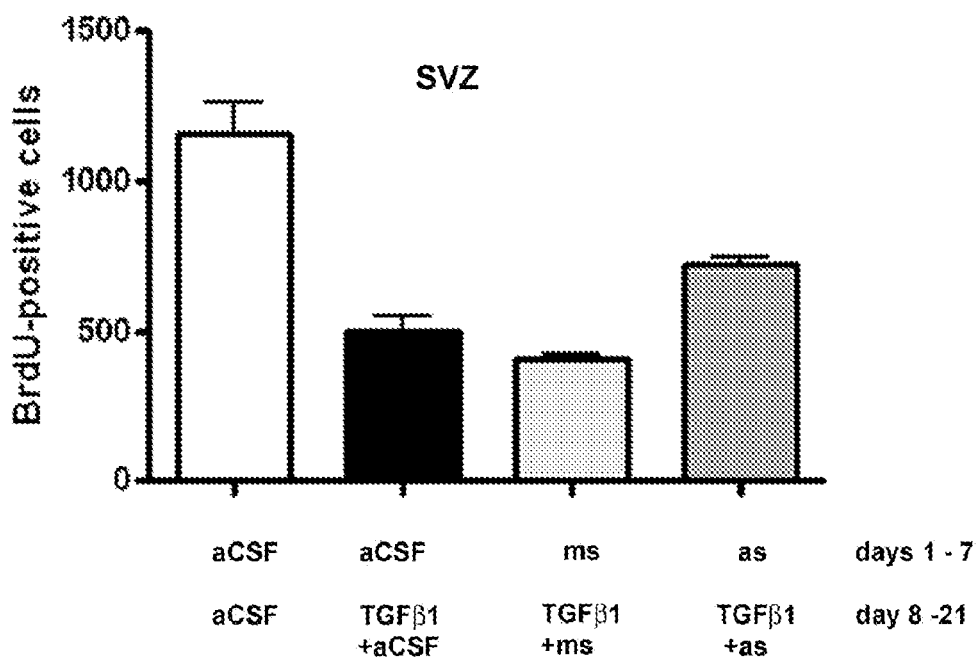

FIG. 8: In Vivo Treatment with TGF-RII Specific Antisense Oligonucleotides Prevent from TGF-β1 Induced Blockade of Cell Proliferation in the Adult Brain FIG. 8 demonstrates that the TGF-β1 induced down-regulation of cell proliferation in the hippocampal dentate gyrus (FIG. 8A) and in the subventricular zone (FIG. 8B) can be prevented by pre-treatment with TGF-βRII antisense oligonucleotide treatment.

In the disorders described above, microglial cells, and potentially perivascular resting macrophages, are attracted from protein aggregates, cell debris, inflammation, inflammatory response in atherosclerosis, or acute trauma/hypoxia associated cell death. This may be an acute, subacute or chronic process. During the activation process the activated microglial cell population (including macrophages from the vessel wall or other sources) releases a number of inflammatory cytokines into the extracellular matrix, draining either into small venules or directly into the CSF-space. These cytokines will reach the CSF-compartment and will be immediately available at all locations, which are surrounded to some extend by CSF. Among these cytokines is TGF-beta. It was demonstrated (Monje, M. L., H. Toda, et al. (2003). "Inflammatory blockade restores adult hippocampal neurogenesis." Science 302 (5651): 1760-1765) that neuroinflammation inhibits neurogenesis and that inflammatory blockade with indomethacin, a common nonsteroidal anti-inflammatory drug, restores neurogenesis after endotoxininduced inflammation and augments neurogenesis after cranial irradiation.

However, the prior art does not disclose TGF-beta as the main regulator down-regulating neurogenesis and neurorepair after injury or under pathological conditions. In contrast, the prior art considered TGF-beta as a neuroprotective agent preventing injured or lesioned neurons from cell death, and tried to up-regulate TGF-beta in CNS disease conditions.

Zhang et al. (Zhang, J. M., R. Hoffmann, et al. (1997). "Mitogenic and antiproliferative signals for neural crest cells and the neurogenic action of TGF-beta1." Dev. Dyn. 208(3): 375-386.) demonstrate that TGF-beta has an effect on developing quail neural crest cells. Here, TGF-beta inhibited proliferation of both pluripotent neural crest cells (and/or their immediate derivatives) and of committed melanogenic cells, causing a decrease in colony size. In addition, and in contrast to the present invention, neurogenesis increased significantly in the presence of TGF-beta. The number per colony of both adrenergic cells and sensory neuron precursors increased in TGF-beta-treated neuroblast-positive colonies.

TGF-betas have important roles in cell growth and differentiation, organ development, matrix formation, wound repair and immune function. While TGF-beta is a potent growth-inhibitory substance for many cell types, it stimulates proliferation of fibroblasts and osteoblasts. It is also a potent stimulator of extracellular matrix production by fibroblasts and osteoblasts, inhibits matrix degradation and up-regulates receptors for matrix interaction. TGF-beta1 has been implicated as a key causative factor in the pathogenesis of liver fibrosis and at least as one crucial mediator of both the beneficial and detrimental effects of cyclosporine A on the immune system and the kidney. In addition, various chronic progressive fibrotic kidney disorders in humans and experimental models have been shown to be associated with stimulation of the TGF-beta system.

TGF-beta1 down-regulates G1 and G2 cyclin-dependent kinases and cyclins in terms of both kinase activity and protein amount. TGF-beta1 also inhibits phosphorylation of the product of the retinoblastoma tumor suppressor gene pRb at multiple serine and threonine residues in human myeloid leukemia cells. The under-phosphorylated pRb associates with transcription factor E2F-4 in G1 phase, whereas the phosphorylated pRb mainly binds to E2F-1 and E2F-3. Because TGF-beta1 up-regulates p130 (pRb family member)/E2F-4 complex formation and down-regulates p107 (pRb family member)/E2F-4 complex formation, with E2F-4 levels remaining constant, these results suggest that E2F-4 is switched from p107 to pRb and p130 when cells exit from the cell cycle and arrest in G1 by the action of TGF-betaI. The "cdk inhibitor" p27 is both a positive and a negative regulator of TGF-betaI-mediated cell cycle control. Although TGF-beta1 has been reported to be a selected inhibitor of normal primitive hematopoietic stem cells, TGF-beta inhibits both primitive and more differentiated myeloid leukemia cell lines. Most attention was drawn on TGF-beta1's neuroprotective activity, its role in neural development and on its role in modulating immune responses. TGF-beta1 has been shown in a number of studies to be neuroprotective in vitro and in vivo. Agonist studies have demonstrated that TGF-beta1 reduces neuronal cell death and infarct size following middle cerebral artery occlusion (MCAO), while conversely, antagonist studies have shown increased neuronal cell death and infarct size after MCAO, suggesting that TGF-beta1 has a neuroprotective role in cerebral ischemia. Recent work with adenoviral-mediated overexpression of TGF-beta1 in vivo in mice has further implicated a neuroprotective role for TGF-beta1 in cerebral ischemia, as evidenced by a reduction in neuronal cell death, infarct size, and neurological outcome. Additionally, numerous in vitro studies have documented the neuroprotective ability of TGF-beta1 in neurons from a variety of species, including rats, mice, chicks, and humans. Of significant interest, TGFbeta1 was shown to be protective against a wide variety of death-inducing agents/insults, including hypoxia/ischemia, glutamate excitotoxicity, beta-amyloid, oxidative damage, and human immunodeficiency virus. The neuroprotective effect of TGF-beta1 has been related to its ability to maintain the mitochondrial membrane potential, to stabilize $Ca^{2+}$ homeostasis, to increase the expression of the anti-apoptotic proteins Bcl-2 and Bcl-xl, to inhibit caspase-3 activation and to induce plasminogen activator inhibitor-1. Studies in embryonic stem cells have demonstrated a primitive neural stem cell as a component of neural lineage specification that is negatively regulated by TGF-beta-related signalling. Endogenous expression of TGF-alpha, another TGF family member, has been shown to positively regulate adult neurogenesis. TGF-alpha is necessary for the full proliferation of progenitor cells present in the subependyma and the full production of the neuronal precursors that migrate to the olfactory bulb. In TGF-alpha knock out mice, proliferation of these progenitor cells also is diminished with age, likely because of a lengthening of the cell cycle. Senescence or the absence of endogenous TGF-alpha does not affect the numbers of neural stem cells isolated in vitro in the presence of epidermal growth factor.

The use of TGF-beta for immunomodulation in humans is severely limited by its toxicity, including excessive stimulation of matrix production, nephrotoxicity and other detrimental effects. TGF-beta has oncogenic potential and has been implicated in glomerulopathies, pulmonary fibrosis, scleroderma and chronic graft versus host disease. In addition, while TGFbeta is an extremely potent immunosuppressive cytokine, several lines of evidence indicate that chronic stimulation of TGF-beta expression—both disease-related or in transgenic animal models—can paradoxically lead to or enhance autoimmune inflammation.

There is increasing evidence that the powerful anti-inflammatory properties of TGF-beta as a negative regulator of T-cell immune response play a key role in the pathophysiology of a variety of CNS pathologies. Therefore, this cytokine is regarded as an injury-related peptide and a potential target for therapeutic intervention. Neuroinflammation and microglial pathology are associated with many neurological diseases. Here, the most classical ones are clearly neuro-immunological diseases such as Multiple Sclerosis. But it includes also diseases of cognition in which memory loss features prominently, such as Alzheimer's Disease, Lewy Body Dementia, AIDS Dementia Complex, Vascular Dementia, or less prominently, such as Pick's Disease, Progressive Supranuclear Palsy, Corticobasal Degeneration, and Creutzfeldt-Jakob Disease. In addition, inflammatory programs are activated after acute lesions such as stroke, traumatic brain and spinal cord injuries. In different animal models for Creutzfeldt-Jacob Disease activation of microglia and up-regulation of TGF-beta1 has been reported (Baker, C. A., Z. Y. Lu, et al. (1999). "Microglial activation varies in different models of Creutzfeldt-Jakob disease." J Virol 73(6): 5089-5097).

Among the hundreds of different neurodegenerative disorders, the attention has been given only to a handful, including Alzheimer disease, Parkinson disease, Huntington's disease, and amyotrophic lateral sclerosis. It is worth to mention that the same neurodegenerative process can affect different areas of the brain, making a given disease appear very different from a symptomatic standpoint. Neurodegenerative disorders of the central nervous system (CNS) can be grouped into diseases of the cerebral cortex (Alzheimer disease), the basal ganglia (Parkinson disease), the brain-stem and cerebellum, or the spinal cord (Amoyotrophic Lateral Sclerosis).

Examples for neurodegeneration and neurodegenerative disorders are: Alzheimer's diseases, Parkinson's disease, Creutzfeldt Jakobs disease (CJD), new variant of Creutzfeldt Jakobs disease (nvCJD), Hallervorden Spatz disease, Huntington's disease, multisystem atrophy, dementia, frontemporal dementia, motor neuron disorders, amyotrophic lateral sclerosis, spinal muscular atrophy, spinocerebellar atrophies (SCAs), schizophrenia, affective disorders, major depression, meningoencephalitis, bacterial meningoencephalitis, viral meningoencephalitis, CNS autoimmune disorders, Multiple Sclerosis (MS), acute ischemic/hypoxic lesions, CNS trauma, head trauma, arteriosclerosis, atherosclerosis, microangiopathic dementia, Binswanger disease Leukoaraiosis, retinal degeneration, cochlear degeneration, macular degeneration, cochlear deafness, AIDS-related dementia, retinitis pigmentosa, fragile X-associated tremor/ataxia syndrome (FXTAS), progressive supranuclear palsy (PSP), striatonigral degeneration (SND), olivopontocerebellear degeneration (OPCD), Shy Drager syndrome (SDS).

Influencing the Levels of TGF-beta1

Up-Regulation of TGF-beta1 and its Effects

Many studies tried to increase TGF-beta1 levels for neuroprotective or immunoregulatory purposes. Agonist studies have demonstrated that TGF-beta1 reduces neuronal cell death and infarct size following middle cerebral artery occlusion (MCAO), while conversely, antagonist studies have shown increased neuronal cell death and infarct size after MCAO, suggesting that TGF-beta1 has a neuroprotective role in cerebral ischemia. Recent work with adenoviral-mediated overexpression of TGF-beta1 in vivo in mice has further implicated a neuroprotective role for TGF-beta1 in cerebral ischemia, as evidenced by a reduction in neuronal cell death, infarct size, and neurological outcome. Additionally, numerous in vitro studies have documented the neuroprotective ability of TGF-beta1 in neurons from a variety of species, including rats, mice, chicks, and humans. Of significant interest, TGFbeta1 was shown to be protective against a wide variety of death-inducing agents/insults, including hypoxialischemia, glutamate excitotoxicity, beta-amyloid, oxidative damage, and human immunodeficiency virus. The neuroprotective effect of TGF-beta1 has been related to its ability to maintain the mitochondrial membrane potential, to stabilize $Ca^{2+}$ homeostasis, to increase the expression of the anti-apoptotic proteins Bcl-2 and Bcl-xl, to inhibit caspase-3 activation and to induce plasminogen activator inhibitor-1.

The use of TGF-beta for immunomodulation in humans is severely limited by its toxicity, including excessive stimulation of matrix production, nephrotoxicity and other detrimental effects. TGF-beta has oncogenic potential and has been implicated inglomerulopathies, pulmonary fibrosis, scleroderma and chronic graft versus host disease. In addition, while TGF beta is an extremely potent immunosuppressive cytokine, several lines of evidence indicate that chronic stimulation of TGF-beta expression—both disease-related or in transgenic animal models—can paradoxically lead to or enhance autoimmune inflammation.

Our main finding is that the identical TGF-β described in it's protective effects upon the CNS above, is the main negative regulatory molecule of CNS-stem cell repair in physiology and in almost all CNS pathology: TGF-β-produced by microglial cells (either at low physiological levels or at higher levels in response to disease) leaks through the intercellular matrix into the CSF. There it may freely and directly interact with highly regulated and expressed TGF-RII and TGF-RI on the precursor/stem cell population of the CNS at the sub-ependymal progenitor-containing cell layer zone or potentially other areas of CNS-stem cell renewal. The finding consists of a negative regulation, resulting in low stem cell renewal in case of high CSF-TGF-β levels and vice versa. Unusual and most remarkably, the extreme high expression level and activity of TGF-RII is located at the site of precursor/stem cell proliferation, in our experiments the SVZ or the hippocampus. Unusual is also the transmission of the signal through a buffering solution, as for example cerebrospinal fluid (CSF). It is therefore a complete regulatory circle, where physiological and pathological regulation are very similar, but vary only by intensity (in other words: the level of TGF-β in the CSF, and level of TGF-R expression at the target cells). The individual disease pathology phenotype is characterized by such diverse changes, as genetic deficits (e.g. Synucleinopathies, Superoxide Dismutase Mutations, Trinucleotide Repeat Disorders) or trauma, hypoxia, vascular disease or inflammation, or CNS-ageing. The executor of the disease pathology, however, is always the microglial cell/macrophage population—produced TGF-β: On one hand it is neuroprotective and immunosuppressive, helping to deescalate the acute inflammatory damage to the parenchyma and the neuronal loss potentially inflicted by the disease pathology. Indirectly—as a Janus Head—the same molecule prevents the CNS from damage repair by the own stem cells/precursor cells through interfering with the TGF-β-TGF-R loop at the precursor or stem cell level, thereby significantly suppressing stem cell proliferation. In this case, as stem cells not only those cells derived from precursor cells from within the CNS should be looked at, but conceivably also those stem cells/precursor cells that try to invade the CNS parenchyma from the vessels respectively the bone marrow. This also means that by simply decreasing TGF-β levels in the parenchyma, the neuroprotective/immunosuppressive effects upon the CNS would be annihilated leading to severe acute damage by inflammation and/or direct neuronal apoptosis.

A local intervention at the TGF-R-level therefore seems the only attractive pathway for stable intervention in favour of repair, not endangering the beneficial effects of TGF-β for the brain. Thus, the present invention relates to antisense oligonucleotides interfering with the biological activity of TGF-beta1 upon the precursor/stem cell pool expressing TGF-R. Said oligonucleotides or pharmaceutical compositions including at least one of said oligonucleotides are useful for the diagnosis/prophylaxis/prevention or treatment of a disease, wherein neurogenesis or neuroregeneration has a beneficial effect. They are also useful in the therapeutic prevention (for example after stroke or head injury)—as shown in our experiments—before the mechanisms described hereafter will be effective.

The term "interfering" as used herein means modulating, preferably reducing or eliminating, the biological activity of TGF-R and/or TGF-$R_{II}$ or its expression. The modulation of the biological activity can be effected by direct interaction or binding of a compound to TGF-R, preferably, TGF-$R_{II}$ or by indirect interaction, e.g., by interacting with a compound that is associated with the biological activity of TGF-R and/or TGF-$R_{II}$. Suitable compounds acting as agents targeting TGF-beta$R_I$, -$R_{II}$, -$R_{III}$, or its signal transduction to interfere with this regulatory circuit with the aim to improve neuroregeneration or increase neuronal/hematopoetic stem cell or precursor cell recruitment to the CNS, including all types of local or systemic transplantation (e.g. ex vivo propagation, allogeneic cells) are listed below:

(a) Plasmids, vectors or natural/synthetic/mutated viruses, oligonucleotides of various types of modification (e.g. PTO, LNA, 2'F-ANA, protein-nucleotide complexes, RNAi, sRNA or mikro miRNA, Methylmetoxy-, Phosphoroamidates, PNA, Morpholino, Phosphoramidate, Cyclohexen (CeNA), gap-meres, ribozymes, aptamers, CpG-oligos, DNA-zymes, riboswitches, or lipids or lipid containing molecules, (b) peptides, peptide complexes, including all types of linkers, (c) small molecules, modifyers of rafts or caveoli, (d) modifyers of golgi apparatus, (e) antibodies and their derivatives, especially chimeras, Fab-fragments, Fc-fragments, or (f) carriers, liposomes, nanoparticles, complexes, or any other delivery systems containing the above named constructs, can be used to target the above mentioned circuit to restore or improve neuroregeneration.

However, most preferred among the above-mentioned agents are antisense oligonucleotides, since they interfere with the formation of TGF-R or TGF-R$_{II}$ at a very early stage. The main advantages of these molecules rest in their extremely high target specificity, combined with their extremely good systemic and local tolerance; they are very well suited for local application into the CNS, either into the parenchyma or the CSF-space. In addition, they are very stable, and may thus be easily applied from an implanted pumping system. Their cost-efficacy is also remarkable.

Thus, in preferred embodiments of the present invention, the compound useful for interfering with the expression of the gene encoding TGF-R or TGF-R$_{II}$, is an antisense oligonucleotide.

The generation of suitable antisense oligonucleotides includes determination of a site or sites within the TGF-R gene or TGF-R$_{II}$ gene for the antisense interaction to occur such that the desired effect, e.g., inhibition of expression of the protein, will result. A preferred intragenic site is (a) the region encompassing the translation initiation or termination codon of the open reading frame (ORF) of the gene or (b) a region of the mRNA which is a "loop" or "bulge", i.e., not part of a secondary structure. Once one or more target sites have been identified, oligonucleotides are chosen which are sufficiently complementary to the target, i.e., hybridize sufficiently well and with sufficient specificity, to give the desired effect.

Thus, the present invention relates to antisense oligonucleotides having a sub-sequence of SEQ ID NO 1 or SEQ ID NO 2 or SEQ ID NO 94 or SEQ ID NO 95 or SEQ ID NO 96 comprising 8 to 50 nucleobases and mimetics thereof. Said oligonucleotides represent a part of the SEQ ID NO 1 or 2 or SEQ ID NO 94 to 96 with 8 to 50 nucleotide bases. Furthermore, the antisense oligonucleotides comprising 8 to 50 nucleobases do not have to be an exact sub-sequence of SEQ ID NO 1 or 2 or SEQ ID NO 94 to 96. It is sufficient if the antisense oligonucleotides are at least 80%, preferably 84%, more preferably 88% and most preferably 92% identical to a sub-sequence found in of SEQ ID NO 1 or 2 or SEQ ID NO 94 or 95 or 96. Preferred oligonucleotides have a sequence at least 80% identical to a sub-sequence of SEQ ID NO 1 or 2 or 94 or 95 or 96 comprising 8 to 50 nucleobases, wherein said sequence is capable of hybridizing sufficiently with the region encompassing the translation initiation or termination codon of the open reading frame of the gene encoding TGF-R or TGF-R$_{II}$, or a region of the mRNA encoding TGF-R or TGF-R$_{II}$ which is a "loop" or "bulge" and which is not part of a secondary structure. That means, these antisense oligonucleotides have a sequence at least 80% complementary with the corresponding region of the gene encoding TGF-R or TGF-R$_{II}$, or preferably have a sequence at least 80% complementary with (a) the region encompassing the translation initiation or termination codon of the open reading frame of the gene encoding TGF-R or TGF-R$_{II}$, or (b) a region of the mRNA encoding TGF-R or TGF-R$_{II}$ which is a "loop" or "bulge", i.e., not part of a secondary structure.

Preferred are antisense oligonucleotides of 8 to 50, preferably 15 to 25 nucleobases, able to hybridize sufficiently with the region encompassing the translation initiation or termination codon of the open reading frame of the gene encoding TGF-R or TGF-R$_{II}$, or a region of the mRNA encoding TGF-R or TGF-R$_{II}$ which is a "loop" or "bulge" and which is not part of a secondary structure.

Preferred are the following elongated sequences of SEQ ID NO 3 which can be represented by the following general formula:

```
5'-XCAGCCCCGACCCATGZ-3':     SEQ ID NO 101
``` wherein X is selected from the group comprising the following oligonucleotides:

```
ACAGGACGATGTGCAGCGGCCACAGGCCCCTGAG:  SEQ ID NO 102
CAGGACGATGTGCAGCGGCCACAGGCCCCTGAG:   SEQ ID NO 103
AGGACGATGTGCAGCGGCCACAGGCCCCTGAG:    SEQ ID NO 104
GGACGATGTGCAGCGGCCACAGGCCCCTGAG:     SEQ ID NO 105
GACGATGTGCAGCGGCCACAGGCCCCTGAG:      SEQ ID NO 106
ACGATGTGCAGCGGCCACAGGCCCCTGAG:       SEQ ID NO 107
CGATGTGCAGCGGCCACAGGCCCCTGAG:        SEQ ID NO 108
GATGTGCAGCGGCCACAGGCCCCTGAG:         SEQ ID NO 109
ATGTGCAGCGGCCACAGGCCCCTGAG:          SEQ ID NO 110
TGTGCAGCGGCCACAGGCCCCTGAG:           SEQ ID NO 111
GTGCAGCGGCCACAGGCCCCTGAG:            SEQ ID NO 112
TGCAGCGGCCACAGGCCCCTGAG:             SEQ ID NO 113
GCAGCGGCCACAGGCCCCTGAG:              SEQ ID NO 114
CAGCGGCCACAGGCCCCTGAG:               SEQ ID NO 115
AGCGGCCACAGGCCCCTGAG:                SEQ ID NO 116
GCGGCCACAGGCCCCTGAG:                 SEQ ID NO 117
CGGCCACAGGCCCCTGAG:                  SEQ ID NO 118
GGCCACAGGCCCCTGAG:                   SEQ ID NO 119
GCCACAGGCCCCTGAG:                    SEQ ID NO 120
CCACAGGCCCCTGAG:                     SEQ ID NO 121
CACAGGCCCCTGAG:                      SEQ ID NO 122
ACAGGCCCCTGAG:                       SEQ ID NO 123
CAGGCCCCTGAG:                        SEQ ID NO 124
AGGCCCCTGAG:                         SEQ ID NO 125
GGCCCCTGAG:                          SEQ ID NO 126
GCCCCTGAG:                           SEQ ID NO 127
CCCCTGAG:                            SEQ ID NO 128
CCCTGAG:                             SEQ ID NO 129
CCTGAG:                              SEQ ID NO 130
CTGAG:                               SEQ ID NO 131
TGAG:                                SEQ ID NO 132
GAG, AG, G,
``` and wherein Z is selected from the group comprising the following oligonucleotides:

| | |
|---|---|
| GCAGACCCCGCTGCTCGTCATAGACCGAGCCCCC: | SEQ ID NO 133 |
| GCAGACCCCGCTGCTCGTCATAGACCGAGCCCC: | SEQ ID NO 134 |
| GCAGACCCCGCTGCTCGTCATAGACCGAGCCC: | SEQ ID NO 135 |
| GCAGACCCCGCTGCTCGTCATAGACCGAGCC: | SEQ ID NO 136 |
| GCAGACCCCGCTGCTCGTCATAGACCGAGC: | SEQ ID NO 137 |
| GCAGACCCCGCTGCTCGTCATAGACCGAG: | SEQ ID NO 138 |
| GCAGACCCCGCTGCTCGTCATAGACCGA: | SEQ ID NO 139 |
| GCAGACCCCGCTGCTCGTCATAGACCG: | SEQ ID NO 140 |
| GCAGACCCCGCTGCTCGTCATAGACC: | SEQ ID NO 141 |
| GCAGACCCCGCTGCTCGTCATAGAC: | SEQ ID NO 142 |
| GCAGACCCCGCTGCTCGTCATAGA: | SEQ ID NO 143 |
| GCAGACCCCGCTGCTCGTCATAG: | SEQ ID NO 144 |
| GCAGACCCCGCTGCTCGTCATA: | SEQ ID NO 145 |
| GCAGACCCCGCTGCTCGTCAT: | SEQ ID NO 146 |
| GCAGACCCCGCTGCTCGTCA: | SEQ ID NO 147 |
| GCAGACCCCGCTGCTCGTC: | SEQ ID NO 148 |
| GCAGACCCCGCTGCTCGT: | SEQ ID NO 149 |
| GCAGACCCCGCTGCTCG: | SEQ ID NO 150 |
| GCAGACCCCGCTGCTC: | SEQ ID NO 151 |
| GCAGACCCCGCTGCT: | SEQ ID NO 152 |
| GCAGACCCCGCTGC: | SEQ ID NO 153 |
| GCAGACCCCGCTG: | SEQ ID NO 154 |
| GCAGACCCCGCT: | SEQ ID NO 155 |
| GCAGACCCCGC: | SEQ ID NO 156 |
| GCAGACCCCG: | SEQ ID NO 157 |
| GCAGACCCC: | SEQ ID NO 158 |
| GCAGACCC: | SEQ ID NO 159 |
| GCAGACC: | SEQ ID NO 160 |
| GCAGAC: | SEQ ID NO 161 |
| GCAGA: | SEQ ID NO 162 |
| GCAG: | SEQ ID NO 163 |

GCA, GC, G, and wherein X and Z together comprise not more than 34 nucleobases and mimetics thereof.

More preferred are the following oligonucleotide sequences and variants or mimetics thereof:

SEQ ID NO 3:
5'-CAGCCCCCGACCCATG-3'

SEQ ID NO 4:
5'-GCTGATGCCTGTCACTTGAA-3'

SEQ ID NO 5:
5'-GCCATGGAGTAGACATCGGT-3'

SEQ ID NO 6:
5'-GCAACAGCTATTGGGATGGT-3'

SEQ ID NO 7:
5'-GTGCAGGGGAAAGATGAAAA-3'

SEQ ID NO 8:
5'-GTATCAGCATGCCCTACGGT-3'

SEQ ID NO 9:
5'-GGATCCAGATTTTCCTGCAA-3'

SEQ ID NO 10:
5'-GGAGAAGCAGCATCTTCCAG-3'

SEQ ID NO 11:
5'-GAGCTCTTGAGGTCCCTGTG-3'

SEQ ID NO 12:
5'-GAGACCTTCCACCATCCAAA-3'

SEQ ID NO 13:
5'-TAGCTGGCTGTGAGACATGG-3'

SEQ ID NO 14:
5'-TTTTGAAACGCTGTGCTGAC-3'

SEQ ID NO 15:
5'-TCAGCCAGTATTGTTTCCCC-3'

SEQ ID NO 16:
5'-TCACACAGGCAGCAGGTTAG-3'

SEQ ID NO 17:
5'-TCAGGAATCTTCTCCTCCGA-3'

SEQ ID NO 18:
5'-TGGTAGTGTTTAGGGAGCCG-3'

SEQ ID NO 19:
5'-TATCCCCACAGCTTACAGGG-3'

SEQ ID NO 20:
5'-AGCCTCTTTCCTCATGCAAA-3'

SEQ ID NO 21:
5'-ATGTCATTTCCCAGAGCACC-3'

SEQ ID NO 22:
5'-AGGAATCTTCTCCTCCGAGC-3'

SEQ ID NO 23:
5'-AGCCATGGAGTAGACATCGG-3'

SEQ ID NO 24:
5'-ATGCTACTGCAGCCACACTG-3'

SEQ ID NO 25:
5'-CCTTCTCTGCTTGGTTCTGG-3'

SEQ ID NO 26:
5'-CCAGGAGAAATAAGGGCACA-3'

SEQ ID NO 27:
5'-CAGCAGCTCTGTGTTGTGGT-3'

SEQ ID NO 28:
5'-CCCACTGTTAGCCAGGTCAT-3'

SEQ ID NO 29:
5'-CAGCCCCCGACCCATGGCAGACCC-3'

SEQ ID NO 30:
5'-CAGCCCCCGACCCATGGCAGACC-3'

SEQ ID NO 31:
5'-CAGCCCCCGACCCATGGCAGAC-3'

SEQ ID NO 32:
5'-CAGCCCCCGACCCATGGCAGA-3'

SEQ ID NO 33:
5'-CAGCCCCCGACCCATGGCAG-3'

SEQ ID NO 34:
5'-CAGCCCCCGACCCATGGCA-3'

SEQ ID NO 35:
5'-CAGCCCCCGACCCATGGC-3'

SEQ ID NO 36:
5'-CAGCCCCCGACCCATGG-3'

SEQ ID NO 37:
5'-GCAGCCCCCGACCCATGGCAGACC-3'

SEQ ID NO 38:
5'-GCAGCCCCCGACCCATGGCAGAC-3'

SEQ ID NO 39:
5'-GCAGCCCCCGACCCATGGCAGA-3'

SEQ ID NO 40:
5'-GCAGCCCCCGACCCATGGCAG-3'

SEQ ID NO 41:
5'-GCAGCCCCCGACCCATGGCA-3'

SEQ ID NO 42:
5'-GCAGCCCCCGACCCATGGC-3'

SEQ ID NO 43:
5'-GCAGCCCCCGACCCATGG-3'

SEQ ID NO 44:
5'-GCAGCCCCCGACCCATG-3'

SEQ ID NO 45:
5'-AGCAGCCCCCGACCCATGGCAGAC-3'

SEQ ID NO 46:
5'-AGCAGCCCCCGACCCATGGCAGA-3'

SEQ ID NO 47:
5'-AGCAGCCCCCGACCCATGGCAG-3'

SEQ ID NO 48:
5'-AGCAGCCCCCGACCCATGGCA-3'

SEQ ID NO 49:
5'-AGCAGCCCCCGACCCATGGC-3'

SEQ ID NO 50:
5'-AGCAGCCCCCGACCCATGG-3'

SEQ ID NO 51:
5'-AGCAGCCCCCGACCCATG-3'

SEQ ID NO 52:
5'-GAGCAGCCCCCGACCCATGGCAGA-3'

SEQ ID NO 53:
5'-GAGCAGCCCCCGACCCATGGCAG-3'

SEQ ID NO 54:
5'-GAGCAGCCCCCGACCCATGGCA-3'

SEQ ID NO 55:
5'-GAGCAGCCCCCGACCCATGGC-3'

SEQ ID NO 56:
5'-GAGCAGCCCCCGACCCATGG-3'

SEQ ID NO 57:
5'-GAGCAGCCCCCGACCCATG-3'

SEQ ID NO 58:
5'-TGAGCAGCCCCCGACCCATGGCAG-3'

SEQ ID NO 59:
5'-TGAGCAGCCCCCGACCCATGGCA-3'

SEQ ID NO 60:
5'-TGAGCAGCCCCCGACCCATGGC-3'

SEQ ID NO 61:
5'-TGAGCAGCCCCCGACCCATGG-3'

SEQ ID NO 62:
5'-TGAGCAGCCCCCGACCCATG-3'

SEQ ID NO 63:
5'-CTGAGCAGCCCCCGACCCATGGCA-3'

SEQ ID NO 64:
5'-CTGAGCAGCCCCCGACCCATGGC-3'

SEQ ID NO 65:
5'-CTGAGCAGCCCCCGACCCATGG-3'

SEQ ID NO 66:
5'-CTGAGCAGCCCCCGACCCATG-3'

SEQ ID NO 67:
5'-CCTGAGCAGCCCCCGACCCATGGC-3'

SEQ ID NO 68:
5'-CCTGAGCAGCCCCCGACCCATGG-3'

SEQ ID NO 69:
5'-CCTGAGCAGCCCCCGACCCATG-3'

SEQ ID NO 70:
5'-CCCTGAGCAGCCCCCGACCCATGG-3'

SEQ ID NO 71:
5'-CCCTGAGCAGCCCCCGACCCATG-3'

SEQ ID NO 72:
5'-CCCCTGAGCAGCCCCCGACCCATG-3'

Still more preferred are the following oligonucleotide sequences as well as variants and mimetics thereof:

SEQ ID NO 33:
5'-CAGCCCCCGACCCATGGCAG-3'

SEQ ID NO 34:
5'-CAGCCCCCGACCCATGGCA-3'

SEQ ID NO 35:
5'-CAGCCCCCGACCCATGGC-3'

SEQ ID NO 36:
5'-CAGCCCCCGACCCATGG-3'

SEQ ID NO 41:
5'-GCAGCCCCCGACCCATGGCA-3'

SEQ ID NO 42:
5'-GCAGCCCCCGACCCATGGC-3'

SEQ ID NO 43:
5'-GCAGCCCCCGACCCATGG-3'

SEQ ID NO 44:
5'-GCAGCCCCCGACCCATG-3'

SEQ ID NO 49:
5'-AGCAGCCCCCGACCCATGGC-3'

SEQ ID NO 50:
5'-AGCAGCCCCCGACCCATGG-3'

SEQ ID NO 51:
5'-AGCAGCCCCCGACCCATG-3'

-continued

SEQ ID NO 56:
5'-GAGCAGCCCCGACCCATGG-3'

SEQ ID NO 57:
5'-GAGCAGCCCCGACCCATG-3'

SEQ ID NO 62:
5'-TGAGCAGCCCCGACCCATG-3'

SEQ ID NO 73:
5'-ATGTGAAGATGGGCAAGACC-3'

SEQ ID NO 74:
5'-ATCTCCATGTGAAGATGGGC-3'

SEQ ID NO 75:
5'-AACGGCCTATCTCGAGGAAT-3'

SEQ ID NO 76:
5'-AACATCGTCGAGCAATTTCC-3'

SEQ ID NO 77:
5'-AATCCAACTCCTTTGCCCTT-3'

SEQ ID NO 78:
5'-AAACCTGAGCCAGAACCTGA-3'

SEQ ID NO 79:
5'-AGGGCGATCTAATGAAGGGT-3'

SEQ ID NO 80:
5'-AGTGCACAGAAAGGACCCAC-3'

SEQ ID NO 81:
5'-ACACTGGTCCAGCAATGACA-3'

SEQ ID NO 82:
5'-TTCCTGTTGACTGAGTTGCG-3'

SEQ ID NO 83:
5'-CACTCTGTGGTTTGGAGCAA-3'

SEQ ID NO 84:
5'-CAAGGCCAGGTGATGACTTT-3'

SEQ ID NO 85:
5'-CACACTGGTCCAGCAATGAC-3'

SEQ ID NO 86:
5'-CTGACACCAACCAGAGCTGA-3'

SEQ ID NO 87:
5'-CTCTGCCATCTGTTTGGGAT-3'

SEQ ID NO 88:
5'-TCAAAAAGGGATCCATGCTC-3'

SEQ ID NO 89:
5'-TGACACCAACCAGAGCTGAG-3'

SEQ ID NO 90:
5'-TGATGCCTTCCTGTTGACTG-3'

SEQ ID NO 91:
5'-TTCCTGTTGACTGAGTTGCG-3'

SEQ ID NO 92:
5'-TTCTCCAAATCGACCTTTGC-3'

SEQ ID NO 93:
5'-GGAGAGTTCAGGCAAAGCTG-3'

Excluded from the scope of the present substance claims are the following two known sequences: 5'-GATCTTGACTGCCACTGTCTC-3' (SEQ ID NO 97) (J. Clin. Endocrinology & Metabolism 2003, 88(10), 4967-4976) and 5'-CATGGCAGCCCCCGTC-3' (SEQ ID NO 98) (Developmental Biology 1996, 180, 242-257).

Especially preferred is the sequence SEQ ID NO 3: 5'-CAGCCCCCGACCCATG-3'.

Consequently, the present invention is also directed to sequences which are closely related to any one of SEQ ID NO 3 to SEQ ID NO 93. Said sequences are referred to as "variants" herein. The antisense oligonucleotides can be modified by several different ways. Modifications within the backbone are possible and refer to oligonucleotides wherein the phosphorus atoms in their internucleoside backbone are partially or completely replaced by other atoms. Preferred modified oligonucleotide backbones include, for instance, phosphorothioates, chiral phorphorothioates, phosphorodithioates, phosphotriester, aminoalkylphosphotriesters, methyl, ethyl and $C_3$-$C_{10}$-alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acids forms thereof are also included.

Preferred are also variants of SEQ ID NO 3 to SEQ ID NO 93 wherein at the 3' terminal end and/or at the 5' terminal end 1, 2, 3, 4, or 5 further nucleobases are added. Such further nucleobases are preferably the five nucleobases within the SEQ ID NOs 1, 2, 94, 95, or 96 which come directly prior or after the respective sequence. Furthermore, said preferred variants may have 1, 2, 3, or 4 nucleobase exchanges, i.e. within said preferred variants, one, two, three or four nucleotides may be substituted by another nucleobase. It should be stressed that these variants may also contain any of the modifications of the backbone or the base or sugar moiety disclosed herein, such as phosphorothioate backbones.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages. These include those having morpholino linkages (formed in part from the sugar portion of a nucleoside); siloxane backbones, sulfide, sulfoxide and sulfone backbones; formacetyl and thioformacetyl backbones; methylene formacetyl and thioformacetyl backbones, alkene containing backbones, sulfamate backbones; methyleneimino and methylenehydrazino backbones; sulfonate and sulfonamide backbones; amide backbones, mixtures of the aforementioned types of backbones and other backbones having mixed N, O, S, P, and $CH_2$ component parts.

Further preferred embodiments of the present invention comprise oligonucleotides with phosphorothioate backbones or heteroatom backbones, and in particular with —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester backbone is represented as —O—P—O—$CH_2$—). Also oligonucleotides having morpholino moieties in their backbone or having a morpholino backbone structure or having a aminoalkylamide backbone are preferred (cf. below). Oligonucleotides may also have sugar mimetics such as cyclobutyl moieties in place of the pentofuranosyl sugar.

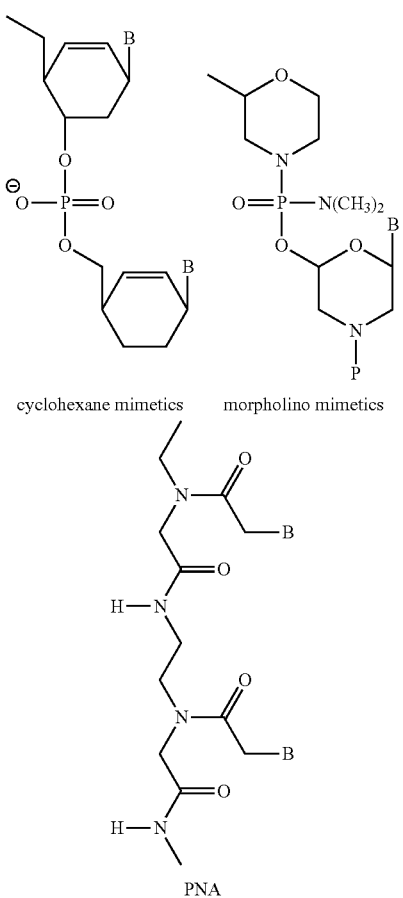

cyclohexane mimetics    morpholino mimetics

PNA

B refers to the base moiety such as the purin or pyrimidin group which may be further derivatized.

Another modification of the oligonucleotides of the present invention involves chemically linking to the oligonucleotide one or more moieties or conjugates which enhance the activity, cellular distribution or cellular uptake of the oligonucleotide. Modified oligonucleotides may also contain one or more substituted or modified sugar moieties. Preferred oligonucleotides comprise one of the following at the 2' position: —OH, —F, —O-alkyl, —S-alkyl, —N-alkyl, —O-alkenyl, —S-alkenyl, —N-alkenyl, —O-alkynyl, —S-alkynyl, —N-alkynyl, —O-alkyl-O-alkyl, wherein the alkyl, alkenyl and alkynyl may be substituted or unsubstituted $C_1$ to $C_{10}$ alkyl or $C_2$ to $C_{10}$ alkenyl and $C_2$ to $C_{10}$ alkynyl. A particularly preferred modified sugar moiety is a 2'-O-methoxyethyl sugar moiety (2'-OCH$_2$CH$_2$OCH$_3$, also known as 2'-O-(2-methoxyethoxy) or 2'-MOE) and 2'-dimethylaminooxyethoxy such as O(CH$_2$)$_2$ON(CH$_3$) (known as 2'-DMAOE). Also particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, O(CH$_2$)$_n$ON[(CH$_2$)$_n$CH$_3$], where n and m are independently of each other integer from 1 to 10. Other preferred modifications include 2'-methoxy, 2'-aminopropoxy and 2'-fluoro. Other preferred oligonucleotides comprise one of the following groups at the 2' position: —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —NO$_2$, —F, —Cl, —Br, —I, —N$_3$, —CN, —OCN, —NCO, —SCN, —NCS, —COCH$_3$, —COC$_2$H$_5$, —COC$_3$H$_7$, —CO-cyclo-C$_3$H$_5$, —COCH(CH$_3$)$_2$, —CF$_3$, —SH, —SCH$_3$, —SC$_2$H$_5$, —SC$_3$H$_7$, —S-cyclo-C$_3$H$_5$, —SOCH$_3$, —SOC$_2$H$_5$, —SOC$_3$H$_7$, —SO-cyclo-C$_3$H$_5$, —SO$_2$CH$_3$, —SO$_2$C$_2$H$_5$, —SO$_2$C$_3$H$_7$, —SO$_2$-cyclo-C$_3$H$_5$, —NH$_2$, —NHCH$_3$, —NHC$_2$H$_5$, —NHC$_3$H$_7$, —NH-cyclo-C$_3$H$_5$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$—CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —C$_2$H$_4$—C(CH$_3$)$_3$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —CH(CH$_3$)—C(CH$_3$)$_3$, C$_7$-C$_{10}$ alkyl, substituted C$_1$-C$_{10}$ alkyl, alkylaryl, arylalkyl, O—C$_1$-C$_{10}$ alkyl, O-arylalkyl, heterocycloalkyl, heterocycloalkylaryl, aminoalkylamino, polyalkylamino, substituted silyl, an RNA leaving group, a reporter group, an intercalator, a group for improving the pharmacokinetic and/or pharmacodynamic properties of the oligonucleotide, or substituents having similar properties. Also preferred are the deoxy nucleobases.

Similar modifications may also be made at other positions on the nucleotide, particularly the 3' position of the sugar on the 3' terminal nucleotide or in 2'-5' linked oligonucleotides and the 5' position of 5' terminal nucleotide.

Preferred modifications can be represented by the following structure fragment:

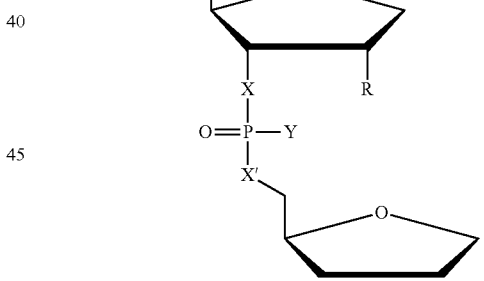

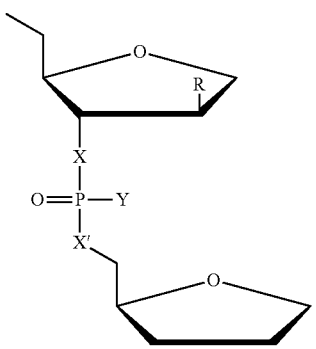

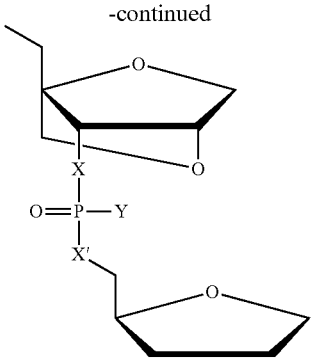

wherein
R represents any of the above-mentioned substituents for position 2' and especially —H, —F, —OH, —NH$_2$, —OCH$_3$, —OCH$_2$CH$_2$OCH$_3$,
X and X' are independently of each other —O—, —NH—, —S—, —CH$_2$—, and
Y represents —O$^-$, —S$^-$, —N(CH$_3$)$_2$, —OCH$_3$, —SCH$_3$.

More preferred are variants wherein X and X represent oxygen and Y represents sulfur.

Furthermore, pure diastereomeric oligonucleotides or mimetics or variants thereof are preferred. Especially preferred are Sp- and Rp-diastereomers:

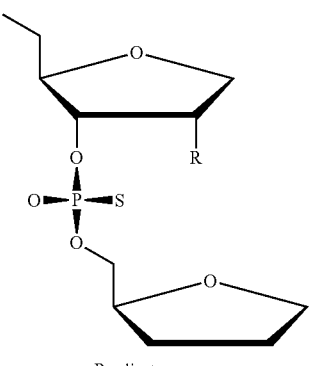

Rp diastereomer

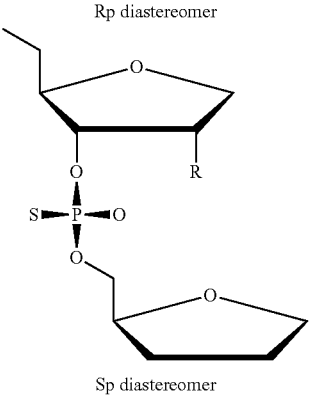

Sp diastereomer

Most preferred are also the sequences SEQ ID NO 3 to SEQ ID NO 93, and especially SEQ ID NO 3, wherein one or more of the modifications disclosed herein are present. Preferred are phosphorothioate moieties in the backbone or complete phosphorotioate backbones and within said phosphorothioates the Rp and Sp diastereomers are preferred.

The oligonucleotides of the present invention may also include nucleobase substitutions. Nucleobases are the four standard nucleotide bases adenine (A), thymine (T), guanine (G), and cytosine (C). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine; uracile (U), 6-carboxyuracile, N$^6$-methyl-adenine, 5-halouracil, 5-halocytosine, 5-propynyl uracil, 5-propynyl cytosine, 6-azo uracil, 6-azo cytosine, 6-azo thymine, 5-uracil (pseudouracil), 4-thiouracil; 8-halo-, 8-amino-, 8-thiol-, 8-thioalkyl-, 8-hydroxyl- and other 8-substituted adenines and guanines; 5-halo—particularly 5-bromo-, 5-trifluoromethyl- and other 5-substituted uracils and cytosines; 7-methylguanine; 7-methyladenine, 8-azaguanine, 8-azaadenine, 7-deazaguanine, 7-deazaadenine, 3-deazaguanine and 3-deazaadenine, 2-thiouracil, 2-thiothymine and 2-thiocytosine etc., with 5-methylcytosine substitutions being preferred since these modifications have been shown to increase nucleic acid duplex stability.

Preferred are variants having the sequence of any one of SEQ ID NO 3 to SEQ ID NO 93, wherein one, two, three or four nucleobases are substituted by other nucleobases or chemically modified nucleobases. A variant shall refer to a sequence of SEQ ID NO 3 to SEQ ID NO 93, wherein one to four nucleobases are, for instance, substituted by uracile (U), 5-halouracil, 5-methyl-cytosine, and/or N$^6$-methyl-adenine. Especially preferred are variants of SEQ ID NO 3, wherein one, two or three nucleobases are substituted by the above-mentioned moieties.

"Oligonucleotide" refers to an oligomer or polymer of ribonucleic acid (RNA) or deoxyribonucleic acid (DNA) or mimetics or variants thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms, because of desirable properties such as, for example, enhanced cellular uptake, enhanced affinity for nucleic acid target and increased stability in the presence of nucleases. While antisense oligonucleotides are a preferred form of the antisense compound, the present invention comprehends other oligomeric antisense compounds, including but not limited to oligonucleotide mimetics such as are described below. The antisense compounds in accordance with this invention comprise from about 8 to about 50 nucleobases (i.e. from about 8 to about 50 linked nucleosides), preferably 9-42, 10-36, 11-32, 12-30, 13-28, 14-26, and most preferably 15-25 nucleobases.

Particularly preferred antisense compounds are antisense oligonucleotides, even more preferably those comprising from about 15 to about 25 nucleobases.

Antisense compounds include ribozymes, external guide sequences (EGS), oligonucleotides (oligozymes), and other short catalytic RNAs or catalytic oligonucleotides which hybridize to the target nucleic acid and inhibit its expression.

The term "salts" refers to physiologically and/or pharmaceutically acceptable salts of the compounds, especialls the antisense oligonucleotides of the present invention. Pharmaceutically acceptable base addition salts are formed with inorganic bases are bases. Examples for suitable organic and inorganic bases are bases derived from metal ions, e.g., aluminum, alkali metal ions, such as sodium or potassium, alkaline earth metal ions such as calcium or magnesium, or an amine salt ion or alkali- or alkaline-earth hydroxides, -carbonates or -bicarbonates. Examples include aqueous LiOH, NaOH, KOH, NH$_4$OH, potassium carbonate, ammonia and sodium bicarbonate, ammonium salts, primary, secondary and tertiary amines, such as, e.g., tetraalkylammonium hydroxide, lower alkylamines such as methylamine, t-butylamine, procaine, ethanolamine, arylalkylamines such as dibenzylamine and N,N-dibenzylethylenediamine, lower alkylpiperidines such as N-ethylpiperidine, cycloalkylamines such as cyclohexylamine or dicyclohexylamine, morpholine, glucamine, N-methyl- and N,N-dimethylglucamine, 1-adamantylamine, benzathine, or salts derived from amino acids like arginine, lysine, ornithine or amides of originally neutral or acidic amino acids, chloroprocaine, choline, procaine or the like.

The compounds of the invention which are basic, may form pharmaceutically acceptable salts with organic and inorganic acids. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphersulfonic acid, china acid, mandelic acid, o-methylmandelic acid, hydrogen-benzenesulfonic acid, picric acid, adipic acid, D-o-tolyltartaric acid, tartronic acid, α-toluic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

Alternatively, the pharmaceutical composition of the invention contains a vector allowing to transcribe an antisense oligonucleotide of the invention, e.g., in a mammalian host. Preferably, such a vector is a vector useful for gene therapy. Preferred vectors useful for gene therapy are viral vectors, e.g. adenovirus, bacculovirus, herpes virus, vaccinia, or, more preferably, an RNA virus such as .a retrovirus. Even more preferably, the retroviral vector is a derivative of a murine or avian retrovirus. Examples of such retroviral vectors which can be used in the present invention are: Moloney murine leukemia virus (MoMuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific. This can be achieved, e.g., by inserting a polynucleotide encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the persons skilled in the art; see, e.g., WO 94/29469 or WO 97/00957. In order to achieve expression only in the target organ, e.g., brain tissue, the DNA sequences for transcription of the antisense oligonucleotides can be linked to a tissue specific promoter and used for gene therapy.

Within an oligonucleotide structure, the phosphate groups are commonly referred to as forming the internucleoside backbone of the oligonucleotide. The normal linkage or backbone of RNA and DNA is a 3' to 5' phosphodiester linkage. Specific examples of preferred antisense compounds or variants useful in the present invention include oligonucleotides containing modified backbones or non-natural internucleoside linkages. Oligonucleotides having modified backbones include those that retain a phosphorus atom in the backbone and those that do not have a phosphorus atom in the backbone. Modified oligonucleotide backbones which can result in increased stability are known to the person skilled in the art, preferably such modification is a phosphorothioate linkage or the replacement of one or more phosphate groups (phosphoric acid group) by a phosphonate (phosphonic acid) group or by sulfate (sulfuric acid) group or by a sulfonate (sulfonic acid) group or by a sulfoxide. A preferred oligonucleotide mimetic is an oligonucleotide mimetic that has been shown to have excellent hybridization properties, and is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone (see, e.g., Nielsen et al., Science 254 (1991), 1497-1500.)

In the context of this invention, "hybridization" means hydrogen bonding, which may be Watson-Crick, Hoogsteen or reversed Hoogsteen hydrogen bonding, between complementary nucleoside or nucleotide bases. As used herein, the term "complementary" refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound does not need to be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., in the case of therapeutic treatment.

In other preferred oligonucleotide mimetics, both the sugar and the internucleoside linkage, i.e. the backbone of the nucleotide units are replaced with novel groups. The base units are maintained for hybridization with an appropriate nucleic acid target compound. An example for such an oligonucleotide mimetic that has been shown to have excellent hybridization properties, is referred to as peptide nucleic acid (PNA). In PNA compounds, the sugar-backbone of an oligonucleotide is replaced with an amide containing backbone, in particular with an aminoethylglycine backbone. The nucleobases are retained and are bound directly or indirectly to aza nitrogen atoms of the amide portion of the backbone.

Another modification of the oligonucleotides of the invention involves chemically linking to the oligonucleotide one or more moieties or conjugates which enhance the activity, cellular distribution or cellular uptake of the oligonucleotide. Such moieties include lipid moieties such as a cholesterol moiety, cholic acid, a thioether, hexyl-S-tritylthiol, a thiocholesterol, an aliphatic chain, e.g., dodecandiol or undecyl residues, a phospholipid such as dihexadecyl-rac-glycerol or triethylammonium-1,2-di-O-hexadecyl-rac-glycero-3H-phosphonate, a polyamine or a polyethylene glycol chain, or adamantine acetic acid, a palmityl moiety, or an octadecylamine or hexylamino-carbonyl-oxycholesterol moiety. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers.

Especially, the present invention relates to the use of the antisense oligonucleotides disclosed herein or variants or mimetics thereof for prophylaxis and treatment of neurodegenerative disorders, neurotrauma, neurovascular and neuroinflammatory incl postinfectious disorders. The term "neurodegenerative disorders and neuroinflammatory disorders" refers to Alzheimer's diseases, Parkinson's disease, Creutzfeldt Jakob disease (CJD), new variant of Creutzfeldt Jakobs disease (nvCJD), Hallervorden Spatz disease, Huntington's disease, multisystem atrophy, dementia, frontemporal dementia, motor neuron disorders, amyotrophic lateral sclerosis, spinal muscular atrophy, spinocerebellar atrophies (SCAs), schizophrenia, affective disorders, major depression, meningoencephalitis, bacterial meningoencephalitis, viral meningoencephalitis, CNS autoimmune disorders, Multiple Sclerosis (MS), acute ischemic/hypoxic lesions incl stroke, CNS trauma, head trauma, arteriosclerosis, atherosclerosis, microangiopathic dementia, Binswanger' disease, leukoaraiosis, retinal degeneration, cochlear degeneration, macular degeneration, cochlear deafness, AIDS-related dementia, retinitis pigmentosa, fragile X-associated tremor/ataxia syndrome (FXTAS), progressive supranuclear palsy (PSP), striatonigral degeneration (SND), olivopontocerebellear degeneration (OPCD), Shy Drager syndrome (SDS).

More general, the present invention relates to the use of the antisense oligonucleotides disclosed herein or variants or mimetics thereof for treating diseases which are associated with up-regulated or enhanced signalling of TGF-R and/or TGF-$R_{II}$, e.g. through elevated levels of TGF-beta. The antisense oligonucleotides thereby inhibit the expression of TGF-R and/or TGF-$R_{II}$. Instead of the antisense oligonucleotides or in combination with the antisense oligonucleotides, antisense compounds may be used. Antisense compounds refer to vectors as disclosed herein allowing to transcribe an antisense oligonucleotide or to ribozymes, external guide sequences (EGS), oligozymes, and short catalytic RNAs or catalytic oligonucleotides which hybridize to the target nucleic acid encoding TGF-R or TGF-$R_{II}$. Said antisense compounds inhibit the expression of TGF-R or TGF-$R_{II}$. Thus, in said cases the amount of TGF-R and/or TGF-$R_{II}$ present during disease state is decreased.

The antisense oligonucleotides and the antisense compounds disclosed herein are useful for regeneration and functional reconnection of damaged neural pathways and for treatment of various neurodegenerative disorders and neuroinflammatory disorders.

In a further preferred embodiment of the present invention, the compound useful for interfering with the biological activity of TGF-R and/or TGF-$R_{II}$ is a compound reducing or inhibiting the binding of TGF-β1 to its receptor. Preferred examples of such compounds are (neutralizing) antibodies directed against a TGF-β receptor; see Lin et al., 1992, preferably the TGF-β receptor II. The term "antibody", preferably, relates to antibodies which consist essentially of pooled monoclonal antibodies with different epitopic specificities, as well as distinct monoclonal antibody preparations. Monoclonal antibodies are made from an antigen containing, e.g., a fragment of TGF-R or TGF-$R_{II}$ or a corresponding receptor by methods well known to those skilled in the art. As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24: 316-325 (1983)). Thus, these fragments are preferred, as well as the products of a FAB or other immunoglobulin expression library. Moreover, antibodies useful for the purposes of the present invention include chimerical, single chain, and humanized antibodies.

Further preferred compounds for the use of the present invention are soluble TGF-β receptors. Such soluble TGFβ receptors are fusion proteins between Fc regions of antibodies and the extracellular domain of TGFβ receptors. Such molecules have a high affinity to soluble TGF-b1. Therefore, the concentration of free TGF-b1 is drastically reduced. According to the manufacturers protocol (R&D Systems, Germany), a DNA sequence encoding the 159 amino acid residue extracellular domain of human TGF-β$R_{II}$ (Lin et al., Cell 1992, 68(4), 775-785) was fused to the Fc region of human IgG1 and the chimeric protein was expressed in a mouse myeloma cell line NSO.

The term "soluble" as used herein in the context of receptors preferably relates to fragments of the receptor only comprising the extracellular domain(s) of the receptor or a part thereof which can still bind its natural ligand, e.g., TGF-β1. The person skilled in the art can determine such fragments based on the known amino acid sequences of the receptors and the determination of the extracellular domain of the receptors can be carried out by use of well known methods, e.g., by computer programs (hydrophilicity plot). In a particular preferred embodiment of the use of the present invention, said soluble TGF-β receptor is the TGF-β receptor II.

The present invention also relates to a method for identifying a compound interfering with (a) the biological activity of TGF-R and/or TGF-$R_{II}$ or the expression of TGF-R and/or TGF-$R_{II}$, or (b) the TGF-β1/TGF-R signaling, comprising the steps of:
(a) incubating a candidate compound with a test system comprising TGF-β1 and neuronal precursor cells; and
(b) assaying the expression of active TGF receptors or the proliferation of the neuronal precursor cells; wherein
(c) an abolition of (i) the suppression of expression of active TGF receptors or (ii) suppression of proliferation of the neuronal precursor cells compared to the test system in the absence of said test compound is indicative of the presence of a candidate compound having the desired properties.

Examples of such candidate molecules include antibodies, oligonucleotides, proteins (e.g., receptors), or mall molecules. Such molecules can be rationally designed using known techniques. Preferably, said test system used for screening comprises substances of similar chemical and/or physical properties, most preferably said substances are identical. The compounds which can be prepared and identified according to a use of the present invention may be expression libraries, e.g., cDNA expression libraries, peptides, proteins, nucleic acids, antibodies, small organic compounds, ligands, hormones, peptidomimetics, PNAs or the like. More recently, WO 98/25146 described further methods for screening libraries of complexes for compounds having a desired property, especially, the capacity to agonize, bind to, or antagonize a polypeptide or its cellular receptor. The complexes in such libraries comprise a compound under test, a tag recording at least one step in synthesis of the compound, and a tether susceptible to modification by a reporter molecule. Modification of the tether is used to signify that a complex contains a compound having a desired property. The tag can be decoded to reveal at least one step in the synthesis of such a compound. Other methods for identifying compounds which interact with TGF-R and/or TGF-$R_{II}$ according to the invention or nucleic acid molecules encoding such molecules are, for example, the in vitro screening with the phage display system as well as filter binding assays or "real time" measuring of interaction using, for example, the BIAcore apparatus (Pharmacia). All these methods can be used in accordance with the present invention to identify a compound interfering with the biological activity of TGF-R and/or TGF-$R_{II}$ or the expression of said receptors, or TGFβ1/TGF-R signaling.

It is also well known to the person skilled in the art, that it is possible to design, synthesize and evaluate mimetics of small organic compounds that, for example, can act as a substrate or ligand to a TGF-β receptor. For example, it has been described that D-glucose mimetics of hapalosin exhibited similar efficiency as hapalosin in antagonizing multidrug resistance assistance-associated protein in cytotoxicity; see Dinh, J. Med. Chem. 41 (1998), 981-987. The gene encoding TGF-β1 or TGF-R can also serve as a target for screening inhibitors. Inhibitors may comprise, for example, proteins that bind to the mRNA of the gene encoding TGF-R, preferably TGF-$R_{II}$, thereby destabilizing the native conformation of the mRNA and hampering transcription and/or translation.

Furthermore, methods are described in the literature for identifying nucleic acid molecules such as an RNA fragment that mimics the structure of a defined or undefined target RNA molecule to which a compound binds inside of a cell resulting in retardation of cell growth or cell death; see, e.g., WO 98/18947 and references cited therein. These nucleic acid molecules can be used for identifying unknown compounds of pharmaceutical interest and for identifying unknown RNA targets for use in treating a disease. These methods and compositions can be used for identifying compounds useful to reduce expression levels of TGF-β1 and/or the corresponding receptor(s). The compounds which can be tested and identified according to the method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879-880; Hupp, Cell 83 (1995), 237-245; Gibbs, Cell 7 (1994), 193-198 and references cited supra). Furthermore, genes encoding a putative regulator of TGF-β1 and/or which excert their effects up- or downstream of TGF-P1 may be identified using, for example, insertion mutagenesis using, for example, gene targeting vectors known in the art. Said compounds can also be functional derivatives or analogues of known inhibitors. Such useful compounds can be for example transacting factors which bind to TGF-R or TGF-$R_{II}$ or regulatory sequences of the gene encoding it. Identification of transacting factors can be carried out using standard methods in the art. To determine whether a protein binds to the protein itself or regulatory sequences, standard native gelshift analyses can be carried out. In order to identify a transacting factor which binds to the protein or regulatory sequence, the protein or regulatory sequence can be used as an affinity reagent in standard protein purification methods, or as a probe for screening an expression library. The identification of nucleic acid molecules which encode polypeptides which interact with TGF-R or TGF-$R_{II}$ can also be achieved, for example, as described for TGF-β1 in Scofield (Science 274 (1996), 2063-2065) by use of the so-called yeast "two-hybrid system". In this system TGF-β1 is linked to the DNA-binding domain of the GAL4 transcription factor. A yeast strain expressing this fusion polypeptide and comprising a lacZ reporter gene driven by an appropriate promoter, which is recognized by the GAL4 transcription factor, is transformed with a library of cDNAs which will express plant proteins or peptides thereof fused to an activation domain. Thus, if a peptide encoded by one of the cDNAs is able to interact with the fusion peptide comprising a peptide of, e.g., TGF-R or TGF-$R_{II}$, the complex is able to direct expression of the reporter gene. In this way, e.g., TGF-R or TGF-$R_{II}$ and the gene encoding each receptor can be used to identify peptides and proteins interacting with TGF-R or TGF-$R_{II}$. It is apparent to the person skilled in the art that this and similar systems may then further be exploited for the identification of inhibitors. Finally, the present invention relates to the use of a compound identified by the method described above for the preparation of a pharmaceutical composition for the prevention or treatment of a disease, wherein neurogenesis or neuroregeneration has a beneficial effect. The below example explains the invention in more detail.

The present intervention also relates to methods for identifying the effects of treatment or prevention/prophylaxis at the stem cell/precursor cell population, induced by the modulation of the TGF-R- or TGF-RII-System. This may be especially helpful in establishing successful treatment in the individual patient, allowing for example individualized dosing. The diagnostic methods comprise (a) systemic application of specific antibodies directed against TGF-R or TGF-RII and labelled with either specific nuclids for nuclear medicine diagnostics (Iodine, Technetium, Fluor 18) or with gadolinium salts, perfluorcarbons or other rare earth products/paramagentic compounds/iron particles for use in Magnetic Resonance Imaging. In this context it may be necessary to shortly open the blood brain barrier at the subependymal layer, in case there is not enough signal over noise ratio; although this area is highly vascularized, and contrast may be enough for visualisation with a 3 Tesla machine, opening of the BBB may be of additional help. This may be either done with i.v. hyperosmolar solutions (e.g. glycerol) or with VEGF (Vascular Endothelial Growth Factor).

(b) systemic application of oligonucleotides (same molecules as mentioned above) specific for TGF-R or TGF-RII: They would be labelled as follows: Gd or $^{111}$In-DTPH (5'XXXXXXXXXXXXXXXXX3'-Biotin)—(SA—either OX 26, 8D3 or Ak-HIR) (whereby Gd is used for MRI, $^{111}$In is used for radiodiagnostics; OX 26 is used for mouse experiments and targets the mouse transferrin receptors, 8D3 is a mouse anti rat transferrin receptor antibody, AK-HIR is an antibody directed at the human Insulin receptor). These compounds would only hybridize and signal in those cells that have the active mRNA for TGF-R or TGF-RII. DTPH is used as a chelate-building agent, the Ak-HIR uses the Insulin receptor to shuttle the oligonucleotide through the different barriers, in case of the transferrin receptor antibodies the latter is used for the transmembrane shuttle. There is a differential hybridization stability in those cells where a large number of mRNA is available and therefore a much stronger signal may be detected (Susuki T, Schlachetzki F, et al. J. Nucl. Med. 45: 1766-1775, 2004, Susuki T, Zhang Y, Zhang Y-f, Schlachetzki F, Pardridge et al., Mol. Imaging 2005, 3, 356-363).

(c) systemic application of oligonucleotides (same molecules as mentioned above) specific for Doublecortin (DCX) with identical labelling as in (b) (cf. WO 2004067751)

Preferably, in a pharmaceutical composition, such compound as described above is combined with a pharmaceutically acceptable carrier. "Pharmaceutically acceptable" is meant to encompass any carrier, which does not interfere with the effectiveness of the biological activity of the active ingredient and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and the active compound can be administered to the subject at an effective dose. An "effective dose" refers to an amount of the active ingredient that is sufficient to affect the course and the severity of the disease, leading to the reduction or remission of such pathology. An "effective dose" useful for treating and/or preventing these diseases or disorders may be determined using methods known to one skilled in the art. Administration of the suitable compositions may be effected by different ways, e.g. by intravenous, intraperetoneal, subcutaneous, intramuscular, topical or intradermal administration. The route of administration, of course, depends on the kind of therapy and the kind of compound contained in the pharmaceutical composition. Furthermore, the compounds of the present invention may be mixed and administered together with liposomes, complex forming agents, receptor targeted molecules, solvents, preservatives and/or diluents.

Preferred are pharmaceutical preparations in form of infusion solutions or solid matrices for continuous release of the active ingredient, especially for continous release of at least one antisense oligonucleotide or variants or mimetics thereof. More preferred are pharmaceutical preparations in form of solutions or solid matrices suitable for local administration into the brain.

The dosage regimen will be determined by the attending physician and other clinical factors. As is well known in the medical arts, dosages for any one patient depends on many factors, including the patient's size, body surface area, age, sex, the particular compound to be administered, time and route of administration, the kind of therapy, general health and other drugs being administered concurrently.

The present invention relates to pharmaceutical preparations comprising at least one oligonucleotide, variants or mimetics thereof, as disclosed above. Instead of or in addition to the at least one antisense oligonucleotide at least one antisense compound could be present. Antisense compounds refer to vectors allowing to transcribe an antisense oligonucleotide, especially one of the antisense oligonucleotides as disclosed herein or to ribozymes, external guide sequences (EGS), oligozymes, and short catalytic RNAs or catalytic oligonucleotides which hybridize to the target nucleic acid encoding TGF-R or TGF-$R_{II}$. Said antisense compound inhibits the expression of TGF-R or TGF-$R_{II}$ and preferably of is capable of decreasing the amount of TGF-R or TGF-$R_{II}$ formed, respectively.

In a preferred embodiment of the present invention, the disease that can be prevented and/or treated is a neurodegenerative disorder, a neuroinflammatory disorder of the CNS, an acute ischemic or traumatic brain hypoxic brain lesion. Preferred examples of neurodegenerative or neuroinflammatory disorders are Alzheimer's diseases, Parkinson's disease, Creutzfeldt Jakob disease (CJD), new variant of Creutzfeldt Jakobs disease (nvCJD), Hallervorden Spatz disease, Huntington's disease, multisystem atrophy, dementia, frontotemporal dementia, motor neuron disorders, amyotrophic lateral sclerosis, spinal muscular atrophy, spinocerebellar atrophies (SCAs), schizophrenia, affective disorders, major depression, meningoencephalitis, bacterial meningoencephalitis and viral meningoencephalitis (prevention of postinflammatory depression of stem cell proliferation), CNS autoimmune disorders, like Multiple Sclerosis (MS), acute ischemic/hypoxic lesions, CNS trauma, head trauma, arteriosclerosis, atherosclerosis, microangiopathic dementia, Binswanger' disease, leukoaraiosis, AIDS-related dementia, fragile X-associated tremor/ataxia syndrome (FXTAS), progressive supranuclear palsy (PSP), striatonigral degeneration (SND), olivopontocerebellear degeneration (OPCD), Shy Drager syndrome (SDS); retinal degeneration, macular degeneration, retinitis pigmentosa, cochlear degeneration, cochlear deafness. Also age dependant decrease of stem cell renewal may be addressed.

EXAMPLES

Example 1

TGF-β1 Inhibits Proliferation of Adult Rodent Neural Stem and Precursor Cells

Adult female mice (various strains) or Fischer-344 rats (3-4 months; Charles River, Germany) are killed, and brains and spinal cords are removed and put in 4° C. DPBS (PAN, Germany) with 4.5 gm/l glucose (Merck, Germany) (DPBS/glu). Overlying meninges and blood vessels are removed. Hippocampus and ependymal zones, including subependymal and subventricular zones from the lateral wall of the lateral ventricle (SVZ), are aseptically removed. The dissected tissue is transferred to fresh DPBS/glu, washed once, transferred to Petri dishes, and dissociated mechanically. The cell suspension is washed in DPBS/glu to rinse off excess blood and resuspended in PPD solution containing 0.01% papain (Worthington Biochemicals, England), 0.1% dispase II (Boehringer Mannheim, Mannheim, Germany), 0.01% DNase I (Worthington Biochemicals), and 12.4 mM $MgSO_4$ in HBSS (PAN) without $Mg_2/Ca_2$ (PAA, Germany) and digested for 30 to 40 minutes at room temperature. The cell suspension is triturated every 10 minutes. Dissociated cells are collected and resuspended in serum-free DMEM/F12 medium containing 2 mM L-glutamine and 0.1 gm/l penicillin/streptomycin and washed three times with accurate trituration. Finally the single-cell suspension is resuspended in NB medium (Gibco BRL, Germany) supplemented with B27 (Gibco BRL) (NB/B27), 2 mM L-glutamine (PAN), 0.1 gm/l penicillin/streptomycin (PAN), 2 g/ml heparin (Sigma, Taufkirchen, Germany), 20 ng/ml bFGF-2 (R&D Systems, Germany), and 20 ng/ml EGF (R&D Systems, Germany). Viable cells are counted by trypan blue exclusion assay in a hemocytometer. Cells are seeded in T-25 culture flasks and cultures are maintained at 37° C. in an incubator with 5% $CO_2$. Single cells begin to form spheres within 5 to 7 days of suspension culture and continue to grow in mass and number during the next weeks. Half of the medium is changed every 7 days. Cells from passage numbers 3 to 20 are used for the experiments (Wachs, F. P., S. Couillard-Despres, et al., Lab Invest 2003, 83(7), 949-962). The cultures of neural stem and precursor cells are further referred to as NSC's. For the dissociation process, the culture medium containing floating neurospheres is collected in a 15-ml centrifuge tube and centrifuged at 120 rcf for 5 minutes. The pellet is resuspended in 200 μl of Accutase (Innovative Cell Technologies Inc., distributed by PAA) and triturated approximately 10 times using a pipette. Then, the cell suspension is incubated at 37° C. for 10 minutes. Dissociated spheres are again triturated and resuspended in 800 μl of NB/B27 medium. Dissociated cells are centrifuged at 120 rcf for 5 minutes and resuspended in NB/B27 medium. An aliquot is counted by trypan blue exclusion assay in a hemocytometer to determine the amount of viable cells. Cells ($10^5$) are plated in T75 culture flasks for long-term passaging (10 ml of culture medium per flask) in NB/B27 medium. The cells obtained after Accutase treatment of primary neurospheres proliferate and yield secondary neurospheres. Secondary neurospheres are passaged 7 to 9 days after plating primary neurosphere cells. Similar to primary cultures and primary neurospheres, single cells obtained after dissociation of secondary neurospheres proliferate and yield tertiary neurospheres (Wachs, F. P., S. Couillard-Despres, et al., Lab Invest 2003, 83(7), 949-962).

Figure 1:
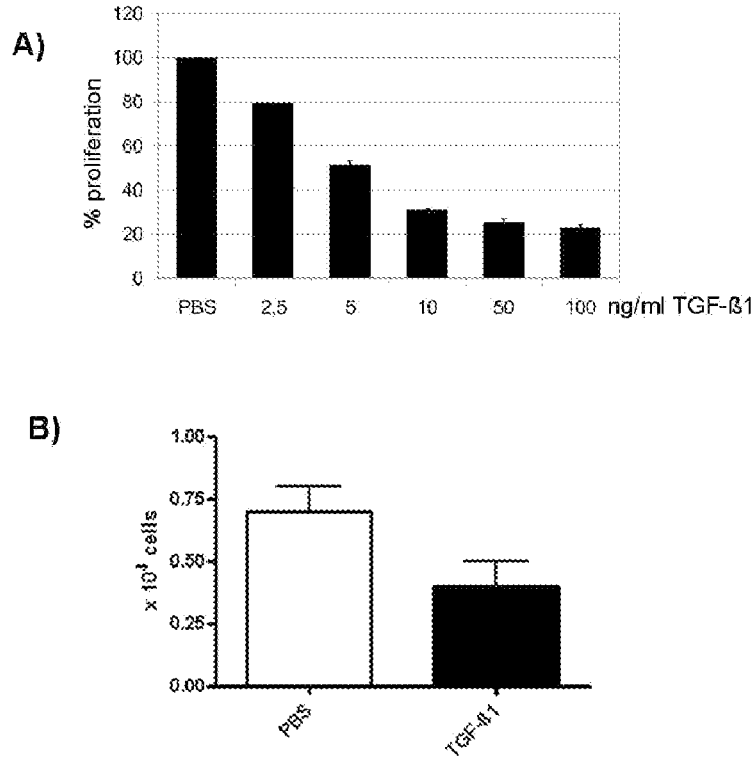
FIG. 1: TGF-Beta1 Inhibits Proliferation of Adult Rodent Neural Stem and Precursor Cells A) Adult rodent neural stem and precursor cell (NSC) cultures were treated with various concentrations (0, 5, 10, 50 ng/ml) of recombinant human TGF-beta1 for 7 days. On day 7 viable cells were counted by Trypan Blue exclusion assay in a hemocytometer. The data are expressed as average cell numbers±SD from three experiments performed in triplicate. B) shows the effect of TGF-beta1 on human fetal neural precursor cells.

$10^4$ NSC's are seeded in 12-well plates in NB/B27 medium in a volume of 1 ml and grow for 7 days. 2 hours, 3 days and 6 days after seeding the cells are stimulated by addition of various concentrations (0, 2,5, 5, 10, 50 and 100 ng/ml) of recombinant human Transforming Growth Factor β1 (TGF-β1) (R&D Systems, Germany). On day 7 the cultures are dissociated by the use of Accutase™ and viable cells are counted by trypan blue exclusion assay in a hemocytometer. In vitro TGF-β1 inhibits the proliferation of adult neural stem and precursor cells in a dose dependant manner (FIG. 1A).

A similar effect was observed on human fetal neural precursors cells. Treatment with 50 ng/ml of TGF-b1 reduced cell proliferation to about 50% of controls within 7 days (FIG. 1B).

Example 2

The Effect of TGF-β1 on Neural Stem and Precursor Cells is Reversible

Figure 2:
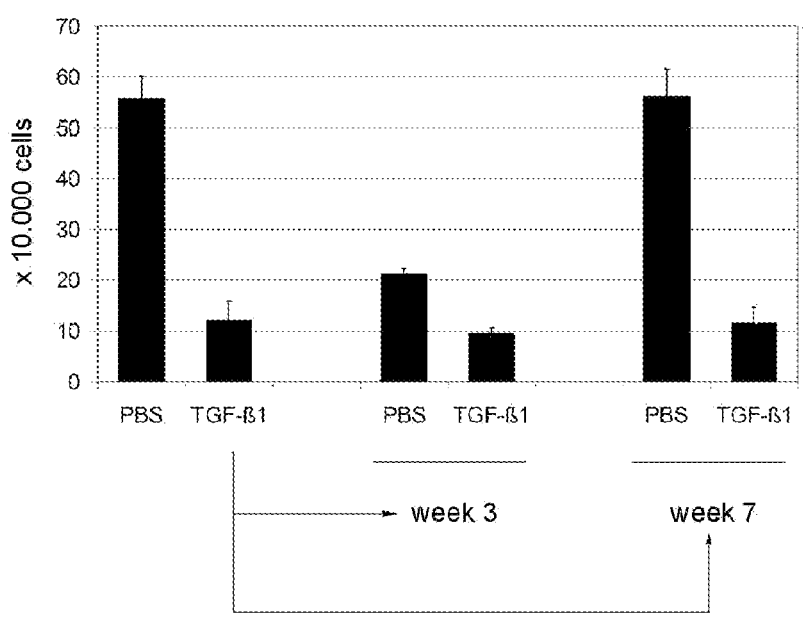
FIG. 2: The Effect of Tgf-Beta1 on NSCs is Reversible

To determine, whether the TGF-β1 induced growth-inhibition is a reversible effect, NSC's are stimulated with 10 ng/ml TGF-β1 for 7 days according to the protocol described in example 1. After dissociation, viable cells are counted by Trypan Blue exclusion assay in a hemocytometer and $10^4$ growth factor-stimulated NSC's are reseeded and cultured with or without 10 ng/ml TGF-β1 according to the protocol described in example 1. This dissociation/counting/reseeding procedure is performed every 7 days. As shown in FIG. 2, after 3 weeks of culture the proliferation rate of initially TGF-β1-treated cells now grown without TGF-β1 returns to normal when compared to formerly untreated cells. This indicates that the effect of TGF-β1 on adult neural stem and precursor cells is reversible. Long term incubation with TGF-β1 does not further decrease cell proliferation.

Example 3

Antibodies Against TGF-βR$_{II}$ can Reduce TGF-β1 Effects on Adult Rodent NSC's Unstimulated seven-day-old neurospheres of low passage number are dissociated by the use of Accutase™ as described in example 1. The resulting single-cell suspension was used for blocking analysis. Adult rodent NSC's were seeded at a density of $10^4$ cells in 12-well plates in NB/B27 medium in a volume of 1 ml. 2 hours after seeding and 1 hour prior to stimulation with 10 ng/ml TGF-β1, various concentrations of neutralizing anti-TGF-βR$_{II}$ antibodies (R&D Systems, Germany) were added to the culture medium. 3 days and 6 days after seeding the cells are re-stimulated by addition of anti-TGF-βR$_{II}$ antibodies and TGF-β1 identical to the procedure performed on day 1. On day 7 the cultures are dissociated by the use of Accutase™ and viable cells are counted by trypan blue exclusion assay in a hemocytometer. Interestingly, addition of the anti-TGF-βR$_{II}$ antibodies itself reduces proliferation of NSC's. Antibodies against TGF-βR$_{II}$ are only able to partially inhibit TGF-β1-induced effects even in the highest concentrations used (10 μg/ml) (FIG. 3).

Example 4

Soluble TGF-R$_{II}$ Completely Inhibits TGF-β1 Induced Suppression of NSC Proliferation According to the manufacturers protocol (R&D Systems, Germany), a DNA sequence encoding the 159 amino acid residue extracellular domain of human TGF-βR$_{II}$ (Lin et al., Cell 1992, 68(4), 775-785) was fused to the Fc region of human IgG1 and the chimeric protein was expressed in a mouse myeloma cell line NSO. Unstimulated seven-day-old neurospheres of low passage number are dissociated by the use of Accutase™ as described in example 1. The resulting single-cell suspension was used for blocking analysis. Adult rodent NSC's were seeded at a density of $10^4$ cells in 12-well plates in NB/B27 medium in a volume of 1 ml. 2 hours after seeding and 1 hour prior to stimulation with 10 ng/ml TGF-β1, various concentrations of bioactive soluble recombinant human TGF-βsR$_{II}$/Fc Chimera (R&D Systems, Germany) were added to the culture medium. 3 days and 6 days after seeding the cells are re-stimulated by addition of TGF-βsR$_{II}$/Fc Chimera and TGF-β1 identical to the procedure performed on day 1. On day 7 the cultures are dissociated by the use of Accutase™ and viable cells are counted by trypan blue exclusion assay in a hemocytometer. Interestingly, addition of the TGF-βsR$_{II}$/Fc Chimera are able to completely block TGF-β1-induced effects in a dose dependant manner (data not shown). Clearly, abrogation of active TGF-β1 in the cell culture supernatant by pre-administration of a soluble recombinant human TGF-βsR$_{II}$/Fc Chimera (soluble TGF-βR$_{II}$) completely blocks TGF-β1-induced growth-suppression of adult neural stem and precursor cells (FIG. 4).

Example 5

TGF-βR$_{II}$-Expressing Cells can be Isolated Using Cell Sorting Techniques

Figure 5:
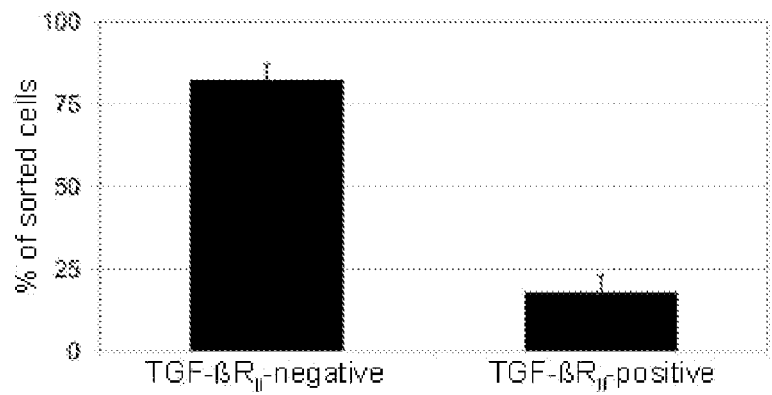

Current methods do not allow fast and reliable isolation and purification of neural stem and precursor cells. To investigate the possibility of isolating pure neural stem and precursor cell populations based on the expression of defined surface markers, we isolate neural stem and precursor cells due to the expression of the TGF-βR$_{II}$ by different techniques. It is possible to isolate TGF-βR$_{II}$-expressing neural stem and precursor cells with two techniques: i) FACS-sorting (data not shown), and ii) MACS-sorting. Dissociated adult neural stem and precursor cells are incubated with 10 µg/ml of primary antibodies against TGF-R$_{II}$ (R&D Systems, Germany) for 20 min at room temperature. After 1 washing step with PBS the cells are incubated with the secondary antibody rabbit-anti-goat-PE (1:500) (Dianova). After 1 washing step with PBS the cells are stained with tertiary antibodies against PE coupled to paramagnetic beads according to the manufacturers protocol (Miltenyi Biotech, Germany). The cell suspension is magnetically sorted using the MACS-system according to the manufacturers protocol (Miltenyi Biotech, Germany) and negative and positive cells after sorting are counted and taken in culture (FIG. 5). Approximately 20% of all sorted cells stained positive for TGF-βR$_{II}$.

Example 6

Antisense Oligonucleotides Against TGF-βRII Inhibit the TGF-β1 Induced Down-Regulation of Adult Neural Stem and Precursor Cell Proliferation in vitro Cells were prepared, dissociated and plated as described in example 1. Cells were then incubated for 1 week with or without 10 ng/ml TGF-b1, 10 µM TGF-βRII antisense oligonuceotide 5'-cagccccgacccatg-3' (SEQ ID NO: 3), sense oligonucleotide 5'-catgggtcggggctg-3' (SEQ ID NO 99), or missense 5'-catccccggacccgtg-3' (SEQ ID NO 100). Oligonucleotides were phosphotihioate-modified and medium with oligonucletodides was changed daily. Note that the TGF-β1 induced inhibition of neural stem and precursor proliferation was completely and specifically blocked by the antisense (SEQ ID NO: 3) treatment (FIG. 6).

Example 7

In vivo Treatment with TGFRII Specific Antisense Oligonucleotides Rescues the TGF-β1 Induced Blockade of Cell Proliferation in the Adult Brain This example demonstrates i) the effect of TGF-β1 infusion on neural stem and progenitor cell proliferation in vivo and ii) the rescue of this effect by TGFβRII antisense oligonucleotide treatment. Therefore, the following experiment was designed:

TGF-β1 was infused intraventricularly for two weeks followed by a co-infusion of TGF-β1 with oligonucleotides. Animal experiments were carried out in accordance with the European Communities Council Directive of 24 Nov. 1986 (86/609/EEC). Stainless steel canules connected to osmotic minipumps (Model 2001, Alza, Stadt, Land) were implanted into two months-old male Fischer-344 rats (n=24) for intracerebroventricular infusion as described. The animals received either recombinant TGF-β1 (500 ng/ml present in the pump) or artificial cerebrospinal fluid (aCSF) as control (n=8 each) at a flow rate of 0.5 µl/hr for two weeks. After the second week, the pumps were changed and aCSF, TGF-β1 (500 ng/ml present in the pump), or TGF-β1 (500 ng/ml present in the pump) in combination with phosphothioate oligonucleotdies (1.64 mM concentration present in the pump) was infused into the ventricles for the following two weeks. Oligonucleotides were as described in example 6. On day 27, animals received a single intraperitoneal injection of 200 mg/kg bromo-deoxyuridine (BrdU). One day later, animals were intracardially perfused with 4% paraformaldehyde. Tissue was processed for chromogenic or epifluorescence immunodetection in 40 µm sagital sections as described. Epifluorescence analysis was done using a Leica microscope (Leica Mikroskopie and Systeme GmbH, Wetzlar, Germany) equipped with a Spot™ digital camera (Diagnostic Instrument Inc, Sterling Heights, USA) or a confocal scanning laser microscope (Leica TCS-NT, Bensheim, Germany). Primary antibodies were: rat α-BrdU 1:250 (Oxford Biotechnology, Oxford, UK). Secondary antibodies were: donkey α-goat, mouse, rabbit or rat conjugated with fluorescein (FITC), rhodamine X (RHOX), CY5 or biotin 1:500 (Jackson Immuno Research, West Grove, Pa., USA). For counting, a systematic and random procedure was used. BrdU positive cells were counted within three 50 µm×50 µm counting frames per section located at the lowest, middle and upper part of the SVZ. Positive profiles that intersected the uppermost focal plane (exclusion plane) or the lateral exclusion boundaries of the counting frame were not counted. The total counts of positive profiles were multiplied by the ratio of reference volume to sampling volume in order to obtain the estimated number of BrdU-positive cells for each structure. All extrapolations were calculated for one cerebral hemisphere and should be doubled to represent the total brain values. Data are presented as mean values±standard deviations (SD). Statistical analysis was performed using the unpaired, two-sided t-test comparison—Student's t-test between the TGF-β1 treated and control groups (StatView Software, Cary, N.C., USA). The significance level was assumed at p<0.05.

FIG. 7 demonstrates the TGF-β1 induced down-regulation of cell proliferation in the hippocampal dentate gyrus (FIG. 7A) and in the subventricular zone (FIG. 7B). Treatment with missense oligonucleotide did not block this effect. In contrast, antisense oligonucleotide treatment (SEQ ID NO: 3) blocked the TGF-β1 effect (FIGS. 7A and B).

Example 8

In vivo Treatment with TGF-RII Specific Antisense Oligonucleotides Prevents from TGF-β1 Induced Blockade of Cell Proliferation in the Adult Brain This example demonstrates that antisense oligonucleotide treatment against TGF-βRII can prevent from TGF-β1 induced down-regulation of cell proliferation in the adult brain.

Oligonucleotides were infused intraventricularly for one week followed by a co-infusion of TGF-β1 with oligonucleotides. Animal experiments were carried out in accordance with the European Communities Council Directive of 24 Nov. 1986 (86/609/EEC). Stainless steel canules connected to osmotic minipumps (Model 2001, Alza, Stadt, Land) were implanted into two months-old male Fischer-344 rats (n=24) for intracerebroventricular infusion as described. The animals received either phosphothioate oligonucleotdies (1,64 mM concentration present in the pump) or aCSF during the first week, and aCSF, TGF-β1 (500 ng/ml present in the pump), or a co-infusion of TGF-β1 (500 ng/ml present in the pump) and phosphothioate oligonucleotides (1.64 mM concentration present in the pump) during the second and third week. Oligonucleotides were described in example 6. On day 20, animals received a single intraperitoneal injection of 200 mg/kg bromo-deoxyuridine (BrdU). One day later, animals were intracardially perfused with 4% paraformaldehyde. Tissue was processed and analyzed as described in example 7.

FIG. 8 demonstrates that the TGF-β1 induced down-regulation of cell proliferation in the hippocampal dentate gyrus (FIG. 8A) and in the subventricular zone (FIG. 8B) can be prevented by pre-treatment with TGF-βRII antisense oligonucleotide (SEQ ID NO: 3) treatment.

Example 9

Pharmaceutical Formulation Comprising at Least One Antisense Oligonucleotide

Three representative aqueous formulations for the antisense oligonucleotides:
1. in aCSF: 148.0 mM NaCl, 3.0 mM KCl, 1.4 mM $CaCl_2$, 0.8 mM $MgCl_2$, 1.5 mM $Na_2HPO_4$, 0.2 mM $NaH_2PO_4$, pH 7.4, 100 μg/ml rat serum albumin, 50 μg/ml Gentamycin
2. in 0.9% NaCl
3. in $H_2O$

The invention claimed is:

1. An oligonucleotide consisting of SEQ ID NO:3:
5'-CAGCCCCCGACCCATG-3'
wherein said oligonucleotide is capable of hybridizing sufficiently with the region encompassing the translation initiation codon of the open reading frame of the gene encoding TGF-$R_{II}$, and mimetics, salts and optical isomers of said sequence.

2. Pharmaceutical preparation comprising at least one oligonucleotide according to claim 1 as well as mimetics, salts and optical isomers thereof and/or at least one antisense compound comprising a vector allowing to transcribe at least one said oligonucleotide together with at least one pharmaceutically acceptable carrier, excipient or diluents.

3. Pharmaceutical preparation according to claim 2, wherein the pharmaceutical preparation is an infusion solution or a solid matrix for continuous release of the active ingredient.

4. Pharmaceutical preparation according to claim 2, wherein the pharmaceutical preparation is suitable for local administration into the brain.

* * * * *

SEQUENCE LISTING

<160> NUMBER OF SEQ ID NOS: 163

<210> SEQ ID NO 1
<211> LENGTH: 89014
<212> TYPE: DNA
<213> ORGANISM: Homo sapiens

<400> SEQUENCE: 1

```
cagccacact gtctttaact ctcagcccac ccacactgag gagggtgcct agaggttcta      60
tttccaaacc tttgcatgta tcttaaaaat ctcaataaaa tgagaccttc caccatccaa     120
acagagctga tattctcact accagtccct ctctaatatt cctatttggc tgaaaataag     180
tagcttcaaa aagtttaaa aaagagatta cttgcagcat taacacttct ttgttgatta     240
acaagtttcc tatggagttt taaagctcat actttgttct tgtccttgtg gacacaaatt     300
ttctaactgc aaatgggacc tttgtgtccc acattcaaat cctctctagt aatttctgca     360
aaggttgaga aggctggcat gatggagaga acggtaacca tgaggaaagc ttcttggagt     420
aaagcactcc tctctccaat gcagagggta aaactattaa catataagca aaagaaactt     480
gggctaactg agacccttaa aggagttccc ctttagtcca ataaaaggcc aacttcaaat     540
cttaacacca gataaggtag tcaaaatcat attatatacc cagagaatga ctgcttgaat     600
ggacatttct tacaagggac cttggttagg tgcagattta attcctagac tggggtccag     660
gtaggcagtg gaaagagcta atgtttacag tgagaagtga ggcagctttg taagtgtctc     720
cacaccttca cattttgtga acgtggactg gagataactg aaaaccatct gctatcctta     780
cctggggatc cagattttcc tgcaaaatct ccaaatattt ataaagtggc ttcactttt     840 gaaacgctgt gctgaccaaa caaaacatat gtttagagtg cctgaggtca tagtcctgac     900
aatgatagta ttgtgtagtt gaaatcctct tcatcaggcc aaactgtgct tgagcaatca     960
ggagcccaga aagatggaac ccattggtgt ttgtatagaa aactagaaaa tcaagtcaag    1020
tgtaatgaaa aagtaaacac gataaagcct agagtgagaa tttgctcctt tttagaaaag    1080
gatgaaggct gggagcagag aatagtaaca taagtgcagg ggaaagatga aaaaaagaac    1140
aatttttcat tagtagatgg tggggcaatc gcatggatgg ggacatctgt tctgattttt    1200
ctgcaaccca tgaaggtaaa aagtgggggtt caaaacattc aaggtattaa agatggggta    1260
gagtttctaa actaggttga gggagagttt ctaaactagc cccccagatt tggggcttgg    1320
```

```
agcttaaatg aaaagtccag gagaaataag ggcacacagg aacccgggaa cactggtcc    1380 tcaaacagtg ccactgtact tagttccatg gccagaagag aagtgctagg cagggaatga    1440
ttattttgca aaagcaagtg caatgtggtc atagctggct gtgagacatg gagcctcttt    1500
cctcatgcaa agttcactgt tttacagtca gagaaccact gcatgtgtga ttgtcaaatg    1560
ctaatgctgt catgggtccc ttccttctct gcttggttct ggagttctcc aataaaacca    1620
atttcctggg aatatttgat gttttccttt gtctcttttc aaggtatggc tatatatata    1680
gagctataga catatataga tatatatata tatatataaa acatagctat tcatatttat    1740
atacaggcat taataaagtg caaatgttat tggctattgt aaaaatcaat ctcatttcct    1800
gaggaagtgc taacacagct tatcctatga caatgtcaaa ggcatagaat gctctatgtc    1860
acccactccc tgctgctgtt gtttctgctt atccccacag cttacaggga ggggagtgac    1920 cccccttggtt ttccaggaag catcagttca ggggcagctt cctgctgcct ctgttctttg    1980
gtgagagggg cagcctcttt ggacatggcc cagcctgccc cagaagagct atttggtagt    2040
gtttagggag ccgtcttcag gaatcttctc ctccgagcag ctcctccccg agagcctgtc    2100
cagatgctcc agctcactga agcgttctgc cacacactgg gctgtgagac gggcctctgg    2160
gtcgtggtcc cagcactcag tcaacgtctc acacaccatc tggatgccct gtagcgggaa    2220
agagatccaa agggcaccat gagttggtgg gctccgcgga aggcaaggtg gcctgctgac    2280
cttgttgcta tagtgagtgc aagcagggtc caaaagtgcc tgtgcattta acatgtgctg    2340
actgagtgcc tgctgctgca ggccagccag ttccatgtgg aaagggtggt gggggggtttg    2400 tgctggtggc agctgtgctc aaaacctacc atactttttg gctctggtgc tatctgatca    2460
caataggtcc tgacagcaca atgatcctct gctgggcttc tggggtacac taacactccc    2520
aacacctgaa aattccccat gtagtggccc ttaatatcat ttcaacacct ttctatttag    2580
agaagttctc gcttcacagc aaaattgagt ggaaagtaca gagagttttc acaaaacccc    2640
ttccccataa aggcacagcc ttctccacct tgacatcatg catgcatcta tgaggtacat    2700
ttgttataac tgatgaacta acactgacgt atcattatca atcaaattca tagttttacat    2760 tagggttcac tcttggtgtt gtatattcca ggggttttga caaatgtata atgacatgta    2820
tctaccatta tagtatcatg cggaatagtt tctctgcccc tcaaattccc tgcattccac    2880
ttattcatcc ctccctccat tcccctaaat ttctggcagc cactgatttt gtactgtctc    2940
tgtagttttt gccttttcca gagtgtcata tagttgggtc atatacactg ttctatttta    3000
acagggctga ttaccccccgt cagaattgta tgcaggcatt agcatggttt cattttctat    3060
aggccacaca ttttgtagag tgattcagta gcagcttcta cgagctgcca aggatgacct    3120
ctgggatgct ccattcctct ccaacaacat tgggttgaac cctgtgaaac agctgcctat    3180
gtgggtcagg catgcttaac tctatgccat ttcctagggt tcaccctaac cgaatcaagc    3240
tcccatccaa ggagaccatc caggagatcc tgcccaggaa ggtggcaaga gttttctctc    3300
actggcttaa ttttatttt gcattgcaaa tattttgtt atcatttcaa atccttttg    3360 gaaataaagc aggcaggagt taagtaaatg gtctgatagg tggaaataga gtgtgctcct    3420
cccaattgta agatcaacat tgctaatggg atccctcaca caggtggctg ggagtgggat    3480
ggataaatct caaaactacc tgggagagct ggcactttt ctacttgttt tctaatacca    3540
acaactttcc aaacacacct aggagcctat ctctccctcc ccacccgatg agttcatgat    3600
gttaaattaa ttgcataatt cacctaattg acagtattga cagatggccc tgttaagagt    3660
agagtgctat tgttggtaca caagtaacat ttattttatt ctggcactgt aattacaggc    3720
```

| | |
|---|---|
| agtaaattaa attaaatatt aagcattaac ttgaaatcaa tagggcaaca aatctcatta | 3780 |
| tgagaaaaaa tgtattatgc aaattctttt cagaatttta tcatcatgaa taatggcttc | 3840 |
| attacgagaa ctatacagca gaggaggcaa cagagtttga agaaacata acactccagc | 3900 |
| acattctgat ttcagaattt atgcaaaata ttcttacagt tttagtgtca aagaggattt | 3960 |
| gctcaaaact ccagagaagc ctgtgaccca ccacagcctg gttcccccctc gccaacctcc | 4020 |
| tcggacttta ttaaggtctg tctgctgaag tggctctggg ccaggactgg cacagaccag | 4080 |
| acttcctgct ccatttgtct tcccgattgt gcctgatttg ttgtttctgt ttcttatctg | 4140 |
| aatttgcctt gcccttaggg aaaccaacaa cttagcctcg gccttcatgg ttgagggaat | 4200 |
| tcatccaaaa gaggcaataa aaggttttag tcagtagaaa gaacagtctt ctcagtgaga | 4260 |
| tagggccaca ctgttctctc tcattcttca ctaagggctc cttcctgggt gtgtcagaca | 4320 |
| tatagctggt tctgactcac tcacaaccta tcgttttctt ttttctctga ccattgccct | 4380 |
| catcaaagtg cccccaaaca aacaatttgg atcagcctct ttatgagtcc agaatgactg | 4440 |
| ccctgctatg gacagcctta gctagcattt cttaacaagg aaaataaga ggccattagg | 4500 |
| atgttcccaa cagacagatt tctcgttcct tccaggcat tctcctcttc tttgctttcc | 4560 |
| ttaattccag agtgaggagt cggtctcctc tttcccacgc gtgctcactc aggcctctcc | 4620 |
| caagtctgtg agcacagcct gcaaacacct gtacacagcc ttctgcatgc cacagtcact | 4680 |
| tctcactaca gctgcctgac aaaccctgct tgttttgcat ctgctaagta tttccttatg | 4740 |
| gagctgaaga ttcccagaag aaaacatttg aatccagag ggaatcaaat ataaactcct | 4800 |
| gacgtgaagg cccaggagta agtagcagag gctgcaaaca aatgttttta acccaggacc | 4860 |
| aagggggctt ggaaaatgtg gcaaatgtcc tccgaatggc tatttgtgaa ctctcagagt | 4920 |
| acatatcagc tggttggagc ctataataat tgggttatcc actgtattga aatttgcttt | 4980 |
| ataaacaaaa tttaacaggg ccatagaaca caatgggacc ttccctcaga tttaagctca | 5040 |
| atattccaga attctctgcc acctaagagg caacttggtt gaatcttact gacctttgta | 5100 |
| aacactcact ccttacctgg tggttgagcc agaagctggg aatttctggt cgccctcgat | 5160 |
| ctctcaacac gttgtccttc atgctttcga cacagggtg ctcccgcacc ttggaaccaa | 5220 |
| atggaggctc ataatctttt acttctgtga agaaagccag caaacacagg gtcactgaga | 5280 |
| atggcatgtg cagccaaagg aaatgagcat ggtgagatgc ctggctgggg agcatgaagc | 5340 |
| actaagtaac aaatacatac gtaattactc taagagcaaa ttttaataat aatggctaag | 5400 |
| ataagaagga aggagtggtt ggggaagggc tagagaagta ttcaataaat gattgttgag | 5460 |
| tacttaaaat gtgctaggtg ttatgctggg ggacacagtg gacaacaaga tagagagggt | 5520 |
| cacggagctt aggttttaac acaggcattt tctacagggg gatattgcag caaaagggtg | 5580 |
| aaactggttc ttgggaagtg gaaaaatctt atgtattaca atggtttgtg agcctccaaa | 5640 |
| gcccagagt atacaaagag attttaaaatg tggtattaaa tttcatgtag gtattgaggc | 5700 |
| ataaaaagga atgaaactct ggcacatgct acaacatgga tgaatcttga agacattatg | 5760 |
| ctaagtgaaa taagccagac acaaaaggac aaatattgta tcattccact tgtatgaagt | 5820 |
| accttgtaca ggtatattca gagacagtat aatggtggtt gtccagggg caacctggga | 5880 |
| ggaagggta ggaaaagtta tccttttaagg ggtaaagaat ttcagttgag caaatttcag | 5940 |
| tacagaaaaa tgaataatgg tgatggttgt agagcactgc gaaggtactt aatgccagta | 6000 |
| aactgtacac ttaaaaatgg ttaagatggt acatttttata ttatgccttat tttgctacag | 6060 |
| aaaaacatca tggagagtag tgtttagaaa aaaagttgtc tacaggccag gtgctgtggc | 6120 |

```
tcatgtgtgt aatcccagca ctttaggagg ctgaaggagg atatcttgac tccgggagtt    6180
tgagaccaac ctgggcaaca tagcgagatc ctctatctat acaaaataaa aaacaaaaca    6240
agcaaacaaa aaaagttgtt taaaaaggct ccttacgata tcactgattt taaaaaaggt    6300
tgagaaatgc tgttttagtg ggaagacaga ggggacagat taacaacatc aacaaaattt    6360
taaaacgata attttcctct gatggtatat tcaataaaga aaatgataaa ggaggaggta    6420
acccttcacc ggggcctcag gcttcaacta aggtcaaatt ctttataaaa acttccttga    6480
acatccttag ggtcaatctt ggttagatat cctgggcagg gctctattcg tgcatatacc    6540
atattttatt taatatattc acctgcttat ttttctcacc taactggact gtgagcattt    6600
gggtgcaagt tgagtccctt tctcattctt gtattcttgg tgccaattgc aagggtctcc    6660
catgccaaca ggctgtcaac aaatgctttg ttgagtgagt gaatgaatga atgaatgaat    6720
gaatcttaga ttctctccaa agtggcagtg cataaactct ggccaaacat taaaacaaaa    6780
caccaattta aatgagcaga ttaatatagt gtaaacagag cacaggacac ttaaaaagat    6840
agaaaacatc ccagtactaa acatgcctg ggctgaaagg agagattggg ctggattcaa    6900
cactgttctc caaagtaagt aggatctttg gcctttagct tcaaaataat cttatttaat    6960
gagtaaaact ttcaatacat ttgcacttct aggtaacgaa ttgaagaagc tttcatggca    7020
agatgacatt ttgaaaaggg acggcttgtt tttgttcttt gttcatttgc ttttttcccc    7080
ttttccagaa ctctacttga atatttatct tttcagctt caccaaatag tagagctgcc    7140
aggatatttt ctttttttata gttttaaata caggggaatt tgggatgaag gcctcccatc    7200
acattaagac aaaccacaaa ctatcctcct gtgtgtcatg cttttttgcct caaaggaccc    7260 aagcatttaa tccacattgc tcttgggtga gatctgaatt gtgatttgca tagcatttat    7320
actcttattt ttttctttca ttccttatct tcaaccagac tgtaaatgcc taaggcacaa    7380
ggcagtggct gaatttggtg tcttttcactt atctgctcag tgcctaaaat cgtgccttat    7440
acgtagtaag aatttaataa atatgagttc ggttgaattc aagcaaaaga gaaaactgag    7500
aatcagatct ggttcccagt aagtgtttac tctcatgtac ttcttctctt ctataaaatg    7560
aatatactga actgagctac ctccatgttc ctcttcagat ttatcttgta atccaatcta    7620
atcaaatatg atgcccccctt ggtaccatac cttgagatat atgtactacc atataatagt    7680
aaaggatagg atttgtatat gatataaatt gttccttaga taaggtacag tccacagacc    7740
ttccatcttc aattgttttg gcttatgtag cagctgcagt tggtgcctgc caaggtcccc    7800
ttgaccaagc tagggccagc agcctacagc tgccacaggt gttggctcat aagggctcac    7860
accttcaccc ttttctgggg gattgtcctt ggccaatggg agttgcctat cctagagatt    7920
cgtggacatg accgccttac tctcagaggc agcgtatagc cgatgacaaa ttaatgttga    7980
agtttaacag tccaattctc ttggctcttg gtgggtaact atggtgcaat tcacactctc    8040
cagagcttcc agtgagatca agctgaggtt agacctctct tgaaatacaa gttcacttaa    8100
ctccttccat gctcttcct gcttctctta cttccttctc atgagagctt atcctcaata    8160
aatcattgca caaaagtgtg tcagactcca cttctagtaa agctggccca acacagccgc    8220
caaggaagtg ctttctcctc tctccctagg cctttgtctc agtgaatctg cacaatctga    8280
ctgtagctgc aaagctaccc tggggaagcc ttgatgtagc cccttcttgt gaaggtgaaa    8340
ttactaaacc aggaagaaca ttctgaatct cacattgtat taccgttact ctgatgaaac    8400
tcctttacct ttctagaaag ctttcatgct ttttcctttc taccaagcat ttcagagagt    8460 tcttttctcct ctgactatca acaacaatcc ctatactcat ggtcagaagt gacagaggag    8520
```

```
gacatgacca acatcagagg aggaaaatgt tgggatcaga ataaacccca gctgtcaatc    8580
tcatggctga tagtccttga gaacaaagac aaagtctttg tccttgagac tataaacgca    8640
gagccaattc attccaagtc ctaatcttcc tagttacaaa cactacacaa tttattgtaa    8700 tttttttat aggtactctg tggatcaaag caagtttcca tggggaatga gagaagatgg     8760
cattgggcat attttactt aagaaaat taatgaatgc tattttagaa aggaagacaa       8820
aggcaataat cccttcccaa aacaaacaga cttataaata ggttacttcc tacttttcct    8880
aaaatcttgg aaagttgtga gactcccta tattcccaag ggatacaagg cctgcttccc     8940
atcttcgact tatgggtaat ttcacaagga agggaggtca cgggtagtct gaaaggtgct    9000
ggcaaaagga ctggctcctt gtgccccact gggagaattt atgactcttc tgcctcctcc    9060
taagcttaaa atagacaagt ctggggaggg aggatcatca tttgacctaa actgtcatac    9120
tctaatcctt taatattagt ttttcagatt aggagtacgg atggggatct gcagtgtgtg    9180
catgatttag gctgaccttt ctttaacttc tgaaaaatgt cctatttatg taacatagat    9240
tttccaaaac agctaaatgc atgtttgctt ttttctttct aattatggat ttttgcaatt    9300 cttcttcct taccctttctc tctcattttg gacatcctac tcccaacctc cattttttt    9360 tttctcatgc cctgcaatgt gtaggaagat ggtttaatgt ttggcagtgt gtatacatgt    9420
gcctctcagt taacatcttt gatattcaat tgcagcgatc aggcaacatt gctcattttt    9480
cctactatgg ccattaaggc aatgccattc tcagggcctc cattaggact tgtaggatga    9540
ccatgtaaca tggaggccag tccctcctgg agggcatttc ttaattgctc ctcagttcta    9600
agtgtccctc agaatgcctc agatatttgc tttgactcag cagaagaagg gaagatcgtg    9660
gccagagata gcctgaaccc tgcgagagga ggttagaaag cagaaagccc tctgccagcc    9720
aggtgggtac caatggtcgt tcctaggatg agacctcatg taacagagcc caggcagtcc    9780 tgggaactg gacagagctg gtgattggca acaagttgat ggcctgagac ctttgacact     9840
cccaactttt tccccagggt ttcaggcagc tggagactgg gatgtttaat ccactttggc    9900 aaaatcttg ggtccaaact gtgtatctta tttattttc atgatggtgc ttaaaatatt      9960 tttatttgg aaaatgcatg tgattaaac tatgaaatga ctaaacaaat atgtataaag     10020
aaatgtaaat ctctccccaa ctcctaacca ctgtttctt cacaaaagtg gcttaggtgg    10080
aatagtgaga ttaaaagtga ttaaaatttt tcccttatta cttgcaaatg agcacttctc   10140 aatcaattt ttataaaagc ccagatgttt tgccctcaat tcattgggaa taaaggcttt    10200
ggtaaaatac agtagaaatg aattacaaga aaaatgaatc ccacttgagt gttgtggcaa   10260
catcaaactg ctattaaagg cacaaaacac atcttggttt ctgtccttat attgcaaatc   10320
tgtaacagag agtttgagga ccagcacctg ccaaagacca cacttggagc aacattgccc   10380
taaatgcttc ttaaggaatg tgagatgcat tttgacacag gaaaaaagag cacaagttat   10440
taaacatatt ttaagggttt caaatgagtc agacaaagaa tattgaaaag gtcttcagag   10500
acgggatcca acatcctcat tttacagttg agaaaactga ggcccaaata gtacactgga   10560
ttccaggaag agcatttaga attgtgcact ttattactgt tactctgaag aaatttgcct   10620
ttgccttttt aggaagcttt catgcttgct catctctgcc aagcattgca gagatttctc   10680
ccctaaccag agcaagtaca gctggggcag tccctggtat gaacatgccc ttcccaaatg   10740
tgacaagtgt gtccctccct gccttgatgg ggccctcctc agcatacaac cttgagaagg   10800
ggaaccttat gggatctgct gggtggttgt tatttgtaat ttctaagcca gctatgcaaa   10860
aaaacaatta caaagagcag ccctctcctt agctggtatt atttacccac attaaaccca   10920
```

```
aacacttgtc ctttctgggt ttagggaagt agatgtgact ggtggtggag gtgaggtaag   10980
gatgagaatc tcattttagc tacaggcatc agattggggc atagttggca atagaattaa   11040
tgcagttcct ctttgcacat ttgatcaaat gatgcttgac cttgggcctc tctcttgtga   11100
agaactgcat aaaaagcaag ttcaggagtg tgtgggctga gtccagagaa aatgttacac   11160
ctggctaacc tataacaaga accacctttt taaaaaaaat tggaattgcc tctaagagaa   11220
aaagcgaagg cttagagagt atgactgagt ttagcacttc aaaagtggaa gagctaacaa   11280
tatgcattgt aagtattatt tgttgttttt gccctgactc cttaaaaag tagatatgag    11340 gacttagaaa agagatgcca agagtttgtg cctcacttcc tatatccaca aaataagaat   11400
agtcacatat gcccctaca attattcagt gtgatgctgc agggccagct gcaccgccac    11460
ctcccaaccc cattgcactg gctcttccgg ttaggctggc ccaactccag gaggaacagg   11520
cagaagggct ggagtgaacc ctcccagctc ggcctggagc agccctccag caaactgatg   11580
ggaattggaa agataaaaca cccagcttcc tttgagtcag gtggtatgac actgaggtgt   11640
gtgttctgct cgtagttata ctccagttgc ccatggtggt aacccacttg ataagatatc   11700
ctttactggt ttccttccct ttcctgactc atttcctcat tctcttactg gcatttcctg   11760
caatctcttc ccaaataaac tactagtact caaattcttg ttccagggtt ggaggcactc   11820
cacccaagac atatgcctac acagcagaat tagttcatca aaccaagtct ttgtctcacc   11880
ctcagactgt ttctgaagcc agacagacgg ggctgaacac ctcagaattt ccctgagtgc   11940
ctcaaacgga atcttttcta aaaacctct ttatttcact gcttgagaac gactttctct    12000
tacttccatc tccctcccgc cacctctctc tgcagtcttt tcactgatgg aagccacccg   12060
caaccgcccg gccctcgcag cttcttttaa tttgtctcaa aaggctctta agagaaaact   12120
acgcttgcct gtctcttccc agttccacaa ccctcagagg gcaggtctct gggacagcaa   12180
tggtattcct cggaaagtca gcatctggtg cacagctgct gttttgactg tagtcccaat   12240
gtaacagggc agcaaagttg ttgatggttt tccccaaagc agtaccccg agttttcata    12300 tctgcttttcc agactgtgct cccttgaaat ccaggaaaat gaagcgtttc aatcctggtc   12360
tctcctcagc cgtctctcca acgcctcctt ttttctgtc tctttcttcc cccagcccct    12420 tcccttttctt tttggttcat ttgcacttttt tttttttttt tttttttcat ctcacaaggc  12480
tgcagcaact tgacaataca ctaaggagcc cttcttggag ttgtgttgct cctcattaaa   12540
tacttgttca gctggctgct acgtgtcagc ttctattcaa aggcctaaat gctagggatg   12600
tggaagtcag tgtgcttgca ggccagtttg gctggggatg acgagagtat tttgcctgct   12660
gtgttcacca aaggggggccc tgaacaggac cgccttcacc cgccttcacc cgccttccac   12720
acaacacaca aacacttgta tgaacaccaa acagactgaa agcctgggac agagatttct   12780
ttgtaaaaga gaagccatct ccagttctgt ccttgctgaa tggcgatttc atgaagcttt   12840 ttctccttttt tcgtagaaca gtaacacacc aatcacctcc tcttgtcttg ttcttacttc    12900
aaacaattct gaaagatttg ttttctttttt ttttcttttt gtattctttc agaggattaa    12960
aatgtctgaa atgacagcct cttttcattat ctatccccca agtctatttt tctttctaaa   13020
atcatcccac ccacccccacc caactccaac attatattac ataatctctt tgttcattac    13080
ctgtccctaa aatactggct cttcactaga cttcctgtct ctcaaagaaa gacactgctt   13140
tttaaactgc tgtatccctg gcatttttaaa caatgcctgc gacacaatag gtactcaata   13200
aatacttttt gagtgaatga atgaataaat atatctttag ggaaataaag ataaaacagt   13260
tatctcaaat tttaaggtat caatactgtg acctgctaca caaattaaca gccttggatt   13320
```

```
ctgttaacag ggattcaccc agagaagtga ggccatcact gaatgttcct caaacatgtg    13380
attgtctcct cagcttctgc tggaaggctt catatctact gccaggatgc acagagtagc    13440
tctgactatc gtatccatac tgatcatagg aatcatagct actattttt ttgggggcg      13500 gggggatgg agtctcgctc tgtcgcccag gctagagtgc agtggcacga tctcagctca     13560
ctgcaacctc cgcctcccgg gttcaagcaa ttctctgcct cagcctcttg agtagctgcg    13620
attacaggca cccgccacca tgcctggcta atatttaat ttttagtaga gatggcattt     13680
caccatcttg gccaggctgg tcttaaactc ctgacctcat gatctgcctt cctcagcatc    13740
ccaaagtgct gggattacag gcgtgagcct gtacctgtac atggccatag ctactatttt   13800
aaatacgttc tccattggcc aggctagcag tataccagga atactaaggc ctgtgagcta   13860
cagagtcaga caacagggct tgattcctg gctccacaac tttcgcactt cctgagcctt    13920
cagttctctt attgtaaaat gggattaata acagtacagg cctcaaagag ttttggtaga   13980
ttaaatgagt tgatgtgtgg agcaagtgct taagaagtgg taattattcc tttatggctt   14040
tctttatctg gaccaaatgt actttcaata agaagccttt ctctctgacc actctcttca   14100
cctaactgca acacatctcc cgaggcccct ggtggaattt tgtgcgaaat gaagctgtac   14160
cacctggctt tgaagagct ctattatcat ctgtttatgt tttctcacct gataaaagtg     14220
aggcttctcc agtgtagtgc tgttctttct ctgttttccc tgtgctcccc tgcattcagg   14280
ggagactggc tagtaaagaa gtaactcaga aggatgcccc agagtcttcc tcttccttta   14340
agagctgacc taagtctcat tccctgacca taacactgca ctccctgtag ccaacctggg   14400
cattcagtcc tttgagctca ctgccttccc ttcctaagca tttatcacaa ctgaaccaca   14460
cttgcctgtt aaaaacagac tagttaagtg ttccagtgcc agtaaatagc atgagacaaa   14520
gcctggaggt aagacctaaa agacatccat catgatgaag tgatgaacac agaatgagaa   14580
tgtggcgtgg aggtgagctt ggagccttaa tatccatgtt tatgagtcac ttaaaggcag   14640
gctaggtggg acttcacagt tttctgtgaa atcttctgtc cctaatcctt gtatcctact   14700
tcattcagtt agaccttctg ctgcttagaa catttttctt caagtagtga gtactgtaat   14760
gttaacatcc aagaaagtaa aacaaatagt cacctctgca atagctcatt aacaactggg   14820
aacagagagg ttaatgttcc atagcttaaa aaagtatcaa tacaactagg gactctctca   14880
gtacaggatg gggtgctata tccatattac caatggcagt catcccgaga aatccaagca   14940
gccacactta ctctccttca gtgggtagat ccactatact tgtcatgtag attagctgtt   15000
ttcactggag acttgcatcc catcatcctt ctgcacacag ttgaggtgga ccatacctct   15060
tttttttttt tttttttttt tagacgcagt cttgctctgt cgcccaggct ggagaacagt   15120
ggcatgatct tggctcactg caagctctgc ctcccgggtt cacaccattc tctggcctca   15180
gcctcctgag tagctgggac tacaggcgcc tgctgccacg cccggctaat ttttttgtat   15240
ttttagtaga cgggggtttt caccatgtta gccaggatgg tctcgatctc ctgacctcat   15300
gatccacccg cctcggcttc ccaaagtgtt gggattacag gcgtgagcca ccgcgcccgg   15360
caggaccata cctcttgagc aggcttctct gcaggtgctt ggtagctggc tcgatgggtc   15420
agatcataag cctttcatgt cacagaagtg gccctgatcc atgatcccac aagcacacag   15480
actcagagcc tacagagaag atgactctgg agatctggtt ccctttactg tccatctatg   15540
attcatcata caaaggtaag cacattccac atttcctttt ttgaaataag actgctgatt   15600
ttaaaaaaat ggtaattaca tctgctatac tgcaaactgc agaagttcaa gcttaaggaa   15660 agaccttta catccttccc tcttccttat accttaaaat taaagtctaa catcaaacag    15720
```

```
ggggattcat tatttaattt gtaagataag aaacatatct gcatgtgtaa gttttttaaa    15780
aagaagggag aggaaacaaa caactgtttc ctgtagacta caagcttctt gaggtcaaaa    15840
cctgtccttc catctgtgtt tctacaaaag ctacagcagg gacaacatca agatgaatgc    15900
agttggaggg aatccatctg tcttcaggct tcgtgtactt tccaaaggac cttttgaatg    15960
taaaagaaaa gcctctgaaa ctaagactag gctgaaaatc tgtctttaag gtttttgaga    16020
catgccaaaa agaaacaaac aaaaaccact aatgcttttta aaagaagaag tcaaggtggg    16080
agaaggagct tactacgtga gttcacacgc ttaatcaagt gaacggcttt gtgtcaggac    16140
gaacgtgagg atggataaat aaccttggtg tctgcagccc gagcaaagat gggagaaata    16200
ggactgtggg cttaagatca acgaaatga gaactgggat ggcctctttc cggttcccca    16260
gggctgtctc ttcttatcct aaggttataa aaggtttttt gagactagct gaataaacca    16320
tatcctgttc cttccttggg aaacttgtt tatattctaa ctgtttttag accttgtaaa    16380
atttggtgaa ctccttcctc attagcttaa attcttccac actcagcaaa tatcaacagg    16440
caagggtttt agtcagtgat aacaatgaaa gctgggagct cacctagggc cttaataagc    16500
tggctgcact gacagaggga aagacagaga cacaatctcc agctcatgtt tatagaataa    16560
cagagttgaa aggatagga atgatactga aatctaggta aatttattct gacagtgaca    16620
acagcattgt ctctgataca actcataccc ggctaaagat tcattttgga actgtcaaag    16680
ctttcaagca taaaattatt ctcagtggct gaaacttggt taaacaaatt tcactgtgca    16740
aggaaaaaca aagttaactt ttggaagtgt tttggggggaa gaaatctcag tcaagaaact    16800
agataataat aactatgtca gctagatagg aagtgccatc cccatgcggg ggtctcagga    16860
aaacatgtga ggttcagcag ggtgcaggat gggagggggt gacccggacc cacgctggag    16920
aattggctat gcatattctg aacaggatga agaatcagag ccagcagtgg tgccaactga    16980
atctgccttg ggcaaaatgt tgggtagttt ggaccagtga cccaagctgt ggcaacctga    17040
gcaacaaaat aaataatgac aatactggat actcatataa tgaaacaaat accccaaatc    17100
ccctgctgat ataaatacat aattagtaaa caaagaacag gggatggtgt cagaagagac    17160
agatcttttt taaaggagaa tgcatattaa taaatataga aggaacaaga aaaacagaaa    17220
atcttcctta agtaaacatt atagtaataa ttgttatagg caggaattag tcatagatca    17280
tcaaattagt gggtaaatga tgaataagaa agttctagta cctttgctaa acaggtattt    17340
agtatcttta gaaacaggtc aaaggcatgt attacttaca aatggacaaa tagcagcagg    17400
tcccacttta accaaaggac caaatttaac attaataacc agacacatgg acatcttatt    17460 cccctgata tgacgcactg aagataggca cactatcatt tctgtggtaa ttttgcccaa    17520
aatatgtaat ctcaatctaa tcatgagaaa acattagtga aacccaaagt gagagaccgt    17580
ctaaataact gtcttaaact ttttacaagt gtcaaggtca taaaagacaa aaatcgactg    17640
aggaactctc acaaggtcaa ggagactaag gaggcatgca cattagatca atgcgggatc    17700
ctagactgga tcctgtttca gaaaagaaca ttactgggga cttggaagta caaatacgta    17760
tatggattaa ttaagaacac tgaatccagg ttaatttgct gttttttgata gccatactat    17820 ggtttaggtt agatattaac aacaggcaaa gttgagttaa gagtatacag aaactccact    17880
atttttacaa ctattttcta agtctaaaat tatcacaaaa caaaaagtta aacatggaat    17940
ggaggctggg tgcagtggct cacgcctgta atcccagcac tttgggaggc cgaggtgggc    18000
agatcatgag gtcaagagtt cgatatcagc ctgatcaaca cggtgtaacc ctgtctctac    18060
taaaaataca aatattagct gagcgtggtg gtgcatgtct gtaatctcag ctactcaaga    18120
```

```
ggctgagcta ggagaattgc ttgaacccgg gaggcagagg ttgcagtcag ccgagattgc    18180
gccattgcac tccagcctgg gtgacagagc gagactgtct caaaaaaaaa aaaagggtgg    18240
agttagtttg gcttcatttg gcagccaacc aggatgaact tgggtgcaca gatttctcag    18300
gtgagaccta agaccctgtc tcacctaaga ataagaagg acatgaatag aaacacatag     18360
tggacaggag acagcgaaag gcagttctag ttcaatgaga gcttgcgttg ggctgctttc    18420
attggacaag catgccagaa ttctattgct ttatgtgtca tgcatctgtc ctccaaggta    18480
ctgagaagag agtcaggaaa gggtatagta atgtagacct caactgttct tgccttctgg    18540
acaacaaggg ataatacttc ctagaacaat agcctcaccc tggcacccca gatgtttgtt    18600
gcccattcta tctacagtct catggtcaat agtagtaaca gcctctaaca gtgaaaagga    18660
ctcagcatac aactgcagag aagacatagc agagggcacc tgggaggcta tgacagtgtg    18720
ttcaggaaaa aatgatccta aagaaaaaa aaacagtag gtggctgaac ttggggataa      18780
aaagagcaag ccagcttttc aggagaaaag taggtctcct aatcagtctt gcaggcttaa    18840
gcagtaagaa gacggccttc ctcaataacc tcttcactag aattttcaaa acctaaacaa    18900
atatctcaaa caatgatttt ttttttgccc aataaaacaa tgtcatgtcc ataaaagtaa    18960
attttgaatc aaatcttttt cccagacata attctgaaaa atcttaaaac acaaagtaaa    19020
agaaatcaga tgcttatctg aatattaccc acatgatcat tagagataat tcttatacat    19080
ttattagtat tcgtctcttg ccagatattt aaataactgt gaagagatgt gtcaagagaa    19140
gagtaattat acaaaggttt ataaaaggag atacaaagct ttatgctcca aatgtggctt    19200
tcagtttaaa aacctaggct gtttagcata accccaaata gttctgggat ggttgtataa    19260
tatcagatct caactagctc taataactgc tttgtaaccc ctggaataat gctcgaagca    19320
acacatgatc ttattttgaa gacaagttta ccactacaca atgatgctgg tccacaccta    19380
cctcccactg cattacagcg agatgtcatt tcccagagca ccagagccat ggagtagaca    19440
tcggtctgct tgaaggactc aacattctcc aaattcatcc tggattctag gacttctgga    19500
gccatgtatc ttgcagttcc cacctatagc aaaaacagac agtgaggccc atcatttaat    19560
tccagctgcc ttttttatttt cacaatatag ctgatggtgg cccctgacac gtgcagagga    19620 ttttttttaaa aaatcaaagt gctgttttaa agaatgagaa atgcacagaa aggtacagat    19680
agatggttat ttttttaaaat agatgttctc tccctgaaaa ccctctaaag accataaaca    19740
aagcatgcca aaataaggaa gtgccaaacc ccagagctgc cttatctaac cccatgactt    19800
atgtcatcac atttttcaat aacatcctta cagataacct gagagacaat atttgtgata    19860
ttttaaatgt ttattttgc tttccaaaat tgaattttt ttattcctg aaactccaag       19920 acttatggta aaaataataa ttgctatcag ttttgatcac tttaggactg agtcttaatc    19980
tttgtttatc ccatggcaca ttccagtgtg caaaggatat agtacaattg cataacatct    20040
ctactaaatt aaattgtata aaagcatttt cacagtaaaa gaccaaatct ggatcacttt    20100
ataattttaa cttgtgggcc atgtagtttt attttgactt ttaggcctgt gctaatctct    20160
atgactgata atatgcaaac gtcggatcca tatgaaaaag gaaaaaaata ttccagaaa    20220 tggctcactt aaatatttag tgttgtagta tgtataaact gactaaataa caataaagtc    20280
ctaccttccc aaggatctag ggaagccaag tgagttgata ttatcattcc aaggaatgtt    20340
tcttattggc atgtattaga gaatttttt cttctcaaga ggtcattgca tggctcatta    20400
ctctggcaca ttagtctgtc catattcga tgtttacctc aacactgcgt gcgctgccat    20460
ggacacaggg ctgactgagc agtaaccgag tgcttcaaag tgtgtcctgc cacctggcta    20520
```

```
aagaagacag tgctgctctc catggactcc actgtgtgaa acactgggc tcatcattta    20580 taagggatgt tgtggtgatt tccaatcacc ttccaatagt ttcttagcca aaaacatttc    20640
cattttaatc tgtgagagtg cttcaagagt ggaagtgctc actcagtcga caagtactta    20700
ttttactttc aatgttcaag gcattgtgct acatatcttg ggtgaccatg tggatgtaga    20760
tttggacttc agggagattg ccttccacga tgcttttaat acaaagaaac caacacaact    20820
acagctagta tagagcagaa aggactgagt acaaccataa gagagggaaa aaatagaggt    20880
aaagtactaa cagtgcttga aacaaagaaa aaacatttgc tggaagagaa atgaggattg    20940
atccaggagg aaaaaatgtg ctgaactggg aaggatttga agataggagg agaaatgctg    21000
tccattagca aaaatgctca ggcaggacag agcagagtat gctcaaggca gactccatac    21060
tttggctaga ttccctagac cagtgtccag agtacagggc tgtttgagat aagagccagg    21120
agatatggat caagaggtag ggtgaggcca ggctcaaggt aaaggggatc tagcactagc    21180
tctaacttac ctgcccactg ttagccaggt catccacaga cagagtaggg tccagacgca    21240
gggaaagccc aaagtcacac aggcagcagg ttaggtcgtt cttcacgagg atattggagc    21300
tcttgaggtc cctgtgcacg atgggcatct tgggcctccc acatggagtg tgatcactgt    21360
ggaggtgagc aatccccccgg gcgagggagc tgcccagctt gcgcaggtcc tcccagctga    21420
tgacatgccg cgtcaggtac tcctgtaggt tgcccttggc gtggaaggcg gtgatcagcc    21480
agtattgttt ccccaactcc gtcttccgct cctcagccgt caggaactgg agtatgttct    21540
catgcttcag attgatgtct gagaagatgt ccttctctgt cttccaagag gcatactcct    21600
catagggaaa gatcttgact gccactgtct caaactgctc tgaagtgttc tgcttcagct    21660
tggccttata gacctcagca aagcgacctt tccccaccag ggtgtccagc tcaatgggca    21720
gcagctctgt gttgtggttg atgttgttgg cacacgtgga gctgatgtca gagcggtcat    21780
cttccaggat gatggcacag tgctcgctga actccatgag cttccgcgtc ttgccggttt    21840
cccaggttga actcagcttc tgctgccggt taacgcggta gcagtagaag atgatgatga    21900
cagatatggc aactcccagt ggtggcagga ggctgatgcc tgtcacttga aatatgacta    21960
gcaacaagtc aggattgctg gtgttatatt ctgatgggga aacaaaacaa ggagagaagg    22020
agttggatgt ggtaggtaag tactgtcagg aagtgggttc atgcctgagc atctatagat    22080
tttagcatct gcatagtttt tgtagatacg atattgttaa ttttttatttc agggatgcaa    22140 gtgcatgctc gttcagcctt ccctgcctct ggccatctgt tcgtcatccc ctgctcttcc    22200
ttcaaacttc agcttaaatg tcactgctta agagaggcct agaaaaactt ggaaaactgt    22260
cttattttat acattttcat agcaccttat acttttccta ggtaacaatt cagtacaact    22320
taaactaaat gaactatgac tctacctctt gatttcacat ctgtctttcc ctactcttgc    22380
catcccccac ggacagggaa ctccatgctg gaaggtacca tgtcttcttc actactgtaa    22440
actgcactta gcacacagca ggtcctcaat attgccaaat aaaaagacaa accatttact    22500
gagtgttatc taagctcagg acattgggaa catgaaaaaa aatgacacag cttctgcctt    22560
caaaaaatct gcatgtatga catctggtaa aaacacagag cgtgccacag tttgcaccaa    22620
aatctttgct cttttcaaa ctccaacttg ttctgctctg atcagcattc aggctaccct    22680
gggcccatgg gtgacaggga gaggagtcca tggaaaggat ctctttggac agttatctta    22740
catccaccca acattcctct tttcagtgtg catacgaatt gtagtttcat ggaactgaaa    22800
tatttaatag caacaatgga aacatggccg caaaggtaaa acaagttaaa aatggaaatg    22860
ctgcagtttt ttgacttgga attctgaagc aggcccctgt gggctgacaa ggagagtcct    22920
```

```
tagcaccaga tatctaacta taatatcttg tgcctcaaac tttgtttcat gtgctggcct   22980
tgttggctct ggtgaaatag ttttcctttt tggaagaagg acatgaatag aaacagacag   23040
tggacaggag agagcaaaag gcagctctag ttcactggga gcttgtgctg ggctgctttc   23100
attgggcaaa catgcagaat tctattgctt tatgtgtcat ccatctgccc tccaaagtac   23160
ccattaatga gcaggcctca tgctcagatc ctagaatcat tcattaaata tatcactact   23220
gagtgtctat gatgggcatg gcactgccct cagagagtac ccagtagagg acttagggca   23280
tatatacaag taagcaatat atggcatctg ggatagggc taaatgtaca atgtaatcta   23340
tatattagtg gaatgtggaa aagcttagag aaacatggaa ggcacagtag caaaaaactg   23400
cctttaagtt ggtctctgaa gaatgggaaa agtcagtgat gagtggaaag agtgctatgt   23460
taaggagaaa gaatatatga tctacttaag gaagagcaat tatcccatac tgaccactct   23520
gcacctgcgg aatagaaagg aaaaaaatgg gtaggtggta tggaaccaaa ctccgtgtca   23580
gaaaggatc ttttgattat tcatttgtca gttttcacct acagtaggtg tttaaagaga   23640
aaaaaaaaag tgatgagaat atagtccagg tagaatgagg atataaccaa attctctcaa   23700
ggggaaccca ttacctaaat gatactgata aaggagttaa aagaaatta cttgggcaga   23760
tagtaagggt atggaagtcc tcggtaaggt gtttctttt aatgaaaagc agccccaaat   23820
cattttctaa caaagagcag cctgtaaagt tgagcttcag acatagacag gcaagctggg   23880
agcttgcacg ggtgaatgcc agcaggaact aaggacatgt tcaagatggc agctccatct   23940
tcccttctct ttgtcagcca tgtgtacaac aaagaacaga ccagatggtg ctgatcaact   24000
ggaaagccca tttgcataat aagattaggg tggggtgacc agtcttcccc atgcactatg   24060
taaacgtcat acctgattga accaatctgt gagccctatg taaatcagac accgcctctt   24120
caaacgggac tataaaatcc agcacattca ccactggccc gtccttccg cttggagact   24180
cctttctcta cagagagaat tgtttctctt tctcttctct tctgcctatt aaacctccac   24240
tcctaaactc ctcatgtgtg ttcatatcct aaattttcct ggctcatgat gatgaacccc   24300
aggttatata ccccagtcta catagctact tcagcatctg atactttctt ttttttttct   24360
cgagatggag tcttgctctg ttacccaggc agcagtgcaa tggcacgatc tctgctcact   24420
gcaaccttgc ctcctgggtt caagccattc tcctgcctta gcctctatgc ccagcttttt   24480
tttttttttt tttttttttt tttttgtat tttagtgga gacggggttt caccatgttg   24540
gccaggctgg tcttgaactc ctgaccttgt gatctgcccg ccttggcctc caaaagtgct   24600
gggattacag gcgtgagcca ctgcgcttgg cccagcatct gaaactttca tctaacgaaa   24660
cagtgagaaa tgaagctggt acatatccat ttttaaggtt tatgtgtaat atgattactt   24720
gttcttaagg taagtctgag tggaaatgcc aacttccact gactatatat tctagatgaa   24780
aatcttgggt ctagtaacca gagaagtaac cccaagatat cagaattcca gcaaccaaga   24840
gggaaaaaaa aaatcaccat ttttggaaa gatatatgaa tgcattttaa aagtataggg   24900
aaagtgagaa aatttggtga ttgatcctta aaaacataaa ttcttacact gggaggcttg   24960
gattgggaca aagaacaggc aagagtaggg cagaaatggg gtgggacaaa gcaattacag   25020
aatgattgaa tgcaaaagaa aaaaagatg ctcttgtgga gatgtatgga ctgtccctgt   25080
tgtacagcaa acaaaattaa gggggcagat gaacacaaca caaattcaaa cacaacagcc   25140
gatccagcag tcggcatttc cacttaggct taccacttcc acaatgctcc ctgcctgaaa   25200
ctccacctct attatatgtg gtatccaatg aatgtgtttg cttgaagtac ccacttgtct   25260
ccggtctctg tgtctgtaac tacatggaat gtcttataat cagaaatcca cttgattatc   25320
```

```
tgattgcttc tctcctgaca aagcagggta gtggccaggt ctgttttgat catcatgata    25380
tacacagcac ctggggcaga atggggcaat ttatggtatt caacaaacgt ttgttttaga    25440
agctgaatga ttacttacgt ggaatgatac ttctcaaatt ttttatattt tacagcaagg    25500
tttgacaaac tatggctcag aagtccatgg cctgcttttg tatagtccta tgacctaaga    25560
atgatttcca tccccatttt taaagagttg tttaaaaaac aataaaacta agaggttcat    25620
gcaacagaga tcttatctgg cccagaaagc ctaaatatt tactatctgg cccttcacag     25680
aaaaactttg ctgaccccctg ttctagaggt gttattttaa taacctcatt ggcagaatct   25740
ggagagactt cactttggcc aaatgtgaat atgtagtcaa ttttttttca catatgagaa    25800
atacaatttg aaaaaattta atattaact gcataattac ttagctttgt ccttaattca     25860
ctaaaacgtc cagatgaaat gttgattcat catggataat tttattttac aattcctaaa   25920
tatctataaa aacagtcgta tttgctaatt tcaattcctt tttagcctaa aggaaacaca   25980
aaaacagaaa tcccttaag tttatgtgtg gcactgactg aagaagattc tagaaatccc    26040
cagttcaatg tcagaaacca aagttttact ttctcctaaa atttcctgtt atttctttag   26100
aagacttaca cttaaaaaat ttgaggggga ggaattcttg aataacatct gtcaatcttg   26160
aaacttcaaa gaggtggtga aaaactctaa caatagcaac cagggctgga aggaagcttt    26220
gggatgtggc tttatctaaa caggagccac ccacaccctc tggcagtatt aacccttggg   26280
ttgctactag aaaacccaac agctgttggt gtaggtacaa gccagcatct cctttagtcg   26340
aagaccaaca ggaaatgctt cttttcatca gccgccagtt acagagaaac tcataaactg    26400
aacacttact aagttcctgg ctgtgtgcta aggattttat agaatattta aatttaattg    26460
atagaaaaac cctatgaggt agaaactgct attattataa accccatttt acagataggg   26520
aagctaaaga tcagacagtt taagtaattt tcccagatga taaatttagg caacagcaaa   26580
gctggtattt acaatgagca ttgcctgatt ggagagactt ctgatctcaa ccccatacct   26640
gatctctaaa cttcatattg gtgagagcca actaagaatg gcaatgacct taggctgggt   26700
gtggtggctc acacctgaaa tcctagcact ttggcgggag aatcacttga gcctaggagt   26760
ttgagactag cctgggcaac atagtgagac tgtctctaca caaacttaaa aaaaaaaaa    26820
attagccaga cactgtggtg cttcctgtag tcccagctat tacggtggct gaggcaggag   26880
gattacttta cttgaggcag gagttcaagg cggcagcaca ctatgatcct gccactgcat   26940
tccagcctgg gtaacagagc aagaccctgt gtttgtgcgg gcggggatgg ggggtaggg    27000
gttgcggggg aggggaagaa tgactttata taagctccca atttgataaa gtgttttct    27060
ttagtgtagc ctggactaag tgattttaca gccatccacc gactgacatt ggcaattctt   27120
gtataatgtg tctaaaggag tatattttgg gtatgggat tatattcctt tgttctgaac    27180
taagaaccac agtttagtag tgtctctgta aatatgcatc tttttcctgc caggaaataa   27240
aaagttttat gtgaaggaga accccccaaat cttttctttt tctcagagcc tattctcatg   27300
gcctagatct tagcagagct caaaacataa ttgttgcact attgggacct tccatgaata   27360
gtaataacat tgaaccagat atagctctga agggcattaa aaataagggt ggaatttatc    27420
caaggcccat aaaaaaatga ggctataata gtaaacattt ttagcctggg ttccataaat    27480
agagttcagt gggtctgtga atttgaatgg gcaaaaattg catctttttt tattttctct   27540
aacctttaat taaaaattaa tatttcctag tatcagctgt acctatgagt tgttgttgc    27600
agacgtctca gcatgtgact tacgctcacc atttagacat ttcaattgtt tagatctgct   27660
gctattgtta tttaaagcat tattatagaa acatatatta ctataacaca aattcatttt   27720
```

```
taaaatattt ggtcattgta tttcaatgta attggttttc tttgaaatac tccatgttct  27780
attttatgca tttaaaaaac atcacagtga aaggggtcc acaggcttcc ctacttcaag   27840
aagtccatgg cacagacaca caaaaaggga agctcccttg gcagagtgaa ggcatttggg   27900
ctctagtctc ttttccagga cttgctagag caggaatttt gagattgatg ggtttctcta   27960
ggaagttggt aactagtgcc aatgggagat ctgcctggct tgatttgttg tgctgcacat   28020
ggacaactgt ggatgctgtc ggagcttctg tggagtggga agggagctcc gcagtgtaga   28080
atttgaggag aagccctcct ttgaaatctt gtaacaataa aaagataac tcatatacga    28140 tgtgctttgt tgggttaggc accggacaat ttattttgta aacatgatct actttatttc   28200
tccaataacc ctatgtatga gttagattct cttaccccg ttttacagag gaggatactg    28260
aaccttggtt gcttctacaa cattttttgtc tacttagtaa ataagtattc ttgttaagta   28320
aaagttgttc ctagtaagta ctcaataaat gaatgctgtc cttttaatgt tataattaac   28380
atgacttgag acaggaagtt cttccttccc ctcagctatc tctctttagc acagtttcct   28440
tctttggatc tcagccagtt gcatatatac tctcgcttta ggtgaacatg ctggcatgtg   28500
aacatccttg cggctagagc ttcactgcca acttcacaag aatctctctt ggcatctgag   28560
gctcattagt gcactaatac accaaggtgt gcgaaaaact gtcatccacg tcccttctca   28620
ttgctcggat aaattagtat cccactaaat gttcaccccta aactccttta ccgagtggag   28680
gaattgccaa actacttcaa atattaaagt aggagcctat ctcccaaatt cagctatgtt   28740
gatttgcttt ttatcaagac acattaactg atccacatag gattttattt accaagttgg   28800
ccttaattta atgcttttat ttttttaacc aagtgacttt tatttaaaat agtggattag   28860
ggaggttcag ttttaagttc cttttaggaa ctggtgtcgg cataacaaag gacataaaag   28920
aggctgagag caacgtgtgt gtgcgcgcac gcgcgtgtgc atgtgtgtgc gcacatgcat   28980
actcaagtta taagacaaat tgtttacttt tcaatcactc caaaggaaag tataccacag   29040
gatttcccct tgaggttttc tgccagtttg tattttttt tatggcatac taacatttat    29100
ctttggaaga cagaaaaaaa aagaatttga catttgtctt taaaaaaata tttatgtaac   29160
aagactctga catttgcaaa tggctcctta tttgcaacta agtctggcct ctatgagtga   29220
cagaagtgac tggaaatttt cagaattatt aaatggatct cacagttcat tgttaaggag   29280
atagcttggt ggtatggaaa gaacaaaagc tttgaagcca ctcagatgat taaaaaaaaa   29340 tgggggaag atatggtgcc tcacacctgt aatcccagca cttcgtgagg ctgaggtggg    29400
aggatcactt gagcccagga gtttgacacc agcctgggca atatattgag accctgtctg   29460
tataaaaaaa aaaaaaaatt agctggatgt ggtggtgtgg gcatgtaatc tgagctactt   29520
aaaaggctga ggcaggagga tcacgagccc agaagttcaa gactgcagtg agctataatg   29580
gtgccactgc attttagcct gggcaacaga acgagaacat ctcccctgc cccccaact    29640 ccccccccca aaaagttag ccctctcttc ctctttcctt tctcctaagg gtatttaaaa    29700
taatatactt ggcccaagag cacagtatgg ccctcaaaac tagagaaatt actctgattt   29760
ctctcttgtg aaaagaatt cattccaaaa taaaacacag atacagaaaa gtgcataaaa    29820
caagtgtctg gcttagtgaa ttactataag atcaacactc ttgtaaccac tggtcaggtc   29880
agaaaatata attttgctgg ccaccccaga agtctgttca tgttccccaa ctcaatcgga   29940
gatccctccc ttcctctaaa aagtaatcac tattcctggc ttttatagtt atcatttct    30000 tgagcttta aacttgtttt atcatccaag tatgcatctg tagtcgtctt gctactaata   30060
tgactgaata caaatggcaa accttgcttt tttgcagaat tactgtttta aaaaaacttc   30120
```

```
ctacaataaa aacaccagaa tctttaaaaa atgtttaatc tgaattaatc aaatcatcag   30180
acaaatctac aaagtgcctt tataaagtac atgaaatggt ctgacctatt caaatcaaag   30240
tcaatgtcat gaaaaccaaa aaaacacact gtagaggcaa aacaatcaat tttaatgtgt   30300
tgtccttgac tggattccga atttaaacaa tagacccatt aaccttgaag aaatctgaat   30360
atggactgta ctgtatatat atttagatgt atatatgtga atgtatctgt gtcttagtat   30420
ctgtatacac acacacacac acagaaagag agtgaaagct aagcactcac atatatgctt   30480
catattgcag agttcaaaga tcttgccatc attttctgta cctttaaaaa ttttgttggc   30540
atgttacata aagaataact tgtcacctcg ttattctaag tgtgcccgca gaccagcagt   30600
catcagcatc ccctgggaac ttactggaaa tgcagagtct tagcgctgtc ctcaactaac   30660
tgaatcagaa tctacattta aaagttctct cagtgattca tttacacatt caagtttcag   30720
aggtaaattt tattcttgct aaacagttta gcaaaaataa agttaagttc tttggtactc   30780
tgccatagag atgcttttcct cctacaaaaa atttcttagt ggaattgttt gcaaagctct   30840
ggtacagctg tattcagcac tagccaatga gaaaatggcc catgataatt ttctagtcaa   30900
ttaactggtg gaggagtgta gaatgagata tgcttcccca tccatcatcc tagtaaaaag   30960
cacaccaatt taggcaaaca ataaaaagtc atttcaatta aacaacaaaa ggacagtaag   31020
ctcactagca atgaaggatt taatttaact tctagctatt gatagcactg tttgacattc   31080
tggatatatt ttgagagtat ttttttcctca aatgatgaaa gaagtcttct ctccaatcaa   31140
tgtggttgtt ttattccaac tgcacatatt tcagaacaaa gctattcgcc acctctccta   31200
tcccatggca cagtctcctt tgtattattt ccttcttatc tctctcccag atggaaaagc   31260
cttgcatgta ttctaatcca gtatgataat ctctttctag aatacccatg agaggtagag   31320
gtgaaacctc tgcctgaaaa tgttatggta gaaggacatc attcctttgt tatcattcca   31380
taatcaaatc acaatatttc taactgcaga tatattggga taaagtctaa atattgggat   31440
atgtttaaaa ttattcttta cattaagtca aatgtagcct ctgtgtgctt ctattattgg   31500
tccttctgct gttctctaaa gcaaaaagta acaaaatgaa tccgttttct atgggatgag   31560
aactattaaa ctcctgctgg atatgaaact cacaacccct agatcatttc attttcaggt   31620
tgaacagcca tgttttcctc ggttactttt caagagatac attgatgaga ctctaaagtc   31680
tgacagattt atcagaccct aaaatcagcc tgcccagcat atagcgccca ataaatgcca   31740 ggacctttt tctaagggta aagtgatctg ttctctgaaa ccacgcttgc tatttaagat   31800
tcttcatcat gtgttttgat agacacagat ataatacttg aatataact tgtgtagcaa    31860 agattacagc aggactctca cctcctcttc caccaagtgg agtttaaggc tcctgatggt   31920
ttgttctttc tgttttgttt tgattcttte agccagatca tcctgatttc aaaatgacct   31980
taactcacct ctaaaccctg gggtcttcat cacatgagca gattcccagc cagtgttttg   32040
acaagtgctc ctttgcaatc gattgtttga acctatatgt ctgattttac atctacctgt   32100
caagttttag aaaattggtc atttcaggcc attaaaaccc tgattcagcc tttgctcttt   32160
taggcatccc ttccactgtg ctttttcaccc tttatgttcc tccttaggat atagattcct   32220
gctacttctc ttgctctgac tttaaaagga gggcaaccaa cattaggagg gtgcctacaa   32280
ggtaccaggc tttgtccagg aaatgatgac acatctgtcc tcccacaaag agagtttcac   32340
acctgatata tgttctttgg aacaagattt tttttcattt tcttttctgt gttattgcag   32400
ttttctgact actaaaagct taggttttgt taggatcccc acacctgccc tgattcttta   32460 attcttttc tggctggctg tctgaattac accttgtact ctgtctaggg gccctcatgt   32520
```

```
tctcaggaaa cctgaaagca aggtacattt cttaagttat ttcaggatgc tctccaacag    32580
ggagaccaga tcgctttgga aaagcatatt cattattcac aatacctgtt aggtcaccag    32640
aatacatcct ctctctctcc ctggctttcc aggtgaacca caggcttctg caattccttc    32700
ccacctgagt ttctcacctc ctaaaatcat gcacacagcc tccctggtcc ctgccttgtc    32760
tctgccaagg cagtagcacc caaaccttgc catccaacct tttggacaca ttaaggttta    32820
aaatgtgctt tcctttaacg tataatttaa tcagttttaa aagctaagat gcctattccc    32880
aatgaggccg ttgaccttgt tccaaagcaa ttgcttgtaa attgttgtag aaaacaaaat    32940
aatatcccct cttaaagtgt cttgctattc ctccaaggat ggggtaaaac aggtgttggt    33000
ttttctcctc ctctaacctt cgaaggcata attttggctc cttcctgtgg tagctgccat    33060
tctttaattg ttaccgtccc tttccaggct acaggggaac cgtgacgaaa aatataaaaa    33120
gatttggcag aacaaactgt cttgagtcca gtggttccca atgtgggctg catattaaaa    33180
tatcttgaag aattaaaaaa taattcctga taccaggccc cagaccaatt aagtcagaaa    33240
ctgcaggagt aagacccagt taatgagtag ttttttaaagc tactcaggtg tttccaatgt    33300
gcagccaagc ctaagcataa ctacatcagc ctggtggaag aaacaggtat ttcgaatagg    33360
atggggcctg gaaaatgaaa gacatgggaa taattttaat gactacattt cagagaaatt    33420
gttcttgaca ttggaaccaa ctatatcctc taattaggca acaaaaggca tatatatgta    33480 tattttaaa agtagataag caaatataaa ttatttctct aaaagttaac atgttttaa    33540 aaaaaagcat aatttgtaat ggcaaaattg atattttcca caacaggtaa catgcaggag    33600
cgatttagaa tacaaaagga cttttccaaag gcaagtcatc cagatgtcca aatggtggtg    33660
aatacagcct ctggagtata cgtgggtgga aataaaagtc aatttcacag tggttagcca    33720
cctccctgag ccttttttttt cccctggtgg gacactgaga cactcgcaaa gcagcaaaag    33780
gtctcagtgg acccttcttg ccattactca tgggtgtgga gtttatggaa cacatggagg    33840
ccgcagtggg agagacctga ggctgcagag gaaccacccg aaccttgcta cagcaccagc    33900
agtatgggtc cgactgcttt cttggccact catatccagt ggatggaatt tgagacagcc    33960
tgtgtccata ctagattcca ctctgctgat tcataccaga atgaggttct agagtacaaa    34020
tattcacaac cagaaagcac atctggcctc agtgcagctt tgtttacttt gctacttagg    34080
aaaaaaaaaa atcttgaaaa gcgagttgct tttgccttaa ttcagttcaa atacattcta    34140
agcttccttc aactgagtca cagtgtcctc tatcatgcaa aatctttatt atttccttgg    34200
ccagacatag ggccatattg atgaattcca agtgtgcttt ctaaccaagg ctggttcaca    34260
acaaaaagct gcttcagctc tgagtcatca cctcaaataa ctgatttctc ttctcaggaa    34320
tgagactagc aactttaatc cataattttc ttcctcttct aacaactttt ctcaaccata    34380
tttccacact tatttttttct tctgcattta gaccagaaag taaatctggt ttgtttcttt    34440
tgaaacaaaa atgcacagct ggaaagccag ctattttgag gcgtgagtgc acagttccaa    34500
ggcagcatac ctaaaatccc ccagagctac caaaacacca tttactcttt tcatttctta    34560
catgcaagaa ctaatcattt ccccaagaag ccagctccct ggtgttggag ctgaacaaac    34620
ataaaatgag atttgggaga aagagggcag catttctaag acttccctta ctcggaaaac    34680
aacggaagtc aacaaaatgc tcaatgcatg cgatcagtac acagagtggg tttgctggat    34740
ggtgtaaagc aacgacatta aggacacaat gggtccagag ggaaccagct ggctgagatg    34800
ttctgctagc aagttaaaca tagacaggaa accgcgtgtc tgatactgta aaaaaataat    34860
ttgtcttcct gccagagata ggctagcaaa ccaaaaaggc tgttttcact taaaagaaat    34920
```

```
gctacaacaa tgagagagga aggaatgaaa ctttgtggct acaagaagtc ttcttctctg   34980
cccctctctc aacatctcag gttagagggc acacatcacc acactaaatg ctaaagcctg   35040
cacatagctt gcgagtcagc aacgtgcacc actgggcata catcttatgg tctgcttccc   35100
tatttaacca catagattga actttgagtc agaagtggtt actcaagtcc tggtttctaa   35160
gctagcaaga tataattgat ttatttactt acagtcctat cccattccca aaaacaacaa   35220
caacgacaac aacaaaaaac acagtgaaag aagatacagt caagacagga gctataatta   35280
tgacaaatgg aatataaatg tgagaaaaca gggtaaaaac tggtaagcaa gagtgatatt   35340
agtatgctaa atgtgtaggt acatatttgc tagaagcatg attcagattt gactctaagc   35400
ttttctggta gttagcattt gagagagaaa cacaaaaacc atgaatatct ctatcagggg   35460
ttggcctgag ccctgttttt gtaaatgaag ttgtactgga acacagccac gtccaatcac   35520
ttacacactg tctgtggctg ctaccacaga agagttgagt agctgtgaca gagactctgc   35580
cctgcaaagc tgaaaatatt tactatcttg cctgttatca aagaagtttg cagacccctg   35640
ctcggtatgc ttcaaagtgt ccttaagatc agaggcaaac aggtcgtcat gaggagaaca   35700
cctttctaaa acagagagcc aaaataaatg tctcctggct tcctcatgaa gataacaata   35760
caatgcagtg aacagcatcc tccacattct ttacagtaaa cataccactt tgattcacag   35820
gactccttat aatggggagc acctcaatag gactcaggtg gaggaatttg cagggaagag   35880
gagaatacat gacgttggta caaatctcct cactcatcca gctaaaggca agataagaa    35940 atttgaatct agtggaacag taataactat ttacagtcaa aattcattaa gtgctcactc   36000
tgtgccaggt gccgtgccaa gttctctaca taaataaata catttatcct caaaataatc   36060
ctattaaaag tattcattat ttctactccc attttcaga gaggtaaaca agtagttacc     36120
ccaagaacca agagcttaca cacggctgag ctgggatctg aacacaggca atcagcaggg   36180
aagccatgct ctcagccctg ccctctgttg tcttcccaac agatgagcat cttactggcc   36240
atcgtttata cacatcattt ctcacggaca tggaaacagt gtcagcctga ggttgtgcct   36300
cttgccaagg acatgctcag tgatgggtct gggctgccgt ttggcaaaca gaacaggtag   36360
cctcttatgt aagttgtgca gcctcccatg ggttaagact gataaaaaag caaacacacc   36420
accaccacgg gaatgtggaa gggtaagggt attccttcta taagagacaa gattatctgg   36480
ttcttctatg attctcctac ggacaaaaag tgaggaacaa actatgagat cttggaaaat   36540
cccagctcct ctctggagac ccactttttt gtcattaaaa tgagaagtct ggaggagcca   36600
attcacgggt ttcacttcat cataaaaatg taatgagtct atgaaacaag acaacacacc   36660
tgaaagtagt tagcacaggt gcacacattc agagtaggct gcaatccaag gcagcgatca   36720
tcactatagt tgttctatga gttcccacag cctaggccat gggcttgcca ccaccttgcc   36780
tacatttcaa ttggaaaagg ggtgggaccc tggtcctgca aacaaactac tgaaagtcta   36840
ggacttgggt ccaatgctat ccctttccta tatggcccca gtgcctctca ttttctagaa   36900
taagcagttc agttctaagt tagcaggaaa agcaagatgg ccaagatcca gtcatttggg   36960
agctggaagt ggtccagcag catgcctccc ttcatcctcc ttggcttacc atcttgtttt   37020
ccacgtaccc accttcagca gacaatctta gcaaacaacc caagaatgaa ctgattcagg   37080
ccaactcttc ttagaaccac actattactc tccagggctt tccaaggcca ccaaacatct   37140
ccttcattga tccagttcaa aacagtatct tgtacaatgc atcttgaaaa cattcgcaaa   37200
tgtcttcttg ttttgggaaa tattaaggga tagtcccaca gataaactaa tacaaataca   37260
ataaactaac atgaacatga tcacagaaac aaaagaaatg cttactgaaa aggtgtctga   37320
```

```
ttttctccac attaagatcc acaccagaac aacatttgtg gagtatattt aaaaaataaa   37380
ctattgtcac tgctgaaaaa gacccacatg ccactggaga gctctgttac acaagctgac   37440
tgagtaaagt atatttagtt catttccaaa tgaccaggct ttagaccaaa tttattcctc   37500
atgggcccat tagctcaggg agttaccagc atgaagttaa taagacctcc atctctggtt   37560
ccatccctac ctggtgagtt cacaccagtg cttctcacac ttcagtgtgc aaacaaatca   37620
ctgaaggcct tgttacaggc agatgctaat gcaataggcc ccagaggacc caaggttgtg   37680
cagttctaat aagctcccgg gtgatcctgc tgctgctggt ctagacactt tcagtagcaa   37740
cggtttatac cgttcagaag aggtatgtgt cttggtgtag agtgttctcc ttaatcaggg   37800
gaagaagaag taagaaagga tgcacctact gtgtgccagc cactgtgctg ggcgctccca   37860
agcatcatct ccttaaatcc cacaacaacc cacaggtacc atttatcagc actacttggc   37920
caataatggc gcagtcattc aaagagaagg ccttgtggcc caaagcaagc tttccatgga   37980
aaaaatgaag agggaatgaa tcccttggc aagtacagaa ctgcgattac cctaatcact   38040
tatgtgaaag gcacttgtgg gttgtttcag ttttatttag ctgcttcctg ctgtgattct   38100
gagtcaaaac aggaacaacg tgtctaattt gtaatattat ccaacaatga cagggatgtg   38160
gttagctttg attagaaatt ctagactcag catgctcccc ttgcctctgt gaaggcatgt   38220
ggagaaaaag agaaactgga tgaaacaggg attaaagcaa agtgagcccc tccaaaacct   38280
tgtggtgtga tatgtaggta tccgaatgct cagtttatgc accacagtca gcactcaact   38340
acaaaacttc agtgttagaa cagaccgaag gctacacagg cctggtttcc tgcattcaga   38400
caagcacaag tcaccagccc tctataaaaa gcccaactac tgctaacagc taacagacag   38460
tgacatgtca ggcaacgttg caagcacttt acatgcatta atctactcaa tcctcacaac   38520
acctcccacc cgctttgtat ttccatttta cagatgaaga gactgaagca tggagatgtc   38580
aagtcactgg cccaacatag cagagctaat aagctgtaga ataagcctta aatccaggag   38640
atctagctca ttcttgagta ttacactaga ccgtttctct cttacctaaa ccagcagaaa   38700
tcacctcttc gctcagtgtt ccacaaatta aatgtctgac tgcacttgga aaccattat    38760 gaaatgaata aaactgagtt gttgtgtttg attcttacag gttcagtgag agatcaataa   38820
ccatatcatg tctttgcaaa gtggggatgt cattggcaag taaacagcat ggctatttgc   38880
tcaggattcc ttcctctcct acctcctgtg ctgctgcctt cagtcctggt gcccatcagg   38940
tctcgtctga ctgacagctg tcaccaggcc atccatcatg accaatccaa caacttctc    39000 ttctaattgg aattttatat gttggttagt acagggatag actctgattt ccttagaatt   39060
ctacacaaaa tgttctggca ggagggaatc ttcagagact gggagggaag catgaatgtg   39120
agagaacagt tgtgcagtgc agaccccagc cccattctag ttgtttcttg accctgcct    39180 gcccttggtc actgtaggga ggcaggggaa ctggcactag gccccactga gggattccag   39240
ggttaagggt aggtacccgg ttcaaagaaa aaaacagcaa ggtttcttta actctttcat   39300
tctaaaaacc atgatctcag tcctctgagg aaagggcatc tatgacacca gtgtctgatg   39360
tcaagatgtt accgtgttcc tctgcctcta cagacaacca agcctcattt acaacaacaa   39420
caaaaggaac aaatgttaaa tctctgcacc attttgtcta gatgtttgaa tttgtctagc   39480
atttgaattt tttatcatat gcatatatta tctctttgga aacatacaga gatataaaga   39540
gaaagaagga aataaaaaga ggaaaaaagg aaagaattaa aaaaggaaaa aaggaaaacc   39600
ttcacaggtt ttagtgcctt acatatccca ttataaatcc tagctttgat acccactagt   39660
tgtttgattg tagacaaagt gttaaatttc tctaagcctg gttttctcat gcataaacag   39720
```

```
ggatcctaac agtgcctact cgcatggggt ggctataaga ttaaatgagg tcatgcttgg    39780
aaagggctga gctccctgca cagcgacagt atgttttctc tgaatattaa ctatcattaa    39840
tagtagcact agaaataaag atccatactt aaaatcttgt ggctcaactt ttttttctta    39900
catattaaaa aaggtagatg tacataatta tcatccattg tgtagctgca gatcaggaac    39960
ttgccaacaa gagtactgta ctactaataa tacagccaca atgcacttca tagcttttgt    40020
gttcaccacc ttgttggact tggagtagac aaatcaacat taagagtttt cattctggcc    40080
gggtgtggtg gctcatgcct gtaatcctag cactttggga ggctgaggca ggtggatcat    40140
ctgaggtcaa gagtttgaga ccagcctgat caacatggtg aaaccccgtc tctactaaaa    40200
acataaaaat tagccgggca tggtggcaga tgcctgtaat cccagctact tgagaggctg    40260
aggcaggaga attgcttgaa tccaggaggc agaggttgca gtgagccgag actgcaccat    40320
tgcactccag cccgggtgac agagtgagac tctgtctcaa aaaaaaaaaa aaaaaaagtt    40380
ttcattcctc aagataaaga agagatggtg gcaataaggg gagaaatgga atataaaatg    40440
ttgctcctaa tgtctgctgt tttaggtgga agaaatatcc caccacacag aaagagatg    40500 cttaaaagc aaacacccccc taccttctgg agcattttag aagactctga atcacccag    40560 acatttgagt cgtcagctgt gaaaggcttc ctgtactgta cagtgagaaa ttgtctttat    40620
gcttattatc tcacttcata agaaagtctg agaataaata agaggaaaaa tatgagggat    40680
gcccatgatg atcacttgag ttgaaagact ctgaaaatgg aagtcattag tatctgaaag    40740
gctcatagta aaatataaaa tgcatgatat attttgacaa agatattcaa tgataaaata    40800
tagatccaac ttgcaggcca tttatcaact tttgtccttt tggaggaaat aaacttgtct    40860
actgtagaca agctggtata cagaaggaga gaaaagtttc ttcaatgcta gtaaacatgc    40920
ctgggtattc tactgtcaga gattaattcc tttggcttag cctaggcctt cttttaaaag    40980
gtgatctact tgaagaaagc tgacctggta agtcagaata tcaggtgtta ccatgtttca    41040
tgtgattaaa ctatttagat ttccctccta actcaaatca cataaagaac atgaggccaa    41100
gcacagtggt tcatgcctgt aattctagca ctttgggagg ccaaggcagg ttattcacct    41160
gaggtcagga gttcgagacc agactgacga acatggtgaa actcgtctct actaaaaata    41220
caaagattag ctgggtatgg tggcacactc ctgcagtccc acctactcag gaggctgagg    41280
caggaggatc acttgaacct gggaggcaga ggttgcagtg agccaagatc gtgccattgc    41340
actccagcct gggcgacaga gtgagactcc gtcaaaaaaa aaaaaaaaaa aaaacaacc    41400 agaaaagaaa acgagagaaa tggaccattt acaggatgag gatgagaaca taggaaggaa    41460
gagtaatctg gaaagcgttg ccctgacaag atgtgcatgc ctgccttcag ttcactgaga    41520
agttggcctg ggggatgttg gacaggaaga tagggagaat ggcagtaggt gaaggacaca    41580
ggaagagaac aagctggatc tgcagtgcta ctgagcacca aacacgaaac acgaggacac    41640
atagcttctc gcaggtggaa tgcacatggc cgcagagata gggtgtagag ccagcatttg    41700
tatttcaaaa agatttttta attaaatcag acctattgtt gactaaacta acatttacac    41760
taccacgctg gtaaaattaa aagacttatc cattcccagt gttggagaag gtacacgaa    41820 atccatatgc ttcatccctt ttcaggagga gaatagttta gtagtgctta ttcaaattta    41880
aaatacacat atttctaatc tagaaatttc acttctggca atctgccttg cagaaatatt    41940
agcacaaatg catgagatat ttttacaaag atattcaatg tagcattaag tggaaaaact    42000
gaagacaatc catcaacagg gacatgataa gatccatcgt gggagataat atgaaattcg    42060
agactaaatt aaaagatgta cagtatatct atgtgttcta tcttgtttag aaggaattgt    42120
```

-continued

```
aaaagtggtt gggtataaaa aagtgttgca aaataatatt tatagtatga tcagatagtt   42180
gtactgaaag atggatgagt ggatggaagg atggacagat ggatgaaagg agggaaagag   42240
aaaggaagac agggagagat tgggagagag gatggagtgg gagataatat gaatgaatga   42300
tagagacgtg tgtgcatcta atacattgtc aatacagatg atctgttgca ttgggagtga   42360
ggggaggacg aaaatgtact ttcatttttt attttcacac actgttggat tgtttgaaat   42420
ttttgatgac gagcatatac tacttttgta attaaaaacc actgaattct cttcttatta   42480
aaaattgagg gaatagtgta tgccttcctt tcaagctgag taaacgctga acttcaaaga   42540
tggaggctag tatctaatct actcttctcc tggctctagg ggtaaacttt ggcttattat   42600
ttcctctctg tattgcaatg tttctctcaa atgggatcga tgacaagtac cctaaagaca   42660
aatcctggga ctatgtacaa gaaacaacat cagttataaa gaaagtcctc ctccaagatt   42720
aaacaacccc atccaaatct ttagaacaat agttaccaaa ttttagctgc acagaattac   42780
tgggagggct tgttaaaata cagatagctg gggttcaccc tctatgtttc tcatttagtg   42840
gggcctgaga atctgcattt ataacaggtt cccaggtgat actgatgctg gctgctcaag   42900
gggccgcact ttgagaaaca ctgctctagg tgaaagaaac tatttgtcaa agacaaataa   42960
taatgtttgc cccagtcaac catatttgat gagaaccaga acaaaccctg ctactcccca   43020 agccctctt tccaccagct gaatgagctc ctaatccact gtatgcaatc caccacagga   43080
ggaatgtgct ctatgacact gcagaccaag gatacaaaaa attggcacag atctcaggtc   43140 ccacacccctt aagagaagaa aactcacctt ctgagaagat gatgttgtca ttgcactcat   43200
cagagctaca ggaacacatg aagaaagtct caccaggctt ttttttttcc ttcataatgc   43260
actttggaga agcagcatct tccagaataa agtcatggta ggggagcttg gggtcatggc   43320
aaactgtctc tagtgttatg ttctcgtcat tctttctcct agagtgaaga gattcattgg   43380
aagcgagggg agggagag agagaaagag aataaatgaa taatatggcc tccagacaga   43440
aaggcaatct ggaatacttt tccttcatga agttgttcct aacaacggca gctggttcct   43500
gttctccagc attcgcaggc tgtcctatag tctcctatgc ttttctactc ttttctgttt   43560
ttcctttgtt tattcttgga acccatttgt gattataaac atcacctgga gcagacagcg   43620
ttccacgggg cagtcctggt ggagaatttt acatatttaa gtcttaatta aatcattaaa   43680
ggggaagaca tggaaaaaaa gaacattcct aggtactcag gataattttta aatcttccat   43740 cctgaatgta atgcaaacct cacatcacac ccctagttta actggcaaaa tctgtcctgt   43800
ctagctatac tgttttcaaa gagcatgcct ggggaaatag tcacagttcc tctttttttt   43860
gtttgctggg ccccagagca ttgcgtgtaa agggtatact ccttgtcaac agctggttct   43920
gctgagaaaa acgggaagaa acatcgcaga taaagaactg cagtctttcc caaattacag   43980
aaaggagcaa ttcagaaaaa acaaacaaac aaaaaaaaca aataaataaa agaaatggaa   44040
aaggatgtca gggtgttctt catttacagt tcaatgaaat attttatgct gtcataaact   44100
aactactttg acagtatcac ttcatagcac atatttgaag actaatttag cccagggctc   44160
agagaatttc tcacatagca ttttccttgg gccctaggaa atgctcaatt ggccgtcagt   44220
gtacattaga tttttaaaca acatgattaa tgcccactat tataattgaa caaaagaaca   44280
ttttggctct cttggaaaag ggtatcacct ctctatctac ctcccctctgc tccctcatga   44340 acatactatc ttggatgact gtccaacaag gctagtctga catccaccct ttcacctctg   44400 tccttttag atgcaaaata cctgttgtct tgaatcgcat tctctctgtc tagagaggga   44460
gcggaaggaa gggctaatct ggtccagtca gttttgctag agtaatcttc tatgaagatt   44520
```

```
ctgagtgcac acatgagcca atgcatgcat gtactcactc accaattttc ccctaatcct   44580
ccctgcccca tgcacaaagg ctcactgctc acagcaagga aaacggaagg caggctagaa   44640
gcaagaagca gctaagacac agcttgcacc tataaaagat gcggggccat ccccacgaga   44700
gaaagagcaa cttttgaccaa taccactttt ttagtgctta agtcaaggac attaaaggac   44760
aatatgttga caaagggata agggcaaggg tatgggttag acaatccag gcaggaatgg    44820 tgccagtgtc aacatccatg cagcccagag ttgactccag tggaggtaca tgtgtctgct   44880
tgtgaagggg ctcaagggtt cttaaactag aattccgaaa gacacaagag gagcaaggct   44940
ttgctaagtt ggtccctgct gtgacaggaa gagtgacaag cagaataatt ggttgagggt   45000
ggctatcagg acaccaaatg aaactaaatg aaagttggca tgatcataca acaaatgatg   45060
tataatttgg aaatctaccc atctttaacc ccaaagctac ttggcagtct tcaaatcagc   45120
tgtagtcatg gaacaagaac accttcctcc ctgcccccac agttttgtgt gtgtgtgtgt   45180
gtgtgtgtgt gtgtgtgtgt gtgtgtgtag gttgttttttg gtttgggtaa taaaacgaag   45240
gtatgctgtg cccacagaaa ggcatggtct cttttccttg tgacgcttat agaggcctaa   45300
gaaggaactg tgagccatga agaaagctg ctctataatt attgggcagc tcttccagag    45360
cctccggttt tctacctctt agctactgag agaactaaca tcacagagag aaaacaactg   45420
taatacttga gacctggtaa agcccttaac tgctttctcc actcactcct gtaacagcca   45480
ggcacagcta actttttcaaa ctctttttgg atatagctga gcataggaaa ggtaaataca  45540
aagaagtaaa tacggacttc ttttttttgtc ctgcaacatt tgctctgagc cactgaagag  45600
gttgtcaatt tccactgaaa gaagaaccaa catgataaaa ttaattttgg aggctgggca   45660
cggtggctca tgcctgtaat ctaagcactt tcagaggccg aggcaggcgg atcacaaggt   45720
caggagttcg agaccagcct ggccaacaca gtgaaacccc atctctacta aaaatacaaa   45780
aaattagcca cgtgatggtg gtgtgcacct gtaatcacag ctactcagga agctgaagca   45840
ggagaatcgc acgaacccgg gaggcagagg ttgcagtgag cccagatcac gccattgcac   45900
tccagcctgg gcaacagtgg gagactccct ctcaatttaa aaataataat aataataatt   45960
ttggttataa aatatttcta tccttggagg cagcttaagc atttatatg gaatgggcac    46020 acaactgaca ttagttaaat gaatgaatga atgaatgaat gaatgaaaaa acactaaaac   46080
tgattaaaaa aacaacaaca ctgaaatcta caatcatagt agagcctttc agtttccaca   46140
ctggctattt ttacaatagc ctcctgtctt agtttaggtt tcctggaaac agaccttgag   46200
gctgtgagag ttctgtgcag gaggtttttg gagatgcatc tgtaagcgac taaaggcaac   46260
agtattgcac agaaggaaaa agctaaacta taatgcaggt tgcagcaaag gcctcagtga   46320
atgccttgga aactctgaaa atgggatgtc cttcaaagat gtaccacatt atggcaaaat   46380
aaccaggaat ttgttttctct gcatcaacta gccatgggat gatggctacc catgaaaagt   46440
gtccaacgtg aatgaggcag ctcccatcac tggagggaag gctcagcagt gatccttcaa   46500
cagccaacac tcccagggaa tgagtgcctt ggtcatgaag gaggatcaag gagggcacta   46560
tagcgtaccc tatacttccc cttctcatta tcaacacccc tggcttcacg ggagaatttt   46620
ctttggccag cacaggtcaa aataatgttc attgtattta ccctttatag ctgggacaca   46680
gaaaagacag ggaggcctcc tctcttcgac atgctcacat ttttttgagg ctagcaaagc   46740
ctctattcta gagagacttg attcacattt aatgatttgg gcttgtatta ctggtcagga   46800 aaacaaaat cttaattaaa agagccttttt tgggttgcaa aagcaagtgc tcacaccacc   46860
gtagatattt aagaaaccac ggaaggaagc tttgaggcca tctagtctgg tgtctcaatc   46920
```

```
tttcctgcat tctatttgac atatggtcat ccagcctctc ctgaacttca cttggtgctt    46980
acagaaaagg aagcctgttc tgctgttggg aaaccatgat tgtgaaaatg tctaaactta    47040
tgctgagcac aagtctgcct gccttgcaaa tgttatggat cctccctcta cccttcagag    47100
ttatgcagaa tatgtttatt atattttcta cctgagagcc tttcaatttc atcagcagaa    47160
cccacgatct ctcttcactg tactaaccat gtctaattgc ccaggccatt cctcagacag    47220
catgatttct aggcctctaa ccacactggt ccctctcctc tgaacacatt ctttgtccaa    47280
atcctttctt tgaaagcgtt acctagaagt ggacatggac aggtatcata tcatattggc    47340
aagtatgtca tgacaagtct ttgctgttaa cattccttca gttcttaaga aaccagttca    47400
tcccgtggta tgtacagaag tttgcaaggt ttccagatct atcatcaagg ctagctttac    47460
atggtctagg ggtctcaaat gactcattcc caaaaaaggg ggagagatat ttgggtttat    47520
attcttgttt gtcaactagc caggagacac ataagttact ttttttaaaa tggccaataa    47580
attaaaaaca tcagaataag tctgcaaaat gtcatatctc attaatgaat ttatgtactt    47640
ttgtaaaatt acaactcttc taaagatcaa ggttatttct tgttcatgct cacaatctat    47700
aaccatgaat taatcaaatg attcatgagt atccactgtg tatgtataat tattatttga    47760
gatgtatgta tgagttggag ggaatgagag agagagagag agagagagga gaaaatgtga    47820
tccgataaaa atatatagtt ctggtcgggc atggtggctc atgcctgtaa ttccagcact    47880
ttgggaggca gaggcgagtg gatcacctga ggtcgggagt tcgagaccag cctggccaac    47940
atggtgaaac cccgtctcta ctaaaaatac aaaacttagc caggtgtggt agtgggcacc    48000
tgtaatccca gctactcgaa aggctgagac aagagaaacg cttgaacctg ggaggtggag    48060
gttgcggtga gccaagattg tgccatggca ctctagcctg aatgacagag caagactcca    48120
tctcaaaaaa aaaaagaaa tatgtagttc tgagctgaga gaaagaagtc atatctatcc    48180
caatggttat atgaataata taaccagaat ttctgactaa aaaaacaggt tgttttttgtg    48240 gttctccaag tagattcccc attttttggct ggtagttttc tcttccaaca gccaacctttt    48300 catcacctct tcttccagac ctgagattgc ctcaagagaa caaagctcct ggtctcacta    48360
tggggtgctg aggaggtgtc ggttaaatga ctactaagcg gcaaatccct cttcttgata    48420
caagaaagag tttccagatt tattatatta aagatcattt tatgatcttt acatttatca    48480
tgatcatttt ataatcatga tacgtttata tacccacata aacgtacaca tacatgcaga    48540
gaacacccct agaaactaca tttaataatc gaaagagaga tggtctaaag gaaagggaaa    48600
tggaacaggt gtttacattt aggagacaga gatacactga ctgtgtgtac tatgagaata    48660
cattatgtaa aaaggggaaa agaaagaata acttcttaaa aggcttgctt accatacagc    48720
cacacagact tcctgtggct tctcacagat ggaggtgatg ctgcagttgc tcatgcagga    48780
tttctggttg tcacaggtgg aaaatctcac atcacaaaat ttacacagtt gtggaaactt    48840
gactgcaccg ttgttgtcag tgactatcat gtcgttatta actgaggaga gagaaagata    48900
tattaaatga ttatccaact gccaggcagc ctgccaatga attcctgaag atgttatgca    48960
atttcaaatg aacttgatgt catgagaatg aatctgaaga aaggcaaaat aattccttca    49020
catcagatta gaattatctg gtgtatgcaa tttgtaataa aatccattgt accgtggtga    49080
ggggtggtga gggggttgggg tggttgagta gccatttgct tttgtcaatg gttgtcataa    49140
ggtccacttt ctacaaaaat cttatcattc aataaagaaa cctagatggg cccactgcat    49200
agtacggagt gctgggccca caaataaaag tacccttaag gaaattatag tttagctggt    49260
gaataagaca ggaaacagac caagtcaggg tgacccaaaa tagagggcag cacagaggat    49320
```

```
gtgggagcca ggcgagcatc accgctcagc tgggcaggga ggctataacc tcacagagtc      49380
atgaagtgcc acaccaaagg aggaaccgtt gctggaggca caagattttg ccgccatttt      49440
cctgacctac tcctgaaaga gctataaggg tcttcttttc aagggactag ttctactgat      49500
ctctctctgt gtttgaggca aatcaattga ttaactaaca cttactgagt gcctcctaga      49560
cacaatccca agcattggtg aggcattgga gttatgatcg cagcaaataa aagctgaatc      49620
cacctcagga tctgccttct gtacctctcc cttatcacca ccatcaccaa tctcctgccc      49680
ccttctggga agaagccaag ttcattccct cctcaggcct ttcacttgct attacctttg      49740
tttagcttcc tgtcactttt ctgatctctg atcaaatgcc acctcttcat cctatagcaa      49800
ctctgtttta tttattgtct gcacaaacta tctgcatcgc atacttgcta ataatctatc      49860
cacaaaaatg taagctccat gaaactttct ccacctcact tacctactat atctccagtg      49920
ccaggaagag aacctttcac atagcaggca tacaaaaatg tttattggat aaatgagtga      49980
acacaggatg aatacaagga gtccatgttt ggcccttgat gccatgtagg ataggataca      50040
gaacttcttc actcagatta gagaggaatg tgattataaa tgtgatattc attcacattt      50100
attcaataaa atatggaaga cagactattc tttgcaaaat acaggctgca aactaggggc      50160
agttcaaata aaggtgtaac accccattcc ccattttctt cctcaatgag atggtgatga      50220
tgtttaagac atgagtttgg acagtcagtg aagtatgaca aggctactag gcactcaacc      50280
agcaaacatg aattaatact tacatgctag actaagaaac attaagcact tagaccgcat      50340
ggggtgctgg aacagttgct gggccacaga agttgtgag gtacttttcc aaggcataac      50400
ccttagagag gcctaagaaa agcctcatgt tccctctgct cttgcctaga gaggaacact      50460
ttcaatgcct ttccacagtc actctctgtc ctgtgaattt taggattctg tcatagatac      50520
tttgccctgc aactgtcttt gtagcttggg catagcacct gtttcctggg tctctaaaaa      50580
tataaacgta tataaattta agatttgctt tcttgtggta acagtaaata tagaagaaaa      50640
aaataaagcc attcatccct ctcgggcctc aagttcattt caggaagttt attttaggt      50700 aacaagctat tttgaaattc tcagtgtctc ccagaccaag agctctatgc ttagctaaaa      50760
atataggcag aaatactctc tgaactgtgt gaaatttggg agaaacacaa caattaatat      50820 gtatttttt ctaacatggt tatacttgga tcaattttg aaacaactaa taacacttta      50880
ggtttcttta acattgttta aagcaaaaaa aaagtgaaac cacgttttgt ttatttcata      50940
catacgtatt ttttgtatag agtatgtttt ggacaagcat ctatttgctg attaggaagg      51000
tttgttgttt gtaaatataa aaccaaattt ccattacttg aaattcagtc ttccaacatc      51060
ttaggatttt agcttagatt ggtggttatc aacttggaga gcatgttgaa atccatcacc      51120
tgaggaaatt taaaaaatac tgaaggggtc ccactcccag atagtctgat ttaattttc       51180 tggaaggtaa ctgaggcatc aggattttta gaagctgccc agatgattct aatgtggaac      51240
caaggttgag aacccagacc tatagttagt tggaaaaaac acaataaaca gaaaacaaaa      51300
cagcaacccc cccactccca ccccaccacc acaaacacat atacaactta tgctgctgag      51360
gggacagcac ctggatatag ctggaattag ttcccttgtg aaaaacatgc acctaaggag      51420
aggtgattag ctcttttcaca cctcagatag aaattcttct ccgtgctggc cagtccttt       51480 ctagcaaaac cttagaaacg tgagaatagt gacaggagtg agcagcgata gataagcag       51540 aaatgaaaac agatgagatg ggtgctggga gcagtggtgg ccacagatgt attgacaaat      51600
gcaagtggtt taagtccgat gcttgcagaa cacaatcaac agggaaaaga aaaaggacc       51660 attagaagaa agaaagggag agaaagggaa gaaggatgta gggagagaga gaggaaggaa      51720
```

```
gggaggaagg gaaacaagga gggaggggga ggagagagaa agagagagaa ggtccaccaa   51780
tttgcacagc tccaggagca ccactgtaac ggggcccctg gcgagatata atacatgtta   51840
cttgatgggt agacccaaca agagaaagcc tttccattga atgttgaaga aaagccaaac   51900
aagcaactgt actgcatata gacacaggca tatggtggga agggcagtgt acaataagaa   51960
tttgcacatg ctgagcaccc actgtatatg aggaaagttg cctaagatac agcatattac   52020
ttcacaagaa cccagccagg gatgccacat ttttctcctt gttacagcag aagctaccac   52080
tgcaagagct taaccagaat ttttttttcaa aagcctgtat gcaggacatg ttcagcacca   52140
gccatcgact ccctattagt tgaccctagg agactcccca ccttaacaat tccaggtagc   52200
ccttgaggtc atatacattc aacctttgt tttaaaccag tattcttttc ctctatatga   52260
tataggtcct caggtccttt tatgcatacc atatgtactg gtggaatagg tagttaagtt   52320
cagagggcaa agctactcta aacctttgct ggagtcacct aagtttgata aaagccttat   52380
gaacacactt tggagttggg gaaaagaaac aaatacaaaa tttgtagatc atctgagaag   52440
gtttgcagat tctctgaggc ccgtaagatc cagttaaggc atcccaagcc aaccccggaa   52500
tcctcaagag tcactaataa catgctaagt ggtatactgc tggtcagagt gggatgaggg   52560
ccagtgggag ggaagggtaa cagtcatttg ctgtatggga cattgcatct gtgcactcca   52620
aaccacagga aaagatgtta ccagccacga cctcagatat caaacaacat ctccttacgt   52680
ttaatacata atgtttaaaa agccaaagga atgggaagga aagtaagtgc atacatgtgc   52740
atagctagga ataagatat tcctctaaac aacgatacaa aacccaccta attaaccctc a   52800 tagcaaaccc taacccaact tcaacattac ttttaatcca gattgttata ttagtctaag   52860
tctctctagt taagatattc ttatattaag gcagtatata gtcagccttc tgtatctgtg   52920
ggttccacat ctgcggtttc catcaaccgt ggatgcaaaa tatttttta aaaaaattga   52980 tgattgtggc tgtactgaat tatgtacaga cttttttctt gtcattattc cctaagcaac   53040
acagtataac aactatttac atagaattta cattgtatta tgtataagta atctagagat   53100
gatttaaagg atatgggagg atgtgtgtag gttatatgta aatattacac aatttttatat   53160 aagggagtta acatctgta gattttggtc tcctcgagga gtcttggaac caatccccca   53220
tgggtaccaa gagatgactg tacttcgatt cctatagact ctctgtgagc agctaaccat   53280
ctttagagaa ttttctaccc ctaataggca aattcgttat tcataaagtt ctccagaaag   53340
aagttccaat aagaatatct gtcacctaga aagccatcca ctaaaggaag tgaacatggg   53400
tagcatctct cagcatatga tagtatcaca tggcccataa tatttcactt ctcttcaaat   53460
aagcccatga gtaatatcaa aaccttcact ctaggtcata ccaccttccc cattttatct   53520
cacattttcc ccacactcac tgcctacaga cagaggttcc aggtcttgag aatatgaatt   53580
gactgcttag ctgtgtctat ttctggaact gtactattgt ctttgagggt cagatgagca   53640
gcctaataag atttagactt atttcagata aatattagaa attctgaata tgaccttagt   53700
ccaaatcttt gaaatagtgt ctattattag ctgaaccatt aggtaaaatc tcaaggttta   53760
acaataacca taaacacttg tcagaaatgc attcatgtat cactgaattc atgcattcgt   53820
gtatcattga attcatgtat ctaccgactg ttgttttctg gagtgttttt tgtgggggga   53880
aactcagaaa tttatttgtt ctacaaatac ctgtggatgt cttgattagt gttatatatt   53940
catagtaaga ccactgaaat tgacacaatt aaataacatc tcaaagaata atccatggaa   54000
actggtggat agaatttact gttttagagt actgcttctc aaatattaat acacaagtac   54060
tttgggaata ttttaacct gcaggtgtag catagtggta ttgtgggggc tggcaagtct   54120
```

```
gaaatttata gggcagactg gcagcctggg aactcaggca gaaatcaatg ctgcagtttt   54180
gaggcagtat ttttctctc agaaacctca gcttttgctc ttaaggctgt tcagttgatt   54240
ggatgaggcc cactcacatt atagagaatg atttcttta cttaaagtca aatgatttta   54300
gctgttaatc acatctacaa catacettca cagcaacaat gagattagtg ggcaccagaa   54360
cctagccaag tacacacgaa actgaccta cagataggaa gggagctgct gccctgggtg   54420
atgccagccc actatatgtt gagtgggaag gctgtggaga acccagtttt taataattgt   54480 ttcccttct ccagtcattt tggagttagt gaaattaaat acctattctt cacctttta   54540 caggcatttc tcatcttcca gttctttcca tatgcttttc tcttgagcct gacctcttaa   54600
atgattgcaa acccagaggc cctgatcacc atatgggccc agaattgaaa gacatgttct   54660
ctgaaaggag gtttttaatt gcctgcagca tttccgagtc agatactgag gcagccatct   54720
ggcagaaagc cgctgtggcc tgtgatgcta gcaacagcag ctccgaccct tgagacaagg   54780
tgggacaagg ctattggcta gtcacacact tcctcccacc cagaacaaag aagaaagtca   54840
agcaatctga gaggattccc tgtataattc ttcaggaaag acatcccaa gccaatcaga   54900 taccttggcc aattactaca accaaccaac caaccaaaca acaccttgt gattaaacca   54960 aagataggaa catttaggaa atagttcttt ttgctgaaca tctattgcac actctaattg   55020
gaacttctaa tacaatacct tctttttagt ttttaaaaat gtgttgaac cctaatgctt   55080 tatctaatta taccttgaga gaagagaggt atcgggcttt ccttcaactg acagtccaca   55140
tggtctctgg ggtaccaagg tcaatactag agataccatc atttagctaa cagggagact   55200
atggcgtgtg caggaagaaa acagagacaa gtgacctgaa ggcatcaatt ctccttctta   55260
tgcaaatatt tttgtagtaa taatacttta aaaccttca gagatgacaa agtgaatact   55320
ctaaaatctc tgtgaaatga caatgcctta taattcttgc ttttaaatag taagtattct   55380
acaagtgcca gaagaattaa tgccatttaa aatcattatc aatgcttatt ggaaacaaat   55440
aacaaatcat atgagttctc tatattgtgt taaaaaacg ctactttaaa tattacttcc   55500
tgatcatatc accagagaat aagctctaaa agcgaagcat gtcaacctca ttgctaacaa   55560
gtgaaatgca gattaaaaat gcataccata tttcacctaa ctcattttga aaaagatcaa   55620
taagtcagat aacacagtga gctgggtaaa gtatggggaa acaaacattc tcataatgct   55680
gtgttgtaaa caggtataac atctcaggag tacatgttat tgatatcaat caacactgca   55740
aacgcaaata gcctttgcc tcgcactttc gcttctaaaa atttatgata ttcattgata   55800
aattcgctgc agtgttgttt gtaaggacaa acaggttttt ttttaacca ctcatcaaga   55860 gaagactagt aaaataaatt agacaaatcc aaacaaggaa cacaacgcaa cgactaaaaa   55920
gcagagggca gctccatgtg gctatcttta taagtgttga agcccaggct atagcattca   55980
agaaaataag caaggtagag accaatgtat agagttactt gggctgggtg tcttctattg   56040
cccttagaga tcagttctcc acccttggtc accagactgt ctgccccagg aggctcatct   56100
ttatggacta catcaaccgg ctctcttgcc ctcaagcttc cagtaagttt ggccaatggg   56160
gtgacccagc ggtatctaag ggaagcaatg aggagcacat ttaaggtatc tgtgttctgg   56220
ctccctctgt ggaatctttt ccagctggcc aagtccctca cttggaggtc acaggttctc   56280
ttcaggaggt catttccaag atttacttct tccctctcct tgccactttg ggcctagcaa   56340
gtcaacatag caattactag tcctaagtat ctgcactatg gtttctccca ttttgtggtg   56400
gtttcccttg actctatcca taccttgta agtacttgtt ttactaaact ctccttaaat   56460
ctccctaatt tgagggtgcc atctgcttgc aactggaacc ctggttgaca caccaccatt   56520
```

```
tctgttttgt tgttattgct tttattgctt tttttttttt ttttcagaca gagtcttgct   56580
ctgtcaccca ggctggagtg cagtggcgcg atctcggctc actataagct ctgcctccca   56640
ggttcacgcc attctcctgc ctcagcctcc cgagcagctg ggactacagg tgcccaacac   56700
cacgcttggc taattttttg tattttagt agagacgggg tttcaccgtg ttagccagga    56760
tggtctcgat ctcctgacct cgtgatctgc ccaccttggc ctcccaaagt gctgggatta   56820
caggcttgag ccaccacgcc tggcctgtta ctgcttttta aagggaatac acacacacac   56880
acacacacac acacgtgcac acacatgcat gcttatatat ttagacggtc tctgggagta   56940
gatgcaagga catgagaatc aaacattatt tggccctgta aaggaaaat aaataggtag    57000 aaaactgagg ttgagaagca acttttatt tcatacccctt ctgttacttt tgaattttct   57060 attattttc tgtacttaaa aaatgttttc attataaatg agcaaatgca aggcagattc    57120
tgtcatggca gatgcatgca gctttcattc aagtgacagc cccacatagc ctctgggcac   57180
caggatcaga agtggagaaa caatacctaa tagggagacc accatgtggg cagaaaataa   57240
agagataagc tcaaaagcat caattttcct tttcatgcac atgttttgt aatactaata    57300 tagttttaa aacctgtcaa gaatgacata atcaatactc taaaatctct tagagcagga    57360
aataattcta gtaaaatacc tagtacgggc cgggtgcggt ggctcacgcc tgtaatccca   57420
gtactataca cacacacaca cacacacaca cacacacaca cacacacaca catacatata   57480
tattttcaca ctgaaactac ctaccatctg gccaacaatt aaggatatca aatgtctggg   57540
atactctcca cacaacaaga catctaaaac aaacaccagg ttggtcccta ccctcctatg   57600
gcttatattc tagtttgaga ggcaacatta acaacggcaa cctcatgtga atcagttact   57660
tgcctttaaa tgcaaacatg aggtcagaaa tggagacaga gctgatacgg gaagtgtgtg   57720
tgtgagtgtg tgtgtttatg catttatgtg tgtgatttcc tcatttggac ttgttcaact   57780
gagggaattt agctttgtag gtttgagttt cactagcatt ttggctcatg aatttagtag   57840
tttgctatga ttgctttaag aaaactgcat aaacataaat ttgtatttac caaacaaatt   57900
aagggattaa ggaatgatta cttgtgtctc aaatgaattc atccaatgag gtactttaaa   57960
ttgaaatctt ggctgtacct ttaaactcaa atttttttaa atgcaattta caaggaagtt   58020
tttttagtct tctacggaat gaaacaagct gtagctgaac ggaaaaataa ttggcttct    58080 ccagtgacaa acataaaata actgagctgg aatttcaatt gcatccttc ctatttaaca    58140 cttaccagcc ccaatgaccc caaataaatc ctaaaaatgc atacttggtt ttcttgcttt   58200
cttgtatcat tgaagaatga agtacaattt gagtcccccc aacgcttgct gaattttcat   58260
ttatttttct gttttttgtt tgttttgtt tttagtggca ggggacctct ctgagataca    58320
ggccacataa caggagacaa aatctaaaca tttaaaatga ctcttgcagg tggaaatatc   58380
tacacattgt tgccaaaggc agtatttcag aattctagca cttgtgccat attcaaaaag   58440
ctgaaacaat tgtaactttc tcaatcatgc tctttcagct ctaataggac ccagtgaata   58500
aaacaaattt ctgaaagctg gggagaagca agcagtttat agtaaatact gtcatcaata   58560
catgaaattc ttaagttttt cattgataaa gctcacttta acgtgccttt atctggcaa    58620 agactgactg cagggactat gagatgagtc aaaaaccaga atgtagggtt tggggctgag   58680
aagaacagga agccagttaa aaaagttaag ccatataaat gcaaatggta tattagatca   58740
agtgaaagag tagaatggag cactatttca tgaactctca aaataataac tttatgcctc   58800
tgctgagaag tgctttaaag ttggtacttt acctaaagtg acagcaactg agaaaacaat   58860 tctcccctcag ttgacaggac ttggagtgct gtagcaacaa ggaaataatt tattattgaa  58920
```

```
aataaaagat gattaaataa ctctcttggt gatggtcaaa acattggtaa atggcacaga    58980
ctgatagagg caagataatg atacacgact gacggagttt tacaacattc caattcaact    59040
aaagtaattt gttacttacc agcaaaatta gtcaacctaa acgaaaatgt gctgctttct    59100
gacagccctc atatttaaac ccttgaggga aggggacag gataagacat ggtcctttcc     59160
tcaagatctt taagttcttc tagggaattt ttaaaaatgc acgaaatgat tttcatcaaa    59220
agagctttgg aaataaggat ggtctaaatg aagatgtgct ttttaattaa gttattcatt    59280
taggatttaa acaattcttt atctcaaagt actgaggcag cttaatggaa aatgcagaaa    59340
ctaacacaaa atctggtaag aacagatttt taaaagatag tgactattag agaatctgaa    59400
aaatcagccc ctgaaatgaa ccatttgcct caactaagca tgggatttgg tccgaatatc    59460
aatgttctgt gagagcagaa ttttcactga taaatttctc cgtggaggct tttgcttcag    59520
tttttcaaaa tatgctgcgg ggttcttgtg catgcctggt acctgaaagg tttttcaatt    59580
acagttttat taaacatgtg aaaatattgg tcaaaacaga tgatttccat attttctctg    59640
gaaaagggcc agagtactac catatttggg aaaggcatcc ctttaaaaag taatataacg    59700
aggtccaagg cgcttggttt ctaacaacca ataacttgg gcacagactg agaagctaaa     59760
gcagaaattg ctacagtggg tacaagagct ggatacagag cacagatgtg ttctgtttgg    59820
cctgaactct tttcttttta aaatataaac caagttttaa aattcagaga tttcacatgc    59880
aaaactggtt ttctaattcc acttaaagaa ataaaaaga cttggaaaca gtgggcccac     59940
accatcccaa gacaacagtc agctgactgt gagctgagat gctcctcttg agaaagtctc    60000
tgtgtcctca aatttgcctc ctccctgaca ctccttcatg tcacctactc ccctgccagg    60060
cccctgtggc cacctgaatg tttacaatta atgattattt cacctgcaca ttcaattctc    60120
tcttctaata ttagggttta actagaatgc aaaaagtcat gatttaactc tctaatatga    60180
atattttaa catgcatgta attctctaat gtgtataatc acatttcagt tcaaggccag     60240
aggacatcta ctttagaaat cagatctatg tgatgttaat aattattatt accatgatca    60300
tgatttatcg aatgcagacc aaatgcttag tccagtatta agtactgtga tgattatttc    60360
atttacttat cacaaccacc atgcaatttt gtcattaaca ttttatagat ggagaaatta    60420
agggtcaaag agatgaaata acttatcata tcatatcaat gagagaaagc aaataaaaga    60480
caaagccaat ggtgacacac aagccctcat ccttcctgat actccacaat gaaatagata    60540
ttccatcaaa aagtttaaga gtagaacttt acacacattc cagtacaagg caaagacaca    60600
ggtgtgacta ctaggagttg aagaaagtat acaaggggtg gggaagcaat aagtttctta    60660
gacaaaagct ttggttcttt gtaattactt cacttatttt aggagacata tataataagg    60720
tcagcttggt gaagcccaag agtttaagg taaaaacttg agtgtgaatt caggctctta     60780
catgtattag ctgtgggcca cttaacttct tgaaacctcc atttcctgat ttatgaaatc    60840
gtcccatgta ggatcatgat gaagagcaaa catgcttgaa gtacctgtga aaatcctcta    60900
gacagtaaaa aatgccacac aagcattcac ttgctagaaa ggtaacattc catgcaatgc    60960
tctctcacac caaagaaaat tgcaggaaac aaatgacaag ataagtatga gtttggtaaa    61020
tctattccta ctcatcaata gaatgtagca gtttgatgac ttctaaaaaa cctttcagga    61080
aatttgaatg aatagacaaa ttgaaatata ataatttttt gttaccactg tgccctgatg    61140
ctttcaaata tacaatggaa tcaatcatcg ttacaataaa gttgccaaga gtgtttagga    61200
tctagaacca aataatctgg ttttgaaata ttgttcataa ccagcatagg tctgcaaac     61260
aggcagtaac ttgagaatcc agttcaattt tcaaatcctc tgcttactcc tgcacattta    61320
```

```
tcaggcgaga gctgatctac tttggctttg agacacttag tgtgttattt cgcaacatgc   61380
taataaaatt agtaagtttg acatgcagag atgggaaggc aatgatgtgt cttaagattg   61440
tggaattcta aaatattgaa ataaaatcat gtttggctta cttttcaagg aaataaaact   61500
gctgtacttt cattcacagc tgatgaaaga attacagaag aatatgggca acaacaattg   61560
tagtagattt ttaagtacct agttaaaaag tgttctgggc catccagata tatggaaagc   61620
aatattcctt aatcttctct cctggagctc atttgctcac gtaaaagtta attataaaac   61680
attgctatat gacttctact ggaggagaat tcaccatgct gggaatggca gcaggttgca   61740
gtggagaagg ctctgaatcg accatgaggg ggctttgagt tcaagggcaa ttacccaacc   61800
actctctgtg cctgttctcc aaccagtcaa acaaatgggt tggacatgat gaacttaaag   61860
gtccctttca ttttgaaaaa tgacacaaaa aggacagaaa gacacattca gattcacttt   61920
ggtttctaag ataacaccaa acactttgaa acttcccccct tcatgttttt caagcagagg   61980
aagtaaaaaa aaaaaaaaaa aaaaagaaa gaagttgcaa gtattgttaa ggcttctaga   62040
aaggacaaca aagggcagga aatttgaaac aaaatctgag aatctgccct taaactgggc   62100
aattttgctt gttttctcac agtgcagtta gatgaaaaag tgtaaggttg atcttcgcct   62160
ttcctgggca ttactcattg ctgtcatgac cttgatgcaa tttgcagtaa acatcataaa   62220
ggtctctctt gtggtgagta gctgcaactt ttctgatgct acctcctgtg attaaaatat   62280
ctactcccgg cctggcacgg tggctcacgc ctgtaatccc agcactctgg taggccgagg   62340
tgggtgaatc acgaggtcaa gaaatcaaga ccatcctggc caatatggcg aaaccccgtc   62400
tctactaaaa atacaaaaat tagctagggc ttgatggtgc gtgcctgtag tcccagctac   62460
tcaggaggct gaggcaggag aatcacttga acccaggaga cagaggttgc agatggccaa   62520
gactgtgcca ctacattcca gccttacgac agagcaagac tctgtattta aaaaaaaaa   62580 aaaaaaaaaa aggctactcc tttccaagtc ctagcaatcc cactaaggtt ggtaacttag   62640
tctgtttggc tgccatacaa aatatgtgag actgggtgat ttataaagga cagaaatttt   62700
tcacagttct agaggctgac aagtccaaaa tcaaggcact ggcagttctg atgtctcgta   62760
agagccccct ttcctgcttc caagatggtg ctttgttgct gtgtcctcta gagaggacca   62820
gtactgtgtc atcacatagc agaaaatgga agggcaaaag gatccaggct ggttacctcc   62880 agcccttta tgtgggacta atccactcat gacttaatca cttcccccaa atctccgtct   62940
cttgatacca ccacaatggg gattaagttt caacataaat tttggagggg agacatcagc   63000
cacagtagtt ggtgagaaaa aaggacagta tttacataat gacagttgtc aatgggctgt   63060
ggaaaagtca agatagattc cagcagtgat tttaagatgg aaaatgagaa ccatgcacac   63120
agtcttcaag gtgcaatctt ccaacatagt tctggaacac agctggctcc ttccatccat   63180
ggggaatgac cacatttgtg tgctgaaata acatttagta ctagagataa aactggaata   63240
agtgatctaa actttgaaat gttttgaatg accttggct acaaagtcaa attataatgc   63300
tttctatttc ttaagacaac tcttatggaa agttctagta tgtacctaac tttggcacct   63360
tagatttgcc ccacactgaa tcttatctat taaacctatc tcattctggg gtgagaaccc   63420
agatgtgtaa aatcgtatgg ccagaggtga ctgagaagtg cattttgact atgtttcata   63480
gtcttttatc catcttagca taatcttttt accagcacca gtggagttgt gaactcgctc   63540
aatttcttgt gatgtccagt gtaaaaatgt atgcctataa atgtaactct tagaaagaga   63600
agcaaaaatg agaaaccatg ggggaggagg ggaggaaatg acaagcacag tctgttttta   63660
ggacactgta cttgctgttc cctccaacta gaatgcgctt aacccagaga tctgccttct   63720
```

```
tcatcccgat tcataccaa ttactgctca aatatcacat tatcaaagat gccattcttg   63780
acaaccgctt ctaaaattac aagcatctac cattgttctc agaccctcgc gctgtactta   63840
tctgctgaca tgttgataga atcttgttta ttagcttgta cacatggact ttaattcact   63900
ctgtattccc caaatctcaa acattggctg gcacacggtg gttggtactc tataaacact   63960
tggtgatggc tttcctatcc ctaagtcctc caaagccaag tttcatacct cttccttaag   64020
ttccaaagga aaccttatct gcagaaaatt aatgcatatt tgctgttgct ggataaagaa   64080
taaggatata gtcacagaga aaaaggaca tgttgaggcc aggtatggag ggtataaaca   64140
gttggtgaag agttttaagc tcaaggccta gcctgtctaa cttagcaata aaggaagtc   64200 agttctgaag tcaaagagag ttcttctttc cccactggga ggagctggtt catgaaagtg   64260
gagggccaga gccaagagaa ctctcccaag acacattgtt caaaagtcaa gggcataatc   64320
tagatagagc tacacagtag ccatgaggac acatggattt ataaatttaa attaactaaa   64380
gttaaatgaa atcatacatt cagttccaag tcagaccagc cattttcaag tgcttaatag   64440
ccacatgtgg ccaggaatag acaggatact ttcatcattg cagaaagtcc tataggacaa   64500
cactgatcta aagaaattca aaaggacctg cgttcctcgg cttctgagga gatctgaaaa   64560
cgaaggccca gagggaaatg aaggagaag cagggcagag cttgaaaagt aatcgcattg   64620
gaaagggccc tgactgctgg cttggatgcc ttgtgtaatt aaagttctat cccaacttct   64680
taaggaatga gtctcgtatt aaatgactgg ctgtctgtag tgtcactgct gaggtaggga   64740
gagaagacaa ttagggacaa ggagtagtgt tccatggaaa acacgttagc tatgagtggc   64800
agcagcaaaa ggtctcagaa gtgagagaaa tggacccaac taggtttgca acaagctgaa   64860
acctgtaaag gctcatgtca gctggcacaa cctctcaaaa tgcaaatccc tgagcccaag   64920
ataaatgtaa ggctcgtctg actcctaagg tatcaagtaa ttcttattaa gccccatttc   64980
aatgactgaa acctaatgca gagcccaggc acacagatta gtttccagt caaagcccac   65040 acaagcctaa agaaaggaaa ttaacatttt agagaaaaaa aaaaaaaaa aaaaaaaac   65100 ccacaggctt tttcaaaggc tttttttttt ttttggagga tttaagtcac agcatgccaa   65160
ataaaggtga gtttctagga gaatacagca cagaggtgac caaggtgggt gaaatttatt   65220
cacaggggaa aatccaaatg ccttcaggga aaccactttt gcagggttct tctgataaat   65280
actgaaccca attaaaagca tcccttcagg gcaagttttc tcctaggaga tttctattgg   65340
ccgctttaac ttccctttcc ccagaatttc caggagaagt ttgtaacggt ttataatccc   65400
taccactcca tgctcataga cttaagcat attttctcc cacaaggcag tactatttt   65460 ataatccttt taagattaaa actaaaaaca cagatgatta aaaaaaaaa aaaaggcct   65520 ggctgcatcc tcctacaata aagtattata attgcagtgc actactaagt agtatttcca   65580
caaacattag actatctggt ttccaggaca aagaaacagc ctataattcc aaagcacagg   65640
aatggaaaag tacaagtaat ttaatctgtc ccactgtgat tataggtgct aagaaattac   65700
ctgaacggac ctctttggga cttgagaaga atgggggactt taatgatgct ccataactgc   65760
cctattcatt atgataccca agagccacct gtggctattt aaattcaagt taactgaaat   65820
aaaaatatat ctatatttga aattcagttc cttatttgca cctgctacgt ttcaagccac   65880
atgtatcatc taagatggtc tcagacccac tgttcaatag aacttcctgc aaaggtgaaa   65940
atatcttata ccagtgctgt ccttaaacct taacacagcc caggtataag atattttcat   66000
ctctgcagaa agttctattg aacagtggat ctaagaccat cttagagaga taattacata   66060 attttttccca atttcataat agagattatg aagtaacagc ctccaaaata cagggttttt   66120
```

```
aggctactgg ctaccttcta cactcaggtg aacttttgt agtggtttac acatgtgtac   66180
caattgccct catctcccca gtttcaagta cattaaaatg gcattagatg taataaaata   66240
catgccactg agactcagct caattgaaac ttgagtttct tcagaattcc aaacgatggt   66300
gcatctcttt ctgaaacctg aagtggggac ttgtcaggaa aatgtctatg agggaggcct   66360
aggaaaaaga aggcatttc caaaattaat aaatttattt ccttgttttt tgtcacacct   66420
tattccagag gtgtctctag gctactgtgt gcggaacgag gtctggacag aacctaatga   66480
taaattgggg gatactgaaa gtcctggcac tctaaggagc ttccccacac atctttagat   66540
ttttatttcc catgtgggaa aaaagaaag ggatttccta tcttcccatc acaaactcct   66600
ggctttgcag tggttttatt acgtcattcc cctacttaca atctgccagt gactcagaga   66660
atttagccca aactggcact taaggctccc ataatctgat taccttctg ctgaataact   66720 ccttttatca gaaacccttt gacctgataa ttgctggctt tcctaccacc aaaatttcta   66780
cctccctacc agatctatca ggtggatttt aaggtcaaga agagcatgcc caaggcagcc   66840
tgctcagccc ctggaaggag ttcagtgcct tcactgttgg ctgtgaggtt tacgtgatgg   66900
agggaagaga ctccaagaat ggtgtctgaa aggatgcctg gtgtctgatg ctgcccctca   66960
ggagtggtcc aaggtggttc aaatactgcc tgctttggcc atggctgaca gagctgaaga   67020
actgcctcta tatggtgtgt ggacacacac cccaggcagc cacttgccgg cttccctctg   67080
tttccttgaa ggaagtggag tagcatggcc ctggggctaa caagtgaaca atagtgcctg   67140
ccttaaatca tacccagcct ttcagaccca ggtcaagtgt tttctctttt ggaaaatcat   67200
ccattccccc cactaccagc cccaccaaga gtactctgcc tcctccggtt ttggttttta   67260
accatcttta ctgtgaggta tgcttttaga taggcctgta tttgctctgt tctgcagatg   67320
agtttccaaa accttctaaa accttgctca tatttgttat gctggattta aagtcaacag   67380
atgggagttt tcaacccagt aaatggaatt tctttgctgt gggaaatcaa gtactttgac   67440
ctctctggtg aaattcttca tttgtaacct cactgggtta ggctagatta tgtttctca   67500 acatggttcc acatcggaat catctgggga tctttaaaa caataatgat gccaaagtcc   67560
taccccaggg caatgagtca gaacttctag gtgcttggct caggctttgg aattctttta   67620
gaagttcgca ggtgatccta acgtgcagcc agggttagaa aaataaactg agttcaggaa   67680
gggacttatg ctacatggac tggagaattc aataggaaaa aatgtagtag ttagagatgg   67740
ggcatggtag tactgacag aggcagtcag gcccataggt gttgcttctc atctttgcct   67800
tgagctgtaa ctagaaaaac tgcaaactgc attataacca gaacattatt atatacatat   67860
acatgtacaa tcaagcccaa cccaattaat tttctcatat gactcaaact ctagtaccat   67920
ttggagatga ggcaggaatc ataaacataa ttggctgcag ggcatttagt tgccattgta   67980
taaattcttc ctgaaaaata atttagatt aattttaag tgtggatttt acaatttcct   68040 atcttttaa agggtgggaa tcctttgcca attcccaaga ggacaataag cttaaaggaa   68100
gataatgtct gaaagatctg aggaccaagt ttcctgagaa agctgtattt ctaaagtttt   68160
gaccctacaa ggcaacatta aaagtaagtt caaggaaaca aatgtgagaa agcatatctc   68220
cctttagata acctagcaaa gaagttaaga agggaaatag ttccttagat cagaattaac   68280
agttgtggat agccttccct tcagaaaatt gcaatgctaa acagacgtta cacaagcaat   68340
atatccctgc aacttaattt ctcttcctag gatctttaat attttcttt tttattcca   68400 ttaaacaaat atatattgag catcacctat ccaccagatc tgaagaaaca ctattttaa   68460 tatgttcaaa atttgagtct tttcttgata caataacatc tgccttaaca ggaatcagta   68520
```

```
tgtaaaaatt acagttttta aagaattata taaaaggtat tattccagaa gacttgctat   68580
ggaatccctt ttaaaaaggg cgttcagaaa aaggtaacac tgaaatttat tacagtttga   68640
agaaaatcac tccaattata aatccatgaa cccagtcatt gtttaatgaa gctcatcttt   68700
gctggaaaat ccccactgag aacaaagcat cacaatgatc cacacagtcc taatcaagcc   68760
cactggaaaa atcaccctga agaacactgg tggaaaacag aaagaagtcc acaccacagt   68820
gtgagagcta atttaatgtg ttcttcaaga aaaattaaat aaaacaatat gactcaattt   68880
ttcttttatg ttgcaagaaa aataacatttt atataaagct agtagtagaa agcagaagt    68940 atagcttagc tttctatgat ggcaagtgaa atagtttctg ctaatcaaag tgattctttt   69000
ttttttttcc tttgagacgg agtcttgctc tgtcgccagg ctggagtgca gtggcacgat   69060
ctcagctcac tgcaacctcc gcctcccagg ttcaagtgat tcccttgcct cagcctcccg   69120
aatagctggg actagaggca cgtgccacca cgcccagtta attttttgtat ttttagtaga   69180 gacgggtttt caccatgttg gccaggatgg tctcaatctc ttaacctcgt gatctgccct   69240
cctcggcctc ccaaagatcc gggattacag gtgtgagcca ccgtgcctgg ccatcaaagt   69300
gattcttagc cattttcttt gaaaatgtca gtcatagagg taggctctgt tgctcttcaa   69360 tgtataccttt cttttatata aaagcaattt gactaaatat tagatgtctg tgtgagtcgt   69420
gttctgctac tcaaaacact tcttgttctg ttcttctcta tattttgttt atttgtttgt   69480
tttttgagat ggaatcttgg tctgttgccc aggctggagt gcaatggcat gatctcggct   69540
cactgcaacc tccacctcct gggttcaagc gattctcctg cctcagcctc ccgagtagct   69600
gtgattacag gcgcccgcca ccatgcccag ctaattttttg tattttttag tagagatagg   69660
gtttcaccat gttggtcagg ctggtcttga actcttgacc tcaggtgatc cacctacctt   69720
ggcctcacaa agtgctggga ttacaggcat gagccacagc gcccaacctc ttctctgtat   69780
gtttattcag acattcatgt ttaagaattt ctgagaaagg aagccaaaga taataatacc   69840
tgacctctat gtctatatga tgaagaagtg cacttcctat gtaaagatgc ccgtattcct   69900
gattaggtta agcaacttga agttctagtg agggggcaaaa ctacaggact gcagaaactg   69960
gcatagcctt ttacacatgg cagcatttgt ctactgataa tggtgacaca acctccaaga   70020
gggcagacca cacggtgtat taagagaag ctgtccccat aagaaaaggg gaaagtaaa     70080 atgactcatt acatagtttg aaatctctta tgatgggtgg acaaaccct caaagaagaa    70140 attctccagt cttaaattgg gcttttaatg ttcgaggcaa gaacaagtct cctgatgagt   70200
acactgccat cgcctctttta acaatttagc tatgaaaata tgaaaatacg aggagactat   70260
agatttttat cttagattta cttcaaaatt aagcagtgag ggagcatgac taaaaataga   70320
aaaatgatga aagattaat taatgatact ttactatgtc tcagtggatg ggcagtccta    70380
ttacagctgg ggcagatgat ttcatctttc tgggcctcca tttccacatc tgtaaaacag   70440
gataattata tccatctcag agagctgttt ttaaaattac agatgacagg aaagtgaaac   70500
tgttttgaaa ataatgaagc tttctattac tgtgagatta ttaaaagatt attataacta   70560
gacatggtca atatgttttc ttcaaagtta tcagactaga catttttccc tctggtgatc   70620
tttcacccat atgtctcaat catactgaaa ttattcaaat cacttctttt ttctgttttc   70680
ctggtactag tttctctttt tcttttttct tttcctttct ctttttttttt tttttttttt  70740 ttttttttga gacaaagtct cgctctgttg cccaggctgg agtgcagtgg tgcgatatcg   70800
gatcactgca accactgtct cctgggttca agtgattctc ctggctcagc ttcctgagta   70860
gctgggatta taggcgtgtc ccaccactcc tagctaattt ttgtattttt agtaaagaca   70920
```

```
gggtttcacc atgttggtca ggctggtctc aaactcctga cctcgtgatc cgcctgcctc   70980
ggcctcccaa agtgctggga ttacaggcct gagccattgc actggctggt actagttttc   71040
tatctgcctg aagaagtacg caaatgacta ttttcatgac ttttttttt gcctttaata    71100 ttatttaaca gctattttaa caatgaaaga cattttacat attctcaaaa ggtatgtacc   71160
aaagaagggt gtgggcagaa atgttcacaa aatcaggacc tttcattgca tcttggtgac   71220
caccaataaa gtacacagaa acccatagtg aactgaggtc taagtggctg ctatcaacca   71280
acacaatctt gaactgctga gtctgatcat ttcattttct taaaacttca ggacagttca   71340
atttagagag cacaagagtg aagttagcct ccctggtcat ctaaagcaac atgggaaggt   71400
aatttaagaa aagtgacacc atatcaatca ctttcccaag cttttcaggg gctcactcca   71460
aagactttct tgatgataaa ttttattaaa gtgctgatca taatcaaaac agtacattgt   71520
atcagaggtc aagcattgtt tttcacttcc cttcccagaa cttattaaag atgtacctct   71580
gaagaaagac ataaggaaga acaaaattgt tttgactcac agaaaatggc ttacacagac   71640
atctaatact tagtcaagtt gcttatatat atgaaataag ttataccttg ggagtaacaa   71700
agccaatagg cttggctcat agggggctaa ctacggctgc agcagttatt caagaagtta   71760
acatattctc tcctgtcccc tgaagacacc acaggcatct cagtaataaa ctgataacaa   71820
ccaatactca agagtttgtg aaaatgcttt gtaaagtgct gaataatgta agtgattatc   71880
tacttaccac aaacgtcctc accaacatca tcattaaaat cttgaaagat aagtgctttt   71940
cagtagtttt gagagtgaac caatgacatg ctaaattaaa agcattatat ttcaaccatt   72000
tccaataagt gccacagaat attaagactt aagaatatta aaattctggt caggtgcagt   72060
ggcccatgcc tgtaatccca gcactttggg aagccgagga gggtggattg cctgaggtca   72120
gaagttcaag agcagcatgg ccaacatggc aaaaccctgt ctctactaaa aatacaaaaa   72180
ttagccaggt gtggtagtgg gcacctacaa tcccagctac tcgggaggct gaggcaggag   72240
aataacttga acccaggagg cagaggttgc agtgagctga ggtcgtgcca ttgtactcca   72300
gcctgggtga agaacaaa actctgtctc aaaaaaaaa aaaaaaaag aatattaaaa     72360 ttcttatttc atctccttt cctctataga tagagcaggt agggcactac cagtccaaat    72420
ctatgtaatg tgatgtcagt ggtagctcca gaattcccat agaggagtgg ctacatgggt   72480
gatgatctgg ctgaaaggga ggcaggcaac acagctggaa gctgtgcttg cacaagagaa   72540
cactacttgt ggtacctaga ctgcatgttt attcaggatg gatggggact atggtggacg   72600
agaaggctga aggccaaatt caagaccatc cttagaaacc cactcctatt aagcacccag   72660
gtaagaaagg cctcatattt aagtctcctt agcatgtatc attttaacag ggctttccaa   72720
aaagtacaac caggggtcac ctttgcaata tgggattatt taccctcagg taggtagaag   72780
agtatcttca gccactcttc attgcaccaa gacccttca gccatccctc ttccagcaat     72840
cccaatgact gaaatcatct atgactcata aagagaaaag gcaggagtga caaaaaattg   72900
tcctgcgtga gatggtgtga tttactttat gactttgcct ggtctctata gtcataatgc   72960
attgagcctt ctgcaaaaga ttcacacatg agagaataaa tgaatcaaag gcagagccag   73020
tgatggatgg aaaattaacc ttaacaccca cacaccacag ctccccaaaa ttcacagaaa   73080
ctaaagactg cagacagagc aagtctccac tgtaaagaac aatttacaca aagcagatca   73140
tacgagattt tccataagcc tatggttctg tcaaacaata ctacaggtgg ctttaagcca   73200
ttgacattta cacttggtgg tgaaaagcca tctgggagaa aaaaaaatag cactccccgc   73260
cttggatcta aaagcaagtt tcctcggcct ttaaaagcaa tgaattccaa acagcaacaa   73320
```

```
acaaaacaca taaacagaat tagtgagaat ctgtgctaag agctatggca aaatcagaca   73380
gaagtttctc cctcaaagag ttttcattct agtaagagtt ttgttttgtt ttgtttgttt   73440
tgagacagag tctcactctg tcgcctaggc tggagtgcag tggcgcgatc tcggctcact   73500
gcaaactccg cctcccaggt tcacgccatt ctcctgcctc agcctcccga gtagctggga   73560
ctacaggcac cgccaccac gcccagctaa tttttgtac ttttagtaga gacagggttt      73620
catcgtgtta gcgaggatgg tctcgatctc ctgacttcgt gatccgcccg cctcggcctc   73680
ccaaagtgct gggattacag gcataagcca ccacgcctgg ctagtaaaat agtttaaaac   73740
acacagagac agcacaggta gcttggcaaa caaggtcata tgaatgagaa tgcaaggctt   73800
gtcggagagg ctatgggcag gaaaaggaat cacagtggga tggataatca aggaaggccc   73860
actagaaaaa gtaacattta gaccaggcgt tatttcaaag ggtggagccg ttgtagggca   73920
caaatagaga atggtaaaac ttgggggggag gtggtggaga atggtcacaa gctaggaaat   73980
ttgtaagcaa aaaggatgtg tgaggcagct gggttcaagt ggaaccaggg catgagggat   74040
gtgaagggtg gaatagatga tgggcaagag gtttggcttc atctgtgcac gtagtcatca   74100
aactggtcct gtgtcccatc agcacaaggc actctcttag gagccaaggg acactgaggc   74160
agcccccatg ctcaaagaga agggaaggc catgtgatga tctaggattc ataaaatcca    74220
tggaaggctt tctaacagag gccagctatt caaaatgcca tctgggggga gatttaactg   74280
agggcaatgc ctgtgttatt gacagagaaa gaacaaaggg tgtccataag cagagaccaa   74340
ttaggtgatt tttacagatg acaaatataa gagttcaggt ttgtgttacg gtagcataat   74400
tcaagggcaa aaataaaacc aaatggttat agattttgcg taacttttct gatggataac   74460
ttaagatttg atgcaacagg aatcaccatg agatatgagt tgcaatggaa agttttatg    74520 tttttttttc ttgccaagta tagttcagat gtcaaaggca aagaaaaaaa agtcagaaaa   74580
taaaattatt tggaaacatc agaaactgct tgtaaggact ggttattgtg gctactgtta    74640
attaagagca ttaataactg acagggaccc ataattctgg aagacaaaag taactaagtc   74700
acaaaaagct gccttatgat attaaaataa aggagcaaat caatgaaaaa gcctacagtg   74760
gcactctcag aaaagtctaa aacaaatgtt gagcaattca agagaaattt attgggtctt   74820
cactgagcat cagacaaata agttcctcaa gacaaaagag gattaaaaaa tgttgaagag   74880
taaaaccact tcctgaaaac ctgtcatcga atcattaatt tattgggtac ctactttgta   74940
tagagcagag tgctacctat tttaagaaat gctgtggtat aatagctcca gaatgaatta   75000
gggcctacat atgtcaaggc aatctgtgag taaatgccta atgaggtaaa catgattaat   75060
gcagtgagtt cgatatagaa atgggtcctt ggggccggac acgatggctc gtgcctgtaa   75120
tcccagcact ttgggaggcc gaggcgggcg gatcacgagg tcaggagttt gagaccagcc   75180
tgaccaacat ggtgaaaccg tgtctctact aaaaatacaa caacaacaaa attagtcaag   75240
tgtgttggtg cacacctgta atcccagcta ctcaggaggc tgaagcagga gaatcgcttg   75300
aacccaggag gcagaggttg cagcgagccg agattgcgcc actgtacacc agcctgggca   75360
acagagcgag attccatctc aaaaaaaaaa aaaaacaag aaagaaaaa gaatgggtc     75420 cttgggttct acagttcacc atggtcaagg gatggacaat cagtggacaa aagactcatg   75480
aaggatgact ggggaaacag actggttaaa aactgactca tttagttgac ttgctaccag   75540
tgccttctgt cttctgctag ctttagttaa aacggcttag gaagagtcaa aagactctca   75600
taaaactaag ccaactcttc cttgaattct cctcttcttt attgacagaa acaagcctga   75660
tgtgatccac taaaaccact gcagatcatt tggctactct ttggaacatg ctttaatgct   75720
```

```
attacagcag tgttttcaa actgctatgt gtacaggaat cacctgggga ccttgtgaaa    75780
gtgtacattc tgttgcagta ggtctgggga gaggacccac aatcctcatt tccaataaat    75840
tctcagtgat gccagacctc ctgtaagcgg caaggtatta gaacatcttc agttgctgtt    75900
atcagaagat gataggaaac catcattttc ggggtcagaa tgctggagct caagctttgg    75960
gccttgatgc atataataac tcataaaatg taatattcag gaaggaatga ggctcctaaa    76020
gaagtgagaa agtagaatga acaaaggcct aagagaatag aaatgtattc taacaatata    76080
aattataaaa ataaaagtaa gagtgcccag gggtattgag attgttagat tattttataa    76140
tgatataact taagggattc caaaataatg aacataaaat gttattatta gattttttc     76200 cttttcacat acttgaagga caattatat catattgtct ttttttcttc cccaatacta    76260
tgagcgttag agaatgagac gcaaatccga tatgtagtaa caaggtagtc actcacagca    76320
aaagttgaaa gattcctagt ctacgctaac aagtgtctgc aaactctaca gaatgcaat    76380 tagaggttgc ggcagctact cccctgccta aaacagcagt ctgaaaactg ccaatctgtt    76440
gcaaattctg tcttttctga gaatatttta agaaaagtgg tagagaaata tttgaaaggc    76500
aacagaacac taattatatc tagacaagtt tccttttttt tttttcccaa aaaatatgaa    76560
agttccttta ggctttacat ctcctaggca tagcaaagca tttcataact ttctaccta    76620 ggaaaaattt tcacagacat tttaaccaat tcagaggaag gggagaatga aaataccata    76680
attaaccaaa gaggaataat attaccacca aaaccaagta agccttttat ttaggaagga    76740
gtgagctcta gctgaagtaa acatgctatt tagtcaggat gtatgctcag acacctgtag    76800
tcggaaattt tcaaaatagc tatggttttt tttcttctct ttttttaata gtagtcatct    76860
ccaatgaaca ccagtggaag tctgtggtat ttctcagttc tgacctgtca tgacttttgt    76920
tagttttcta ttttgattag ctaaagattt tctaactcaa cttcaatgat ttattctact    76980
aacaaaatag tacagggata acaagaatg aaatgttca gaagagaaaa tactggaaat    77040
cttatttagt ccaattcttg tcactgtata gaaggaaaat gagccccagt gggaagaaag    77100
acagcctggt cacccagaca cctagattcc tggtacaaca taccttagtc tttaccagct    77160
gtctcctagg tagagtcctt ctaatctcaa actaagggtc agagctaggt tatctttcat    77220
ccaagatgaa ggtttgtgat aattacatct ttgcaacttc ttttctactt ggcatggggc    77280
tctaaagtag gaaaatgatg aagggtttag ctaaacctgg aggaaaaata ttttggtttt    77340
gtgaaataac aatgcagatt tcagtctctg tttgcaatgg ggggaaggag gaagaggcat    77400
tttttaacat ttatttcta aaccaacaaa caaatcctac cattagtcaa agactcaggt    77460
ctttggaatc tgaagcttgt aaatttcagg ggcactcttt aagaagaaga atacaaaatt    77520
aagaataaag tgaatataaa attaagaata aagtgaatat ttatttagaa ttaaaatggc    77580
atacaggccg ggtgcagtgg cttacacctg taatcctaac actttgggag gcagaggtgg    77640
acaggttcct ctgagcccca gtgttcaaga ccagacttgg tacatagtaa gacaccatct    77700
ctacaaaaat taaaaacaa caaaaacaa aaaactggcc ggtcttggtg gtgcatgcct    77760
ttagtcccag ctactctaga ggactgcttg aacctaggac tccaaggctg cagtgagtta    77820
tgattatgca actgctttcc agactgagtg acagaatgag atctcatctc tggaaaaaaa    77880 atttaaata gtatcataca aacaacaaat ttttaaaagc tataaatact acaaatgaa     77940 agtgtttaaa aaacaaatat ttttattaac tgattgccat acctctgaaa taattctcct    78000
atattttttg gttgcacact ctttgatcat ctccttccaat aacatttgc aatattctct    78060 attgagagaa tagaaaaata attcagtctt cccctttagaa atgtagatca gaatttgtaa    78120
```

```
tttattcttg aataatttgg aaaagttcct ttcagcttca taattcatta caggtaatgt  78180
catataaatt ttttggattg acttcaaatt tggaaaactt ttatcaggtt tcttttatat  78240
gtgagctgta agattcaggg cactgcaaga tttcgtagta tttgacttga tgacacttgt  78300
taaccacatt gccagggcct ctcctagagc caggagatgg acctatacca gggtataggt  78360
agccttgaag gttaagttca agcacttcac agtaaatcca cctgagcctg gcatttatat  78420
cctcaacata tttgatgcat ctgtgaagtc tcccagtcct ttcaaataaa gtgcctgttt  78480
tactcagaat acctaaactt cctgatggca taattgttcc atgattcagc caagactgta  78540
tcacttgagg tatacacttc attttttccat tgagatcaca agacaggcat gatgtttgac  78600
tacctggtgt ataaaccgag tgttatttta ttacactaag aaaatgcaat gggataatat  78660
atgaagaatg ctaaaacact agaaaaatgt tggatattat tatttctctt aacctctagt  78720
cttccaacac ccatgctata atggacaagt agtttatgtc aattaaggca gactagtctc  78780
agtacagtat aacaattagg aatctagatc cccaaaccag accatcttgg ttccaacccc  78840
agcctaatca ttttctaact aggtggactt aggcaaattt attgactctg gaggatttat  78900
aataagcata atataaccta ccttctaaag ttgttttgag ggttaataca cctgaagtac  78960
tcagcatgat ccgtgcagta gcaagacctc aataagtggt agctactatg attattggga  79020
aattagtcca tgaagtctct tgagaaaagc tacaggggaa ataagcccaa tttcatttcc  79080
ctatgtagaa aagtttgcag gatttgggcg tgacaggtag tcatccacaa agcagcagtg  79140
ttatcgcccc ataggaaatg aagacttcgt aatgatttat actttaataa agagctgctg  79200
cagcatatac tgaaaatatg cacccaaccc atatcttctt tcaaaggcat tcatgttggt  79260
tcaaccaaat ccctagttct ctaaaatgaa gttttgacaa tcttatatct tctaaagcac  79320
tgagaagcct ttttccttgt tttctttaaa gaggcttgag aagaaccaag cctttttttg  79380
gttcaaataa aatatttaca ataggaggaa aaaacattca gataaacttc accttgcccg  79440
cctggtggtc tctcaataca cagaagaaat gcaactaggg cactaggaaa tctaaaaaaa  79500
aaaaaaaaaa aaggaaagaa aaaaagtata gagctaaagt tcacttcagg acaacgcaaa  79560
ctaagaaaaa ctacatttcc caaaggaaat agagcactat gtctacaaag taactcattt  79620
tttctttaat gttcaatgtt gtctattcca gggaaaaaat ggtacaatta accaaaactt  79680
atttctaccc aacatctctg caaaggaatg ttgctgctgc agatccaccc ccaacatggg  79740
aaggcccaag gcaagtgagc aaatagaggc ccatgtacca taagtcaaaa catttaaagt  79800
tacaaatcaa gctagcaaac tgctcaataa aataggtgtt atccttctac ctagactgac  79860
aaatatatct tttcaatgtc ttggaagacc aggtacaact ttagaactcc tacaatgttc  79920
atagtccttc cacagaaatg ggtggtttaa agagagacat catcctgagc cctggtaatc  79980
aatttgcctt cctccccccct gcctgctcca tcctacatca agaggggcct tgtgatatgt  80040
ggacacccaa gctcgctctc tgtctctctc tctctttctc tctctctctc tctctctctc  80100
tcacatacag acacacacac acacagagct atcccttaaa caaccctcgt gcagagattg  80160
cacaaccagt agcaatgaca gccttcagga agatggcttc aaggatccat gcaaactgca  80220
gataccagtt cagggccttc tggacagcga atgtgggttc ccacataacc aaatcatggt  80280
ctaaaaatga aaagagagta agactggaag gcccaaaagt cacctcaccc cataggcatg  80340
gctctgacca gagaagaatg acagcagagt accatctaag gcccaggaca gaggccagtt  80400
gtgttcatat actaggtcta tatttagtt gtagagctga aaaaaattgg aggaaaatat  80460
tccctcagaa aagagaagaa aaaaaaaaaa aaaaagagc tgcatgtctt gacctttccc  80520
```

```
agatagaatc tccccagtca taggtacggg ccctgaagct aaatctcatc taataatgat    80580
agcttcaaac ctacaaacaa aacacagatg ctagggaacc cttaagagtc taagcaggag    80640
gccataagta gactaaactg actacaccca agaggatagt tgctacttgt tgggtgctaa    80700
gacctagaaa gctgactgtg gcaagtaaaa ggcagaagta ctcctgatgt aatgggtgag    80760
gaagagaatc ttaacctcct ataagttttc aaattgtccc cttcaaaagt caaactgtcc    80820
ccttcttctt tgttatgttg gataaagtcg gctcttcttg ccctcatcag cagttgtaca    80880
cgattgtaca caaatgattg tcctacacac tcaaaatttg gggtttacaa tacacatctt    80940
tgcaaatggg gtatgtccaa ctgctataag tggccaaacc acaggtcacc caccatgagt    81000
cctaccacta agacaccatt gtcaaactgt gggctgtaga gtttccttat gcaaagaaac    81060
tctgccttat cttgattttc tgtggtacaa atgtagtcag gaaggaggca gataatgcaa    81120
gcaaaccaaa tcaattaaat caggagcact gaactgatga cattagatgg taagcttccc    81180
ctctctcaaa tctgatatcc attcacccct cttcagcctc cctcccaaca cacgcataca    81240
cacatagaga ccacacgaaa gaacctagca gcatgcaagc acaagaagct tgggccacac    81300
actcatacat gcacccaggc aaaactccag agagaccctg agcaggatcc atctttccat    81360
ccataaaata aagataataa aacttatctt ggagatttct tcctaggatt aaatgagata    81420
cataatatca agtggctgtc tcagggtagg ttctcaaatg ttaattgtct ttctcttcct    81480
tctccctgag atgagacaat ttgcctgtcc agcattccaa acccttggc atgccaagca     81540 aagaagtatg agtcattatc ttgcctcagt cacaagcaac aagtacctgt ggagcaaaat    81600
attaccagga aagtagagag tgcaaaagaa gcggtgagca ttcttgctgc gaatgcatat    81660
ctgttctact gaaaatcata acttaaatct gctgaagttg tacataagga cctggagggt    81720
agaagctaac aaggtaacag agttatgctt ttatgtggaa cttggccaaa taatgccatg    81780
ctgtagccag gaagtatgtt tcccctgcac cctatttaaa actgctttgg tggtttgcat    81840
cagacctaaa taatatccac gctactctag agtaggcagt ggtggctaca agaccacact    81900
tcccttcaac caacgctgct tcacccttat aaaccaaaac ataaaaccca atgaaaaaag    81960
aaacttaaaa aataaattta gatttttagca cttcattcgt aataaaattc tctttccgac    82020
acccttctat gaaaaaaaaa aaaaagagga atcagtatct actggataat tcctctggtg    82080
actttattta aaattttgca gtggctttca aggccctaca ctgattcaaa atttatggct    82140
aaaggaattg catgaaaact tctagcagct ttccatcatg tttgtcagaa gttgaaacat    82200 cttttccat atttcatgag aatacaagaa ccaattccat acttcaaaaa cagtcaaatt      82260
acttattgtg atcagaacta aaactattct aactgaaagt aaagatttta ctatttggac    82320
caaacaccta acaaacagtg actgcttagt taaatgctcg acctcagttg cattagatac    82380
agtaggatga agtggaggct cagctcagca cttcctgggt gctaaatgat gtgtcaggca    82440
ctgccagaga tcccagagat agaaaactga ataagattga gaggattaaa ggtataatgg    82500
gcaagagagt tacgtaaaga tatgactttg gcttggtatt gttaccagct aagtgagagg    82560
tctgtatctc ataggagaca tttacctcaa actgggacat tcaaagcagg tttcctcaag    82620
aagatgacac ttgaactacg tcttaaaaga tgagtgaaaa ttagccaggt agcaggagtt    82680
ccagacatcc tgaacaaagg aacagctgcc taaattgctc acattgtgtg tatgtgtagt    82740
gacacaaata gactgggaaa atgtgggctg tggtgggatg tgaagcagca gagtcaaatg    82800
ggaaccaggt cagaggcccc tggtaagccc aattaaggag ttaatagtaa taacagaagc    82860
tgatatttat tgagcattta ctatgttgca ggcaccatgt taaatacttt aaaacaatat    82920
```

```
tttatttaat cctcaccata actccataat cctcatttta caaatgagac cagggatgac   82980
tagtaggtaa agcaactaca acaggctaca cagccagtac atggcaagtg ggtctggaac   83040
ccaggacggc ctgattccaa agtttatacc ctacactctt ctaccaccag cctatcctca   83100
aagagagcac taaatgaacg cattgggtcc atcatgctgg ctatggaatg gagaatgcaa   83160
ttaaaggctg cccaactggg gctccgtgac aaggcaggga taggaaagag acaacaaatt   83220
gattcaaaaa tacattcaat gggacctaga aggaaacatt caacatgcac atcctcctag   83280
tgcatacaac aacaaaaaaa aatgaggctt tgaaaatga ggtgtagaaa ataaaacacc    83340
agtattccat aatgctttca aatataaaca gttaaaacac gtatccttt ctttacttat   83400
aacatgctcc cagctgttaa attcaatggc aaagaccagg tctgtcttat tcatctgaga   83460
tggtatccca ggtctgagca tcctgcctgg caagagatac tcaataaata tggttgaaaa   83520
ggtagaagaa aaaatgccca gttttttgcaa tgatatcaga ggtgccttat tgatccagag   83580
ttaaaaacta accttactga aaaaattaaa aagtcatgtt cataactgag tagaaaacat   83640
gtagtagtta tgttgactac atagacaaca gtcatcatta gggaatgcta cattgaaaag   83700
aaggcaatga gttcaaaatg tgattagtat tttgtataaa tcataactca ttaaaaataa   83760
gatgttgagt ggcctaaagg tggaaatgtg ttttatgag gcggaaaaaa agcacgagta    83820
gactgaagat cagatttggg gcctaatgat gtctagtctc ttaccctgac aaaataagca   83880
ggttattaaa gtgatgtgaa gaacctgatc actatgacac ttttacaaat tctttgtcct   83940
caataagaat ctatctactt ccaggaacct gaaaagtcat attttcaga cctgaagagt    84000
tattgtgcac tttacagttt tccccaaaag agtcatttct taattttgat catttaggaa   84060
gagtgaatct attaagtcaa aaacgaagaa aaaaaaactt tctatttctt agtgaaattt   84120
gttctttat ttaaatcctt tgcatactac taaacagaag tacagaagct actaaacaga    84180
agacagattt ttgggccttt ttaggtgacg taaaaggagc ttgttgttta ttaaacaatc   84240
tcattacctg atatattatc ttgcattaag atattttgaa aaaatgtttt cagtttacca   84300
attacgttag agaaattctg aaactattta cttacatgaa aaattaaaat gtaagtagaa   84360
ttaggtttct cgtcttcaat atatctgtct tcaaccattg gccaactttg aaaatttaat   84420
ttgaatcaaa tgaatacaaa ttcaaaatga ttcattaatt caaccatttt gaaacttcag   84480
ttctataaaa atatgaaatc tgtgggcctt gtaaaactgt ctaaatacc aaataaaaag    84540
ccaccacgtt tttaagctaa ttgtttaaaa gtgtgtatat tgatgaaatg aaagtgactc   84600
gtgaactatt gggtctggaa tttgcaaatc ataaaccta tccttgtaaa cagaacctaa    84660
ctaacaacat cagggcctgc taatttcctt cttttataat ctggaacaaa agttgtaatg   84720
atttttaaca tccacagaaa attaagggtg ccatttaaa tatttattag caaaatgtca    84780
cttaggtttt aaaagtctgg aggaaaatga gagacaattg aacattctgg tactgcaatg   84840
caggaaaaac gccaagaacg aaacactaag attttattaa aaccatagga ctcaaatgtg   84900
tgtcaagact ttttgcttgc aatagtgcct cttcctaatt tgattaaaag cttccatctc   84960
catgccacct tcaatgtatg ccataatttt taaaaagttc ccaatccact tcaaacactc   85020
taaaatttac aactgaccgt gatgcgcatt ttttctagac aaacctaaag gtaaatctgc   85080
ccatgtccct ggataaataa aatgagtgcc tccgggtgat gtggactgtc aactcctcta   85140
catttcatcc aaagtctaca tgggtcatct ccaagtcacc agaagagcca ggggaaagga   85200
ggggaggggc acgatacgta agatgttaaa catgaagatg atgtaaaatt acccagattc   85260
aagctggcca ttttacagat gaggaaacta aggcccagaa aaagctctat gacttgccca   85320
```

```
aatactcggt tacccagacc acagctgcag atactgttat ttggatcata gctgcaaaaa   85380
gtctaacttt tggccgggcg cggtggctca cgcctgtaat cccagcactt tgggaggcca   85440
aggtgggcgg atcacgaggt caagagatcg agaccaccct ggccaatatg gtgaaacccc   85500
gtctctacta aaaatacaaa aattagctgg gcgtggtggc acgcgcctgt aatcccagct   85560
actcgggagg ctaaggcagg agaatcgctt gaacccagag gcaaagttgc agtgagccga   85620
gattgcgcca ctgcactcca gcctggtgac agagcgagac tccgtctcca aaaaaaaaaa   85680
atctaacttt tgaagtctca gaggttttac actttccata acaaatagtt aagaacccccc  85740 attcctgcat gcatatatat attaatatta tatatattta tatatataat tatatatata   85800
tttatatata tataatatat atatatattt ttttatttt attttttcct taaaaacctt   85860
cagagacagc gatcaggtgg gtagcctagt taggatttta acccttcggt ttccaacaaa   85920
cgataattgc atagaaccat caactccctg aagacaggac tatcttgttc caggcaaaat   85980
ctacagcctc tagcacccag taggcattca gtgagggatt ctcggtttca cctgagcatc   86040
tccactccct atccatccat gccaaggcgt cagtggagcc agctaacttt cttttggaaa   86100
tcgattattt tcttgaaact tgtttccaaa aactccgggc caagaagccg gcctgaggga   86160
aagcgtggcc gtctccagga gctaaggact gaggagctgg cctttttgaac gggtggctca   86220 gaaagagctg ggtgggcacg cggcatcgcc atgggcggag tggcccaggt gcgctggctg   86280
ctttggcagc tcaggctgcc gctccgggcc gctgctcccc ggccgccttc agataaccaa   86340
cttctcaaac ttccctttcc ggggtgggg gctcgcctcg aacgcggcca acacaacgcc    86400
tttcctgctc gcacaaaggg gaccaaacgt gccccgcgcc ccttgcaact gaactttcct   86460 tctcttttc aagaaaaact cacaatccct gcagctacgg gagtcgggct gcgtgagtgt   86520
cgcgggggaa actttcctcg tttccgcccg ggggccgggt tgccgggccc gactgtcaag   86580
cgcagcggag aggcggggac cccaggaaga ccccgcgcgc cccgccgagc ccgggctggg   86640
gaccactcac ccgacttctg aacgtgcggt gggatcgtgc tggcgatacg cgtccacagg   86700
acgatgtgca gcggccacag gcccctgagc agccccgac ccatggcaga ccccgctgct    86760
cgtcatagac cgagccccca gcgcagcgga cggcgccttc ccggacccct ggctgcgcct   86820
ccgcgccgcg ccctctccgg accccgcgcc gggccggcag cgcagatgtg cgggccagat   86880
gtggcgcccg ctcgccagcc aggaggggc ctggaggccg gcgaggcgcg gggaggcccc    86940
cggcggccga gggaagctgc acaggagtcc ggctcctgtc ccgagcgggt gcacgcgcgg   87000
gggtgtcgtc gctccgtgcg cgcgagtgac tcactcaact tcaactcagc gctgcggggg   87060
aaacaggaaa ctcctcgcca acagctgggc aggacctctc tccgcccgag agccttctcc   87120
ctctcctcga cgtccagccc ctagctctct cgtagctgcc aatcatgttt cctagaccag   87180
cccctccgag agctttggcc gactttcagc tgcccctcac cgccctccca caccactcag   87240
gagttcctcg ctccaagtat ttactcaaga atgactaagt gcacacagtt cacaaagtaa   87300
caacagaaaa cgtccacgtt ttccctagta gatcagaaca tctgccgcct cccctcagct   87360
ttcttcagat tgctcctagg tgctttagag atgcgttttc aaattgcaag ttgagatcca   87420
ggagtgaata ctccaatcta ttgagtcgcg agcacatttc tttcccaaat aaaatagtaa   87480
cggtaaattc tacttcatta aatttgtgct tcagttgtgt ctatatgcat gtatgtatgt   87540
gcatacactg tcaagttgta aaatgttttt ctttaggtcg aagtctagag gttttttctca  87600 agttttaatg tacatattga tcacctggaa atcttattta aaaatgcaga ttctaattca   87660
gtaggtctag gaggcaggca gagattctgc atttctaatg agcacctgga tagagcgtcc   87720
```

```
cattttgcac cgcctcttcc cgggactgag tcagtgagta attgtaaatg atcacctatc    87780
acgaagtgat agtggtggga aatgtaattt tcagaatgta tagagtatag cagaaactgt    87840
aaaattaaaa gtgggttggg agtcacctga atgcttgtgc ttttattccc ttaatgcagg    87900
tgaagaaaga gaatacttac cctctcatgt gcaaacgggg taacatggga gcagaacagc    87960
ataaactttc aaatttcctt tcttgctagg gcaaccagat ttgcccaaga cattcctggt    88020
gtacatgttt tgtagtttaa atattaatag aaccccctttt ctctttcaga tatgtcctga   88080
ttggataata aactatgtga tcaacctact tcccactctc aaagatatga ttctgtacag    88140
ccctctggtc agtagatctt ctagcaattc atttaatgaa ttcctttacc tgagaggaag    88200
attgcagagg caagggtttg tgccagggtc tccaggaat aaaggtaaat agccctcccc     88260
caaacccaac tcccaaatct ttcctgtcat tctaagtgtt catttgcttc atcctggaat    88320
tttaactcat gctccaccta gcacccaagc tgcctctgga tgttttgcca cttcccagta   88380
ctcatgttga agatgcagaa agtgcagtga aatcaggagg gctaggcatc ttcttttccca  88440 ccaattaatt gccttgccaa agctggagtg actttgtcaa tggaggaaga ttgagttcca   88500
aatcttctcc ctattccctc ttctgccacc agcccatgcc actgccatgg cttgtgtagg   88560
agtctcccag gagtcaccct cagccacggc cgttctgggc tctttcactc agtttctcaa   88620
acgagagctg aattcagctt ttcaaaatac aaaactagtt ataccaaccc tctgattaaa   88680
atcatttaat ggcttcccac tgctcttgag ataaagagaa gataaaaacc agatccttga   88740
acgtgtcttc aagcctccaa ctctcccgta aactttcatt tggcttctcc ttgcttactg   88800
aaagccttct ccaaatttcg tgaatatgcc tctgtaatcc tcctacccctt tatgcttaga  88860 gccttcccca gtgtggactt ccttcctctg accttttttt cttcacccag ccaactcctg   88920
gtcttcgtgg attgaatcat aacttctttg atgggcaagc tttccctcac ctccatgagt   88980
agatcttgta ttacacgttc tcttggcacc atat                                89014

<210> SEQ ID NO 2
<211> LENGTH: 4636
<212> TYPE: DNA
<213> ORGANISM: Homo sapiens

<400> SEQUENCE: 2 ttttttttttt tttttctag gaatgggaac aggaggcagg atgctcacct gagtattttg     60
ctttattcaa tctaataaac attttatttta tgtaaaagac aaacaatgca tagaataaaa   120
ataagtgctt gagacttttg atataaaaag agtatatagc attcacattc ctattttaat   180
acatgagtac agctgaagtg ttccataaaa gaataaaact ttcccttttat gtatagtagt   240 gaaaaaagtc agtattttta ggaactacag aatgttattc cttggtcttt tttcttgaat    300
aagaaaaaaa aacataaaca aaacaagcca cagtatcctc tgacactaca ttccagttta    360
tgctgataac ccagaagtga gaatactctt gaatcttgaa tatctcatga atggaccagt    420
attctagaaa ctcaccacta gaggtcaatg ggcaacagct attgggatgg tatcagcatg   480
ccctacggtg caagtggaat ttctaggcgc ctctatgcta ctgcagccac actgtctttta   540 actctcagcc caccccacact gaggagggtg cctagaggtt ctatttccaa acctttgcat   600
gtatcttaaa aatctcaata aaatgagacc ttccaccatc caaacagagc tgatattctc    660
actaccagtc cctctctaat attcctattt ggctgaaaat aagtagcttc aaaaagtttt    720
aaaaaagaga ttcttgcag cattaacact tctttgttga ttaacaagtt tcctatggag    780 tttttaaagct catactttgt tcttgtcctt gtggacacaa attttctaac tgcaaatggg   840
```

```
acctttgtgt cccacattca aatcctctct agtaatttct gcaaaggttg agaaggctgg    900
catgatggag agaacggtaa ccatgaggaa agcttcttgg agtaaagcac tcctctctcc    960
aatgcagagg gtaaaactat taacatataa gcaaaagaaa cttgggctaa ctgagaccct   1020
taaaggagtt cccctttagt ccaataaaag gccaacttca atcttaaca ccagataagg    1080
tagtcaaaat catattatat acccagagaa tgactgcttg aatggacatt tcttacaagg   1140
gaccttggtt aggtgcagat ttaattccta gactgggtcc aggtaggcag tggaaagagc   1200
taatgtttac agtgagaagt gaggcagctt tgtaagtgtc tccacacctt cacattttgt   1260
gaacgtggac tggagataac tgaaaaccat ctgctatcct tacctgggga tccagatttt   1320
cctgcaaaat ctccaaatat ttataaagtg gcttcacttt ttgaaacgct gtgctgacca   1380
aacaaaacat atgtttagag tgcctgaggt catagtcctg acaatgatag tattgtgtag   1440
ttgaaatcct cttcatcagg ccaaactgtg cttgagcaat caggagccca gaaagatgga   1500
acccattggt gtttgtatag aaaactagaa aatcaagtca agtgtaatga aaagtaaac    1560
acgataaagc ctagagtgag aatttgctcc ttttagaaa aggatgaagg ctgggagcag    1620
agaatagtaa cataagtgca ggggaaagat gaaaaaaga acaattttc attagtagat     1680
ggtggggcaa tcgcatggat ggggacatct gttctgattt ttctgcaacc catgaaggta   1740
aaagtgggg ttcaaaacat tcaaggtatt aaagatgggg tagagtttct aaactaggtt    1800
gagggagagt ttctaaacta gccccccaga tttgggcctt ggagcttaaa tgaaaagtcc   1860
aggagaaata agggcacaca ggaaccccgg gaacactggt cctcaaacag tgccactgta   1920
cttagttcca tggccagaag agaagtgcta ggcagggaat gattattttg caaaagcaag   1980
tgcaatgtgg tcatagctgg ctgtgagaca tggagcctct ttcctcatgc aaagttcact   2040
gttttacagt cagagaacca ctgcatgtgt gattgtcaaa tgctaatgct gtcatgggtc   2100
ccttccttct ctgcttggtt ctggagttct ccaataaaac caatttcctg gaatatttg    2160
atgttttcc ttgtctcttt tcaaggtatg ctatatata tagagctata gacatatata     2220
gatatatata tatatatata aaacatagct attcatattt atatacaggc attaataaag   2280
tgcaaatgtt attggctatt gtaaaaatca atctcatttc ctgaggaagt gctaacacag   2340
cttatcctat gacaatgtca aaggcataga atgctctatg tcacccactc cctgctgctg   2400
ttgtttctgc ttatccccac agcttacagg gaggggagtg accccttgg ttttccagga    2460
agcatcagtt caggggcagc ttcctgctgc ctctgttctt tggtgagagg gcagcctctt   2520
tggacatggc ccagcctgcc ccagaagagc tatttggtag tgtttaggga gccgtcttca   2580
ggaatcttct cctccgagca gctcctcccc gagagcctgt ccagatgctc cagctcactg   2640
aagcgttctg ccacacactg ggctgtgaga cgggcctctg ggtcgtggtc ccagcactca   2700
gtcaacgtct cacacaccat ctggatgccc tggtggttga gccagaagct gggaatttct   2760
ggtcgccctc gatctctcaa cacgttgtcc ttcatgcttt cgacacaggg gtgctcccgc   2820
accttggaac caaatggagg ctcataatct tttacttctc ccactgcatt acagcgagat   2880
gtcatttccc agagcaccag agccatggag tagacatcgg tctgcttgaa ggactcaaca   2940
ttctccaaat tcatcctgga ttctaggact tctggagcca tgtatcttgc agttcccacc   3000
tgcccactgt tagccaggtc atccacagac agagtagggt ccagacgcag ggaaagccca   3060
aagtcacaca gcagcaggt taggtcgttc ttcacgagga tattggagct cttgaggtcc    3120
ctgtgcacga tgggcatctt gggcctccca catggagtgt gatcactgtg gaggtgagca   3180
atccccgggc gagggagct gcccagcttg cgcaggtcct cccagctgat gacatgccgc    3240
```

-continued

```
gtcaggtact actgtaggtt gcccttggcg tggaaggcgg tgatcagcca gtattgtttc    3300
cccaactccg tcttccgctc ctcagccgtc aggaactgga gtatgttctc atgcttcaga    3360
ttgatgtctg agaagatgtc cttctctgtc ttccaagagg catactcctc atagggaaag    3420
atcttgactg ccactgtctc aaactgctct gaagtgttct gcttcagctt ggccttatag    3480
acctcagcaa agcgaccttt ccccaccagg gtgtccagct caatgggcag cagctctgtg    3540
ttgtggttga tgttgttggc acacgtggag ctgatgtcag agcggtcatc ttccaggatg    3600
atggcacagt gctcgctgaa ctccatgagc ttccgcgtct tgccggtttc ccaggttgaa    3660
ctcagcttct gctgccggtt aacgcggtag cagtagaaga tgatgatgac agatatggca    3720
actcccagtg gtggcaggag gctgatgcct gtcacttgaa atatgactag caacaagtca    3780
ggattgctgg tgttatattc ttctgagaag atgatgttgt cattgcactc atcagagcta    3840
caggaacaca tgaagaaagt ctcaccaggc ttttttttt ccttcataat gcactttgga    3900
gaagcagcat cttccagaat aaagtcatgg taggggagct tggggtcatg gcaaactgtc    3960
tctagtgtta tgttctcgtc attctttctc catacagcca cacagacttc ctgtggcttc    4020
tcacagatgg aggtgatgct gcagttgctc atgcaggatt tctggttgtc acaggtggaa    4080
aatctcacat cacaaaattt acacagttgt ggaaacttga ctgcaccgtt gttgtcagtg    4140
actatcatgt cgttattaac cgacttctga acgtgcggtg ggatcgtgct ggcgatacgc    4200
gtccacagga cgatgtgcag cggccacagg cccctgagca gccccgacc catggcagac     4260 cccgctgctc gtcatagacc gagcccccag cgcagcggac ggcgccttcc cggacccctg    4320
gctgcgcctc cgcgccgcgc cctctccgga ccccgcgccg ggccggcagc gcagatgtgc    4380
gggccagatg tggcgcccgc tcgccagcca ggagggggcc tggaggccgg cgaggcgcgg    4440
ggaggccccc ggcggccgag ggaagctgca caggagtccg gctcctgtcc cgagcgggtg    4500
cacgcgcggg ggtgtcgtcg ctccgtgcgc gcgagtgact cactcaactt caactcagcg    4560
ctgcggggga aacaggaaac tcctcgccaa cagctgggca ggacctctct ccgcccgaga    4620
gccttctccc tctcca                                                   4636
```

<210> SEQ ID NO 3
<211> LENGTH: 16
<212> TYPE: DNA
<213> ORGANISM: Artificial sequence
<220> FEATURE:
<223> OTHER INFORMATION: antisense oligonucleotide

<400> SEQUENCE: 3
cagcccccga cccatg                                                    16

<210> SEQ ID NO 4
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 4
gctgatgcct gtcacttgaa                                                20

<210> SEQ ID NO 5
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 5
gccatggagt agacatcggt                                           20

<210> SEQ ID NO 6
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 6
gcaacagcta ttgggatggt                                           20

<210> SEQ ID NO 7
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 7
gtgcagggga aagatgaaaa                                           20

<210> SEQ ID NO 8
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 8
gtatcagcat gccctacggt                                           20

<210> SEQ ID NO 9
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 9
ggatccagat tttcctgcaa                                           20

<210> SEQ ID NO 10
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 10
ggagaagcag catcttccag                                           20

<210> SEQ ID NO 11
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 11
gagctcttga ggtccctgtg                                           20

<210> SEQ ID NO 12
<211> LENGTH: 20

```
<212> TYPE: DNA
<213> ORGANISM: Artificial sequence
<220> FEATURE:
<223> OTHER INFORMATION: antisense oligonucleotide

<400> SEQUENCE: 12
gagaccttcc accatccaaa                                                    20

<210> SEQ ID NO 13
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 13
tagctggctg tgagacatgg                                                    20

<210> SEQ ID NO 14
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 14
ttttgaaacg ctgtgctgac                                                    20

<210> SEQ ID NO 15
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 15
tcagccagta ttgtttcccc                                                    20

<210> SEQ ID NO 16
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 16
tcacacaggc agcaggttag                                                    20

<210> SEQ ID NO 17
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 17
tcaggaatct tctcctccga                                                    20

<210> SEQ ID NO 18
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 18
tggtagtgtt tagggagccg                                                    20
```

<210> SEQ ID NO 19
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 19
tatccccaca gcttacaggg                                                 20

<210> SEQ ID NO 20
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 20
agcctctttc ctcatgcaaa                                                 20

<210> SEQ ID NO 21
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 21
atgtcatttc ccagagcacc                                                 20

<210> SEQ ID NO 22
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 22
aggaatcttc tcctccgagc                                                 20

<210> SEQ ID NO 23
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 23
agccatggag tagacatcgg                                                 20

<210> SEQ ID NO 24
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 24
atgctactgc agccacactg                                                 20

<210> SEQ ID NO 25
<211> LENGTH: 20
<212> TYPE: DNA
<213> ORGANISM: Artificial sequence
<220> FEATURE:
<223> OTHER INFORMATION: antisense oligonucleotide

```
<400> SEQUENCE: 25
ccttctctgc ttggttctgg                                              20

<210> SEQ ID NO 26
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 26
ccaggagaaa taagggcaca                                              20

<210> SEQ ID NO 27
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 27
cagcagctct gtgttgtggt                                              20

<210> SEQ ID NO 28
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 28
cccactgtta gccaggtcat                                              20

<210> SEQ ID NO 29
<211> LENGTH: 24
<212> TYPE: DNA
<213> ORGANISM: Artificial  sequence
<220> FEATURE:
<223> OTHER INFORMATION: antisense oligonucleotide

<400> SEQUENCE: 29
cagcccccga cccatggcag accc                                         24

<210> SEQ ID NO 30
<211> LENGTH: 23
<212> TYPE: DNA
<213> ORGANISM: Artificial  sequence
<220> FEATURE:
<223> OTHER INFORMATION: antisense oligonucleotide

<400> SEQUENCE: 30
cagcccccga cccatggcag acc                                          23

<210> SEQ ID NO 31
<211> LENGTH: 22
<212> TYPE: DNA
<213> ORGANISM: Artificial sequence
<220> FEATURE:
<223> OTHER INFORMATION: antisense oligonucleotide

<400> SEQUENCE: 31
cagcccccga cccatggcag ac                                           22

<210> SEQ ID NO 32
<211> LENGTH: 21
```

```
<212> TYPE: DNA
<213> ORGANISM: Artificial sequence
<220> FEATURE:
<223> OTHER INFORMATION: antisense oligonucleotide

<400> SEQUENCE: 32
cagcccccga cccatggcag a                                         21

<210> SEQ ID NO 33
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 33
cagcccccga cccatggcag                                           20

<210> SEQ ID NO 34
<211> LENGTH: 19
<212> TYPE: DNA
<213> ORGANISM: Artificial sequence
<220> FEATURE:
<223> OTHER INFORMATION: antisense oligonucleotide

<400> SEQUENCE: 34
cagcccccga cccatggca                                            19

<210> SEQ ID NO 35
<211> LENGTH: 18
<212> TYPE: DNA
<213> ORGANISM: Artificial sequence
<220> FEATURE:
<223> OTHER INFORMATION: antisense oligonucleotide

<400> SEQUENCE: 35
cagcccccga cccatggc                                             18

<210> SEQ ID NO 36
<211> LENGTH: 17
<212> TYPE: DNA
<213> ORGANISM: Artificial sequence
<220> FEATURE:
<223> OTHER INFORMATION: antisense oligonucleotide

<400> SEQUENCE: 36
cagcccccga cccatgg                                              17

<210> SEQ ID NO 37
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 37
gcagcccccg acccatggca gacc                                      24

<210> SEQ ID NO 38
<211> LENGTH: 23
<212> TYPE: DNA
<213> ORGANISM: Artificial sequence
<220> FEATURE:
<223> OTHER INFORMATION: antisense oligonucleotide

<400> SEQUENCE: 38
gcagcccccg acccatggca gac                                       23
```

<210> SEQ ID NO 39
<211> LENGTH: 22
<212> TYPE: DNA
<213> ORGANISM: Artificial sequence
<220> FEATURE:
<223> OTHER INFORMATION: antisense oligonucleotide

<400> SEQUENCE: 39
gcagcccccg acccatggca ga                                    22

<210> SEQ ID NO 40
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 40
gcagcccccg acccatggca g                                     21

<210> SEQ ID NO 41
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 41
gcagcccccg acccatggca                                       20

<210> SEQ ID NO 42
<211> LENGTH: 19
<212> TYPE: DNA
<213> ORGANISM: Artificial sequence
<220> FEATURE:
<223> OTHER INFORMATION: antisense oligonucleotide

<400> SEQUENCE: 42
gcagcccccg acccatggc                                        19

<210> SEQ ID NO 43
<211> LENGTH: 18
<212> TYPE: DNA
<213> ORGANISM: Artificial sequence
<220> FEATURE:
<223> OTHER INFORMATION: antisense oligonucleotide

<400> SEQUENCE: 43
gcagcccccg acccatgg                                         18

<210> SEQ ID NO 44
<211> LENGTH: 17
<212> TYPE: DNA
<213> ORGANISM: Artificial sequence
<220> FEATURE:
<223> OTHER INFORMATION: antisense oligonucleotide

<400> SEQUENCE: 44
gcagcccccg acccatg                                          17

<210> SEQ ID NO 45
<211> LENGTH: 24
<212> TYPE: DNA
<213> ORGANISM: Artificial sequence
<220> FEATURE:
<223> OTHER INFORMATION: antisense oligonucleotide

```
<400> SEQUENCE: 45
agcagccccc gacccatggc agac                                              24

<210> SEQ ID NO 46
<211> LENGTH: 23
<212> TYPE: DNA
<213> ORGANISM: Artificial sequence
<220> FEATURE:
<223> OTHER INFORMATION: antisense oligonucleotide

<400> SEQUENCE: 46
agcagccccc gacccatggc aga                                               23

<210> SEQ ID NO 47
<211> LENGTH: 22
<212> TYPE: DNA
<213> ORGANISM: Artificial sequence
<220> FEATURE:
<223> OTHER INFORMATION: antisense oligonucleotide

<400> SEQUENCE: 47
agcagccccc gacccatggc ag                                                22

<210> SEQ ID NO 48
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 48
agcagccccc gacccatggc a                                                 21

<210> SEQ ID NO 49
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 49
agcagccccc gacccatggc                                                   20

<210> SEQ ID NO 50
<211> LENGTH: 19
<212> TYPE: DNA
<213> ORGANISM: Artificial sequence
<220> FEATURE:
<223> OTHER INFORMATION: antisense oligonucleotide

<400> SEQUENCE: 50
agcagccccc gacccatgg                                                    19

<210> SEQ ID NO 51
<211> LENGTH: 18
<212> TYPE: DNA
<213> ORGANISM: Artificial sequence
<220> FEATURE:
<223> OTHER INFORMATION: antisense oligonucleotide

<400> SEQUENCE: 51
agcagccccc gacccatg                                                     18

<210> SEQ ID NO 52
<211> LENGTH: 24
```

```
<212> TYPE: DNA
<213> ORGANISM: Artificial sequence
<220> FEATURE:
<223> OTHER INFORMATION: antisense oligonucleotide

<400> SEQUENCE: 52
gagcagcccc cgacccatgg caga                                    24

<210> SEQ ID NO 53
<211> LENGTH: 23
<212> TYPE: DNA
<213> ORGANISM: Artificial sequence
<220> FEATURE:
<223> OTHER INFORMATION: antisense oligonucleotide

<400> SEQUENCE: 53
gagcagcccc cgacccatgg cag                                     23

<210> SEQ ID NO 54
<211> LENGTH: 22
<212> TYPE: DNA
<213> ORGANISM: Artificial sequence
<220> FEATURE:
<223> OTHER INFORMATION: antisense oligonucleotide

<400> SEQUENCE: 54
gagcagcccc cgacccatgg ca                                      22

<210> SEQ ID NO 55
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 55
gagcagcccc cgacccatgg c                                       21

<210> SEQ ID NO 56
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 56
gagcagcccc cgacccatgg                                         20

<210> SEQ ID NO 57
<211> LENGTH: 19
<212> TYPE: DNA
<213> ORGANISM: Artificial sequence
<220> FEATURE:
<223> OTHER INFORMATION: antisense oligonucleotide

<400> SEQUENCE: 57
gagcagcccc cgacccatg                                          19

<210> SEQ ID NO 58
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 58
tgagcagccc ccgacccatg gcag                                    24
```

<210> SEQ ID NO 59
<211> LENGTH: 23
<212> TYPE: DNA
<213> ORGANISM: Artificial sequence
<220> FEATURE:
<223> OTHER INFORMATION: antisense oligonucleotide

<400> SEQUENCE: 59
tgagcagccc ccgacccatg gca                                    23

<210> SEQ ID NO 60
<211> LENGTH: 22
<212> TYPE: DNA
<213> ORGANISM: Artificial sequence
<220> FEATURE:
<223> OTHER INFORMATION: antisense oligonucleotide

<400> SEQUENCE: 60
tgagcagccc ccgacccatg gc                                     22

<210> SEQ ID NO 61
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 61
tgagcagccc ccgacccatg g                                      21

<210> SEQ ID NO 62
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 62
tgagcagccc ccgacccatg                                        20

<210> SEQ ID NO 63
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 63
ctgagcagcc cccgacccat ggca                                   24

<210> SEQ ID NO 64
<211> LENGTH: 23
<212> TYPE: DNA
<213> ORGANISM: Artificial sequence
<220> FEATURE:
<223> OTHER INFORMATION: antisense oligonucleotide

<400> SEQUENCE: 64
ctgagcagcc cccgacccat ggc                                    23

<210> SEQ ID NO 65
<211> LENGTH: 22
<212> TYPE: DNA
<213> ORGANISM: Artificial sequence
<220> FEATURE:
<223> OTHER INFORMATION: antisense oligonucleotide

```
<400> SEQUENCE: 65
ctgagcagcc cccgacccat gg                                                  22

<210> SEQ ID NO 66
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 66
ctgagcagcc cccgacccat g                                                   21

<210> SEQ ID NO 67
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 67
cctgagcagc ccccgaccca tggc                                                24

<210> SEQ ID NO 68
<211> LENGTH: 23
<212> TYPE: DNA
<213> ORGANISM: Artificial sequence
<220> FEATURE:
<223> OTHER INFORMATION: antisense oligonucleotide

<400> SEQUENCE: 68
cctgagcagc ccccgaccca tgg                                                 23

<210> SEQ ID NO 69
<211> LENGTH: 22
<212> TYPE: DNA
<213> ORGANISM: Artificial sequence
<220> FEATURE:
<223> OTHER INFORMATION: antisense oligonucleotide

<400> SEQUENCE: 69
cctgagcagc ccccgaccca tg                                                  22

<210> SEQ ID NO 70
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 70
ccctgagcag ccccgaccc atgg                                                 24

<210> SEQ ID NO 71
<211> LENGTH: 23
<212> TYPE: DNA
<213> ORGANISM: Artificial sequence
<220> FEATURE:
<223> OTHER INFORMATION: antisense oligonucleotide

<400> SEQUENCE: 71
ccctgagcag ccccgaccc atg                                                  23

<210> SEQ ID NO 72
<211> LENGTH: 24
```

```
<212> TYPE: DNA
<213> ORGANISM: Artificial sequence
<220> FEATURE:
<223> OTHER INFORMATION: antisense oligonucleotide

<400> SEQUENCE: 72
cccctgagca gcccccgacc catg                                              24

<210> SEQ ID NO 73
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 73
atgtgaagat gggcaagacc                                                   20

<210> SEQ ID NO 74
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 74
atctccatgt gaagatgggc                                                   20

<210> SEQ ID NO 75
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 75
aacggcctat ctcgaggaat                                                   20

<210> SEQ ID NO 76
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 76
aacatcgtcg agcaatttcc                                                   20

<210> SEQ ID NO 77
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 77
aatccaactc ctttgcccett                                                  20

<210> SEQ ID NO 78
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 78
aaacctgagc cagaacctga                                                   20
```

```
<210> SEQ ID NO 79
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 79
agggcgatct aatgaagggt                                               20

<210> SEQ ID NO 80
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 80
agtgcacaga aaggacccac                                               20

<210> SEQ ID NO 81
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 81
acactggtcc agcaatgaca                                               20

<210> SEQ ID NO 82
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 82
ttcctgttga ctgagttgcg                                               20

<210> SEQ ID NO 83
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 83
cactctgtgg tttggagcaa                                               20

<210> SEQ ID NO 84
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 84
caaggccagg tgatgacttt                                               20

<210> SEQ ID NO 85
<211> LENGTH: 20
<212> TYPE: DNA
<213> ORGANISM: Artificial sequence
<220> FEATURE:
<223> OTHER INFORMATION: antisense oligonucleotide
```

<400> SEQUENCE: 85
cacactggtc cagcaatgac                                          20

<210> SEQ ID NO 86
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 86
ctgacaccaa ccagagctga                                          20

<210> SEQ ID NO 87
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 87
ctctgccatc tgtttgggat                                          20

<210> SEQ ID NO 88
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 88
tcaaaaaggg atccatgctc                                          20

<210> SEQ ID NO 89
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 89
tgacaccaac cagagctgag                                          20

<210> SEQ ID NO 90
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 90
tgatgccttc ctgttgactg                                          20

<210> SEQ ID NO 91
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 91
ttcctgttga ctgagttgcg                                          20

<210> SEQ ID NO 92
<211> LENGTH: 20

```
<212> TYPE: DNA
<213> ORGANISM: Artificial sequence
<220> FEATURE:
<223> OTHER INFORMATION: antisense oligonucleotide

<400> SEQUENCE: 92
ttctccaaat cgacctttgc                                              20

<210> SEQ ID NO 93
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 93
ggagagttca ggcaaagctg                                              20

<210> SEQ ID NO 94
<211> LENGTH: 1512
<212> TYPE: DNA
<213> ORGANISM: Homo sapiens

<400> SEQUENCE: 94
ttacattttg atgccttcct gttgactgag ttgcgataat gttttcttaa tccgcaatgc    60
tgtaagccta gctgctccat tggcatacca acattctctc ataatttag ccattactct    120 caaggcttca cagctctgcc atctgtttgg gatatttggc cttaacttct gttcacaaac   180 aactttctc atttcttcaa ctgatgggtc agaaggtaca agatcataat aaggcagttg    240
gtaatcttca tgaattccac caatggaaca tcgtcgagca atttcccaga atactaagcc   300
cattgcatag atgtcagcac gtttgaagga ttcaaaatgt ttcatattta tggaatcatc   360
gagaacttca ggggccatgt accttttgt tcccactctg tggtttggag caatatcaat    420
ggtatctgtg gctgaatcat gtcttactgc cagtcctaag tctgcaatac agcaagttcc   480
attcttcttt accaagatat tctttgattt caaatctcta tgagcaatgg ctggctttcc   540
ttgggtacca acaatctcca tgtgaagatg ggcaagaccg ctcgccgtgg acagagcaag   600
ttttatcatt ccttccacag taactgtgta tctgtttaag taatcaaaaa gggatccatg   660
ctcatgataa tctgacacca accagagctg agtccaagta ccattgtctt tattgtctgc   720
tgctataaat cccaggatgt tttcatgacg taacattaca gtttgataaa tctctgcctc   780
acggaaccac gaacgttctt ctctagagga gaatatctta acagcaactt cttctccccg   840
ccactttcct ctccaaactt ctccaaatcg accctttgcca atgctttctt gtaacacaat   900
agttctcgca attgttctct gaacaagcaa tggtaaacct gagccagaac ctgacgttgt   960
catatcataa attaagtctt tcaacgtagt accctctgaa ataaagggc gatctaatga   1020 agggtcctct tcattggca ctcgatggtg aatgacagtg cggttgtggc agatatagac    1080
catcaacatg agtgagatgc agacgaagca cactggtcca gcaatgacag ctgccagttc   1140
cacaggacca aggccaggtg atgactttac agtagttgga agttctattt tattgcaatg   1200
gtcctgattg cagcaatatg ttgtagtcac agacccagtt tttgaagagg gtgcacatac   1260
aaacggccta tctcgaggaa ttaagtcaat ttcagctata cacatgctgt tgtgtataac   1320
tttgtctgtg gtctctgtga cagagacaaa gcagagccca tctgtcacac aagtaaaatt   1380
gtcttttgta cagaggtggc agaaacactg taacgccgtc gccccgggga gcagcgccgc   1440
cgccgccgcc gccgccgccg ccagcacgag gaggagcagc cggggacgcg gagcagcgac   1500
cgccgcctcc at                                                      1512
```

<210> SEQ ID NO 95
<211> LENGTH: 2308
<212> TYPE: DNA
<213> ORGANISM: Homo sapiens

<400> SEQUENCE: 95

| | | | | | |
|---|---|---|---|---|---|
| aaacactata | ggttttaaca | tagagacttt | cagcaattct | actcatttcc | attagaaaga | 60 |
| cacagaagtg | gcacttactg | gtatagtaca | atcccatttt | gaaggcatgt | aatgttctga | 120 |
| ataagtgaaa | gaacaataat | agtatacaaa | atacaattgc | atgaattatg | ttcctcacta | 180 |
| ctatatgagg | tcattttttag | actcaagata | agagttttat | aagtgttagt | tttaagatcc | 240 |
| tgaaaaacta | tagaacagta | cattcaaagt | ctgaatcaag | gaaactctag | tggttcagaa | 300 |
| tcctctgaga | atgtactaac | caggagtaaa | tcactttctt | tagtaataag | acatgtttca | 360 |
| ttgtaattca | gcaatccaac | tcctttgccc | ttaaagatga | tctccagcac | agcagagtta | 420 |
| cctaaagtta | agaccagcaa | tcatcttttt | aaaaaacaag | ttttgttaat | aaaaaataaa | 480 |
| ggtagactac | acattttctg | tcctgggaaa | gaagcgttca | tagtgcacag | aaaggaccca | 540 |
| catggctgtt | tcctgggtcc | aaagaaatcc | tgggaagttt | ttaattgact | ttattacact | 600 |
| gctgcaaaag | gaagcaatat | ccttctgttc | cctctcagtg | aggtagaaca | attgacctcc | 660 |
| caaattaaaa | cccaggagca | gatctgaaga | aaaaaggaga | gttcaggcaa | agctgtagaa | 720 |
| ttacattttg | atgccttcct | gttgactgag | ttgcgataat | gttttcttaa | tccgcaatgc | 780 |
| tgtaagccta | gctgctccat | ggcatacca | acattctctc | ataattttag | ccattactct | 840 |
| caaggcttca | cagctctgcc | atctgtttgg | gatatttggc | cttaacttct | gttcacaaac | 900 |
| aacttttctc | atttcttcaa | ctgatgggtc | agaaggtaca | agatcataat | aaggcagttg | 960 |
| gtaatcttca | tgaattccac | caatggaaca | tcgtcgagca | atttcccaga | atactaagcc | 1020 |
| cattgcatag | atgtcagcac | gtttgaagga | ttcaaaatgt | ttcatattta | tggaatcatc | 1080 |
| gagaacttca | ggggccatgt | accttttttgt | tcccactctg | tggtttggag | caatatcaat | 1140 |
| ggtatctgtg | gctgaatcat | gtcttactgc | cagtcctaag | tctgcaatac | agcaagttcc | 1200 |
| attcttcttt | accaagatat | tctttgattt | caaatctcta | tgagcaatgg | ctggctttcc | 1260 |
| ttgggtacca | acaatctcca | tgtgaagatg | ggcaagaccg | ctcgccgtgg | acagagcaag | 1320 |
| ttttatcatt | ccttccacag | taactgtgta | tctgtttaag | taatcaaaaa | gggatccatg | 1380 |
| ctcatgataa | tctgacacca | accagagctg | agtccaagta | ccattgtctt | tattgtctgc | 1440 |
| tgctataaat | cccaggatgt | tttcatgacg | taacattaca | gtttgataaa | tctctgcctc | 1500 |
| acggaaccac | gaacgttctt | ctctagagga | gaatatctta | acagcaactt | cttctccccg | 1560 |
| ccactttcct | ctccaaactt | ctccaaatcg | acctttgcca | atgctttctt | gtaacacaat | 1620 |
| agttctcgca | attgttctct | gaacaagcaa | tggtaaacct | gagccagaac | ctgacgttgt | 1680 |
| catatcataa | attaagtctt | tcaacgtagt | accctctgaa | ataaagggc | gatctaatga | 1740 |
| agggtcctct | tcatttggca | ctcgatggtg | aatgacagtg | cggttgtggc | agatatagac | 1800 |
| catcaacatg | agtgagatgc | agacgaagca | cactggtcca | gcaatgacag | ctgccagttc | 1860 |
| cacaggacca | aggccaggtg | atgactttac | agtagttgga | agttctatttt | tattgcaatg | 1920 |
| gtcctgattg | cagcaatatg | ttgtagtcac | agacccagtt | tttgaagagg | gtgcacatac | 1980 |
| aaacggccta | tctcgaggaa | ttaagtcaat | ttcagctata | cacatgctgt | tgtgtataac | 2040 |
| tttgtctgtg | gtctctgtga | cagagacaaa | gcagagccca | tctgtcacac | aagtaaaatt | 2100 |
| gtcttttgta | cagaggtggc | agaaacactg | taacgccgtc | gccccgggga | gcagcgccgc | 2160 |

| | |
|---|---|
| cgccgccgcc gccgccgccg ccagcacgag gaggagcagc cggggacgcg gagcagcgac | 2220 |
| cgccgcctcc atggtcccgc cgccaccgcc tgtggcccgg cccggcccgg ccgcgccgct | 2280 |
| gcctcacccc agcaaacctc gcctcgcc | 2308 |

<210> SEQ ID NO 96
<211> LENGTH: 48775
<212> TYPE: DNA
<213> ORGANISM: Homo sapiens

<400> SEQUENCE: 96

| | |
|---|---|
| cctaggatgg gcagtataaa caactgtgtt tttaaatgac aaaattatta ctctaatcaa | 60 |
| atttatctgc agttatcgac agtaatcatg atccatccca ccttttaagt ttctttcatt | 120 |
| ttcaatatca gccaattgtg gtttatcaaa ccatccctag ccaaaaaagg aattaactgc | 180 |
| agtaatacgt aaagtcaatt tagaactaaa ctccaacttt aaaaaaattc cctgattcat | 240 |
| caaaagtaca ttttatccac ttaggtaaga aaagtataat tgtaactcaa tctttgattc | 300 |
| aataaaaaat atcttcagca aaagtggata accttacatg aaagtgagaa atcatgtatt | 360 |
| acaactttaa atcagacaac ttttggtata ttcttaaaat tatataaaaa tagttttagt | 420 |
| gataaaatgc attggtcccc tggatttcat aaagcagatc tggtaggctt agaaatggcc | 480 |
| caaaacaac aacaaaaaaa aaaaacaaa aaaaaaccc ccacaaaaaa agtacctgat | 540 |
| cacagaatta gagattatta ttaaacaagt aatacaacac aactataaaa acaaacctct | 600 |
| caaactcatt catttgcttc aatgaaatta tggtaactac agaaaaaaac tcaactttgt | 660 |
| agtcaaaata gtaacctcta agcatttttc ccatgatgtt tttaaacaca tgaaattgac | 720 |
| actaaattcc tatgtaatat gtcactcatt ctaaaattac tttggttta agatcaaata | 780 |
| gtctttcaaa tttattctac gtataagaga taagacatta tcagaatgca actcattcag | 840 |
| tgtaaatggc cactttctct tcctgaccaa aatactgtat gggttactct gaccctgtat | 900 |
| cggggaactg atagcactat aaagtcgaag tcttgcctca gagctatgat agttttttct | 960 |
| cccctcagaa taagatcaca gtgataaaag gacttcgaaa actgtaaaag ccctgcagag | 1020 |
| acttcatagc attggaagta aaaaccagtt attataagct agtttcaact taatgtaaga | 1080 |
| agaccatgac aagtttgctt tcaatatttg accaaagaca tctgtaaatg gagaaaaacc | 1140 |
| tatactcaga atgttcttta gctaccacct ctcccaagta acaagggtgc actgaatgca | 1200 |
| ttacataaat tacatgtaag cagttgcaat gtacgcacac ataaggaaac actgaattaa | 1260 |
| aagctgcctt cctcaaagtg tagtgagacc tcaaaaccac actagctcta acctcagtta | 1320 |
| caaagacaga ggatccaccg aacgttact cctacataca taacaaatgt gactttcttg | 1380 |
| cacatctgtt atctattcaa attattaact accttcgcct tcctagaaaa aggcctatta | 1440 |
| tttaatatta accatattct aattttaaat gtaattcatg tcttaaaaaa taagtctttg | 1500 |
| aacagataaa gaaaaaatg gcttacagaa taccacataa cttttcacaa gcagctagac | 1560 |
| agactttccc ttttagaaaa attagtctgt atgctacaaa tattaaagta ctataagcat | 1620 |
| ctagagtgcc acttgatttt ttaaaagtat acttagacaa cacaattaaa atgcaaaagc | 1680 |
| ttgatgtgag aatattcaaa catgaccatg ctaataattt actaattaat gccacttcat | 1740 |
| ttctttagtg gcttaagcac attttggtag gagaaaggca ttttcagaat agaataccaa | 1800 |
| atgacatacc acaaaaaccc ttccaaaaac aaaacagaaa agtttgggt tacccagata | 1860 |
| aataagcttt tgaattcaa acactatagg ttttaacata gagactttca gcaattctac | 1920 |
| tcatttccat tagaaagaca cagaagtggc acttactggt atagtacaat cccatttga | 1980 |

```
aggcatgtaa tgttctgaat aagtgaaaga acaataatag tatacaaaat acaattgcat    2040
gaattatgtt cctcactact atatgaggtc atttttagac tcaagataag agttttataa    2100
gtgttagttt taagatcctg aaaaactata gaacagtaca ttcaaagtct gaatcaagga    2160
aactctagtg gttcagaatc ctctgagaat gtactaacca ggagtaaatc actttcttta    2220
gtaataagac atgtttcatt gtaattcagc aatccaactc ctttgccctt aaagatgatc    2280
tccagcacag cagagttacc taaagttaag accagcaatc atcttttaa aaaacaagtt    2340 ttgttaataa aaaataaagg tagactacac attttctgtc ctgggaaaga agcgttcata    2400
gtgcacagaa aggacccaca tggctgtttc ctgggtccaa agaaatcctg ggaagttttt    2460
aattgacttt attacactgc tgcaaaagga agcaatatcc ttctgttccc tctcagtgag    2520
gtagaacaat tgacctccca aattaaaacc caggagcaga tctgaagaaa aaggagagt    2580 tcaggcaaag ctgtagaatt acattttgat gccttcctgt tgactgagtt gcgataatgt    2640
tttcttaatc cgcaatgctg taagcctagc tgctccattg gcataccaac attctctcat    2700
aattttagcc attactctca aggcctacaa gaaaatataa aaaaaaaaat taatgcatgc    2760
accattttcc attggtctgg ataagaattt ttacgtgtaa attttctttt taaatgacat    2820
atacacttgt tattgtttaa gcattatttg taatagcaaa tgagtagaaa ttacataaat    2880
ttccatcaat agggtactgg tgccagtgct ggaaagcagg tggacaaaga gtgactcatt    2940
tagcaaacct gaaaaggccg aatcctaaac cagagctggg caaagcaaag aagaaatctg    3000
acctcacact gaaattttaa gtttgtactt tgaagtattc acatcaaatt tttctttctt    3060
tttttttttt ttgagacagg gtctcactct gccgcccaaa gtggaatgca atggcatgcc    3120
ctcagctcac tgcagccttg acctcccagg ctccagcaat cctcccactt cagcctccca    3180
agtagatcaa atttctaaaa gacaaaatct agcagcactc tcatttatta aactatgtca    3240
catgcaaatt ccttaagcat gctgaaatac atttttattta tttgggcctg gagatgtgat    3300
tttgttggag gtagcaagct ctcttgctta tcagaggttc tgctgagtcc tacaatagtt    3360
taagacgtaa aatcaactac tgaactgaac agcttttat agcctttta agctacaaat    3420 cttcaaacct ggaggaatat gctctgcttc accaatattg taatagtaac agctagcaat    3480
taaggagagg ttaaataaaa ttcatcttac gaatctttaa atttacaatt acaaaaacgt    3540
ttctaaaact ttttgttaga gctgaagttg agcagctcag atactgctgg aaaaaagcat    3600
tttccctaaa ttcctggtta acggttatct gggcaatcag atgaataaaa cggaaaatca    3660
tttgaaacac ctttgtaatc accttatctg agttcctcac cttgcaaagg gatattaaag    3720
tccagagaac taaagggatt tgttcagagt cagaccctttg aaatggtagc caggctggtc    3780
tagaatacag ggctcctcat tcatgtccgg taactgtcta gtgttctggg ttgccccggc    3840
tgaagggagg cattcattta aaatatgtg ccttagttcg cccggcagat ctaaactatg    3900
ttctgataca ctaaaggcca ctgcaaatgt tccatggccc tttcaatgtg cttacaattg    3960
aatatgaaaa ccaaattatt ctgtttttaa acattggttt gactgctatg aaaaagaaaa    4020
ttcttaaaga aaagttttcc ttaaagaaaa gtagcaaact tttgcttact aagcagaagc    4080
agtttagaaa attgcctaat atcaaaaaga aatactcact tcacagctct gccatctgtt    4140
tgggatattt ggccttaact tctgttcaca acaactttt ctcatttctt caactgatgg    4200
gtcagaaggt acaagatcat aataaggcag ttggtaatct tcatgaattc ctgtatcagt    4260
ttaaaaaaaa ttaaattttg atgaatttat tcagctaatg ccaaggcatt aaaagatcac    4320
ctgagagacc tattacagtg tttcattact aaagtaggta tgtggaacag agattacagc    4380
```

```
tttctctatc tcatccacat ctgtatccac aagccacttc cctgagttga tattccaccc    4440
acaccttgaa actaagtatt gccatgagat caataaagcc tatttgaaat gacagtaaac    4500
tatgagctgt gatgaccaga ttgacatttt cccctagaac cctattgtgc agcaaatgag    4560
attctattct gtaagtgcac aggctctcac ttgcacaggg atatatatac cctatcagtg    4620
agacttgaat cttatgaggc aagtttaagg tgccaagtcc cttctctac ttgcatctgt     4680 caataatata tcctatttac tacaatacag agaaatactc tgtccctcac tgcttcaaaa    4740
acctaaggca ctaggtctca gccaagtcta ggtccccaag cctaagagac tgttcctga    4800 gtaaacatta aaagtactcc atctaaaaag ctagaagtta aaacaaacta actctagaat    4860
acaacacaat ggtaacataa ttgtattctg tgtatgtaac tgtaactatc aagttggaga    4920
aaataaccac aatctcaaag aaaaaaaata agtttgacac ccaggtacat gctagaaaca    4980
gcttcctagg tgagcctctc aagcagctgt ccattctaaa gaactatatt ccaatataac    5040
aaggggttgg gttctgatga gtctccagat tcaaatggaa acaggaagag aatacactag    5100
gctagagctg tgcatgtgca caccatggca ctgtcccctc ccaaaggttt catcgccttt    5160
gttttctctg gcactcggtg acatcctgtt tcagataatg gactgtacat aatttcattc    5220
aattaaaaaa agaagacaat tcttgaacaa cttctgctca tgacaaacta ctgggggaga    5280
ggagagcaat ttaccaccaa tggaacatcg tcgagcaatt tcccagaata ctaagcccat    5340
tgcatagatg tcagcacgtt tgaaggattc aaaatgtttc atatttatgg aatcatcgag    5400
aacttcaggg gccatgtacc taaaaaaaat ttgcaaaaag aactttgaaa atcatcccct    5460
tactgccata tttggatgaa cctcctttca gacatttctt tatacataga catatgtaca    5520
caatattaca taacaaatat tagactcaag aaaaatatta aatatccaca ctggtttgca    5580
cattaatgat gtcaactaaa tcccacaaaa tgctaaaata gcagtttcac actatctgcc    5640
tcatgatctt ggtttccaat gaaagacata cataacaatt gtgactgtta aaggtgtcct    5700
aatgtacacc acctatacac gtactaggta gaaaccatgc atttttaattt agaagtcttc    5760 tcactgagga tgaaaggaag ggcacgaata tactccaggg aaaaaaataa tagatacaaa    5820
agaatgccag tcctcatact gaagcttcaa aaacctacca aaattatggg tcaggaccca    5880
cagagaccta cagcaaccac tgacaaggac cccttagctg gttgagaatt gagagtcatc    5940
tacggccata ccaccctaaa cacgcccgat ctcgtctgat cttggaagct aagcagggtc    6000
gggcctgctt agtacttgga tgggaaaatt gagagtcccc agggaatcca gaaatctcaa    6060
aattatacat gcaatttgaa tagactaatg ctgctggctc tccagctgtc tccaaggcca    6120
agacagtagt ttgaaaaaat gctgtgacag cttgtgataa ggggtttggg tcagaaatgc    6180
ccaggttcaa atctcagctc ttcggcttat catccacatg aagctggcca tattatttaa    6240
cctcctcaag gtggtttcct catctgtgaa ttaagggta ataacaccta cctaattaag     6300
ttcttttgaa gactcatgga ctcaacaaat atctactgag gatctaccat gtattaggca    6360
ctgtgatgga tgctgggaat acaaggctgc tctcaagcag cttgcaccta atagaatata    6420
taggcaaata aataaacagt tacaacataa cgcataagtg cctcaacggt cccagttcag    6480
tgtgctatga cagtccctgg cagggactcc taagattttt gaggactaga aaaacttcc     6540 tacgggaaag gtgggtatga ggctgagaaa cagtagggta agtatgctc caggagacag     6600 catgtgcaaa agttctaaga aagcaagaaa ggcatatttt taggaactga aatatgaaaa    6660
tagcagggct agctactgca cagtatttga gaagggatta aatgaggtaa tatacgtaaa    6720
agacctatta gacgattggc acatagtagg tgccctataa acgttagtta ctactgttat    6780
```

```
tataattaac atgcctaatg atattttctg gaagggcaac ctttcatcag caggcatctt   6840
tttaagtcag gtaactctgg cttcagagca ggcaagacca tgagatcttc ttacctgttg   6900
gcaatctaat aaagtgcaag tttaagctga gtttcagcaa tgatatgtat atatgaaaga   6960
gaagggaaaa aaggtgattt cagaagatat taaatatagt tgttcaaaag tatacctttt   7020
tgttcccact ctgtggtttg gagcaatatc aatggtatct gtggctgaat catgtcttac   7080
tgccagtcct aagtctgcaa tacagcaagt tccattcttc tttaccaaga tattctttga   7140
tttcaaatct ctatgagcaa tggctggctt tcctaaagaa tcaaaaatta acatgactg    7200 cttaaaaggt aataccaatc acaactcaca tctttaggtt caaaagtctc ttctcccaac   7260
ccaaattatc aaagcatttc agcccacatg acctacaata cttacgggca ttattaaact   7320
caagtgaatc actacaccaa aagtcactga atttatattt ctttaaagaa aatgtggaca   7380
ataacatgct ttaaaagatg aacaactcaa agactgggc aaaaaaaaag ttatcagttt    7440
atctgttggt gccttatgaa ttctttttaa gaaacttagc catagactga tattccagca   7500
gcccaggaac caagcatgta gaacatcact tccctatcaa ctgcaatgta ctcagtatta   7560
agtatattat ctttgatgct aaccactaga aaatgttatt aaaaaataat aattataatg   7620
tggaaaacct ggaaccttca tacactgctg gcaggaatgt aaaatggttc aggcactta    7680 agaaaatagt atgcagttc ttcaaaccat taaatagagt tatcatatga tacagtaatt    7740
caactcctag gtatataccc aagataactg aaaacatgaa actacataca acttgtacac   7800
aaatgttcac tgcagcatta gctacaatgg ccaaaagaaa caaaccaaat gtccatcaac   7860
gaacggatat atgacatatg ccatatccat acactgaagt attacttagc catcaaaatg   7920
actgaagtac tcatacgtgc tacaacataa atgaaccttg aaaacatgct aagtgaaaga   7980
agccagtcac aaaagaccac atattgtatg attcatttat ataaaatgtg cagaataagc   8040
aaatctacag acaaaaagga gcagttgttg cctagggcta aggagtttgg gaggaaaggg   8100
gagtgactgc tagtggctac agggtttctc tttggagtga agatattcta aaattgactg   8160
tagtgtttgc tggctgtaca actcttgagt attctaaaaa ccactgaatt ttacacttta   8220
agtgggtgaa ctttatgatg tgaattataa ctcaataaaa ctgttacaat caataataat   8280
aataactaca aagatggagc taagatgtga actagcactt atgctgtatg taaagtgggg   8340
agtgggggag ccattgggtt gcaagtggac aactgctaga gcagagagat atactggcat   8400
ctgaaatccc acatgcacaa aaactacagc atacaaatgt cataactaaa acttagtatt   8460 taattttca actgtaaaac tatctcatgc agtctcctta tctcaaggtc aaatataatt    8520
attagatggc cagataacag ttacctagca tgttgatgtt tacaaagcac tttcacattt   8580
catttgatac tacacataaa aatatattca gttggacctg aattctgaaa ctgagatcct   8640 caaaatcat aagattgaat gctacttta agaactcaaa aaaaatcaca gttttgttac      8700
aacgactaga gaatctctaa acaaatttcc agattcctag ctctacctga aattttgaac   8760
tgaaagataa aatgttctca tctaaaaaat ttgttttaaa tatctccagt taggccacct   8820
actgtttttg ttttttgttttt ttttttctgag acagggtctc tctctattac tcagctggga 8880
gtgcagtggc atgatgtctg ctcactgcag cttcgacctc ccaggctcag gtaatcctcc   8940
tacctcagcc ccctgagtag ctgggactac aggtgcatgc caccatgccc gactaatttt   9000
ttgtatgttg gtagagatgc ggttttgtca tgttgcccag gctggccatg aactcctgag   9060
atcgggcgat ctgcccacct cagcctccca aagtgctggg attataggca tgagccacca   9120
ggcccagcct ccaccttcta ttttcataga cattattcat gaaaatttaa agcttaaata   9180
```

```
atagaactgc ttatagaatt accttgggta ccaacaatct ccatgtgaag atgggcaaga    9240
ccgctcgccg tggacagagc aagttttatc attccttcca cagtaactgt gtatctgttt    9300
aagtaatcaa aaagggatcc atgctcatga taatctgaca ccaaccagag ctgagtccaa    9360
gtaccattgt ctgtaaaaca gaattaacat ttcggttggg ctgcagacca tttatgattt    9420
atttgttcaa tggttattac ttttactct caatcctgag tcacacactg caatataatg    9480
ccaccttaag tctgtatttc cttcacattt tcttctacat tgtttgtttt atacttttat    9540
gtacacatcc tttagttcct cagagtaagc ccctcttctt gagataaggc aagtataatt    9600
aatcccattt aagagacaaa gatggtgact tttttgagtc ttcacagata attggtatca    9660
gagctggcac tcttaagtgc ctagaaaaat ctctgggtcg ggttgggtgc tcagtggctg    9720
ttcctggaag gagagaaggt taaaaaaaag gaaggaacag agagggaagc aaggaggtga    9780
gaagtctccg gagaccagtg tggccacagt gggaatggaa gagtatggga caaaactgaa    9840
agtgagtttc aacaagaaat gacaagcttt agtgacagat tgtgtacaca gttcacaaag    9900
acgcaagaca agatgattat gattccaagg ttgctagctt agaaaaacag aaatagtgat    9960
acctctaaca catggggaag ctgaaatagg aactgaaatg tcaggagcaa aactggaaaa   10020
gctgggacta aactcaaaca acgaggaacg tgggttccaa aatttcctct gtaagccaaa   10080
acacgagttt aaaacatgtt ttctcatagg aataatggta aagacactag ctaggctcct   10140
aagctagact ggtccacgac aatctaattt aacctagaag tagctggaaa accacatgct   10200
taattaagcc atgaagaaaa aaagcattac aacattagga gacagcacaa tccagtaaaa   10260
gatggacgct tagagtcatt ctaacctggt tggaatccac ggcctgcctg ttactgacaa   10320
ggagcctgtt tctccttta tacaagaata aagtcttact ttgtaagact gttaagattt   10380
aaaaaacgga atgctagatt ctttaggtaa gaagtacata aactgtgctc tttctttccc   10440
tgctggttgt aaaccaaaag aaaaaatcca tattgacatg aaacagcttc tattttgaag   10500
gtatttggtt gaagaagaaa accaactctg attagaagag attaagaaag gaatagaaac   10560
ttttcagaag attctggagg agatttctgg gtacatttaa aaggacttag tattaatttg   10620
ttcttcatga actttataaa ctgattctga ccaaactcgc acccttgctt ttccttgata   10680
taggcacatc actagcttat ttgcatgcct cttaaccatt actgaatttt gaaaagctca   10740
caaatacaag aaacaaagtg gaagacaggc agatggaaga aagggaaacc acaggttatg   10800
gacaagatag aaggaaggtt atatgtaagg ggccataaat ataaagggct gccgggggtg   10860
gaattaacta aatcaggaga agataaagga actgaggtgg aggggctagg ctcagagaaa   10920
gtacattaac ccctgacaaa gaagaaagaa ggggagtagg gaagagccag tagggtcagc   10980
tagttcccat ggtgaccacc agatgacagc atcagcctgg ttagaagttc agggcacaga   11040
ctcaccaaca ttttgtgctg ctgtgttgt aacttggaat gtgacaaaat ccagaccctg   11100
ggtgaggttt aagctttcaa atggagattt gagagttgcc aacatggtag agtttgaaac   11160
catgaatgtg gctatgttct taaggaagaa attaccactt ataaaatcag taccttcata   11220
tgaaccagtg agaagagtaa gagttgagaa aacaaagaca actatgaaga agtaagaagg   11280
aacaaggaaa gtctagggtc atcaaacaca gtaaataaag aaaaggttgt tttaagagtt   11340
gggggaggaa ataaatggtg ataaaggcag aaacgaaaat gagaactaag gatttggtca   11400
gactgattac tattttttgt tttgtttttgt tttgttgttg ttttttttttt gagacagagt   11460 ctccctgtgt cgcccaggct ggagtgcagt ggtgcgatct cagctctgac tgcaacctcc   11520
acctcccagg ttcaagcaat tctctgcctt agcttcccaa gtagctggga ttataggcac   11580
```

```
ctgccatcat gcctggctaa ttttttttgta tttttagtag agatggggtt tcatcatctt    11640
ggccagccag gctggtcttg aactcttgac ctcgtgatcc acccaccttg gcttcccaaa    11700
gtgctgggat tacaggcgtg agccactgtg cccggcctgt tttgttttta acttaagagg    11760
tattacattg tcaggtgcca ctgataatcg ctacctacat tcatcatata cctcactgcc    11820
ccgtcttaat caaacactat acacctccac atatgatgca ataggatgta tataatatcc    11880
ttagtatgta ttttgagaaa accaataaaa ctccaattag gtttagcttc taaatctaac    11940
taccagtttt cagaaaagat agaagaacaa gttaagagac actatggaaa tgcaatcagc    12000
aaaatccaga atgtgatagg cccttcagga taaacaatcc aatttcttca acaaataagc    12060
tgcgagagga gaaaaaagat gaaggggggga cctaaatttt aagacacata agagaaatat    12120
caactaaata taacttgtgg acttagaatc ataatttgaa taaataatttt ttttaatagg    12180 agacaattat agaattgaac ctaactggat atttgataac atttaaaaaa ctgacaatgg    12240
tagtgtggtt gtttcataaa aacatttcct catcatttga agatacaaat tacattttat    12300
aagtgtttac agatgaaaac atattgtctg ggaccagctt caaataacac agttagggca    12360
gagtaggtgg gatcagacat caattatgat tggcagtgac ctgacaactg ttgaagctgg    12420
acgatgaggg atcactgtaa ctactctgct tttctacata ttggaaattt tctacaaata    12480
aaagtcaata acaaaaaaaa gcagtacatg cttgtaaata aatttgaaaa cccagagaag    12540
ctaaaagaaa aataataaaa atcacccata attaccaact gaggttaaac actgttaata    12600
tttgaataaa taaatattgc tgaagtaaat ggaaggtggg agaaggaaaa agatgactac    12660
aggtctggcc aagctaagag ataatgacag catttttttt tttttttaaa taggaaagct    12720
gggaaataca tttgattcag gggtagggat gacaagagtg gagctgaaac acaagtctct    12780
gacagaggca gtaaaatag gaatcgtggg ggctgggcac agtggctcat gcctgtaatc    12840
ccagcacttt gggagggtga ggtggtgga tcacgaggtc aagagatgga ggccaacctg    12900
gccaacatgg tgaaacccca tctctactaa aaatacaaac attagctggg catggtggtg    12960
cacgcctgta gtcccagcta ctcgagaagc tgaggcagga gaaccacttg aacccaggag    13020
gcagaagctg cagtgagccg agattgcacc actgtactcc agcctggcta cagagcgaga    13080
ttccatctca aaaaaaaaaa aagtaggaat catgggcata aagtattaa cggaagctaa    13140 gaaagtggca gcagcacagt ctaaggtcac tgcttgcagt ccccactcat tctgactccc    13200
tgctgacagg cttccttcct tcttcagcat ctgacctgac actgggcctc aggcaccagc    13260
atgataggca gaaaagtgtc cgtacagtta ccagggtggt tgaagaaaca atttatctct    13320
ttgagtttgc cagaagattc atctatttag cccttggcaa ctcagaacac tgacaagtta    13380
tttttactct ccccattaat aaggtcaata gtccatattg aaacatccta ctggtcagga    13440
agagattaaa aggaaacagc tatctgagcc ctattctcaa aatttttgagc aagtttatat    13500 atcttttcta tatcatgagt actctcaata actaactgcc ctaaactaaa ccaacaaagt    13560
acatggcttt ttaaaatagc tcttttatat tttataaaac attaagagat tttaggaatg    13620
ctatcaagag tcagaaaat cttgaagaag ttcctagttc taaaagttac taatatattg    13680
tattcgactt aatgggtcta atctacatga gagacatcta tgtctcatct actttgatga    13740
tggttagtca ccatatctgt aaagacttaa agagatcttg ttatatataa cataaggaaa    13800
agcaaatgtt acagaccttt attgtctgct gctataaatc ccaggatgtt ttcatgacgt    13860
aacattacag tttgataaat ctctgcctca cggaaccacg aacgttcttc tctagaggag    13920
aatatcttaa cagcaacttc ttctccccgc cactttcctc tccaaacttc tccaaatcga    13980
```

```
cctttgccaa tgctttcttg taacacaata gttctcgcaa ttgttctctg aacaagcaat   14040
ggtaaaccta aaggtaaaaa taaatagtac tcaacacaat caacaatatt acatgtttca   14100
aacatcatga taggcactaa tgagtgaccc agaaaactga tactttaagc tatcccttta   14160
ggaatttatc tcactgggga gatattatat ttgcaataaa ataactaatt aaaaaaggaa   14220
aataagataa taaatataat aaaagaatcc agaaactcct gctagagggt caaggtaggc   14280
tttgtaaaag taagttgaat tttgactatc ccttaagtac ggtggttagg caggaagaat   14340
gtgcaggcaa aggtagaggg aaatgaatga cacattttta gggaagcagc ttgggcaatc   14400
agagagagga tatatgtggc aaagcagtga aaagagaaag taagctgtca ccagaagatg   14460
aagagtactg aataccaagc tcaaaataac caatgaagag ctttaggtaa aagaggaacc   14520
tttaaagatt tctgagaaaa agggccatgg ctggaagcaa gataatttta aaatcttatt   14580
ttagaaagat gaatctcgta acagtttcac tgatgggagg aaaaaaggat gtgaacgcag   14640
aaacacagaa gtaaattctg ctttttgat aagtcagtaa aaatcaccac agaaactatt    14700
tcaaggaaag caatttactt gctgacaact ggctacatag acaacactag tatcttgaag   14760
aacaaggcta agtaacttac cttggtaatg gagcactgtt tttccactaa tggaacttgg   14820
ctttctccaa aatatgtatt tttaagtatt gccatactta cttcatttaa aagggtttac   14880
taacttacct gcaacattta agtggcacta tatgtgagac catcacttaa tatcctatcc   14940
accatccggt aagtgtcatt ttaaattaca ttgacactaa caaagaaaat gccagtgtac   15000
atcatgttcc tcactcatat cttatttata caatctatgt acatataaat tggtgtcatt   15060
tataatctat actcaaagct gcttactaga tcaaattaac ccaatgacag taaatgaaat   15120
tatctgctct ctttggttcc ctgatgtgaa atgcttataa atccaaacgt taaatcttta   15180
aagcgatcag aagctcttct tcttaagttt ctcaaacggg tccttcttc ctcttgctct    15240
accctcccca cctcctgtaa agtagttagc agtataacta taaataactg tttgtgttta   15300
taaggaggct gctagttaga aacagatctg tcagaaatcc ttatttaaat catagagctc   15360
tttcgcacta tgtataatca attctaatta tgttgtttag tgtagatact aatttattac   15420
atttttatgaa agccttgtag agggccacac cacagactta aaagtacact taagagttaa   15480
tttcaggaga ctaatctgga aattgcaaag acaagtaata aaaagaaaa aggaatcaca    15540
aacacaaatt ctgaaaacac ctgacaggtt caggacttgt gtaaatggta tggtcaagaa   15600
aggccaacag gacgaggaaa ggttttgtct tcccctttat cactggattc tagatgtcaa   15660
ttaaaattaa aaagcaaatc ttgatccact gtattatcta tattggatta cttcacatga   15720
atagttgagc atttttaaaa agttaacaat tggccaggca cagtgactca cacctctaat   15780
cccagcactt taggaggccg acgtggttgg atcactagag atcaggagtt caagatcagc   15840
ctggccaaca tggtgaaacc tggtctctaa taaatataca aaaattagct gggcatggtg   15900
gtgcacacct gtaatcccag ctactcagga ggctgaggca ggagaattgc ttgaacccgg   15960
gaggtgaagg ctgcagagag ctgagatccc accactgcac tccagcctgg gcaacagagt   16020
gaaactccgt ctccaaaaaa aaaaaaaaa aaagtaacaa ttttcttcta aagacaaaac    16080
tgaataggcc taatttagat ctctatattc tctgctctac tcttctgtac ctttagaact   16140
gtttgagaga aaacttcaaa agggaaacag ggactccaca gctttacatg cagtgaacag   16200
gaaataagac ccgaacaaca tgcatatatt acaagagctc ataagctgca cacgccataa   16260
caaacactgg cctagaagac tcacttacaa aagctggcac atatgcacat gtgcacactc   16320
acacacttgg cgtacagctg ccagaaccca gctcttcatt gtattccctg aagttcccaa   16380
```

```
gttaaaagca cagtctttag aggtagagac agggcctttc cttaattatg gtcacggtac    16440
taagtaataa acatatgaat tcagaatgtg aaatgcttat acctttttcct caattaatga    16500 aagaactaaa aacagagtat tacaaacaca cagtttactt attcacaggc actagtctca    16560
tgcctaaggt ggcattaagg atttataatg aatagaaggg aaacagatgg cattttctgc    16620
tattattcac cagaagatgg cttctgcctg gataggtttg gagggaattc agtacacaat    16680
gaactatgac aggcaaagga ggccttaaac taagttttgt acaatgtggt caactgatac    16740
tgtatgttag attttttcctc caagtatgtt ttcaataaga gtaacacttg tcatttggac    16800
ataactctac aatttaccaa gtgctttcat gcaaacattt tgtcttgctt gaactcacaa    16860
caatccaatg atgtgcacag aatccatcac tttcatttta aagatgaaat aactcaagca    16920
tgagacattg gttaactgcc caaagccaca gagctagcaa gcaatgcaga caagtttttg    16980
cagggtaagg catcaaagga gggagagaag ctttcagaga acagagagct atggtccctc    17040
atggatctag aaatatatat atatatatat atatatatat atatatatat atatatatat    17100
ataatggaaa cagaattatt ccattgtttc tcatgtttat atcttaaaag gttaatgaag    17160
atattcttat ccagtaatca actgccaccc acccaccaat tcctttaatc agttaggtgg    17220
gcttattcca ctgtggcaag tggcatgagt gctgtgtctt tccggagtat aagtttagaa    17280
acaagagaac aggtttgagg gattaattcc aaatatctgt agccatcctg attttctgtg    17340
actctggtcc ttgattatca cagttttgag caggatgact tccagaatga gcaaaatctt    17400
tttgaagatc tgaactgaga ataaatggga agtcccagga aagctctaaa ataacctctg    17460
tccaccaggc ctgcctaaag actatcacac cttcagtact aagactgctt catctaagtc    17520
caaactctca ttgtcttcct tgcacaactg tttcaggaat ccctaagctt gccttctggg    17580
acgtgagctc cagtgcgagc ctgtgtgtgt cctagtagtc aaggagagag ctctcttatt    17640
gaatacatat ggccaaattc tatagaagaa taattcaggt aataaaatca gtttcttcat    17700
tcttaaatga atggatatgc atacatacca atatatattc atttccttaa aataaataga    17760
catttgtcat tatatgagct ttctgcaaca ttagatgtga ttttatgctt cagaattata    17820
ttcttaccca gtcacaactt ctgctttaac attccttttaa tatcactcaa ttataaaatt    17880
agtgaaaatt tttttttttt tttttttta gatggagtct gtttcccagg ctggagtgca    17940
gtggtgcgat ctcagctaac tgcaacctcc accccccagg ttcaggtgat tctcctgtct    18000
cggcctcccg agtagctggg actacaggcg catgccacta cgcccggcta atttttttgc    18060
atttttaata gagatgggct ttcaccaaaa ttagtgaaat tttcattata tacgctttac    18120
aaattttcac tttattcatg aatttagccc ttatttgaag atgactcata cttttcaaag    18180
gatagtacat ctcatttaaa agtcttaaca aaccacttga agtgttttta tcaacagtat    18240
gggttccata ttttttgatga ggaaacagaa gcccaaagag gaaacatgtt ctaaccaagg    18300
ttatacagcc aatcaatgac aaagcttgcc ttgaaaccta gatctatta ttcttcacca    18360 agtgtcaaat tctaaaaaca caggggatag gagtgttcct ctcttaatat ttttccaaac    18420
cacatacatg caagaaaaag taaaagataa ccccctttca gtttaaacat gaagcactgc    18480
tatgccaaaa tccaccttgg gatgactctg acaattagct catctacttc tgatgccaca    18540
aatatcaaca aatagaactg agaaaagaaa acgtcattag gggccaaaac tacattaaat    18600
aagaaggtgg ttagacattt ttctcaagtg agaaaatgac ataagagttc attagtttaa    18660
ttttaaaaaa ccaggcctat acgaaagaca atttcatata atgttaaaaa agtaaataac    18720
cttcacaatt ctgaatacat ttctgtcatg cctgttttca aatgtaaaca tcaagctgct    18780
```

```
aaacaatcct gaatagaatg ggttagctgc agatcatgtg aatatctttg accttcagct   18840
tcatctatat gagaataatt gttcttatcc tttctacctc acagtgatga aaagcaaatt   18900
agattataca agtgagaacg ctttgaaatt tataccacca tggagctgac ttattgattc   18960
gctttaacag ttaaagttaa gttccaatct atttaaacc agccacagtc atatatacat    19020
caagcttaaa gatttttatt aggttcaaac ctgcaatatt atttatacta tctcacattc   19080
tagcaagttg gcttattaga aaactaataa aataagtatc gcttaatttt aaaaagatgt   19140
cttaggaaaa aggagaaaca attatgttac ctgagccaga acctgacgtt gtcatatcat   19200
aaattaagtc tttcaacgta gtaccctctg aaataaaagg gcgatctaat gaagggtcct   19260
cttcatttgg cactcgatgg tgaatgacag tgcggttgtg gcagatatag accatcaaca   19320
tgagtgagat gcagacgaag cacactggtc cagcaatgac agctgccagt tccacaggac   19380
caaggccagg tgatgacttt actgaaaaag ggcctcgagt gaaataaaca tcaacaacga   19440 caaaacact gtaggtggca acccccattt tcccaatcct acacaattcc tgcagctggc    19500
cactgccacc acttagccaa agagcctcat tacagcagtt tacagggctc aaacccagaa   19560
caagtgaatc agtcttctcc cactaggcct ccttttatgc acaccagctc tgtcagcacc   19620
cacttactcc tgtattcttc agccatcatt acaaggccaa ctgccgccaa tatcatagga   19680
ccttccccac ttatcacatc aggtcactaa taccaataac ctgtaacaat acctattaac   19740
atctccttaa aaatcatatt ttttttaatg tttggcttgt cttcttgttc caaggccagt   19800
acatgctcat agcaagaaaa acaacaacaa aaaaacaac aaaatatcaa aacaagcgaa    19860
aaaaaaaacc acatacatct tcatcacttc taaacaactc acatttcagt atatatctct   19920
ccaccaattt tttttttttt tgagatggat tttcactctt gttgcccagg ctggagtaca   19980
gtggtatgat gttggctcac tgcaacctcc gcctcccggg ttcaagcgat tctcctgcct   20040
gagcctccca gtagctggg attacaggca tgtgccacca cacctggcta atttttgtat    20100
cttaatagag acggggtttc accatgttgc tcaggctggt ctcgaacccc taacctcaag   20160
tgatccacct accttggctt cccaaagtgc tgggattaca ggcatgagcc atgcccggcc   20220
aataggtcca ccaatttttt aaaggcagaa catatctttt acttttttt tttaacagag    20280 tttgcatata tatactttt atactatctt aacctcctgg acttttaagt ccagatcatt    20340
ttcttgtaac ttctattaat aattaagatt ttctggttgt ttcagaaaat tacaattatt   20400
ttgacattca tcctgagtct tactggttta ctgcttacca ccatttcttt catatcacat   20460
ctttcccatt cttaagatct tcagtagatt aatctcttat catacagaat cctatttcta   20520
gtaatttctt tcaggaagag tccatgcacc cttgtacact gaacttagtt gtggcaagaa   20580
ggctgttgcc tttgtatatg aaaaatcttg gcctatttca agaatttag gtgatcgtaa    20640 aaatgttcca tttgcccttt gatatttaag cagaaaatct gaacctgttt ttttttttca   20700 cctttacag gtaaccaatg tttatgtgtg ttaaatgctt atataattct tttattcttg    20760
aaattgatac ttttattat atgtgtttgg attaatattt tttcattaat tttgcctggt    20820
attctgtctt ctttatgatt tcatgccttt ttctggaatt ctgataataa gcatattgga   20880
tcatctaaat ctgttcccta tatctcttaa tatgctcacc aactgtcttt tctctgaatt   20940
gtaacacagt ttcttaaaac ttgtcccaaa cttgactata aaattatggc atccagtctg   21000
ttgttcgctc tcaatagtgc attttaaaa acattcatca gttgggcttt tcttctgaaa    21060 gcaacctta acaactgtga aatgttctca tttcatagtg aataactgaa aatagaccct    21120
gtactgtttg aaagttcttc cctatcatgt ggtaaaccta tttcacagga tgacatctaa   21180
```

```
tctatctagt tcagactact tcttttgaac tcctaacttt tcattggtaa ttttttgctg   21240
tttgcttatc ctagagctgg aaatgagaag tttatatatg ttcattagaa acatgagaaa   21300
taaggtgact tcttcacaag gttttgtaaa tatctattca gatatttcaa gctcaaatga   21360
tggaaatggg aaattctgga attatccttt tctttgccac attataactg cagatgcttt   21420
catcaaagtc acaaagatat tgtagtccga ccaacccctta ccacagggga gctgcattat  21480
catgctgaac aggtggagga ctggcctttt ccttctgcgc tacagcagtg cttcctcctt   21540
taattagcac aaggcctgga ccaactttga gtggagagtg agcaactgtg tctgctcctc   21600
tgagcactga agccaggtgc ttcctaaaag ggaactgaga gtttgccccc atacctaac    21660 ctcacccccc aaatcctttg tctaagttat tggctggact tttcgatgac taacctttct   21720
tatatggcta gtcaattctt tactagtctg gtgtcatctg tactgtaaat tgcagaagtt   21780
cctcacaagt gctggcatgt gggtggcatt ctaccattaa tcccactagc attaatacag   21840
gttgccctca tttttatatt cctttgggat ctggggaaag aggtaagagt taaatacatg   21900
tgctcagact tccatattaa accggaatct taaaattaaa agtttatga agtcttcaaa    21960 ctgctggttc tgccaggaaa ttttattat ttatttatta tcttttttt ttagacagag    22020 cctcactctg tcacccaggc tggagtgcag tggcacaatc ttggctcact gcaacctctg   22080
cctcccaggt tcaaagattg ttgtgcctca gccacccaag taggtgggat tacaagcatg   22140
tgccaccatg cccagctaat ttttgttatt ttagtagaga tagggttttg ccatgttggc   22200
caggctggtc ttgaacttct ggcctcaagt gatctgccca cctcaggcct tccaaagtgc   22260
tgggattaca ggcatgagcc accgcaccca gccccaggaa attttaaatg taaactacag   22320
gtgaaggacc aaaatctag aaatcatgta taattaattt acgcaaaaag atcataaaac    22380
aagctgaaat tacaaaatga aaacatctag actgttaagt gctgctctga atccccactc   22440
attaaaagac tgtgattgct ttaaaagata ggagcattat acaaggaaga agaaattcac   22500
tctgagaaca aagtagagac aatctgaaga tgttgttgtg ggctttgtca gagtttgctt   22560
ttatctatcc tttttaggtat aacagaccctc agaggaagtc caccctggaa ccaccttctt  22620
aaacaacaca tacccaggag gcaggatctt ggttactctt ataagtctgt aacaatggac   22680
aagtcacttc ttgcctctaa acggaatgag ctggattaga caattttttat gatcccttcc   22740 agttctaaaa tcacagagta tgaagagttt ttcttgtagt atctaggaaa aaaattttat   22800
acaacttacc agtagttgga agttctattt tattgcaatg gtcctgattg cagcaatatg   22860
ttgtagtcac agacccagtt tttgaagagg gtgcacatac aaacggccta tctcgaggaa   22920
ttaagtcaat ttcagctata cacatgctgt tgtgtataac tttgtctgtg gtctctgtga   22980
cagagacaaa gcagagccca tctgtcacac aagtaaaatt gtcttttgta cagaggtggc   23040
agaaacactg taacgctgga aaagagaaa gattcttaga aaaatctca aggttaacag    23100 tttgaaatta ccaatattc acctctaata atacattctt gatcctatta tcacacaatt   23160
tctatgcact gtttgttgct cttagaagca aaaacaact atttgttgct cttagaagtt   23220
tcaaattata ttaagaacca catacacgtg gaagcccaag gaaatgtagc aacatttgga   23280
cccaggtttt ttcctgaagt tttttgcttc caagtataga aaaatttgt tatgttcaat    23340 ttcatcaaag caaggcaagc atttgccttc ccattagaaa caaagtacat ttaaatttgt   23400
aatggttata ctttttttt tttttttttt ttttaccag gcccaaacta aacattcaca    23460
tactcctcct ttgagaagca atgtgtgaaa acactaccac ccattaagtg taggctaatg   23520
ccatttcagt ggctttctgg ataatggagt aacggaaaca gatttgtact gagccagaca   23580
```

```
ctctctattc cccttggtgc aaaccctaaa aaagacatgt atattctggc caggactggg   23640
gcattctctt agggaagcca agcagactac acctgtaaca atacatacat gctccaacca   23700
cataggcaac ctaactacag aaatgactgg cagcaaaata ctagcttcat gcccacttgt   23760
atctacttga tctttatggc tcaaccccag gagtgacctc tttagggaag ccttctaatt   23820
atcaccaaca ccttctcata cacacagata caccttcaac catgctctct gatgaagtta   23880
agtgctctcc aaaacacata ctgcttacca gaattgctag ttttgttttt ctttctccta   23940
tgaaactgta aactccttga ggccagatac ctgtattagt catttctgtc aatctgccat   24000
ctaacaccat gcctcatgca cagcagcatt caaaaaatac ttgttgaatc acaatgatag   24060
aatgtgtgca taatttcacc atggtcacat gaaattgcaa agcacagaca tgttcttaaa   24120
tccaaacatt ccaattactt gttggcaaag gaataaaaag gagtctaggt acacggaatg   24180
gccatctatg acgtgaacag caaggtccac tctacctaga aaaggagtgg ctaggcagac   24240
aggggcagga tagacagagc taactccctg aagagctaac ttgctgtaca agaaagggtt   24300
aactcagcag gactgagttg ctcaaaccct gcatattccc aagaaagact tgtcttcaaa   24360
actggccttg gctggctcct ggtagatgag ctctgaacct ttggaatatt ctccctgata   24420
agaatatttc tgtatgcctg aggccttggg tcacatggta ccaattttgt cagacagctt   24480
attctaacaa tgtgatttac agtgaacacc tattactgct gggggggccgg gtaggagaag   24540
tctgagggggc tgaagcctgt catgcagatg ctgcaagcct aagtgactga ccaacagtaa   24600
aaaccctgga caccaaggct caagcgaact tccctggttg acaacttcgt gcatgctgtc   24660
acacattgtt gttgagagaa ttaaggccat ctatgctatg ccactggaat gggacacctg   24720
gaaacctgtg tctgatttct cctagacttc accccgggtg ccttttgctt ttgctgatgt   24780
taactgtatg gttttgctgt aatacactat aaccatgact gtaacagctt ttctgagtcc   24840
tgtgagtcct tctagcaaac caagtctgag gatggccctg cagactccca actcacttgc   24900
tcaactcaaa ttcaggaatg tcaggttctc cctcaagtag ctgtttcttg gttgctggct   24960
taattcacat acttgtctat tatctttaca gaccagtaaa gttttacctt aatcattatt   25020
aaaaacgctt tctttattca tagacaggtc agctatttgc ttcctaagta tgaaagaaac   25080
tcaaggaaat gacaagaaag agacacaatc gtaataaaga ctgctaaaag agacagtaat   25140
tattcatgac aaggtgtgat ggtgatggct gtctgggtat gatttcctaa ggaggaattc   25200
tgaaccagga attcatggac tggcttcaga ggtacatgaa tcccataaaa ctataagcca   25260
aatgttatat gtatttacat tttcaaggaa aagctttcca agtcaatcac aatggagtct   25320
gtgacccaca aagcattaaa actaccaccg aaggacattg tcataattct ctcctaaatc   25380
ctctttactc atgattagtc attcaaccca tgttttctaa gcattacttt tatcagttac   25440
tctaccaaaa gcttagcaca caaagattaa taactaatgg tcacagcact tgaagagctc   25500
caatgacaag tgaaggagaa cactgtaata caatgtggta accgctatac ataaaaaata   25560
ttgccctgaa tactctccca gttctcagat caccatggct cccctatgct gatgagataa   25620
gggctaaaca cctagcctaa caagacttttt agtttggggt tccaatttac ttctcacatg   25680
gcaaatgcta tctagggcca cacacctctc accattataa taataatgtc tttcatgacc   25740
ttggtcttta catataccat ctctctgtct agtttaaacc tatcttctta tctgactcat   25800
cctttaagac cctatttcaa caggatcttt gccattatgt gctctaaacc tcgcccttac   25860
cttcacaata attggtatct cctttcaata tgttccatag tgctctttgc ataccttag    25920
aacagcacaa atcaatctat ttatagcttg ctgttaaagg gtctttcatt gcctcaggaa   25980
```

```
gggccaagct tgttttgttt ttcacatctc tgaatcctgg ctccttagat agtgatcaga    26040
aaaatatttg ctaaaacaat gtctcccaaa tatgctggga gaaaaaaagg atgtataagt    26100
tgggtacaag gtttgagaac atattttcac ttcaaagata atctaaaaac aaggataaac    26160
attcaagatc atgagtagcc actgtctcaa cactggcact aggctttcac tgctgcttct    26220
tcagctgtgt gaagatcccc ttcaggccaa atgtccttgt ggcacactac acacagcata    26280
agtttcatgg tcattgtaaa agaaagagta aaaaataaag ggaatttgaa tcgaccatat    26340
ggcaatacag gcatggcatg catattcaaa agccaaatagc ctaacagcca ataccatata    26400
tgtactttat tatatgcaag tgctatatgg gtcctacatg tgtagtacaa tttgcaaaca    26460
tttgttagca gtaaatataa ttgtaggtat gcaatgtttt tccattctca tttccagcaa    26520
taactggttt agaaaatcat ttaatgaaga tttcaataat gtcaagatat taaccttatc    26580
ttccaatgaa caaatggat gacatctcag taaaacttat aagcctgtat ttgaggaatg    26640
cttgctgtca agtgttttgg ttaggtatga tgtctcatcc tgaacttacc aacaaggcct    26700
tgaagtcatt aatgccctcc tgcataacat tactgatgag aagaggcact actcacagct    26760
tttattatca ctgaagttaa aatacagaaa cacatttaaa atggaattag acctaaagct    26820
atttttttct actgcaaaac ctaaacatca tctgtcacat ggaataattg tattcatttg    26880
aattttgttt ttttttgtag ttgtctttgt atttaatttg cagatttggt ttatagtggt    26940
gtatgagcca agaacataag ggttttatat ctagtttcat gtctacagaa tttaagtaac    27000
attatgaaaa atacactctg tacttctcct ttcaaagagg tcattacatt acggtaaatt    27060
tgaaaaagtc agtactaaag ggttttctt aactactctt tcaatcagaa gaggtcacta    27120
gacaaataaa aacatcaaga taacacaaag cttaactagg taaagatttc tctcttcagg    27180
gaattaaaaa attccatttc accacttgaa gtcagtcttg attgactaca agactgctgt    27240
tatgtgatac ggcaagatcg tttagggaaa aactaaaata agaacttaat tttttccatg    27300
aacatgagtt ttaattgcca ttttttttaaa aaattcaaat ttattttatt aatagataga    27360
tttggcccct ggatactgcc cccccaacc ttttattcaa ctaggtttta aatttttaaa    27420
cgcatataca tggcaaaatt tcaatctaaa aaacgtaaac gaagacacct ccttccgcca    27480
gcccaaagcc caagttctcc tcactctgca acacatcacc ttgactcttt catttaattc    27540
tgcaattatt cactaagcat ctctatatgc caggtacagt gtgggctatg aggtgcagag    27600
atgagtaaga caaggtattt gcacttgagt agttcactag ggtggaaggg aaaggcatta    27660
aacagataat taaaatcctg agtcctgaga agaatgatca aagtgtttct actctgctgc    27720
ggtagaagag attatcaaga aaagcttcac cagcattcaa gtcagaactt ggagaatatg    27780
tacaatttgt tagatagata agggtgagaa agctttcctg actgggtttt ctttctcagt    27840
ggcaggattt catccttagt ggctggcata ccaagtaaga tgatcaaatt taaattgttc    27900
aagatgctaa ctacgatgtt ttatttcatc aggaaaataa acataatacc tctctgacct    27960
atttcatcat ctgagctaat caaatgagat actgtacttt attaacacat ttggaaacga    28020
acataaatga ttatataaac acacagaatt atcccatatg ataaatggca ttgtgccaat    28080
gtggttttta ttcgtaggcc accaaaggta aacttcttcc caaaagtagt gacaaaattc    28140
cactgtagaa tcccagacta acagaaccac atgaaacttt gaatatcatc taggcaattc    28200
agttctgtca ttttattaat gtagaaacca aaacttaaga aaagcaaaac aattttaaaa    28260
attttaaaaa gaaaaccaaa aaaccaaaat gatttataca aatattctac ccagattaca    28320
ggcggatgtg aatcctcact atattatcac cagcccacga gtgaaaccta cgcaactatt    28380
```

```
tgctatacca ctatccccat gctaagtaac cctgaacttt aaagactccc aggtggacct    28440
gatttggttt agactcctac agttttgact cttctgcttg atagcaaaaa taagaaccaa    28500
atcccctgtt taggaccttt ctactacact gtccaacttt gtttccatgc cccagtcttt    28560
aacagtgggc atagctttct taatcttgag atgcacattt ctctaagctt tacatttcta    28620
aaatctgaat acaatttaca atcaaagtaa aagaaaact ccagcctcca gactgaaagg     28680
ttaagacatg atgggttgtt gtaacctatg tatgtgcaaa cttggctata catagaaaag    28740
attacaagtt gagtatccct catgcaaaat gctcaggacc agaagtgttt tggatttggg    28800 attttttca gattttggaa tatttgcata tacataatga gacatcttgg gaatgggacc     28860
caagtctaag tataaaattc attcatgttt catatatgct ttatatatat agtctgaagg    28920
taatttaata taatatttga aataattttg agcatgaaac aaaggtcatg ttaagtactt    28980
atgtgcagaa ttttccactt gtggcatcat gttggtgtgc tcaaaaggtt ttgaatttca    29040
gattgggatg tttgacttgt attcacttca ccatcactgt aattatttgt cttgatagct    29100
cccttgcaac tataacttag gttaaacaag gatttcagtg tgattcagca ctaaaaggaa    29160
aagctactgt gtcacagaa aattatatca gaaccatgcc aggaaataca attactagca     29220
gtgaaatttc caaatattgc agaataaatc agaattttca agtttgcag atgttagcat     29280 ggtgacagtt agtaccaaag gaagtgacat gaggaaaaag agacaacagg acccttgggg   29340
ttattattca tggtattata gtatcggggt aacaactctc ggggtaacat atcccaagtt    29400
gagatcttgg ctcttggtcc caatataaag gatttccttg gttgcctcat ttcagtacgt   29460
ctcgaggtca catatggaag cactattaat tctatctaat gccagggcta cccagggtta    29520
attcacaagc ccatatgtct tgctagaaaa gctgagaggt aaacagttgt gtatagtatt    29580
aatatatgga acagatattt ctatcacccct tgttaaagaa ataaaaatta gcaccgaaac    29640
cttgtcttcc caggcttagt gtgtcatcat ctacacaacc tacccgtagt ctttttatgc    29700
atacgcttga atactctttc ctttttcaac ccttgttact ggccctctcc agccttctat    29760
cacccatctt cctccagttc agagctcaac tgaaatctct ctttgaaatt cactagcaat   29820
gcccttctgg tcaaattcaa tattctttc aaaacgtttc aggatatgag acagagtacc     29880 acccttctt tattagttttt tatatgacac taaacttccc aaacttactt tgcacttggc    29940
cctttggtac atctcagatg tacatctcca agcctcttgg cctttaccct gtgctccaag    30000
cttgtatttt aactacatcc aggaaacact ctgcttggct tacttatcta tgcaaagtca    30060
agcagagtgt tgtaatccag ttttttcatc actctgactt tgctggtgat gacccttatt    30120
ttcctcaccc tacccactac agcacaacta acttttctt cgcagtgaga gtatttccaa     30180
atattacaaa catgtaccaa caggcaagta aaagacctaa catgcacaat gtcctttatg    30240
cagtttgctt cactacagct gaaagcagat cacatcactg ctggcaaagg tgaaggcaaa    30300
agttggaagt tatttaaaaa aaactttcag ggactaatgt cagccccttt tatcatccaa    30360
cctattcttc tacccagtt cttctgagta atctgcctta cccctttct ccattctcaa      30420 cacatgcccc cttctcaagg agacgtgtcc tcttttctcc ctcatccagc tttggagtaa    30480
agcatactat atagattctc cttttctttt tattaaatat gttgcttatc tctgtataca    30540
tggctaaaac cctgacctcc aattccctcc agcctactat cctaggtttt gttcctcaaa    30600
atactcagtt cttctcaatt caaccctcct ggggctacct tgcagcagta atatcaaagt    30660
aagcttgtca aaatagagaa caccatataa tgtacataaa atttcctct agtccagata     30720 atatttcacc cctgaattta gggcatcaga ataaacgcct gatttttttc cagataaatt    30780
```

```
ccatttactt ctgccacttt taaagaattt aagatgcatt gtttatcatt taacccacat   30840
cacatcttaa aagaacaggg cactcccaaa ttcacaagct cttgtttttc cacattatct   30900
tcattttcca gtctcctagt ttctatggaa ttagccaata taatgttaac tgatatcaga   30960
gaaaacacac taagaatagg ctgcccaaat ggcaagatgg gatttaacag ggtaactaat   31020
acaaaggctt tcacttagat tcgaaataaa tcacacaagt acagcataaa gatctggtta   31080
gcagatctga ggagtttaac aacacatttt agaagagtca gagcctttaa aaagtatctt   31140
ttaatccatc aattctacta cttcagttg tctgaggaaa caataggtga gagcaaaaat    31200
ctaaacttgc agatgttcat tacagtatt  tatgattgaa acaacctat gtgaatgaca    31260
atacaatgac agaatgaatc cttatacaat cataaatgaa agactatata gccattaaaa   31320
ctggtatttt agaagcatgt ttaaggacaa gggaatggtc ctactactaa agggcaggaa   31380
gtaaagctgt atagtgtgat tacaattaca gtcctgtcaa gtgaccttgt ttttgttcca   31440
cttcaatgag ttgaggggat atttaatat acagagcaga tgtgcacact ttgccttacc    31500
ccaggccctg aaaagaaatg agaaacttc tatgtctaaa ggtgagtgct aaaacaataa    31560
ccaaatttct tatttcctct caatctaagt atgcttttac acagtttctt attagatttt   31620
aatttgacta gtgggtaggt attataagga tatggtagtt aagttgatgg aactcagaga   31680
cagaaaaact taagttaaaa tcctatcttt gccagtcagg cactgagtaa tcctgaggaa   31740
gtcacttaac ttatttgaac ctaaattct  tcaacttact tcctaaattt ataacatact   31800
aacaaacagt accaatctca gaaggtttga gggttaatga aataacatac atagaatact   31860
tagcacagtg cccagcacat aataaaatgt tcaaaaatta gtttatgcac ttttttcaaca   31920
agtatttctt tggagctcct attacgtgcc agtctctggt ctagatgcta gacagagaat   31980
cagagctaat gttgagacag ctctggtagg caatactgac acagaacaca atataaacca   32040
tatgcatata caacagtgaa tgttcatggt acctatcagc tctttctcct tcataaatat   32100
tcatacagtt tttcaacaat atgactgaac agacctggct caagaacttc actacagtag   32160
cagtaggcac acacagaaag tatattttca gttccaaccc aaattaacag tgtagggaca   32220
cacccagtgt gtatatgtaa tatccctaat aaataagtta atatctaatt agccataaaa   32280
tgttcatgct ggaaggaata tgaacagaaa tatcagatcc cagctccttt agagatgaag   32340
aaacagaaat gtcctaacag ttacatcaac ataatctaga tttattccaa aagtacacaa   32400
agaaaaaaag gattacttga taatctacag tgatttccac ccctactccc cacaacccct   32460
cacgtaggac aaaaccgaaa atttcaacct ttccctttgg aaagcacgag tggctgtagg   32520
agagactggc ttggttgcac agataataag gtgtaataat gaacgtaaat gaaagtggct   32580
gatcatcctg ggctagggga atgacataca aaacagaact gtggtagaga aggaactgtg   32640
gtaagagaag gaagtggtaa ccactcccag ctgccattga ctcggggcag aggagagcaa   32700
tacctgggcc agcaaacagc gaaagatctg ttggagccac agttgaagaa atgaactgat   32760
ggtcctgggc agttagtaat tttagaagca gaaagcaagg cctgaacacc tttctcaga    32820
acacaacagt gaatgtaacc tgtgtaggaa gaaagaaaaa acctttagga ggatagagat   32880
aattaggatt gagattcctg ccctcagatt cacaatgcag agaacacacc actgataaat   32940
gatgatgcaa agtgcacaga tcagaggaca gaaagggag atttctctga aatatgacac    33000
ctaaactaag acttaaggaa agctagtgaa gaaaggaaag tcattttagg tagaggatat   33060
acaaaaacat tgtacaaaag atgccaaaat aaaagtttga gccaggtgtg gtggcacgca   33120
cctgtagtcc cagctatttg ggaggctggg gcacaaggat cacttgagcc ccaggagttt   33180
```

```
gaggctgcag tgagccatga tcaggccaca gcactccatc ctgggcaaca gagtgagatc   33240
ctgtctcaaa aaaaaaaaaa aaaaaagaa agaaaacagt aagggagttt ggcagtttag   33300
gtgatgtaaa caaaaacaaa aaaactgata aaattcaaca gctattcatg attttttaaaa  33360 atcttagtaa actgataaaa ttcaacagct attcatgata tttaaaaatt tcagtaaatt   33420
gcagaattta aaaaaaattc tgaaataatc agattaaata aaaggcataa agtaggcat    33480 tacatttaat gttgcatgac tgtcattttc ccttgaaatc acaataaga aagagatatc   33540 catcactact tctcaacatt gtattagaag tctgagtgta gtaagtcaga ataaacaaa    33600 aggaagatag actggaaaga cacagaacta tcattacttg cagaggacaa ctatgtacat   33660
ggaaaatcca aaagtgacct acagatcaac tattagaatc aattagtcaa tctagcaagg   33720
tcactaatat aaggttactc actataccaa aaaaaattaa attaaaaaat cattcttaaa   33780
ccagtaataa atagaaaacg ttttttaaaa atctaaaaac taggaataaa cctaacaaaa   33840
gacaggtaaa gacctctgca gagaaagctt aaaaaatatt acttattgat agaaattaca   33900
aaggagataa aataaaattt taaaatgtat ttataaatgg agaaaagtga caagttccta   33960
actggaagat tcaatactgt aaagaggtca atattccata aagtgatctg tagattcaat   34020
aaaatcaaat cagaatcccc acagggtttt tttattcagt gggaactgac aagttgattc   34080
tgaaatttat atgaaaaaac aacatcgcaa gaataaccaa agcaatcttt gaaagactta   34140
acactactcg atatcaagac tcctaacatc ataataatta agacagtatg gtaatggcac   34200
aaggacaaat gggcaaacag aacagagatt acagagaaac agaccctcac atatacaacc   34260
tcttgattta tgatgaaggt gattgtacac tgggggaaaa aaggttttac caataaatgg   34320
ttctgagtca accagatatc cgtattttaa aaataataaa aatctcatac cataataaat   34380
aaccaactcc agatacatct caatgtgaga ggtaaaacca atcttttaaa tgaaaacaca   34440
ggaaaacatt tttaaaacat ttgggtcaga aaaagtaagc aaacaggatt ctaacttaaa   34500
gcaaaaaatt gaaggccggg cacggtggct cacgctgtaa tcccaatact tgggaggcc    34560 gaggcaggca gatcacctga ggtcaggaat tcgacaccag cctggccaac acggtgaaac   34620
cccatctcta ctaaaaatac aaaaaaaaaa aaaaaatag ccaggcgtgg tggcagatgc    34680
ctgtaatccc agctcacgg gaggctgaga caggagaatc acttgaaccc aggaggcaga   34740
ggttgcagtg agccaagatc gcgccactgc attccagcct gggtgacaac agtgagactc   34800
cgtctcatct gaaacattca tctcccttgt caaacaaaat accaaagcaa agcagttaaa   34860
ttgtggttgc agtctcctag aagaacacag ctgaattgaa ccaagcaagg acagaaaagc   34920
ccaccaaaag gaaggagctt ttgtattatt tctatatttg cattttttata atattttttaa  34980 tcattaaatt ttggactccc ttggagccta aagatataag catctagtgt tgactgaact   35040
cctttcaggg aaacatttgc cctttgagac taaactatgt gtatatgaaa acttaggctt   35100
gagatgtact gtaaccaagc taataaagtt ttcagacctc aaaatctaca tgccgagact   35160
tggcattagg aatatgggtt tccaattgct ggtagcattg atacagtagc atcatggcta   35220
ctgaagaaag tgggggggttg gttattaaaa gataaggatc tatcaggctc agaggcataa   35280
gggtcttgat gttatttata ccttggataa ctgatgatac aacaccgaag actatcttgc   35340
agaattatga aatctatatg taagtcaata atcactagtc tctagataat agtttagaat   35400
ggttcacagg tgattatact catttcttcc ataagatttt cctttttccc agttacagag   35460
actaagctaa atcagatgga agcacccaat tgcttagggc aactacgcta tttcctcagg   35520
gacacaccat ctgtttgcaa tgcacagcta attctgagcc tgttggtcct cgcagagttt   35580
```

```
tcccttaaga cttctgcctg atgcctaaaa tcccttaaaa ctcctccctc ctttcccttc    35640
tcccatggta aggcaagagc aggctggatc tgacaaaact taaatgatag atgagatcta    35700
cataaaatac ttatgtggcc ttttttttt tttttaagaa taaagtgaag aaacaattat     35760
gatcatgggg agaaagaatg tgagagcaga aaggctcaag tttatacatg catcgaaata    35820
agagggaaga aaacaaaagg acaatgcacc atggaaagaa ggaaagcaaa ataatggaaa    35880
gggagaaaaa aggagcatct cttcctagga aagtaatcta caatgctgtg ttaatctgcc    35940
aacgctttgg tgggactggc aatcagaaat tgtctttcct cactgacaaa catgaccaga    36000
ctctggcccc tgatttgtaa ttttttttccc aaatgtaaaa tgagacaaaa taactaaaac   36060
tactttaact tgtttatttt gataaaataa ttatatataa ttattgttga aggaaatcta    36120
caatacacaa tcttgggtgt ttttatttaa atctatcaca cattgaataa caaaattaaa    36180
atgtcagttt ttcaactgga gaaagtactc aaatcaacaa ccacgtgctg aacaaagaga    36240
cccaattaga gcacattata gtttgatttg gaaatgaata catcaagcaa aaaataaaaa    36300
acccatacat atatcgtgtg cttgcataca aatgaaaggg cagttgctgc ttttctatct    36360
ctgtatgtct tttcaagttt aactctatcc tccatgttca gtgctcccaa atatctatat    36420
tagtcctagt ttctcgcaga aaaagccatt cgttttttgcc ttttccctgg ggacctattt   36480
gtaattcaat gcatatttaa gaatcttata atgtagaaat gtaacaggat gcctgaagaa    36540
ggtgtcctag aactataaat atacactatt atgtaatcag tgaggtttac acctaggaaa    36600
tctagatgga atggttttcc tgaagcaaat gaacaaaaat aaggaggttc agtcttggtg    36660
gtgagaacaa ggaaacactg aacagacct gaagtagtac agcaactgca gaaaaaagga    36720
aaagtgaatc cttacaaatc atgagtgata aacccgaatt gttcacttta ttttttcaatg  36780
gcccatgtac aaagacttct ataaaagctt ctgctcaaga acagagagaa gcttgttttt    36840
cccaatgaaa tcagaatgct tctaaccaca gaatgccctc atgctaatgt acgtgcctat    36900
cttttccatg aatactggga ttactgtgag accagtacag tagggccaca ctctcagata    36960
agtgtggtct ctcctaaagt aatcattccg aacgtccatt actcagaaat gaagcagttc    37020
ttcaaacaag aaacccaagc aaagacactc tggatcttac tgacttgcac ctgtttgaag    37080
gtaaatgtct ggctctgcct ttggtagcag tactctgatg aagtgtatca aatggagaca    37140
caccaaaaga taagggcatg agaaaaatgt ctttgtaagc cagactaaat agtttcatgt    37200
tgctctctat tcattatcct ccagctttta gcaaagcttg atttaaatgt cctagcctta    37260
catcagctgt tccattggca ttagggaaag actaatgtgt tcatacttgg atcagagact    37320
taaactggag aagaaagatg gaggcagcag cactaaattg aaccctcaat acgtgttaaa    37380
ggggaagcct cagaacaaga atcagattat tgccagatcc agcaataacc ccttaccact    37440
tggagattct ccctgtatga caatcttggc atttggggct ccactttatt aaggaaggtg    37500
gcagtctcct catgaattct cgataggcaa tgagatctat gcaaattatc agtcttcctt    37560
acttgccttg gttaccagaa aactcagagc taagtattgt gttcaacttc taaagctttc    37620
ctcagctaaa cttacggata attgttctct ttttctttcc ctttttgact tactgattct    37680
tatcttttgt ggtcagtaga tttggtctta ctgaatttgc tattatttca agcttccaaa    37740
atccttttt ggaaaatgac caaaataaaa gccaatcaat ggataaacta acttttctcg     37800
tataatacag gagcaacaag atactgctca tcttgaagcc atgaatccta gggatattta    37860
gactatattt ggctaaaacc agtaagcaag gaagcttgga ttatgcccaa aagtacagaa    37920
ttttagagga gaaacagagc ttagagataa acaagtccga cctcctacct aatgtaagaa    37980
```

```
attccttcta caatttctca gacagaaggt tatctagcct ctgcctgaat agttccaggg    38040
tgacagggaa catactacct tacaatgttc cattttgaca gctatggtag agagtcattc    38100
cttacattga gctgaattct gcctttcagt ctaccaatta attctagttc ttcattacac    38160
agacatgtat ttcttctttc agaagacatt ctttcactta tttaaatata taataattcc    38220
cctttattga acacctactg gtgtcaggct atgtactaag tgtaaatact actgtacact    38280
atcttcacaa cgatcaggta aattaggaac tatcctcttt tgaaaagtga gtcacagata    38340
cactgattag actctaatta cagccagata tgttggtgct tatatactac tcctataaac    38400
aaatatttca ttaaatttct gacaaccaag tcacatgaat ttaatctgcc ttcaaaactg    38460
aaagaaaaac ttaagttaga tcaatccaaa tagaaaaaga gagatggtct agggatacaa    38520
ctgcaccagt gtttggttca ttgagaaaaa caacaggaaa agcatttaaa aggatagcca    38580
tcagggagct ccaggagata gtaaagctga cacctgtaac atcagcaacc atgacctgag    38640
gcctaggccg caagcaggaa acttcctctc ttttatctca gccaagaacc acactcccaa    38700
aagatcaaac gcattactgc agagaaagca gcactgtctg aaggttaatt tcaatacaac    38760
cagaagatca caagtaattc tgaatatata catctttact aagagaggtg ggggaaaaat    38820
agcatgaacc tgcaaaacag gaaagaacca tatcccagca aacggaccag gactccagat    38880
acaagctagg acttcagggt ctaaataaaa actccattta aggtagcgtt ttaggacact    38940
agaatcctcc tacccccaaa agagaaagac agagagagag agagagaata tgaggtgaat    39000
gctagatgct agtagccatt tctttgctta aggtgctctc ccatttccaa ctaggttcca    39060 tttttttttta atctttgctg actactgagc aattttattt ggctaccttc acctcaaact    39120
caacatgctt aaaccagaat tcgtctcccc ttaatcctcg tgccaaatta ctcattaagt    39180
taaaggcatt atccagccta aaaaagcttg gagtcattct ttttctttc atggagtcac    39240 tctgaatttc tgtactccac ctctttacag ctaagaccta ctgccactca acaaatattt    39300
actgagtgcc taggatgcac caggcacttt ccatacactt gagatacatt agtgaacaaa    39360
acgaagacat ccactttcac aaagcataga atgataggaa ggagacaata aacagtaaat    39420
aagtacatat gataagtaaa taaatacagt atgttagaag gtattgttac agagaaggaa    39480
agcactgtag gatgatgaca atattttaaa aggtggcagg ataagcctca ctgagaaaaa    39540
ggtgtcatct gagcaaagac ttgcaggagg tgagggagga agccatgcag gtatgtgagg    39600
gaagagcaca caagcaaggg aacagccaca cacaggccct actactaatt cctctgattt    39660 cttttgtttca aatgtcatac agtcaccatt tcaccccgtt ctcaatgcca tcaaaccaac    39720
tgggtagcca ccctgatcca ttccctctgc ggcacaatta gacattcttt ttccacatta    39780
aaaccactct cctgatttc aaggcccata attctctgag cccaccctt acaccatgaa    39840 cttccatttc tcctcttaga aatcctgaaa cttagaatgc tctttctcca cacatgccat    39900
cctctccagc caagaagtgc ctcctttcca ccacacatcc actcaaagcc ctatcctcct    39960
gcaaggcaga gagatcaagt cctacctcct ctgtaaagca gtccctgtgg ttgctagtac    40020
tgagtctgta gtcatatttc ctcagcatca attttttcaa aagcaagact gcctcttact    40080
tttcctatat ttctcatcat gttgatcact actaaatatt tgctaagaat agatgagcta    40140
tttcctctgt aaactgaagc tctttcctct gtaaactgaa gctgtttgtc aatttaaaca    40200
cttttattag ctttcataaa ctgctgaaat agaatgatta aagaatggtt tgttgctgtt    40260
tttttgtttg tttgttttg ttgagatgga gtttcactct gtcgcccggg ctggagtgca    40320
gtggcgcaat ctcggctcac tgcaaactcc acctcctgag ttcaagtgat tctcctgcct    40380
```

```
cagcctccca agcagctggg attacaggtg cctgccacta cgtccagcta atttttttgtt  40440
atttttagta gagacagggt ttcatcatgt tggccaggct ggtctcgaac tcctgacctc  40500
gtgattcgcc cacttcggcc tcccaaagtg ctgggattac aggtgtgagc tactgtgccc  40560
agcccaagaa tggttttta tactcaaaaa aaaaaaaaaa aaaaaaaaaa aaaaagcatg  40620
ggtgcaggat atgccaaatg ttaataatgg ctggtgatgg tttttttcct ttctctaata  40680
caaattttca gtcctgtgct tatgtaactt ttagaagaaa agaatttgct atgaatatat  40740
gtataaatca atacaaatag taagtgatca actatcactg gactcgtcag gaagattcaa  40800
attcctaaa aatataatgt taagaaaga ctgttagtat ctgaatggcc tgcagttgca  40860
aagaaatagt aaaactgtaa tcaaggcaat ctgaagcaaa ttctcatggt ttgcaaaaaa  40920
gggaaaggaa actttcctgc tgaagtggct ctaacaatgt atttactcta tatgaaagga  40980
gcatggacgt acgtgacccc atcataagta gaggagcatt tgtataggaa aagagtacat  41040
accctggagt gcttaactga aggctccacc tttcattaac agcataactt cagtttcctg  41100
gtctataaaa tggaaacaaa gagggtcttc tttcatagat atgaactagg ttccaatctg  41160
agcaaaattg tgtcaattct gcctgcccag gcagatgggg tttatggtaa tacaaaatca  41220
tttgagtctc agtggctgaa ctactgttag tctacatctg tgccattcaa agcagtgtct  41280
ttcttttata tatatattta cgattagacg atgaaaaaat actaacaccct ttggataatg  41340
tttagagttg aaaagaatct tggggtagag ccgatgttat caaaacctac agttatcttc  41400
tgagcactgg tcacctgtat ctgggaacaa atgggcttaa gagtttggaa attaagcagc  41460
aaataagtaa gaagttttgg tactctatac aactaccatt caaggttggt tatgagaact  41520
aaatgatgcc gtattagcca tggtcaaaga aaaaaaaga gagaagagag aattaaacga  41580
gacaagacag atagaatatg tagcatattc ttgcaaccct tcaagaaatt tcaaagcaac  41640
ctgtgtgtat actttgcaag tcaatttttt taagttaga ttagaaattg ttctttgagg  41700
gagcagcttt ataaaagact tgatctgatc tataaaattg gaccataaaa ccaactgaac  41760
ttagtccact agtatttaag aaagtgatgt ctgagatgaa taattacaag tctaccaacc  41820
aattttcttc atgatgaaga agggtagcca taagaaactt acctggaaag caaacaaaac  41880
acataaaatt ggatctaatt cagagtggta aacaattta atgtttatgg agactgcctg  41940
gatttgacat tgagaaaatt cagctaagaa tggcattaaa tgtaatccta agtattggag  42000
ttaggctggg tcaaaactga ccataaattc tgagaagact ccaaaacttt tcctcaagct  42060
agttctatgg gacaaagcat taaaaaatcc ctgagaaata tgccagcatc tgccctcaat  42120
tccaaaagca ggaagcaaag atgtgaccca atcacatgat atcaaaccac agtccatctg  42180
ttcagagaac tctgtgttac gtaagccatg accaaggaag aactgcaaaa ggcaagaggt  42240
gtgtcgacat ttgcaagggg ctctgtggtt tgaagagaca cgttctcaca tcagaagggc  42300
catccatagg ataatggcat tttcaaaatt ccatttatta cacatgaaca tatttggtgc  42360
aataaaatga cactacaaga atggtgttga gtccctgtaa ctgctcaact aaggcctaga  42420
acctttgac aggggtcttc cctacatgag cggccctcct cacaggaaca agatttatct  42480
tcctcttgat tattttatg tcaattcctc tcttaatttc aacaacaaag cggatcatct  42540
aatattctaa accaaagcct tctaactaca ccccaattca attaactgta cttactcaag  42600
accatcttcc aaactactat aggcctactt ttctcaatca ataagtatat accaggtcct  42660
tttatcagca attaaaaaaa aattgacctt tccttgaga actttaaggc tttaatcatt  42720
cccctccct tccacctta gaattcactt ttcataaatt ctgtgaagtt caaggcctac  42780
```

```
ttcacttaag gaagtcactc atcccttcgt ggatgccaac cacctatccc aaccctgtcc   42840
cactcccacc tccaagtcct tcacatttta aagcaccata tagggcacaa gatatggaat   42900
cagaaaatca aagttcctgt ctctgttctg cccctgtgcc accctaagaa attcacctga   42960 gtcgttttt  catctgtaaa ttgaagtgat aatatactta ggacttccac catttgaatg   43020
cctagtccta ctgggcatcc cataatgtta ttctccctca ctcattccac tttgattact   43080
tttatgtttt gtttccagct atgtactata gcttttagga ttggggaaaa aatgatagag   43140
gttaatacat ccaaattcca cagtacagaa taaggaacct aactctgaag agtaacttgc   43200
cagtcagtca gtaaaagcct tgtttcctcc cttggagtag gccccaggac agttggggac   43260
acaacttcaa aagaactttc acactcatca aatcccctc  tgaattctac ccacccttca   43320
aagtcagtgt aagtcctaaa gtgtccaaga agcctccccc aatcattcca gcttacacta   43380
atcatttccc tttttgaata ctaatgcctc cctatagaaa tgatattaaa aatatttaac   43440
aactggcact acaagggtac caaccaatca gaaaggatgt ttaaccaaaa cacacatggc   43500
ccagtgggaa ctgcttattg aacatcagtc ctgctctttta gcaacaacac agaatagcaa   43560
cctcaaactc aaataccact ttctcatgtg atcttcacaa tctcatgaat taggcaaaag   43620
taggtattgc cccatttct  gcataactgc tggtgaaggt aggacaaata accaattgct   43680
ttcaacacgc catacaactt ttcctgatta tttatcgga  attacaagtt aatattgcat   43740
aaactggact tacataaaac agtataaata ttaaaggaat gctcaaatag aaatcaacaa   43800
gcatttatgt ggaatagaat ataaaacaca gtgctaagtt ctgaggccac aaaagaaaga   43860
aatggcatga atcttgtcct ctgggtacct ataacgcatt caagtagagt taagtagcag   43920
cacaggcagt agaaatggac aacacaaact gttaagtgtt gcagagttct ggaagacaaa   43980
gaattcaaga actaaaccag cacaggaagt cagggctgag aacttctcgc actcccaaaa   44040
aaaggggcaa aactaaatgt gtagtgaaaa ggctgaacag tcaggagtca gtgagaaaga   44100
gaaattgctc gaaggtctgc agtaatgaga aatgagatcc ctggtaggat actcagagat   44160
ggccccaatc ataagctgct aagtgttgtt ctaagtgctg aatacaaatg ggaaatctta   44220
taaaccttca cggggaaggc tgaggaagat tagtttggca gtagccatag aaaagcctag   44280
atgagaaaaa catgggaaag caactagatt tggaggataa caggcaggat taagctgaag   44340
gctgcatacc aagaaaggag gagacattca agaggcattc atagaagagt tggattgggg   44400
gcacgttttc aaagaaaaaa agttatgaaa tggcagaaag gaagcaaata gcattctcag   44460
atgggatata catatagaca tagtggtact aaactgtgca ctagggataa ggaatcaatt   44520
tccctagaga aacctatgtt ggagacagaa gttgggcaga gaacattaaa acatactcag   44580
aacataaaaa ggtgcaagtc tttaaaaggg aagccaagtt acagaggaaa taaaaagcat   44640
ttgacccttt tcagaatgtt ttttaagggg ggactgaggc atcatcataa ccaacagggg   44700
aggcagacaa gctgaggcag tctgggctta gagtaataag cacctggaca gctttgtatt   44760
ttgtgcatac catggagact gtaaactcct ccaggacatg gactgagcaa tgttctgtgt   44820
cttcaactaa gtccactact gttacttgaa tacatgaacg cttcttgtgc tacttctggt   44880
ggaaaagagt gcactgtgtt attcaagtta atagcggtgt ggaaatgtta cctgtgtttc   44940
atgcctaact atactgattc tcccaaatgt ccacacagtt atcctgcctt cctccctagg   45000
ccaatgtcaa aaatccattg tttcctctaa tgcaggccca cgtgaaggga ctcaacaatg   45060
tgctaagagt cggaatgaag cctatctgat actcaaatca tgaggacaga atccaaagtg   45120
gataataaag accaattgct catcagacga ctgaagaaga aaaatgggct acgccagata   45180
```

```
gtatgatgta tacatattta tatatatata tgacatacag gtttgggaaa ctgagatctg    45240
agtgaaaatc ctagctttag cacttaagtt attgggtact taacgtgtct gtaccccact    45300
ttgcacatct gtaaagtggg gcaaatgcca ctactcctgg gagtttactt gtggtgatta    45360
aataatgtaa ttatacaata gtgtatgcat ttacatcgta gtaatgcaca atacatagac    45420
ggtagctatt aggactgatt ataatcgtca ccgtcagtct tgattttta aaaaaatttc     45480 aacatctttt gtccagtttc agaaacagaa atgtactttc actgcatttt agttgctaac    45540
actgaggctg tgtattttag cttctagtgt ctcagttcag ctgctaacga agttttcac     45600 tcatcccttt gtggatacca accacctacc ccaacctgat ttactatttt gaaaaatcca    45660
gccaacagtc ttccttgaaa accagctata cagatgtctg aatcaaacta ttaactgtca    45720
ctcaagaaaa ggaacaacgt gagtgatgtt ccttcgagga aataaaaagc gtttaatcaa    45780
ttcacagtcg ttcccaaaat ttccaaaacc cgcagaatga gcaaacgttc aagtttccac    45840
tatgaaaaca atccgtagcc gtctggttac tggactcact tcaacactcc ccagacgcac    45900
gaaagaagaa acattccgcg catctccgcg cttccttctt ctcacacaaa gccccctgg    45960 ctggaggagc agcccttcc agcagggtcg gctcgggtcg agccgggcgg gagtcagggc     46020
ggcctgcgga cccaggggtc tcaccacacg tcgccccga ctcccactgg acgaagccct     46080
agaggctcgg agctcacacc ccgcccggga gccgccttcc accccaacct caaacccgc     46140 cccgggttcg gcagcctctg gcacggaccc tcttggggcg ggggtcccca gaacaaggtc    46200
acgccgtgcc caggggggcgg cggcgggcag ccacggctct gccagtcccc gccggcctcg   46260
cactctccgc ccctggccct cgcccactca caccccagag ggcagccccg gacctcggac    46320
gactccgccc gactccacct ccccggggag tcccgagcgg ggcggcctcg ggcagccgga    46380
cacgtccgcc cgcgcccgga cacacgcccc tgccccgcct ccgctcccg cttgcggttc     46440 gcccggcagc cgccgagccg cgcggcgcca cgagagcccg gcccgggccc cggcgccgcc    46500
acctgcgccc ccggccccgc gccatgtttg agaaagagca ggagcgagcc agaggccggg    46560
tccgccccgc gcgccccgca gtcgcccgcc cgccgcgccg ccgctcaccc gtcgcccccg    46620
ggagcagcgc cgccgccgcc gccgccgccg ccgccagcac gaggaggagc agccggggac    46680
gcggagcagc gaccgccgcc tccatggtcc cgccgccacc gcctgtggcc cggcccggcc    46740
cggccgcgcc gctgcctcac cccagcaaac ctcgcctcgc cccacctccc tagccgccgc    46800
ggcggcctcg ctccggccct ttgtaactgc tcggaggacg cgcgtccatt ggctgccggg    46860
ctcccgccgg ccccgcctcc ccgccgccgc gagctgccaa gcgggaccca gccgggagcc    46920
ccgcctgcgg gcccgccagg cagccaatcc gcagccgcga gcgccggttt ctggccacgc    46980
cccacgctcc ccggggctg gccgccaga ccccagcccc ggcccgatcg gctcccggct     47040
ccgagaggcc gcgtgggggc ggggtctgcc agccccagca ccgctcagcc gctagccccg    47100
gagggccggg tagagcgatg ggtgtgtctg tgtgagtctc tttcggaaaa aggctgtggc    47160
cgttcgacgc tctttctctc taacctcctc taggcgcgga agatctggta ctgcctcagc    47220 cccacccctga ccccattcac agctccgcat tggcaatccc agcacatgcc acccagatcc   47280
gctgcagcgc caggcccctg catccacttc aacttcccct ctccaagtcc acgcatcaac    47340
ttcagcattc ccccgaagat ccctcctcag tgcccttcac atgcgactca ctctcctatt    47400
tcctcctgct cccagcggtc accccaaaacc cagctccccc acccagttcc aaacccagaa    47460
agtcctcaga tcccagcgtc agaccagat cctgagccca aacacacccc caaatagcct    47520
cccgcctccc tccagcacag atccaggatg gggatccaag ccgcactcct ctcaaacccc    47580
```

-continued

```
ttcccgatcc aggttggaaa gggaggatcc ccacccaac ccctcaaagg aggggttccc    47640
ccttcttagc acccagctcc cgcggggcgg aggggagca gtcatcatta ctttgagctg    47700
tgtctgacac tgctgtataa taatcctgag gtgtcactaa aaacccaaat aaactctacg    47760
ttttcattct gaattcctaa tttactgcga gacgctccac ccaccttccc tctgcgacgc    47820
caaaatgagc tccagatttg taattcttcc tgtcagacta gtcctttctt cagacacaaa    47880
cacagccaag gaggctgtta cgtagaacag agaatatttt tccgcagaac cttttaagga    47940
ggaaatttta ttttctgtgt catttgagct tagaattaaa taaaccttga tagcaggaat    48000
cagaatggtt ctgattaatg ccaatttgtg cactacttta gagtcactgg gtgagcattt    48060
tccccacctg tgaaggcttc cttccgggag atgaaaaggg aaaaggcgtg gatattggag    48120
ctgggatctg agacccgcgc gctttctccc tcctgtctag gacacttact taagcaagtc    48180
agctaacctt tctgaacctc aacaggctc agaggcctgc aacttgctct acaccgcagc    48240
tccagcagcc tcagcagcaa actcccctct tgctcaggct gagggattcc agagagatgg    48300
cttctggcag gctccagtcc caatttgccc tctcagttcc agtttcttca atggagattt    48360
ggtggacttt gtgccacctg aggtccctag actgcctttt tgctgctcta tttgcaatgt    48420
ctttcataag ataagagcta atgagatttt tattgtatga atgaatgaat gatctcagaa    48480
agtgactgtt tttctctggc cattagcttc ttcatctcta aaatgtaaat aataatagta    48540
cctaccccgt ttataaataa aagggattga atcacttgtc ttgggcccct aaatgacgt    48600 aatgtgtctg gtacagtgtc tggaacatag taaatattta gctaatgcca tttctttgcc    48660
catccccttc cagctctgta tgattctaat cagcatgtat gttcatgtca gtctgtgcct    48720
ttgacgtacg gagcctagat taatcagtgt taatcacacc tccagttcct taaca         48775
```

```
<210> SEQ ID NO 97
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 97
gatcttgact gccactgtct c                                              21

<210> SEQ ID NO 98
<211> LENGTH: 16
<212> TYPE: DNA
<213> ORGANISM: Artificial sequence
<220> FEATURE:
<223> OTHER INFORMATION: antisense oligonucleotide

<400> SEQUENCE: 98
catggcagcc cccgtc                                                    16

<210> SEQ ID NO 99
<211> LENGTH: 16
<212> TYPE: DNA
<213> ORGANISM: Artificial sequence
<220> FEATURE:
<223> OTHER INFORMATION: sense oligonucleotide

<400> SEQUENCE: 99
catgggtcgg gggctg                                                    16

<210> SEQ ID NO 100
<211> LENGTH: 16
```

```
<212> TYPE: DNA
<213> ORGANISM: Artificial sequence
<220> FEATURE:
<223> OTHER INFORMATION: missense oligonucleotide

<400> SEQUENCE: 100
catccccgga cccgtg                                                      16

<210> SEQ ID NO 101
<211> LENGTH: 16
<212> TYPE: DNA
<213> ORGANISM: Artificial sequence
<220> FEATURE:
<223> OTHER INFORMATION: Partial antisense sequence of TGF-RII gene
<220> FEATURE:
<221> NAME/KEY: X
<222> LOCATION: (1)..(1)
<223> OTHER INFORMATION: oligonucleotides representing group X appear
      before the nucleotide at location 1
<220> FEATURE:
<221> NAME/KEY: Z
<222> LOCATION: (16)..(16)
<223> OTHER INFORMATION: oligonucleotides representing group Z appear
      after the nucleotide at location 16

<400> SEQUENCE: 101
cagcccccga cccatg                                                      16

<210> SEQ ID NO 102
<211> LENGTH: 34
<212> TYPE: DNA
<213> ORGANISM: Artificial sequence
<220> FEATURE:
<223> OTHER INFORMATION: oligonucleotides representing group X

<400> SEQUENCE: 102
acaggacgat gtgcagcggc cacaggcccc tgag                                  34

<210> SEQ ID NO 103
<211> LENGTH: 33
<212> TYPE: DNA
<213> ORGANISM: Artificial sequence
<220> FEATURE:
<223> OTHER INFORMATION: oligonucleotides representing group X

<400> SEQUENCE: 103
caggacgatg tgcagcggcc acaggcccct gag                                   33

<210> SEQ ID NO 104
<211> LENGTH: 32
<212> TYPE: DNA
<213> ORGANISM: Artificial sequence
<220> FEATURE:
<223> OTHER INFORMATION: oligonucleotides representing group X

<400> SEQUENCE: 104
aggacgatgt gcagcggcca caggccctg ag                                     32

<210> SEQ ID NO 105
<211> LENGTH: 31
<212> TYPE: DNA
<213> ORGANISM: Artificial sequence
<220> FEATURE:
<223> OTHER INFORMATION: oligonucleotides representing group X

<400> SEQUENCE: 105
ggacgatgtg cagcggccac aggcccctga g                                     31
```

```
<210> SEQ ID NO 106
<211> LENGTH: 30
<212> TYPE: DNA
<213> ORGANISM: Artificial sequence
<220> FEATURE:
<223> OTHER INFORMATION: oligonucleotides representing group X

<400> SEQUENCE: 106
gacgatgtgc agcggccaca ggcccctgag                                         30

<210> SEQ ID NO 107
<211> LENGTH: 29
<212> TYPE: DNA
<213> ORGANISM: Artificial sequence
<220> FEATURE:
<223> OTHER INFORMATION: oligonucleotides representing group X

<400> SEQUENCE: 107
acgatgtgca gcggccacag gcccctgag                                          29

<210> SEQ ID NO 108
<211> LENGTH: 28
<212> TYPE: DNA
<213> ORGANISM: Artificial sequence
<220> FEATURE:
<223> OTHER INFORMATION: oligonucleotides representing group X

<400> SEQUENCE: 108
cgatgtgcag cggccacagg cccctgag                                           28

<210> SEQ ID NO 109
<211> LENGTH: 27
<212> TYPE: DNA
<213> ORGANISM: Artificial sequence
<220> FEATURE:
<223> OTHER INFORMATION: oligonucleotides representing group X

<400> SEQUENCE: 109
gatgtgcagc ggccacaggc ccctgag                                            27

<210> SEQ ID NO 110
<211> LENGTH: 26
<212> TYPE: DNA
<213> ORGANISM: Artificial sequence
<220> FEATURE:
<223> OTHER INFORMATION: oligonucleotides representing group X

<400> SEQUENCE: 110
atgtgcagcg gccacaggcc cctgag                                             26

<210> SEQ ID NO 111
<211> LENGTH: 25
<212> TYPE: DNA
<213> ORGANISM: Artificial sequence
<220> FEATURE:
<223> OTHER INFORMATION: oligonucleotides representing group X

<400> SEQUENCE: 111
tgtgcagcgg ccacaggccc ctgag                                              25

<210> SEQ ID NO 112
<211> LENGTH: 24
<212> TYPE: DNA
<213> ORGANISM: Artificial sequence
<220> FEATURE:
<223> OTHER INFORMATION: oligonucleotides representing group X

<400> SEQUENCE: 112
```
gtgcagcggc cacaggcccc tgag                                          24

<210> SEQ ID NO 113
<211> LENGTH: 23
<212> TYPE: DNA
<213> ORGANISM: Artificial sequence
<220> FEATURE:
<223> OTHER INFORMATION: oligonucleotides representing group X

<400> SEQUENCE: 113
tgcagcggcc acaggccct gag                                            23

<210> SEQ ID NO 114
<211> LENGTH: 22
<212> TYPE: DNA
<213> ORGANISM: Artificial sequence
<220> FEATURE:
<223> OTHER INFORMATION: oligonucleotides representing group X

<400> SEQUENCE: 114
gcagcggcca caggccctg ag                                             22

<210> SEQ ID NO 115
<211> LENGTH: 21
<212> TYPE: DNA
<213> ORGANISM: Artificial sequence
<220> FEATURE:
<223> OTHER INFORMATION: oligonucleotides representing group X

<400> SEQUENCE: 115
cagcggccac aggccctga g                                              21

<210> SEQ ID NO 116
<211> LENGTH: 20
<212> TYPE: DNA
<213> ORGANISM: Artificial sequence
<220> FEATURE:
<223> OTHER INFORMATION: oligonucleotides representing group X

<400> SEQUENCE: 116
agcggccaca ggccctgag                                                20

<210> SEQ ID NO 117
<211> LENGTH: 19
<212> TYPE: DNA
<213> ORGANISM: Artificial sequence
<220> FEATURE:
<223> OTHER INFORMATION: oligonucleotides representing group X

<400> SEQUENCE: 117
gcggccacag gccctgag                                                 19

<210> SEQ ID NO 118
<211> LENGTH: 18
<212> TYPE: DNA
<213> ORGANISM: Artificial sequence
<220> FEATURE:
<223> OTHER INFORMATION: oligonucleotides representing group X

<400> SEQUENCE: 118
cggccacagg ccctgag                                                  18

<210> SEQ ID NO 119
<211> LENGTH: 17
<212> TYPE: DNA
<213> ORGANISM: Artificial sequence -continued

```
<220> FEATURE:
<223> OTHER INFORMATION: oligonucleotides representing group X

<400> SEQUENCE: 119
ggccacaggc ccctgag                                                    17

<210> SEQ ID NO 120
<211> LENGTH: 16
<212> TYPE: DNA
<213> ORGANISM: Artificial sequence
<220> FEATURE:
<223> OTHER INFORMATION: oligonucleotides representing group X

<400> SEQUENCE: 120
gccacaggcc cctgag                                                     16

<210> SEQ ID NO 121
<211> LENGTH: 15
<212> TYPE: DNA
<213> ORGANISM: Artificial sequence
<220> FEATURE:
<223> OTHER INFORMATION: oligonucleotides representing group X

<400> SEQUENCE: 121
ccacaggccc ctgag                                                      15

<210> SEQ ID NO 122
<211> LENGTH: 14
<212> TYPE: DNA
<213> ORGANISM: Artificial sequence
<220> FEATURE:
<223> OTHER INFORMATION: oligonucleotides representing group X

<400> SEQUENCE: 122
cacaggcccc tgag                                                       14

<210> SEQ ID NO 123
<211> LENGTH: 13
<212> TYPE: DNA
<213> ORGANISM: Artificial sequence
<220> FEATURE:
<223> OTHER INFORMATION: oligonucleotides representing group X

<400> SEQUENCE: 123
acaggcccct gag                                                        13

<210> SEQ ID NO 124
<211> LENGTH: 12
<212> TYPE: DNA
<213> ORGANISM: Artificial sequence
<220> FEATURE:
<223> OTHER INFORMATION: oligonucleotides representing group X

<400> SEQUENCE: 124
caggcccctg ag                                                         12

<210> SEQ ID NO 125
<211> LENGTH: 11
<212> TYPE: DNA
<213> ORGANISM: Artificial sequence
<220> FEATURE:
<223> OTHER INFORMATION: oligonucleotides representing group X

<400> SEQUENCE: 125
aggcccctga g                                                          11
```

```
<210> SEQ ID NO 126
<211> LENGTH: 10
<212> TYPE: DNA
<213> ORGANISM: Artificial sequence
<220> FEATURE:
<223> OTHER INFORMATION: oligonucleotides representing group X

<400> SEQUENCE: 126
ggccctgag                                                              10

<210> SEQ ID NO 127
<211> LENGTH: 9
<212> TYPE: DNA
<213> ORGANISM: Artificial sequence
<220> FEATURE:
<223> OTHER INFORMATION: oligonucleotides representing group X

<400> SEQUENCE: 127 gccctgag                                                                9

<210> SEQ ID NO 128
<211> LENGTH: 8
<212> TYPE: DNA
<213> ORGANISM: Artificial sequence
<220> FEATURE:
<223> OTHER INFORMATION: oligonucleotides representing group X

<400> SEQUENCE: 128 ccctgag                                                                 8

<210> SEQ ID NO 129
<211> LENGTH: 7
<212> TYPE: DNA
<213> ORGANISM: Artificial sequence
<220> FEATURE:
<223> OTHER INFORMATION: oligonucleotides representing group X

<400> SEQUENCE: 129 ccctgag                                                                 7

<210> SEQ ID NO 130
<211> LENGTH: 6
<212> TYPE: DNA
<213> ORGANISM: Artificial sequence
<220> FEATURE:
<223> OTHER INFORMATION: oligonucleotides representing group X

<400> SEQUENCE: 130 cctgag                                                                  6

<210> SEQ ID NO 131
<211> LENGTH: 5
<212> TYPE: DNA
<213> ORGANISM: Artificial sequence
<220> FEATURE:
<223> OTHER INFORMATION: oligonucleotides representing group X

<400> SEQUENCE: 131 ctgag                                                                   5

<210> SEQ ID NO 132
<211> LENGTH: 4
<212> TYPE: DNA
<213> ORGANISM: Artificial sequence
<220> FEATURE:
<223> OTHER INFORMATION: oligonucleotides representing group X

<400> SEQUENCE: 132
```

```
tgag                                                                    4
```

<210> SEQ ID NO 133
<211> LENGTH: 34
<212> TYPE: DNA
<213> ORGANISM: Artificial sequence
<220> FEATURE:
<223> OTHER INFORMATION: oligonucleotides representing group Z

<400> SEQUENCE: 133

```
gcagaccccg ctgctcgtca tagaccgagc cccc                                  34
```

<210> SEQ ID NO 134
<211> LENGTH: 33
<212> TYPE: DNA
<213> ORGANISM: Artificial sequence
<220> FEATURE:
<223> OTHER INFORMATION: oligonucleotides representing group Z

<400> SEQUENCE: 134

```
gcagaccccg ctgctcgtca tagaccgagc ccc                                   33
```

<210> SEQ ID NO 135
<211> LENGTH: 32
<212> TYPE: DNA
<213> ORGANISM: Artificial sequence
<220> FEATURE:
<223> OTHER INFORMATION: oligonucleotides representing group Z

<400> SEQUENCE: 135

```
gcagaccccg ctgctcgtca tagaccgagc cc                                    32
```

<210> SEQ ID NO 136
<211> LENGTH: 31
<212> TYPE: DNA
<213> ORGANISM: Artificial sequence
<220> FEATURE:
<223> OTHER INFORMATION: oligonucleotides representing group Z

<400> SEQUENCE: 136

```
gcagaccccg ctgctcgtca tagaccgagc c                                     31
```

<210> SEQ ID NO 137
<211> LENGTH: 30
<212> TYPE: DNA
<213> ORGANISM: Artificial sequence
<220> FEATURE:
<223> OTHER INFORMATION: oligonucleotides representing group Z

<400> SEQUENCE: 137

```
gcagaccccg ctgctcgtca tagaccgagc                                       30
```

<210> SEQ ID NO 138
<211> LENGTH: 29
<212> TYPE: DNA
<213> ORGANISM: Artificial sequence
<220> FEATURE:
<223> OTHER INFORMATION: oligonucleotides representing group Z

<400> SEQUENCE: 138

```
gcagaccccg ctgctcgtca tagaccgag                                        29
```

<210> SEQ ID NO 139
<211> LENGTH: 28
<212> TYPE: DNA
<213> ORGANISM: Artificial sequence

```
<220> FEATURE:
<223> OTHER INFORMATION: oligonucleotides representing group Z

<400> SEQUENCE: 139
gcagaccccg ctgctcgtca tagaccga                                    28

<210> SEQ ID NO 140
<211> LENGTH: 27
<212> TYPE: DNA
<213> ORGANISM: Artificial sequence
<220> FEATURE:
<223> OTHER INFORMATION: oligonucleotides representing group Z

<400> SEQUENCE: 140
gcagaccccg ctgctcgtca tagaccg                                     27

<210> SEQ ID NO 141
<211> LENGTH: 26
<212> TYPE: DNA
<213> ORGANISM: Artificial sequence
<220> FEATURE:
<223> OTHER INFORMATION: oligonucleotides representing group Z

<400> SEQUENCE: 141
gcagaccccg ctgctcgtca tagacc                                      26

<210> SEQ ID NO 142
<211> LENGTH: 25
<212> TYPE: DNA
<213> ORGANISM: Artificial sequence
<220> FEATURE:
<223> OTHER INFORMATION: oligonucleotides representing group Z

<400> SEQUENCE: 142
gcagaccccg ctgctcgtca tagac                                       25

<210> SEQ ID NO 143
<211> LENGTH: 24
<212> TYPE: DNA
<213> ORGANISM: Artificial sequence
<220> FEATURE:
<223> OTHER INFORMATION: oligonucleotides representing group Z

<400> SEQUENCE: 143
gcagaccccg ctgctcgtca taga                                        24

<210> SEQ ID NO 144
<211> LENGTH: 23
<212> TYPE: DNA
<213> ORGANISM: Artificial sequence
<220> FEATURE:
<223> OTHER INFORMATION: oligonucleotides representing group Z

<400> SEQUENCE: 144
gcagaccccg ctgctcgtca tag                                         23

<210> SEQ ID NO 145
<211> LENGTH: 22
<212> TYPE: DNA
<213> ORGANISM: Artificial sequence
<220> FEATURE:
<223> OTHER INFORMATION: oligonucleotides representing group Z

<400> SEQUENCE: 145
gcagaccccg ctgctcgtca ta                                          22
```

```
<210> SEQ ID NO 146
<211> LENGTH: 21
<212> TYPE: DNA
<213> ORGANISM: Artificial sequence
<220> FEATURE:
<223> OTHER INFORMATION: oligonucleotides representing group Z

<400> SEQUENCE: 146
gcagaccccg ctgctcgtca t                                              21

<210> SEQ ID NO 147
<211> LENGTH: 20
<212> TYPE: DNA
<213> ORGANISM: Artificial sequence
<220> FEATURE:
<223> OTHER INFORMATION: oligonucleotides representing group Z

<400> SEQUENCE: 147
gcagaccccg ctgctcgtca                                                20

<210> SEQ ID NO 148
<211> LENGTH: 19
<212> TYPE: DNA
<213> ORGANISM: Artificial sequence
<220> FEATURE:
<223> OTHER INFORMATION: oligonucleotides representing group Z

<400> SEQUENCE: 148
gcagaccccg ctgctcgtc                                                 19

<210> SEQ ID NO 149
<211> LENGTH: 18
<212> TYPE: DNA
<213> ORGANISM: Artificial sequence
<220> FEATURE:
<223> OTHER INFORMATION: oligonucleotides representing group Z

<400> SEQUENCE: 149
gcagaccccg ctgctcgt                                                  18

<210> SEQ ID NO 150
<211> LENGTH: 17
<212> TYPE: DNA
<213> ORGANISM: Artificial sequence
<220> FEATURE:
<223> OTHER INFORMATION: oligonucleotides representing group Z

<400> SEQUENCE: 150
gcagaccccg ctgctcg                                                   17

<210> SEQ ID NO 151
<211> LENGTH: 16
<212> TYPE: DNA
<213> ORGANISM: Artificial sequence
<220> FEATURE:
<223> OTHER INFORMATION: oligonucleotides representing group Z

<400> SEQUENCE: 151
gcagaccccg ctgctc                                                    16

<210> SEQ ID NO 152
<211> LENGTH: 15
<212> TYPE: DNA
<213> ORGANISM: Artificial sequence
<220> FEATURE:
<223> OTHER INFORMATION: oligonucleotides representing group Z

<400> SEQUENCE: 152
```

```
gcagaccccg ctgct                                              15

<210> SEQ ID NO 153
<211> LENGTH: 14
<212> TYPE: DNA
<213> ORGANISM: Artificial sequence
<220> FEATURE:
<223> OTHER INFORMATION: oligonucleotides representing group Z

<400> SEQUENCE: 153
gcagaccccg ctgc                                               14

<210> SEQ ID NO 154
<211> LENGTH: 13
<212> TYPE: DNA
<213> ORGANISM: Artificial sequence
<220> FEATURE:
<223> OTHER INFORMATION: oligonucleotides representing group Z

<400> SEQUENCE: 154
gcagaccccg ctg                                                13

<210> SEQ ID NO 155
<211> LENGTH: 12
<212> TYPE: DNA
<213> ORGANISM: Artificial sequence
<220> FEATURE:
<223> OTHER INFORMATION: oligonucleotides representing group Z

<400> SEQUENCE: 155
gcagaccccg ct                                                 12

<210> SEQ ID NO 156
<211> LENGTH: 11
<212> TYPE: DNA
<213> ORGANISM: Artificial sequence
<220> FEATURE:
<223> OTHER INFORMATION: oligonucleotides representing group Z

<400> SEQUENCE: 156
gcagaccccg c                                                  11

<210> SEQ ID NO 157
<211> LENGTH: 10
<212> TYPE: DNA
<213> ORGANISM: Artificial sequence
<220> FEATURE:
<223> OTHER INFORMATION: oligonucleotides representing group Z

<400> SEQUENCE: 157
gcagaccccg                                                    10

<210> SEQ ID NO 158
<211> LENGTH: 9
<212> TYPE: DNA
<213> ORGANISM: Artificial sequence
<220> FEATURE:
<223> OTHER INFORMATION: oligonucleotides representing group Z

<400> SEQUENCE: 158 gcagacccc                                                      9

<210> SEQ ID NO 159
<211> LENGTH: 8
<212> TYPE: DNA
<213> ORGANISM: Artificial sequence
```

```
<220> FEATURE:
<223> OTHER INFORMATION: oligonucleotides representing group Z

<400> SEQUENCE: 159 gcagaccc                                                                    8

<210> SEQ ID NO 160
<211> LENGTH: 7
<212> TYPE: DNA
<213> ORGANISM: Artificial sequence
<220> FEATURE:
<223> OTHER INFORMATION: oligonucleotides representing group Z

<400> SEQUENCE: 160 gcagacc                                                                     7

<210> SEQ ID NO 161
<211> LENGTH: 6
<212> TYPE: DNA
<213> ORGANISM: Artificial sequence
<220> FEATURE:
<223> OTHER INFORMATION: oligonucleotides representing group Z

<400> SEQUENCE: 161 gcagac                                                                      6

<210> SEQ ID NO 162
<211> LENGTH: 5
<212> TYPE: DNA
<213> ORGANISM: Artificial sequence
<220> FEATURE:
<223> OTHER INFORMATION: oligonucleotides representing group Z

<400> SEQUENCE: 162 gcaga                                                                       5

<210> SEQ ID NO 163
<211> LENGTH: 4
<212> TYPE: DNA
<213> ORGANISM: Artificial sequence
<220> FEATURE:
<223> OTHER INFORMATION: oligonucleotides representing group Z

<400> SEQUENCE: 163 gcag                                                                        4
```